US012545934B2

(12) United States Patent
Kumaran et al.

(10) Patent No.: US 12,545,934 B2

(45) **Date of Patent: *Feb. 10, 2026**

(54) METHODS FOR PRODUCTION OF OXYGENATED TERPENES

(71) Applicants: Givaudan SA, Vernier (CH); MANUS BIO INC., Cambridge, MA (US)

(72) Inventors: Ajikumar Parayil Kumaran, Cambridge, MA (US); Chin Giaw Lim, Allston, MA (US); Liwei Li, Arlington, MA (US); Souvik Ghosh, Cambridge, MA (US); Christopher Pirie, Cambridge, MA (US); Anthony Qualley, Beavercreek, OH (US); Geoff Marshall-Hill, Buckinghamshire (GB); Martin Preininger, Nuess (DE)

(73) Assignees: GIVAUDAN SA, Vernier (CH); MANUS BIO INC., Cambridge, MA (US)

( * ) Notice: Subject to any disclaimer, the term of this patent is extended or adjusted under 35 U.S.C. 154(b) by 91 days.

This patent is subject to a terminal disclaimer.

(21) Appl. No.: 18/373,659

(22) Filed: Sep. 27, 2023

(65) Prior Publication Data

US 2024/0141392 A1 May 2, 2024

Related U.S. Application Data

(60) Continuation of application No. 17/456,126, filed on Nov. 22, 2021, now Pat. No. 11,807,890, which is a continuation of application No. 16/669,051, filed on Oct. 30, 2019, now Pat. No. 11,180,782, which is a division of application No. 15/505,022, filed as application No. PCT/US2015/046421 on Aug. 21, 2015, now Pat. No. 10,501,760.

(60) Provisional application No. 62/040,284, filed on Aug. 21, 2014.

(51) Int. Cl.

| | |
|---|---|
| ***C12P 7/26*** | (2006.01) |
| ***A01N 27/00*** | (2006.01) |
| ***A23L 27/12*** | (2016.01) |
| ***C12N 9/02*** | (2006.01) |
| ***C12P 5/00*** | (2006.01) |

(52) U.S. Cl.

CPC ................ *C12P 7/26* (2013.01); *A01N 27/00* (2013.01); *A23L 27/13* (2016.08); *C12N 9/0073* (2013.01); *C12P 5/002* (2013.01); *C12Y 114/13078* (2013.01); *A23V 2002/00* (2013.01); *C07K 2319/03* (2013.01)

(58) Field of Classification Search

None

See application file for complete search history.

(56) References Cited

U.S. PATENT DOCUMENTS

| | | | | |
|---|---|---|---|---|
| 5,847,226 | A | 12/1998 | Muller et al. | |
| 6,200,786 | B1 | 3/2001 | Huang et al. | |
| 6,890,960 | B1 | 5/2005 | Henderson et al. | |
| 7,211,420 | B1 | 5/2007 | Wong et al. | |
| 7,273,735 | B2 | 9/2007 | Schalk et al. | |
| 8,097,442 | B2 | 1/2012 | Hitchman et al. | |
| 8,415,136 | B1 | 4/2013 | Gardner et al. | |
| 8,512,988 | B2 | 8/2013 | Ajikumar et al. | |
| 8,927,241 | B2 | 1/2015 | Ajikumar et al. | |
| 9,284,570 | B2 | 3/2016 | Stephanopoulos et al. | |
| 9,359,624 | B2 | 6/2016 | Ajikumar et al. | |
| 9,494,130 | B2 | 11/2016 | Ko et al. | |
| 9,796,980 | B2 | 10/2017 | Ajikumar et al. | |
| 9,957,527 | B2 | 5/2018 | Ajikumar et al. | |
| 10,501,760 | B2 | 12/2019 | Kumaran et al. | |
| 10,774,314 | B2 | 9/2020 | Donald et al. | |
| 11,180,782 | B2 * | 11/2021 | Kumaran | C12P 7/26 |
| 11,807,890 | B2 * | 11/2023 | Kumaran | C12P 5/002 |
| 2011/0189717 | A1 | 8/2011 | Ajikumar et al. | |
| 2012/0107893 | A1 | 5/2012 | Ajikumar et al. | |
| 2012/0164678 | A1 | 6/2012 | Stephanopoulos et al. | |
| 2012/0246767 | A1 | 9/2012 | Amick et al. | |
| 2017/0002366 | A1 | 1/2017 | Ajikumar et al. | |
| 2017/0002382 | A1 | 1/2017 | Ajikumar et al. | |
| 2017/0332673 | A1 | 11/2017 | Philippe et al. | |
| 2018/0135081 | A1 | 5/2018 | Kumaran et al. | |
| 2018/0251738 | A1 | 9/2018 | Donald et al. | |
| 2018/0327789 | A1 | 11/2018 | Kumaran et al. | |
| 2020/0224224 | A1 | 7/2020 | Kumaran | |

FOREIGN PATENT DOCUMENTS

| | | |
|---|---|---|
| JP | 2004067723 | 3/2004 |
| WO | 2006079020 | 7/2006 |
| WO | 2011060057 | 5/2011 |
| WO | 2016029187 | 2/2016 |

OTHER PUBLICATIONS

Database WPI Week 200423, Thomson Scientific, London, GB: AN 2004-244290, XP002752397, & JP 2004 067723 (Hasegawa Co. Ltd.) Mar. 4, 2004.

International Search Report and Written Opinion dated Dec. 14, 2015 for international application PCT/US2015/046369.

International Search Report and Written Opinion dated Mar. 22, 2016 for international application PCT/US2015/046421.

International Search Report and Written Opinion for international application PCT/US2016/047692.

"Beta-Nootkaton", Product information from Pubchem, downloaded from pubchem.ncbi.nim.nih.gov/compound. Nootkatol (Year 2018).

"Predicted: en-kaurene oxidase, chloroplastic-like [*malus domestica*]" Database Genpept XP002752377, Jun. 20, 2014.

(Continued)

*Primary Examiner* — Anand U Desai

(74) *Attorney, Agent, or Firm* — Curatolo Sidoti & Trillis Co., LPA; Floyd Trillis, III; Salvatore A. Sidoti

(57) ABSTRACT

The present disclosure relates to methods for producing oxygenated terpenoids, and preparation of compositions and formulations thereof. Polynucleotides, derivative enzymes, and host cells for use in such methods are also provided.

10 Claims, 79 Drawing Sheets

Specification includes a Sequence Listing.

(56) References Cited

OTHER PUBLICATIONS

Ajikumar, et al., "Isoprenoid Pathway Optimization for Taxol Precursor Overproduction in *Escherichia Coli*", Science, 2010, vol. 1, No. 330 (6000), pp. 1-11.
Chang, et al., "Engineering *Escherichia Coli* for Production of Fictionalized Terpenoids Using Plant P450s" Nature 2007, Chemical Biology, vol. 3, No. 5, pp. 274-277.
Drew, et al., "Transcritome Analysis of Thapsia Laciniata Rouy Provides Insights into Terpenoid Biosynthesis and Diversity in Apiaceae", 2013 International Journal of Molecular Sciences, 2013 vol. 14, pp. 9080-9098.
Hotze, et al. "Cinnamate 4-hydroxylase from Catharanthus Roseuseand and Strategy for the Functional Expression of Plant Cytochrome P. 450 Proteins as Translational Fusions with P450 Reductase in *Escherichia Coli*" FEBS Letters, 1995 vol. 374, pp. 345-350.
Humphrey, et al. "Spatial Organization of four enzymes from Stevia rebaudiana that are involved in steviol glycoside synthesis", Plant Molecular Biology (2006) 61:47-62.
Humphrey, et al., "Subname: full-ent-kaurene oxidase CYP701A5", Unirot Database, Feb. 19, 2014.
Humphrey, et al. "Subname, Full-kaurene ociidase" Uniprot Database, Jul. 9, 2014.
King, "Production of Bioactive Diterpenoids in the Euphoribiaceae Depends on Evoultionary Conserved Gene Clusters", The Plant Cell, 2014, vol. 26, pp. 3286-3298.
Kumaran, et al. Notice of Allowance dated Apr. 4, 2019 for U.S. Appl. No. 15/505,022.
Kumaran, et al., Notice of Allowance dated Aug. 5, 2021 for U.S. Appl. No. 16/669,051.
Kumaran, et al., Office Action dated Mar. 19, 2019 for U.S. Appl. No. 15/505,503.
Kumaran, et al. Office Action dated Mar. 3, 2021 for U.S. Appl. No. 16/669,051.
Kumaran, et al. Office Action dated Nov. 23, 2018 for U.S. Appl. No. 15/505,022.
Kumaran, et al. Restriction Requirement dated Dec. 20, 2018 for U.S. Appl. No. 15/505,503.
Kumaran, et al. Restriction Requirement dated Oct. 9, 2018 for U.S. Appl. No. 15/505,022.
Lange, et al. "Isoprenoid Biosynthesis: The Evolution of Two Ancient and Distinct Pathways Across Genomes" PNAS 97:13172-13177, 2000. (Year 2000).
Leonard, et al. "Functional Expression of a P450 Flavonoid Hydroxy Lase for the Biosynthesis of Plant-Specific Hydroxylated Flavonaols in *Esherichia Coli*" Metaboic Engineering, 200. vol. 8. pp. 172-181.
Schuckel, et al. "A gene-fusion approach to enabling plant cytochromes P450 for Biocatalysis" Chembiochem, vol. 13, No. 18, Nov. 5, 2012, pp. 2758-2763.
Seifert, et al. "Rational design of a minimal and highly enriched CYP102A1 mutant library with improved regiostereo and chemoselectivity" Chembiochem, vol. 10, No. 5, Mar. 23, 2009.
Singh, "Chemistry of Terpenoids and Carotenoids", Discovery Publishing House, New Delhi, 2007, pp. 3 and 4 (Year 2007).
Wriessenegger, et al., "Production of the sesquiterpenoid (+)-nootkalone by metabolic engineering of Pichia pastoris", Metabolic Engineering, vol. 24, Apr. 16, 2014, pp. 18-29.

* cited by examiner

Figure 3A

>VvVS [Vitis vinifera]

MSTQVSASSLAQIPQPKNRPVANFHPNIWGDQFITYTPEDKVTRACKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMHGVYFEP
QYLRGRRILTKVIAMTSILDDIHDAYGTPEELKLFIEAIERWDINSINQLPEYMKLCY
VALLDVYKEIEEEMEKEGNQYRVHYAKEVMKNQVRAYFAEAKWLHEEHVPAFEEYMRV
ALASSGYCLLATTSFVGMGEIATKEAFDWVTSDPKIMSSSNFITRLMDDIKSHKFEQK
RGHVTSAVECYMKQYGVSEEQVYSEFQKQIENAWLDINQECLKPTAVSMPLLARLLNF
TRTMDVIYKEQDSYTHVGKVMRDNIASVFINAVI (SEQ ID NO: 1)

ATGGCTACGCAGGTCTCAGCCTCGTCACTGGCACAAATCCCGCAGCCGAAAAATCGTC
CGGTGGCGAACTTCCATCCGAATATCTGGGGTGACCAGTTTATCACGTATACCCCGGA
AGATAAAGTGACCCGTGCGTGCAAGGAAGAACAAATTGAAGACCTGAAAAAGGAAGTC
AAACGCAAGCTGACCGCAGCAGCAGTGGCAAACCCGTCTCAGCTGCTGAATTTTATCG
ATGCGGTTCAACGTCTGGGCGTCGCCTATCATTTCGAACAGGAAATTGAAGAAGCACT
GCAACATATCTGCAACAGCTTTCACGATTGTAATGATATGGACGGCGATCTGTATAAC
ATTGCTCTGGGTTTCCGTCTGCTGCGCCAGCAAGGCTACACGATTTCCTGTGACATCT
TTAATAAATTCACCGATGAACGTGGTCGCTTTAAGGAAGCGCTGATCTCAGACGTTCG
TGGCATGCTGGGTCTGTATGAAGCTGCGCATCTGCGCGTCCACGGCGAAGATATTCTG
GCCAAAGCACTGGCTTTCACCACGACCCACCTGAAGGCGATGGTCGAATCTCTGGGTT
ACCATCTGGCAGAACAGGTGGCACACGCCCTGAACCGTCCGATCCGCAAAGGCCTGGA
ACGTCTGGAAGCGCGCTGGTATATTAGTGTGTACCAGGACGAAGCATTTCATGATAAA
ACCCTGCTGGAACTGGCTAAGCTGGATTTCAACCTGGTTCAATCTCTGCACAAAGAAG
AACTGAGTAATCTGGCCCGTTGGTGGAAAGAACTGGACTTTGCGACCAAGCTGCCGTT
CGCCCGTGATCGCCTGGTTGAAGGCTATTTTTGGATGCATGGTGTCTATTTCGAACCG
CAGTACCTGCGCGGTCGTCGCATTCTGACGAAAGTGATCGCAATGACCTCGATTCTGG
ATGACATCCACGACGCTTACGGCACCCCGGAAGAACTGAAACTGTTTATTGAAGCGAT
CGAACGTTGGGATATTAACAGCATCAATCAGCTGCCGGAATATATGAAACTGTGCTAC
GTGGCCCTGCTGGATGTTTACAAGGAAATCGAAGAAGAAATGGAAAAGGAAGGTAACC
AGTATCGTGTTCATTACGCGAAAGAAGTCATGAAGAATCAAGTGCGCGCCTACTTTGC
AGAAGCTAAATGGCTGCATGAAGAACACGTGCCGGCGTTCGAAGAATATATGCGCGTT
GCGCTGGCCAGCTCTGGCTACTGTCTGCTGGCCACGACCTCTTTTGTGGGCATGGGTG
AAATTGCAACGAAAGAAGCGTTTGACTGGGTTACCAGTGATCCGAAGATTATGAGTTC
CTCAAACTTTATCACCCGTCTGATGGATGACATTAAATCCCATAAGTTCGAACAGAAA
CGCGGTCACGTCACCTCAGCCGTGGAATGCTATATGAAACAGTACGGCGTTTCGGAAG
AACAAGTCTATAGCGAATTTCAGAAACAAATCGAAAACGCATGGCTGGATATTAATCA
GGAATGTCTGAAACCGACGGCAGTCTCCATGCCGCTGCTGGCTCGTCTGCTGAATTTT
ACGCGCACGATGGATGTGATCTATAAAGAACAGGATTCGTACACCCATGTGGGCAAGG
TTATGCGCGATAACATTGCAAGCGTGTTCATTAATGCTGTTATCTAA (SEQ ID
NO: 2)

>Vv1M1 | engineered valencene synthase

MATQVSASSLAQIPQPKNRPVANFHPNIWGDQFITYTPEDKVTRACKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMHGVYFEP
QYLRGRRILTKVIAMTSILDDIHDAYGSPEELKLFIEAIEKWDESSINQLPEYMKLCF
VALIDVYNEIEEEMEKEGNQYRIHYLKEVMKNQVRAYFAEAKWLHDEHVPAFEEYMRV
ALASSGYCLLAVTSFVGMGEIVTKEAFDWVTSDPKLMSSSNFITRLMDDIKSHKFEQK
RGHVTSAVECYMKQYGVTEEQVYSEFKKQIENAWLDINQECLKPTAVPMPLLARLLNF
TRTMDVIYKEQDSYTHVGKVMRDNIASVFINPVI (SEQ ID NO: 3)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCTGCAAAGAGGAGCAGATCGAGGACCTGAAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGCACGGCGTTTACTTCGAGCCG
CAATACCTGCGTGGCCGCCGCATCCTGACGAAGGTGATCGCCATGACCAGCATTCTGG
ACGACATCCACGATGCGTACGGGAGCCCTGAGGAGTTAAAGCTGTTCATCGAGGCAAT
CGAGAAGTGGGATGAGAGTAGCATCAACCAACTGCCGGAGTATATGAAACTGTGCTTC
GTGGCCCTGATTGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGAAGCTGATGAGCAG
CAGCAACTTCATCACCCGTCTGATGGACGACATCAAGAGCCACAAGTTCGAGCAGAAA
CGCGGTCACGTTACCAGCGCCGTGGAGTGCTACATGAAGCAGTACGGCGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGCAGGATAGCTACACCCACGTTGGTAAGG
TGATGCGCGACAACATCGCCAGTGTGTTCATCAACCCGGTGATCTAA (SEQ ID
NO: 4)

Figure 3B

>Vv2M1 | engineered valencene synthase

MATQVSASSLAQIPQPKNRPVANFHPNIWGDQFITYTPEDKVTRACKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMHGVYFEP
QYLRGRRILTKVIALTSILDDIHDAYGTPEELKLFIEAIEKWDESSINQLPEYMKLCY
VALLDVYNEIEEEMEKEGNQYRIHYLKEVMKNQVRAYFAEAKWLHDEHVPAFEEYMRV
ALASSGYCLLAVTSFVGMGEIVTKEAFDWVTSDPRIMSSSNFITRLMDDIKSHKFEQK
RGHVTSAVECYMKQYAVTEEQVYSEFKKQIENAWLDINQECLKPTAVPMPLLARLLNF
TRTMDVIYKEQDSYTHVGKTMRDNIASVFINPVI (SEQ ID NO: 5)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCTGCAAAGAGGAGCAGATCGAGGACCTGAAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGCACGGCGTTTACTTCGAGCCG
CAATACCTGCGTGGCCGCCGCATCCTGACGAAGGTGATCGCCCTGACCAGCATTCTGG
ACGACATCCACGATGCGTACGGGACCCCTGAGGAGTTAAAGCTGTTCATCGAGGCAAT
CGAGAAGTGGGATGAGAGTAGCATCAACCAACTGCCGGAGTATATGAAACTGTGCTAT
GTGGCCCTGCTGGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGCGTATTATGAGCAG
CAGCAACTTCATCACCCGTCTGATGGACGACATCAAGAGCCACAAGTTCGAGCAGAAA
CGCGGTCACGTTACCAGCGCCGTGGAGTGCTACATGAAGCAGTACGCAGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGCAGGATAGCTACACCCACGTTGGTAAGA
CCATGCGCGACAACATCGCCAGTGTGTTCATCAACCCGGTGATCTAA (SEQ ID
NO: 6)

Figure 3C

>Vv1M5 | engineered valencene synthase

MATQVSASSLAQIPQPKNRPVANFHPNIWGDQFITYTPEDKVTRAKKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMMGVYFEP
QYLRGRRILTKVIAMTSILDDIHDAYGSPEELKLFIEAIEKWDESSINQLPEYMKLCF
VALIDVYNEIEEEMEKEGNQYRIHYLKEVMKNQVRAYFAEAKWLHDEHVPAFEEYMRV
ALASSGYCLLAVTSFVGMGEIVTKEAFDWVTSDPKLMSSSNTITRLMDDIKSHKFEQK
RGHVTSAVECYMKQYGVTEEQVYSEFKKQIENAWLDINQECLKPTAVPMPLLARLLNF
TRTMDVIYKEEDSYTHVGKVMRDNIASVFINPVI (SEQ ID NO: 7)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCAAAAAAGAGGAGCAGATCGAGGACCTGAAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGATGGGCGTTTACTTCGAGCCG
CAATACCTGCGTGGCCGCCGCATCCTGACGAAGGTGATCGCCATGACCAGCATTCTGG
ACGACATCCACGATGCGTACGGGAGCCCTGAGGAGTTAAAGCTGTTCATCGAGGCAAT
CGAGAAGTGGGATGAGAGTAGCATCAACCAACTGCCGGAGTATATGAAACTGTGCTTC
GTGGCCCTGATTGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGAAGCTGATGAGCAG
CAGCAACACCATCACCCGTCTGATGGACGACATCAAGAGCCACAAGTTCGAGCAGAAA
CGCGGTCACGTTACCAGCGCCGTGGAGTGCTACATGAAGCAGTACGGCGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGGAAGATAGCTACACCCACGTTGGTAAGG
TGATGCGCGACAACATCGCCAGTGTGTTCATCAACCCGGTGATCTAA (SEQ ID NO: 8)

Figure 3D

>Vv2M5 | engineered valencene synthase

MATQVSASSLAQIPQPKNRPVANFHPNIWGDQFITYTPEDKVTRAKKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMMGVYFEP
QYLRGRRILTKVIALTSILDDIHDAYGTPEELKLFIEAIEKWDESSINQLPEYMKLCY
VALLDVYNEIEEEMEKEGNQYRIHYLKEVMKNQVRAYFAEAKWLHDEHVPAFEEYMRV
ALASSGYCLLAVTSFVGMGEIVTKEAFDWVTSDPRIMSSSNTITRLMDDIKSHKFEQK
RGHVTSAVECYMKQYAVTEEQVYSEFKKQIENAWLDINQECLKPTAVPMPLLARLLNF
TRTMDVIYKEEDSYTHVGKTMRDNIASVFINPVI (SEQ ID NO: 9)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCAAAAAAGAGGAGCAGATCGAGGACCTGAAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGATGGGCGTTTACTTCGAGCCG
CAATACCTGCGTGGCCGCCGCATCCTGACGAAGGTGATCGCCCTGACCAGCATTCTGG
ACGACATCCACGATGCGTACGGGACCCCTGAGGAGTTAAAGCTGTTCATCGAGGCAAT
CGAGAAGTGGGATGAGAGTAGCATCAACCAACTGCCGGAGTATATGAAACTGTGCTAT
GTGGCCCTGCTGGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGCGTATTATGAGCAG
CAGCAACACCATCACCCGTCTGATGGACGACATCAAGAGCCACAAGTTCGAGCAGAAA
CGCGGTCACGTTACCAGCGCCGTGGAGTGCTACATGAAGCAGTACGCAGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGGAAGATAGCTACACCCACGTTGGTAAGA
CCATGCGCGACAACATCGCCAGTGTGTTCATCAACCCGGTGATCTAA (SEQ ID
NO: 10)

>VS2 | engineered valencene synthase

MATQVSASSLAQIPQPKNRPVANFHPNIWGDQFITYTPEDKVTRAKKEEQIEDLKKEV
KRKLTAAAVANPSQLLNFIDAVQRLGVAYHFEQEIEEALQHICNSFHDCNDMDGDLYN

Figure 3E

IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMMGVYFEP
QYLRGRRILTKVIALTSILDDIHDAYGTPEELKLFIEAIEKWDESSINQLPEYMKLCY
VALLDVYNEIEEEMEKEGNQYRIHYLKEVMKNQVRAYFAEAKWLHDEHVPAFEEYMRV
ALASSGYCLLAVTSFVGMGEIVTKEAFDWVTSDPRIMSSSNTITRLMDDIKSHKFEQK
RGHVTSAVECYMKQYAVTEEQVYSEFKKQIENAWLDINQECLKPTAVPMPLLARLLNF
TRTMDVIYKEEDSYTHVGKTMRDNIASVFINPVI (SEQ ID NO: 11)

ATGGCAACCCAGGTGAGCGCCAGTAGCCTGGCACAAATCCCGCAGCCTAAAAACCGCC
CTGTTGCCAATTTCCATCCGAACATCTGGGGCGACCACTTTATCACCTACACCCCGGA
AGACAAAGTGACCCGCGCCAAAAAAGAAGAGAGGATTGAAGATCTGAAGGAAGAAGTG
AAACGCAAACTGACCGCAGCCGCCGTGGCCAATCCGAGTCAACTGCTGAACTTCATTG
ATGCAGTTCAGCGCCTGGGCGTTGCCTATCACTTTGAGCAGGAGATCGAGGAGGCATT
ACAGCATATTTGTAATAGCTTTCACGACTGCAATGATATGGATGGCGACCTGTATAAT
ATCGCCCTGCTATTTCGTCTGCTGCGCCAACAGGGTTACACAATCAGTTGCGACATCT
TTAACAAGTTCACCGATGAAGAGGGCCGCTTTAAAGAAGCCCTGATTAGCGACGTGCG
CGGTATGTTAGGCCTGTATGAAGCAGCCCACCTGCGCGTTCACGGCGAAGACATCCTG
GCAGAGGCACTGGCCTTTACAACCACCCACCTGAAAGCAATGGTTGAATCGCTGGGCT
ACCATCTGGCCGAGCAAGTGAGGCACGCCTTAAACCGTCCGATCCGTAAAGGCATGGA
ACGTCTGGAAGCACGTTGGTACATCAGCATATACCAGGATGAGGCCTTTCATGACAAA
ACCCTGCTGGAGCTGGCCAAACTGGACTTCAACCTGGTGCAGAGCCTGCACAAAGAAG
AGCTGAGCAATCTGGCACGCTGGTGGAAGGAGCTGGATTTTGCCACCAAACTGCCTTT
TGCCCGCGACCGTTTAGTTGAAGGCTACTTTTGGATGATGGGTGTGTATTTTGAGCCG
CAGTATCTGCGTGGCCGTCGCATCCTGACAAAGGTGATCGCCCTGACCAGCATCATTG
ACGACATCCACGATGCCTATGGCACCCCGGAGGAACTGAAACTGTTTATCGAGGCCAT
CGAAAAATGGGACGAGAGCAGCATCAACCAACTGCCTGAGTACATGAAGCTGTGCTAT
GTGGCCCTGCTGGACGTGTATAATGAAATCGAAGAGGAGATGGAAAAGGAGGGCAACC
AATACCGTATCCACTACCTGAAGGAGGTTATGAAAAACCAGGTGCGTGCCTACTTTGC
AGAGGCAAAATGGCTGCACGATGAGCATGTGCCGGCCTTTGAAGAATACATGCGCGTT
GCCCTGGCCAGCAGTGGTTATTGTCTGCTGGCCGTTACAAGTTTTGTGGGCATGGGCG
AGATCGTGACAAAGGAAGCCTTTGACTGGGTTACAAGCGACCCGCGCATCATAAGCAG
CAGCAACACAATTACACGCCTGATGGACGACATTAAAAGCCATAAATTTGAACAGAAA
CGCGGTCATGTGACCAGCGCCGTGGAATGCTACATGAAACAGTACGCCGTGACCGAAG
AGCAGGTTTACGAGGAATTTAAAAAACAGATTGAAAACGCATGGCTGGACATTAATCA
GGAGTGTCTGAAGCCGACCGCAGTGCCGATGCCGCTGTTAGCACGCCTGCTGAATTTC
ACCCGCACAATGGATGTGATTTATAAAGAAGAAGACAGCTATACCCATGTGGGCAAGA
CCATGCGCGACAACATCGCCAGCGTGTTTATCAACCCTGTGATCTAA (SEQ ID
NO: 120)

>CsVS | Citrus sinensis valencene synthase

MASGETFRPTADFHPSLWRNHFLKGASDFKTVDHTATQERHEALKEEVRRMITDAEDK
PVQKLRLIDEVQRLGVAYHFEKEIGDAIQKLCPIYIDSNRADLHTVSLHFRLLRQQGI
KISCDVFEKFKDDEGRFKSSLINDVQGMLSLYEAAYMAVRGEHILDEAIAFTTTHLKS
LVAQDHVTPKLAEQINHALYRPLRKTLPRLEARYFMSMINSTSDHLCNKTLLNFAKLD
FNILLELHKEELNELTKWWKDLDFTTKLPYARDRLVELYFWDLGTYFEPQYAFGRKIM

Figure 3F

TQLNYILSIIDDTYDAYGTLEELSLFTEAVQRWNIEAVDMLPEYMKLIYRTLLDAFNE
IEEDMAKQGRSHCVRYAKEENQKVIGAYSVQAKWFSEGYVPTIEEYMPIALTSCAYTF
VITNSFLGMGDFATKEVFEWISNNPKVVKAASVICRLMDDMQGHEFEQKRGHVASAIE
CYTKQHGVSKEEAIKMFEEEVANAWKDINEELMMKPTVVARPLLGTILNLARAIDFIY
KEDDGYTHSYLIKDQIASVLGDHVPF (SEQ ID NO: 12)

ATGGCCTCCGGCGAAACCTTCCGTCCGACCGCAGACTTCCATCCGTCACTGTGGCGTA
ATCACTTCCTGAAAGGCGCAAGCGACTTCAAAACGGTGGATCATACGGCAACCCAGGA
ACGTCACGAAGCTCTGAAGGAAGAAGTCCGTCGCATGATTACCGATGCCGAAGACAAA
CCGGTGCAGAAGCTGCGTCTGATCGATGAAGTTCAACGCCTGGGCGTCGCGTATCATT
TTGAAAAAGAAATTGGTGACGCCATCCAGAAGCTGTGCCCGATTTACATCGATAGCAA
CCGCGCAGACCTGCATACCGTGTCTCTGCACTTTCGTCTGCTGCGCCAGCAAGGCATC
AAGATCAGCTGTGATGTTTTCGAAAAGTTCAAGGATGACGAAGGCCGTTTCAAAAGCT
CTCTGATTAATGATGTTCAGGGTATGCTGTCTCTGTATGAAGCGGCCTACATGGCGGT
CCGCGGTGAACATATTCTGGATGAAGCGATCGCCTTTACCACGACCCATCTGAAAAGC
CTGGTGGCCCAGGACCACGTTACGCCGAAGCTGGCGGAACAAATTAACCACGCCCTGT
ATCGTCCGCTGCGCAAAACCCTGCCGCGTCTGGAAGCACGCTACTTCATGAGCATGAT
TAATAGTACGTCCGATCATCTGTGCAACAAAACCCTGCTGAATTTTGCTAAGCTGGAC
TTCAACATCCTGCTGGAACTGCACAAAGAAGAACTGAATGAACTGACCAAATGGTGGA
AGGATCTGGACTTTACGACCAAACTGCCGTATGCACGTGATCGCCTGGTTGAACTGTA
CTTCTGGGACCTGGGCACGTATTTTGAACCGCAGTACGCTTTCGGTCGTAAAATTATG
ACCCAACTGAACTATATCCTGTCAATTATCGATGACACGTATGATGCGTACGGCACCC
TGGAAGAACTGTCGCTGTTTACGGAAGCGGTGCAGCGTTGGAATATTGAAGCCGTTGA
TATGCTGCCGGAATATATGAAACTGATTTACCGCACCCTGCTGGATGCATTCAACGAA
ATCGAAGAAGACATGGCTAAACAAGGTCGTAGTCATTGCGTGCGCTATGCGAAAGAAG
AAAATCAGAAGGTTATTGGCGCGTACTCAGTCCAAGCCAAATGGTTTTCGGAAGGTTA
TGTTCCGACGATTGAAGAATACATGCCGATCGCACTGACCTCATGTGCTTATACGTTT
GTGATCACCAACTCGTTCCTGGGCATGGGTGATTTTGCCACCAAAGAAGTTTTCGAAT
GGATTAGCAACAATCCGAAAGTGGTTAAGGCAGCTTCTGTCATCTGCCGTCTGATGGA
TGACATGCAGGGCCATGAATTTGAACAAAAACGCGGTCACGTTGCAAGTGCTATTGAA
TGTTATACCAAGCAGCACGGCGTCTCCAAAGAAGAAGCAATTAAGATGTTCGAAGAAG
AAGTGGCGAACGCCTGGAAAGATATCAATGAAGAACTGATGATGAAGCCGACGGTCGT
GGCACGTCCGCTGCTGGGCACCATCCTGAATCTGGCACGCGCTATCGATTTCATCTAC
AAAGAAGATGACGGCTACACCCATAGTTACCTGATTAAGGATCAGATCGCCTCCGTCC
TGGGTGACCACGTGCCGTTCTAA (SEQ ID NO: 119)

Figure 3G

```
Vv2M5    MATQVSASSLAQIPQPKNRPVANFHPNIWGDQFITYTPEDK-VTRAKKEEQIEDLKKEVK 59
VS2      MATQVSASSLAQIPQPKNRPVANFHPNIWGDQFITYTPEDK-VTRAKKEEQIEDLKKEVK 59
VvVS     MSTQVSASSLAQIPQPKNRPVANFHPNIWGDQFITYTPEDK-VTRACKEEQIEDLKKEVK 59
CsVS     MASGETF------------RPTADFHPSLWRNHFLKGASDFKTVDHTATQERHEALKEEVR 49
         *::  :            **.*:***.:* ::*:. :.: * * :: .:*: * **:**:

Vv2M5    RKLTAAAVANPSQLLNFIDAVQRLGVAYHFEQEIEEALQHICNSFHDCNDMDGDLYNIAL 119
VS2      RKLTAAAVANPSQLLNFIDAVQRLGVAYHFEQEIEEALQHICNSFHDCNDMDGDLYNIAL 119
VvVS     RKLTAAAVANPSQLLNFIDAVQRLGVAYHFEQEIEEALQHICNSFHDCNDMDGDLYNIAL 119
CsVS     RMITDAEDK-PVQKLRLIDEVQRLGVAYHFEKEIGDAIQKLCPIYIDSNRAD--LHTVSL 106
         * :* *     * * *.:** ***********:** ;*:*::*   : *.*   *   *:.::*

Vv2M5    GFRLLRQQGYTISCDIFNKFTDERGRFKEALISDVRGMLGLYEAAHLRVHGEDILAKALA 179
VS2      GFRLLRQQGYTISCDIFNKFTDERGRFKEALISDVRGMLGLYEAAHLRVHGEDILAKALA 179
VvVS     GFRLLRQQGYTISCDIFNKFTDERGRFKEALISDVRGMLGLYEAAHLRVHGEDILAKALA 179
CsVS     HFRLLRQQGIKISCDVFEKFKDDEGRFKSSLINDVQGMLSLYEAAYMAVRGEHILDEAIA 166
          ******** .****:*:**.*:.****.:**.**:***.*****:: *:**.** :*:*

Vv2M5    FTTTHLKAMVES--LGYHLAEQVAHALNRPIRKGLERLEARWYISVY--QDEAFHDKTLL 235
VS2      FTTTHLKAMVES--LGYHLAEQVAHALNRPIRKGLERLEARWYISVY--QDEAFHDKTLL 235
VvVS     FTTTHLKAMVES--LGYHLAEQVAHALNRPIRKGLERLEARWYISVY--QDEAFHDKTLL 235
CsVS     FTTTHLKSLVAQDHVTPKLAEQINHALYRPLRKTLPRLEARYFMSMINSTSDHLCNKTLL 226
         *******::*  .   :   :****: *** **:** * *****:::*:      .: : :****

Vv2M5    ELAKLDFNLVQSLHKEELSNLARWWKELDFATKLPFARDRLVEGYFWMMGVYFEPQYLRG 295
VS2      ELAKLDFNLVQSLHKEELSNLARWWKELDFATKLPFARDRLVEGYFWMMGVYFEPQYLRG 295
VvVS     ELAKLDFNLVQSLHKEELSNLARWWKELDFATKLPFARDRLVEGYFWMHGVYFEPQYLRG 295
CsVS     NFAKLDFNILLELHKEELNELTKWWKDLDFTTKLPYARDRLVELYFWDLGTYFEPQYAFG 286
         ::******:: .******.:*::***:***:****:******* ***   *.******  *

Vv2M5    RRILTKVIALTSILDDIHDAYGTPEELKLFIEAIEKWDESSINQLPEYMKLCYVALLDVY 355
VS2      RRILTKVIALTSILDDIHDAYGTPEELKLFIEAIEKWDESSINQLPEYMKLCYVALLDVY 355
VvVS     RRILTKVIAMTSILDDIHDAYGTPEELKLFIEAIERWDINSINQLPEYMKLCYVALLDVY 355
CsVS     RKIMTQLNYILSIIDDTYDAYGTLEELSLFTEAVQRWNIEAVDMLPEYMKLIYRTLLDAF 346
         *:*:*::   : **:** :***** ***.** **:::*: .::: ******* * :***.:

Vv2M5    NEIEEEMEKEGNQYRIHYLKEVMKNQVRAYFAEAKWLHDEHVPAFEEYMRVALASSGYCL 415
VS2      NEIEEEMEKEGNQYRIHYLKEVMKNQVRAYFAEAKWLHDEHVPAFEEYMRVALASSGYCL 415
VvVS     KEIEEEMEKEGNQYRVHYAKEVMKNQVRAYFAEAKWLHEEHVPAFEEYMRVALASSGYCL 415
CsVS     NEIEEDMAKQGRSHCVRYAKEENQKVIGAYSVQAKWFSEGYVPTIEEYMPIALTSCAYTF 406
         :****:* *:*..: ::* **   :: : ** .:***: : :**::**** :**:*..* :

Vv2M5    LAVTSFVGMGEIVTKEAFDWVTSDPRIMSSSNTITRLMDDIKSHKFEQKRGHVTSAVECY 475
VS2      LAVTSFVGMGEIVTKEAFDWVTSDPRIMSSSNTITRLMDDIKSHKFEQKRGHVTSAVECY 475
VvVS     LATTSFVGMGEIATKEAFDWVTSDPKIMSSSNFITRLMDDIKSHKFEQKRGHVTSAVECY 475
CsVS     VITNSFLGMGDFATKEVFEWISNNPKVVKAASVICRLMDDMQGHEFEQKRGHVASAIECY 466
         :  ..**:***::.***.*:*::.:*:::.::. * *****::.*:********:**:***

Vv2M5    MKQYAVTEEQVYSEFKKQIENAWLDINQEC-LKPTAVPMPLLARLLNFTRTMDVIYKEED 534
VS2      MKQYAVTEEQVYSEFKKQIENAWLDINQEC-LKPTAVPMPLLARLLNFTRTMDVIYKEED 534
VvVS     MKQYGVSEEQVYSEFQKQIENAWLDINQEC-LKPTAVSMPLLARLLNFTRTMDVIYKEQD 534
CsVS     TKQHGVSKEEAIKMFEEEVANAWKDINEELMMKPTVVARPLLGTILNLARAIDFIYKEDD 526
          **:.*::*:.  . *:::: *** ***:*   :***.*. ***. :**::*::*.****:*

Vv2M5    SYTHVGKTMRDNIASVFINPVI- 556
VS2      SYTHVGKTMRDNIASVFINPVI- 556
VvVS     SYTHVGKVMRDNIASVFINAVI- 556
CsVS     GYTHS-YLIKDQIASVLGDHVPF 548
         .***     ::*:****: : *
```

Figure 3H

Figure 4A

>ZzHO [Zingiber zerumbet]

MEAISLFSPFFFITLFLGFFITLLIKRSSRSSVHKQQVLLASLPPSPPRLPLIGNIHQLVGG
NPHRILLQLARTHGPLICLRLGQVDQVVASSVEAVEEIIKRHDLKFADRPRDLTFSRIFFYD
GNAVVMTPYGGEWKQMRKIYAMELLNSRRVKSFAAIREDVARKLTGEIAHKAFAQTPVINLS
EMVMSMINAIVIRVAFGDKCKQQAYFLHLVKEAMSYVSSFSVADMYPSLKFLDTLTGLKSKL
EGVHGKLDKVFDEIIAQRQAALAAEQAEEDLIIDVLLKLKDEGNQEFPITYTSVKAIVMEIF
LAGTETSSSVIDWVMSELIKNPKAMEKVQKEMREAMQGKTKLEESDIPKFSYLNLVIKETLR
LHPPGPLLFPRECRETCEVMGYRVPAGARLLINAFALSRDEKYWGSDAESFKPERFEGISVD
FKGSNFEFMPFGAGRRICPGMTFGISSVEVALAHLLFHFDWQLPQGMKIEDLDMMEVSGMSA
TRRSPLLVLAKLIIPLP (SEQ ID No: 13 | Wild Type)

MALLLAVFFFFITLFLGFFITLLIKRS*SR*SSVHKQQVLLASLPPSPPRLPLIGNIHQLVGGN
PHRILLQLARTHGPLICLRLGQVDQVVASSVEAVEEIIKRHDLKFADRPRDLTF*SR*IFFYDG
NAVVMTPYGGEWKQMRKIYAMELLN*SR*RVKSFAAIREDVARKLTGEIAHKAFAQTPVINLSE
MVMSMINAIVIRVAFGDKCKQQAYFLHLVKEAMSYVSSFSVADMYPSLKFLDTLTGLKSKLE
GVHGKLDKVFDEIIAQRQAALAAEQAEEDLIIDVLLKLKDEGNQEFPITYTSVKAIVMEIFL
AGTETSSSVIDWVMSELIKNPKAMEKVQKEMREAMQGKTKLEESDIPKFSYLNLVIKETLRL
HPPGPLLFPRECRETCEVMGYRVPAGARLLINAFAL*SR*DEKYWGSDAESFKPERFEGISVDF
KGSNFEFMPFGAGRRICPGMTFGISSVEVALAHLLFHFDWQLPQGMKIEDLDMMEVSGMSAT
RRSPLLVLAKLIIPLP (SEQ ID NO: 14)

ATGGCTCTGTTATTAGCAGTGTTCTTCTTTTTCATTACGCTGTTTCTGGGTTTCTTTATTAC
GCTGCTGATTAAACGCTCGTCCCGTAGCTCTGTCCATAAACAGCAAGTGCTGCTGGCCTCTC
TGCCGCCGAGTCCGCCGCGCCTGCCGCTGATTGGCAACATCCATCAACTGGTGGGCGGCAAC
CCGCATCGTATTCTGCTGCAACTGGCGCGTACCCACGGCCCGCTGATCTGCCTGCGTCTGGG
TCAGGTTGATCAAGTGGTTGCAAGTTCCGTGGAAGCTGTTGAAGAAATTATCAAACGTCACG
ACCTGAAATTTGCAGATCGTCCGCGCGACCTGACCTTTAGCCGTATTTTCTTTTATGATGGT
AACGCTGTCGTGATGACGCCGTACGGCGGTGAATGGAAACAGATGCGTAAAATCTATGCAAT
GGAACTGCTGAACAGCCGTCGTGTGAAATCTTTTGCGGCCATTCGTGAAGACGTTGCACGCA
AACTGACCGGCGAAATCGCTCACAAAGCATTCGCTCAGACGCCGGTCATTAACCTGTCTGAA
ATGGTGATGAGTATGATCAATGCGATTGTCATCCGCGTGGCCTTTGGTGATAAATGTAAACA
GCAAGCATACTTCCTGCATCTGGTGAAAGAAGCTATGTCCTATGTTTCATCGTTTTCAGTCG
CGGATATGTACCCGTCCCTGAAATTCCTGGACACCCTGACGGGCCTGAAAAGCAAACTGGAA
GGCGTTCACGGTAAACTGGATAAAGTCTTCGACGAAATCATCGCACAGCGTCAAGCAGCGCT
GGCGGCGGAACAGGCTGAAGAAGATCTGATTATCGACGTGCTGCTGAAACTGAAAGATGAAG
GCAACCAGGAATTTCCGATTACCTATACGTCAGTTAAAGCGATTGTCATGGAAATCTTCCTG
GCCGGCACCGAAACCAGCAGCAGCGTGATTGACTGGGTTATGAGTGAACTGATCAAAAACCC
GAAAGCGATGGAAAAAGTGCAGAAAGAAATGCGTGAAGCCATGCAAGGCAAAACCAAACTGG
AAGAATCGGATATTCCGAAATTTAGCTACCTGAATCTGGTTATCAAAGAAACCCTGCGTCTG
CATCCGCCGGGTCCGCTGCTGTTCCCGCGTGAATGCCGCGAAACCTGCGAAGTGATGGGCTA
TCGTGTTCCGGCGGGTGCCCGCCTGCTGATTAACGCATTTGCTCTGTCTCGTGATGAAAAAT
ACTGGGGTTCCGACGCCGAATCATTTAAACCGGAACGCTTTGAAGGCATCTCTGTGGATTTC
AAAGGTAGTAATTTTGAATTTATGCCGTTCGGCGCGGGCCGTCGTATTTGTCCGGGCATGAC
CTTTGGTATCTCCTCAGTTGAAGTCGCGCTGGCCCATCTGCTGTTTCACTTCGATTGGCAAC

TGCCGCAAGGCATGAAAATTGAAGATCTGGACATGATGGAAGTCTCGGGTATGAGCGCAACC
CGTCGTAGCCCGCTGCTGGTTCTGGCCAAACTGATTATCCCGCTGCCG (SEQ ID NO: 15)

>BsGAO [Barnadesia spinosa]

MELTLTTSLGLAVFVFILFKLLTGSKSTKNSLPEAWRLPIIGHMHHLVGTLPHRGVTDMARK
YGSLMHLQLGEVSTIVVSSPRWAKEVLTTYDITFANRPETLTGEIVAYHNTDIVLSPYGEYW
RQLRKLCTLELLSAKKVKSFQSLREEECWNLVKEVRSSGSGSPVDLSESIFKLIATILSRAA
FGKGIKDQREFTEIVKEILRLTGGFDVADIFPSKKILHHLSGKRAKLTNIHNKLDSLINNIV
SEHPGSRTSSSQESLLDVLLRLKDSAELPLTSDNVKAVILDMFGAGTDTSSATIEWAISELI
RCPRAMEKVQTELRQALNGKERIQEEDIQELSYLKLVIKETLRLHPPLPLVMPRECREPCVL
AGYEIPTKTKLIVNVFAINRDPEYWKDAETFMPERFENSPINIMGSEYEYLPFGAGRRMCPG
AALGLANVELPLAHILYYFNWKLPNGARLDELDMSECFGATVQRKSELLLVPTAYKTANNSA
(SEQ ID No: 16 | Wild Type)

MALLLAVFLGLAVFVFILFKLLTGSKSTKNSLPEAWRLPIIGHMHHLVGTLPHRGVTDMARK
YGSLMHLQLGEVSTIVVSSPRWAKEVLTTYDITFANRPETLTGEIVAYHNTDIVLSPYGEYW
RQLRKLCTLELLSAKKVKSFQSLREEECWNLVKEVRSSGSGSPVDLSESIFKLIATIL*SR*AA
FGKGIKDQREFTEIVKEILRLTGGFDVADIFPSKKILHHLSGKRAKLTNIHNKLDSLINNIV
SEHPG*SR*TSSSQESLLDVLLRLKDSAELPLTSDNVKAVILDMFGAGTDTSSATIEWAISELI
RCPRAMEKVQTELRQALNGKERIQEEDIQELSYLKLVIKETLRLHPPLPLVMPRECREPCVL
AGYEIPTKTKLIVNVFAINRDPEYWKDAETFMPERFENSPINIMGSEYEYLPFGAGRRMCPG
AALGLANVELPLAHILYYFNWKLPNGARLDELDMSECFGATVQRKSELLLVPTAYKTANNSA
(SEQ ID NO: 17)

ATGGCTCTGTTATTAGCAGTTTTCCTGGGCCTGGCTGTCTTCGTCTTTATCCTGTTCAAACT
GCTGACCGGCTCAAAATCAACCAAAAATTCACTGCCGGAAGCATGGCGTCTGCCGATCATTG
GCCACATGCATCACCTGGTTGGCACGCTGCCGCATCGCGGTGTGACCGACATGGCGCGTAAA
TACGGCAGCCTGATGCATCTGCAACTGGGCGAAGTGAGCACCATTGTCGTCTCATCGCCGCG
TTGGGCAAAAGAAGTGCTGACGACGTATGATATTACCTTTGCGAATCGCCCGGAAACCCTGA
CCGGCGAAATTGTTGCGTACCACAACACGGATATTGTGCTGTCACCGTATGGCGAATACTGG
CGCCAACTGCGTAAACTGTGCACGCTGGAACTGCTGAGCGCCAAAAAAGTGAAAAGTTTTCA
GTCGCTGCGTGAAGAAGAATGCTGGAATCTGGTGAAAGAAGTGCGTTCGAGCGGCTCAGGTT
CCCCGGTCGATCTGTCGGAATCCATCTTTAAACTGATTGCAACCATTCTGAGCCGCGCAGCG
TTTGGCAAAGGTATCAAAGATCAGCGTGAATTTACCGAAATTGTGAAAGAAATCCTGCGCCT
GACGGGCGGTTTTGATGTGGCGGATATTTTCCCGTCCAAAAAGATCCTGCACCACCTGAGCG
GCAAACGTGCGAAACTGACCAACATCCACAACAAACTGGATTCCCTGATTAATAACATTGTT
TCTGAACATCCGGGTTCGCGTACCTCGTCGAGCCAGGAAAGCCTGCTGGATGTGCTGCTGCG
CCTGAAAGATTCCGCGGAACTGCCGCTGACCTCGGACAATGTTAAAGCCGTGATCCTGGATA
TGTTCGGTGCGGGCACGGATACGTCGAGCGCCACGATTGAATGGGCGATCAGCGAACTGATC
CGCTGCCCGCGTGCAATGGAAAAAGTGCAAACGGAACTGCGTCAAGCGCTGAATGGTAAAGA
ACGCATTCAGGAAGAAGATATTCAGGAACTGTCCTATCTGAAACTGGTCATTAAAGAAACCC
TGCGCCTGCATCCGCCGCTGCCGCTGGTGATGCCGCGTGAATGTCGTGAACCGTGTGTCCTG
GCGGGTTACGAAATCCCGACCAAAACGAAACTGATTGTGAATGTCTTTGCCATCAATCGTGA
CCCGGAATACTGGAAAGATGCAGAAACCTTCATGCCGGAACGCTTTGAAAACAGCCCGATTA
ACATCATGGGTAGTGAATATGAATACCTGCCGTTTGGCGCAGGCCGCCGTATGTGTCCGGGT

Figure 4B

GCAGCTCTGGGTCTGGCGAATGTGGAACTGCCGCTGGCGCACATCCTGTATTATTTAACTG
GAAACTGCCGAATGGCGCTCGCCTGGATGAACTGGATATGTCGGAATGCTTTGGCGCGACGG
TCCAACGCAAAAGCGAACTGCTGCTGGTCCCGACGGCATACAAAACGGCAAACAACTCCGCA
(SEQ ID NO: 18)

>HmPO [Hyoscyamus muticus]

MQFFSLVSIFLFLSFLFLLRKWKNSNSQSKKLPPGPWKLPLLGSMLHMVGGLPHHVLRDLAK
KYGPLMHLQLGEVSAVVVTSPDMAKEVLKTHDIAFASRPKLLAPEIVCYNRSDIAFCPYGDY
WRQMRKICVLEVLSAKNVRSFSSIRRDEVLRLVNFVRSSTSEPVNFTERLFLFTSSMTCRSA
FGKVFKEQETFIQLIKEVIGLAGGFDVADIFPSLKFLHVLTGMEGKIMKAHHKVDAIVEDVI
NEHKKNLAMGKTNGALGGEDLIDVLLRLMNDGGLQFPITNDNIKAIIFDMFAAGTETSSSTL
VWAMVQMMRNPTILAKAQAEVREAFKGKETFDENDVEELKYLKLVIKETLRLHPPVPLLVPR
ECREETEINGYTIPVKTKVMVNVWALGRDPKYWDDADNFKPERFEQCSVDFIGNNFEYLPFG
GGRRICPGISFGLANVYLPLAQLLYHFDWKLPTGMEPKDLDLTELVGVTAARKSDLMLVATP
YQPSRE (SEQ ID NO: 19 | Wild Type)

MALLLAVFFFSLVSIFLFLSFLFLLRKWKNSNSQSKKLPPGPWKLPLLGSMLHMVGGLPHHV
LRDLAKKYGPLMHLQLGEVSAVVVTSPDMAKEVLKTHDIAFASRPKLLAPEIVCYNRSDIAF
CPYGDYWRQMRKICVLEVLSAKNVRSFSSIRRDEVLRLVNFVRSSTSEPVNFTERLFLFTSS
MTCRSAFGKVFKEQETFIQLIKEVIGLAGGFDVADIFPSLKFLHVLTGMEGKIMKAHHKVDA
IVEDVINEHKKNLAMGKTNGALGGEDLIDVLLRLMNDGGLQFPITNDNIKAIIFDMFAAGTE
TSSSTLVWAMVQMMRNPTILAKAQAEVREAFKGKETFDENDVEELKYLKLVIKETLRLHPPV
PLLVPRECREETEINGYTIPVKTKVMVNVWALGRDPKYWDDADNFKPERFEQCSVDFIGNNF
EYLPFGGGRRICPGISFGLANVYLPLAQLLYHFDWKLPTGMEPKDLDLTELVGVTAARKSDL
MLVATPYQPSRE (SEQ ID NO: 20)

ATGGCTCTGTTATTAGCAGTTTTCTTCTTCTCCCTGGTCTCAATCTTTCTGTTCCTGTCCTT
TCTGTTCCTGCTGCGTAAATGGAAAAACTCAAACTCCCAATCGAAAAAACTGCCGCCGGGTC
CGTGGAAACTGCCGCTGCTGGGCTCTATGCTGCACATGGTTGGCGGCCTGCCGCATCACGTT
CTGCGTGATCTGGCGAAAAAATATGGTCCGCTGATGCATCTGCAACTGGGCGAAGTCTCCGC
CGTGGTTGTCACCTCACCGGATATGGCAAAAGAAGTGCTGAAAACGCATGACATTGCGTTCG
CCTCCCGTCCGAAACTGCTGGCCCCGGAAATTGTGTGCTACAACCGCTCAGATATTGCATTT
TGTCCGTATGGTGACTACTGGCGTCAAATGCGCAAAATTTGCGTCCTGGAAGTGCTGTCGGC
CAAAAATGTGCGCAGCTTTAGCTCTATTCGTCGTGATGAAGTTCTGCGTCTGGTTAACTTCG
TCCGCAGTTCCACCTCGGAGCCGGTGAATTTTACGGAACGTCTGTTTCTGTTCACCTCATCG
ATGACCTGCCGTAGCGCATTTGGTAAAGTTTTCAAAGAACAGGAAACCTTCATTCAACTGAT
CAAAGAAGTCATTGGCCTGGCCGGCGGTTTTGATGTGGCAGACATCTTTCCGAGTCTGAAAT
TCCTGCATGTTCTGACCGGCATGGAAGGCAAAATTATGAAAGCTCATCACAAAGTCGATGCG
ATTGTGGAAGACGTTATCAACGAACACAAGAAAAACCTGGCGATGGGCAAAACGAACGGCGC
ACTGGGCGGTGAAGATCTGATCGACGTTCTGCTGCGTCTGATGAATGATGGCGGCCTGCAAT
TTCCGATCACCAACGATAATATCAAAGCTATTATCTTTGATATGTTTGCGGCGGGCACCGAA
ACCAGCAGCAGCACCCTGGTGTGGGCGATGGTGCAGATGATGCGTAACCCGACGATTCTGGC
AAAAGCTCAAGCGGAAGTGCGCGAAGCCTTCAAAGGCAAAGAAACCTTTGATGAAAATGACG
TTGAAGAACTGAAATATCTGAAACTGGTCATCAAAGAAACGCTGCGTCTGCATCCGCCGGTT
CCGCTGCTGGTCCCGCGTGAATGCCGCGAAGAAACCGAAATTAACGGTTATACCATCCCGGT

Figure 4C

TAAAACGAAAGTGATGGTTAATGTCTGGGCTCTGGGCCGTGATCCGAAATACTGGGATGACG
CGGACAACTTTAAACCGGAACGCTTTGAACAGTGCTCTGTGGATTTCATCGGCAACAACTTT
GAATATCTGCCGTTTGGCGGTGGCCGTCGCATTTGTCCGGGTATCAGCTTCGGCCTGGCTAA
TGTTTATCTGCCGCTGGCGCAACTGCTGTACCACTTTGATTGGAAACTGCCGACCGGCATGG
AACCGAAAGATCTGGACCTGACCGAACTGGTGGGCGTTACGGCAGCTCGTAAATCTGATCTG
ATGCTGGTTGCGACCCCGTACCAGCCGAGCCGTGAA (SEQ ID NO: 21)

>LsGAO |Lactuca sativa|

MELSITTSIALATIVFFLYKLATRPKSTKKQLPEASRLPIIGHMHHLIGTMPHRGVMDLARK
HGSLMHLQLGEVSTIVVSSPKWAKEILTTYDITFANRPETLTGEIIAYHNTDIVLAPYGEYW
RQLRKLCTLELLSVKKVKSFQSIREEECWNLVKEVKESGSGKPINLSESIFTMIATILSRAA
FGKGIKDQREFTEIVKEILRQTGGFDVADIFPSKKFLHHLSGKRARLTSIHKKLDNLINNIV
AEHHVSTSSKANETLLDVLLRLKDSAEFPLTADNVKAIILDMFGAGTDTSSATVEWAISELI
RCPRAMEKVQAELRQALNGKEKIQEEDIQDLAYLNLVIRETLRLHPPLPLVMPRECREPVNL
AGYEIANKTKLIVNVFAINRDPEYWKDAEAFIPERFENNPNNIMGADYEYLPFGAGRRMCPG
AALGLANVQLPLANILYHFNWKLPNGASHDQLDMTESFGATVQRKTELLLVPSF (SEQ ID
NO: 22 | Wild Type)

MALLLAVFIALATIVFFLYKLATRPKSTKKQLPEA*SR*LPIIGHMHHLIGTMPHRGVMDLARK
HGSLMHLQLGEVSTIVVSSPKWAKEILTTYDITFANRPETLTGEIIAYHNTDIVLAPYGEYW
RQLRKLCTLELLSVKKVKSFQSIREEECWNLVKEVKESGSGKPINLSESIFTMIATIL*SR*AA
FGKGIKDQREFTEIVKEILRQTGGFDVADIFPSKKFLHHLSGKRARLTSIHKKLDNLINNIV
AEHHVSTSSKANETLLDVLLRLKDSAEFPLTADNVKAIILDMFGAGTDTSSATVEWAISELI
RCPRAMEKVQAELRQALNGKEKIQEEDIQDLAYLNLVIRETLRLHPPLPLVMPRECREPVNL
AGYEIANKTKLIVNVFAINRDPEYWKDAEAFIPERFENNPNNIMGADYEYLPFGAGRRMCPG
AALGLANVQLPLANILYHFNWKLPNGASHDQLDMTESFGATVQRKTELLLVPSF (SEQ ID
NO: 23)

ATGGCTCTGTTATTAGCAGTTTTCATCGCACTGGCTACCATCGTCTTCTTCCTGTATAAACT
GGCAACGCGCCCGAAATCTACCAAAAAACAACTGCCGGAAGCGAGCCGTCTGCCGATTATCG
GCCACATGCATCACCTGATTGGCACCATGCCGCACCGTGGTGTCATGGATCTGGCCCGCAAA
CATGGCTCGCTGATGCATCTGCAACTGGGCGAAGTGAGCACCATTGTGGTTAGCTCTCCGAA
ATGGGCAAAAGAAATTCTGACCACCTATGATATTACCTTTGCTAACCGCCCGGAAACCCTGA
CGGGCGAAATTATCGCGTACCATAATACGGACATTGTGCTGGCCCCGTATGGTGAATACTGG
CGTCAACTGCGTAAACTGTGCACCCTGGAACTGCTGTCCGTTAAAAAAGTCAAATCATTTCA
ATCGATTCGTGAAGAAGAATGTTGGAACCTGGTGAAAGAAGTTAAAGAAAGCGGCTCTGGTA
AACCGATTAATCTGAGTGAATCCATCTTCACCATGATTGCGACGATCCTGAGTCGTGCGGCC
TTTGGCAAAGGTATTAAAGATCAGCGCGAATTTACCGAAATTGTCAAAGAAATCCTGCGTCA
AACGGGCGGTTTCGATGTGGCAGACATTTTTCCGAGCAAAAAATTCCTGCATCACCTGTCTG
GCAAACGTGCTCGCCTGACCAGTATCCATAAAAAACTGGATAACCTGATCAACAATATCGTC
GCGGAACATCATGTGAGCACCAGCAGCAAAGCGAATGAAACGCTGCTGGATGTTCTGCTGCG
CCTGAAAGACAGTGCCGAATTTCCGCTGACCGCAGACAACGTCAAAGCTATTATCCTGGATA
TGTTCGGTGCAGGCACCGATACCAGCAGCGCAACGGTGGAATGGGCCATTAGCGAACTGATC
CGTTGCCCGCGCGCAATGGAAAAAGTTCAGGCAGAACTGCGTCAAGCTCTGAACGGTAAAGA
AAAAATCCAGGAAGAAGATATTCAAGACCTGGCCTATCTGAATCTGGTGATTCGTGAAACCC
TGCGTCTGCACCCGCCGCTGCCGCTGGTTATGCCGCGTGAATGCCGTGAGCCGGTGAACCTG
GCGGGCTATGAAATCGCCAATAAAACCAAACTGATCGTCAATGTGTTTGCGATTAACCGTGA

Figure 4D

CCCGGAATACTGGAAAGACGCGGAAGCCTTTATCCCGGAACGTTTTGAAAACAATCCGAACA
ATATCATGGGTGCAGATTATGAATACCTGCCGTTTGGCGCTGGTCGTCGCATGTGTCCGGGC
GCAGCTCTGGGTCTGGCAAACGTTCAACTGCCGCTGGCGAACATTCTGTACCATTTCAACTG
GAAACTGCCGAATGGCGCGTCCCACGATCAACTGGACATGACCGAATCATTTGGTGCCACCG
TGCAACGTAAAACGGAACTGCTGCTGGTTCCGAGCTTC (SEQ ID NO: 24)

>NtEAO [Nicotiani tabacum]

MQFFSLVSIFLFLSFLFLLRKWKNSNSQSKKLPPGPWKIPILGSMLHMIGGEPHHVLRDLAK
KYGPLMHLQLGEISAVVVTSRDMAKEVLKTHDVVFASRPKIVAMDIICYNQSDIAFSPYGDH
WRQMRKICVMELLNAKNVRSFSSIRRDEVVRLIDSIRSDSSSGELVNFTQRIIWFASSMTCR
SAFGQVLKGQDIFAKKIREVIGLAEGFDVVDIFPTYKFLHVLSGMKRKLLNAHLKVDAIVED
VINEHKKNLAAGKSNGALGGEDLIDVLLRLMNDTSLQFPITNDNIKAVIVDMFAAGTETSST
TTVWAMAEMMKNPSVFTKAQAEVREAFRDKVSFDENDVEELKYLKLVIKETLRLHPPSPLLV
PRECREDTDINGYTIPAKTKVMVNVWALGRDPKYWDDAESFKPERFEQCSVDFFGNNFEFLP
FGGGRRICPGMSFGLANLYLPLAQLLYHFDWKLPTGIMPRDLDLTELSGITIARKGGLYLNA
TPYQPSRE (SEQ ID NO: 25 | Wild Type)

MALLLAVFFFSLVSIFLFLSFLFLLRKWKNSNSQSKKLPPGPWKIPILGSMLHMIGGEPHHV
LRDLAKKYGPLMHLQLGEISAVVVT*SR*DMAKEVLKTHDVVFA*SR*PKIVAMDIICYNQSDIAF
SPYGDHWRQMRKICVMELLNAKNVRSFSSIRRDEVVRLIDSIRSDSSSGELVNFTQRIIWFA
SSMTCRSAFGQVLKGQDIFAKKIREVIGLAEGFDVVDIFPTYKFLHVLSGMKRKLLNAHLKV
DAIVEDVINEHKKNLAAGKSNGALGGEDLIDVLLRLMNDTSLQFPITNDNIKAVIVDMFAAG
TETSSTTTVWAMAEMMKNPSVFTKAQAEVREAFRDKVSFDENDVEELKYLKLVIKETLRLHP
PSPLLVPRECREDTDINGYTIPAKTKVMVNVWALGRDPKYWDDAESFKPERFEQCSVDFFGN
NFEFLPFGGGRRICPGMSFGLANLYLPLAQLLYHFDWKLPTGIMPRDLDLTELSGITIARKG
GLYLNATPYQPSRE (SEQ ID NO: 26)

ATGGCTCTGTTATTAGCAGTTTTCTTCTTCTCCCTGGTCTCAATCTTCCTGTTCCTGTCCTT
TCTGTTCCTGCTGCGTAAATGGAAAAACTCTAATAGCCAATCCAAAAAACTGCCGCCGGGTC
CGTGGAAAATTCCGATCCTGGGCTCTATGCTGCACATGATTGGCGGTGAACCGCATCATGTG
CTGCGTGATCTGGCGAAAAAATATGGTCCGCTGATGCATCTGCAACTGGGCGAAATCTCTGC
GGTGGTTGTCACGAGTCGTGACATGGCCAAAGAAGTGCTGAAAACCCATGATGTGGTTTTTG
CATCTCGCCCGAAAATCGTTGCTATGGATATTATCTGCTATAACCAGTCGGACATCGCGTTC
AGCCCGTACGGTGATCACTGGCGTCAAATGCGCAAAATTTGTGTCATGGAACTGCTGAACGC
CAAAAATGTGCGCAGTTTTAGCTCTATTCGTCGTGATGAAGTCGTGCGTCTGATTGATTCCA
TCCGCTCAGACAGTTCCTCAGGCGAACTGGTGAATTTTACGCAGCGTATTATCTGGTTCGCA
TCGAGCATGACCTGCCGCTCGGCTTTTGGTCAGGTTCTGAAAGGCCAAGATATTTTTGCGAA
GAAAATTCGTGAAGTGATCGGTCTGGCCGAAGGCTTCGATGTTGTGGATATTTTTCCGACCT
ATAAATTCCTGCATGTCCTGAGCGGTATGAAACGCAAACTGCTGAACGCGCACCTGAAAGTT
GATGCCATTGTCGAAGACGTGATCAACGAACATAAGAAAAACCTGGCGGCGGGTAAATCCAA
CGGCGCACTGGGCGGTGAAGATCTGATTGACGTGCTGCTGCGTCTGATGAATGATACCAGCC
TGCAATTTCCGATCACCAACGACAACATTAAAGCGGTGATCGTTGATATGTTCGCGGCGGGC
ACCGAAACCTCTAGTACCACGACCGTTTGGGCGATGGCCGAAATGATGAAAAACCCGTCGGT
GTTTACCAAAGCACAAGCGGAAGTGCGTGAAGCGTTTCGTGATAAAGTTAGCTTCGATGAAA
ATGATGTGGAAGAACTGAAATACCTGAAACTGGTGATTAAAGAAACGCTGCGTCTGCATCCG
CCGAGCCCGCTGCTGGTTCCGCGTGAATGCCGTGAAGATACCGACATTAACGGTTATACGAT
CCCGGCAAAAACCAAAGTCATGGTGAATGTTTGGGCTCTGGGCCGTGACCCGAAATACTGGG

Figure 4E

ATGACGCAGAATCCTTTAAACCGGAACGCTTTGAACAGTGCTCAGTGGATTTCTTTGGTAAC
AACTTTGAATTTCTGCCGTTTGGCGGTGGCCGTCGCATTTGTCCGGGTATGTCCTTCGGCCT
GGCGAACCTGTATCTGCCGCTGGCCCAACTGCTGTACCACTTTGATTGGAAACTGCCGACGG
GTATTATGCCGCGTGATCTGGACCTGACGGAACTGTCTGGCATTACCATCGCACGCAAAGGT
GGCCTGTATCTGAATGCTACCCCGTACCAGCCGAGTCGTGAA (SEQ ID NO: 27)

>CpVO [Citrus x paradisi]

MELPLKSIALTIVIVTVLTWAWRVLNWVWLRPKKLEKFLRQQGLKGNSYRLLFGDLKENSIE
LKEAKARPLSLDDDIAIRVNPFLHKLVNDYGKNSFMWFGPTPRVNIMNPDQIKAIFTKINDF
QKVNSIPLARLLIVGLATLEGEKWAKHRKLINPAFHQEKLKLMLPAFYLSCIEIITKWEKQM
SVEGSSELDVWPYLANLTSDVISRTAFGSSYEEGRRIFQLQAELAELTMQVFRSVHIPGWRF
LPTKRNRRMKEIDKEIRASLMGIIKNREKAMRAGEAANNDLLGILMETSFREIEEHGNNKNV
GFSMNDVIEECKLFYFAGQETTSVLLNWTMVLLSKHQDWQERARQEVLQVFGNNKPDYDGLN
HLKIVQMILYEVLRLYPPVTVLSRAVFKETKLGNLTLPAGVQIGLPMILVHQDPELWGDDAV
EFKPERFAEGISKAAKNQVSYFPFALGPRICVGQNFALVEAKMATAMILQNYSFELSPSYVH
APTAVPTLHPELGTQLILRKLWCKNN (SEQ ID NO: 28 | Wild Type)

MALLLAVFIALTIVIVTVLTWAWRVLNWVWLRPKKLEKFLRQQGLKGNSYRLLFGDLKENSI
ELKEAKARPLSLDDDIAIRVNPFLHKLVNDYGKNSFMWFGPTPRVNIMNPDQIKAIFTKIND
FQKVNSIPLARLLIVGLATLEGEKWAKHRKLINPAFHQEKLKLMLPAFYLSCIEIITKWEKQ
MSVEGSSELDVWPYLANLTSDVI*SR*TAFGSSYEEGRRIFQLQAELAELTMQVFRSVHIPGWR
FLPTKRNRRMKEIDKEIRASLMGIIKNREKAMRAGEAANNDLLGILMETSFREIEEHGNNKN
VGFSMNDVIEECKLFYFAGQETTSVLLNWTMVLLSKHQDWQERARQEVLQVFGNNKPDYDGL
NHLKIVQMILYEVLRLYPPVTVLSRAVFKETKLGNLTLPAGVQIGLPMILVHQDPELWGDDA
VEFKPERFAEGISKAAKNQVSYFPFALGPRICVGQNFALVEAKMATAMILQNYSFELSPSYV
HAPTAVPTLHPELGTQLILRKLWCKNN (SEQ ID NO: 29)

ATGGCTCTGTTATTAGCAGTTTTCATTGCTCTGACGATTGTTATTGTTACGGTGCTGACCTG
GGCGTGGCGTGTGCTGAACTGGGTTTGGCTGCGTCCGAAAAAACTGGAAAAATTTCTGCGCC
AGCAAGGCCTGAAGGGTAACAGCTATCGTCTGCTGTTCGGCGATCTGAAAGAAAATTCTATT
GAACTGAAAGAAGCGAAAGCCCGTCCGCTGAGTCTGGATGACGATATTGCAATCCGCGTTAA
CCCGTTTCTGCATAAACTGGTCAACGATTACGGCAAAAATTCTTTTATGTGGTTCGGTCCGA
CCCCGCGCGTGAACATTATGAACCCGGATCAGATTAAAGCGATCTTTACGAAAATCAACGAT
TTCCAAAAAGTTAATAGCATTCCGCTGGCGCGTCTGCTGATCGTCGGCCTGGCCACCCTGGA
AGGTGAAAAATGGGCAAAACATCGCAAACTGATTAACCCGGCTTTTCACCAAGAAAAACTGA
AACTGATGCTGCCGGCGTTCTATCTGTCCTGCATCGAAATTATCACGAAATGGGAAAAACAG
ATGTCAGTGGAAGGTAGCTCTGAACTGGACGTTTGGCCGTATCTGGCCAATCTGACCAGCGA
TGTTATTTCTCGTACGGCATTTGGCAGTTCCTACGAAGAAGGTCGTCGCATCTTCCAGTTAC
AGGCGGAACTGGCCGAACTGACCATGCAGGTTTTTCGTTCTGTCCATATTCCGGGCTGGCGT
TTCCTGCCGACGAAACGCAACCGTCGCATGAAAGAAATTGACAAAGAAATCCGCGCCAGTCT
GATGGGTATTATCAAAAATCGTGAAAAAGCAATGCGCGCTGGCGAAGCGGCCAACAATGATC
TGCTGGGTATTCTGATGGAAACCAGCTTTCGTGAAATCGAAGAACACGGCAACAATAAAAAC
GTCGGTTTCAGCATGAATGACGTGATCGAAGAATGTAAACTGTTTTATTTCGCTGGCCAGGA
AACCACGTCAGTTCTGCTGAACTGGACGATGGTGCTGCTGTCGAAACATCAGGATTGGCAAG
AACGTGCCCGCCAGGAAGTCCTGCAAGTGTTTGGCAACAATAAACCGGACTACGATGGTCTG
AACCACCTGAAAATTGTGCAGATGATCCTGTATGAAGTTCTGCGTCTGTATCCGCCGGTGAC
GGTGCTGAGCCGTGCGGTGTTTAAAGAAACCAAACTGGGTAATCTGACGCTGCCGGCAGGCG

Figure 4F

TCCAGATTGGTCTGCCGATGATCCTGGTGCACCAGGACCCGGAACTGTGGGGCGACGATGCT
GTGGAATTTAAACCGGAACGTTTCGCGGAAGGTATTAGTAAAGCAGCTAAAAATCAGGTTTC
CTATTTTCCGTTCGCGCTGGGTCCGCGTATTTGCGTCGGTCAAAACTTTGCACTGGTGGAAG
CTAAAATGGCAACCGCTATGATCCTGCAAAATTATAGCTTTGAACTGTCACCGAGCTATGTT
CATGCGCCGACCGCCGTTCCGACGCTGCACCCGGAACTGGGCACGCAACTGATTCTGCGTAA
ACTGTGGTGTAAAAACAAT (SEQ ID NO: 30)

>AaAO [Artemesia annua]

MKSILKAMALSLTTSIALATILLFVYKFATRSKSTKKSLPEPWRLPIIGHMHHLIGTTPHRG
VRDLARKYGSLMHLQLGEVPTIVVSSPKWAKEILTTYDITFANRPETLTGEIVLYHNTDVVL
APYGEYWRQLRKICTLELLSVKKVKSFQSLREEECWNLVQEIKASGSGRPVNLSENVFKLIA
TILSRAAFGKGIKDQKELTEIVKEILRQTGGFDVADIFPSKKFLHHLSGKRARLTSLRKKID
NLIDNLVAEHTVNTSSKTNETLLDVLLRLKDSAEFPLTSDNIKAIILDMFGAGTDTSSSTIE
WAISELIKCPKAMEKVQAELRKALNGKEKIHEEDIQELSYLNMVIKETLRLHPPLPLVLPRE
CRQPVNLAGYNIPNKTKLIVNVFAINRDPEYWKDAEAFIPERFENSSATVMGAEYEYLPFGA
GRRMCPGAALGLANVQLPLANILYHFNWKLPNGVSYDQIDMTESSGATMQRKTELLLVPSF
(SEQ ID NO: 31 | Wild Type)

MALLLAVFIALATILLFVYKFATRSKSTKKSLPEPWRLPIIGHMHHLIGTTPHRGVRDLARK
YGSLMHLQLGEVPTIVVSSPKWAKEILTTYDITFANRPETLTGEIVLYHNTDVVLAPYGEYW
RQLRKICTLELLSVKKVKSFQSLREEECWNLVQEIKASGSGRPVNLSENVFKLIATIL*SR*AA
FGKGIKDQKELTEIVKEILRQTGGFDVADIFPSKKFLHHLSGKRARLTSLRKKIDNLIDNLV
AEHTVNTSSKTNETLLDVLLRLKDSAEFPLTSDNIKAIILDMFGAGTDTSSSTIEWAISELI
KCPKAMEKVQAELRKALNGKEKIHEEDIQELSYLNMVIKETLRLHPPLPLVLPRECRQPVNL
AGYNIPNKTKLIVNVFAINRDPEYWKDAEAFIPERFENSSATVMGAEYEYLPFGAGRRMCPG
AALGLANVQLPLANILYHFNWKLPNGVSYDQIDMTESSGATMQRKTELLLVPSF (SEQ ID
NO: 32)

ATGGCTCTGTTATTAGCAGTTTTCATCGCACTGGCAACCATTCTGCTGTTTGTGTATAAATT
CGCTACCCGTTCCAAATCAACGAAAAAATCACTGCCGGAACCGTGGCGCCTGCCGATTATCG
GTCACATGCATCACCTGATCGGCACCACCCCGCATCGTGGCGTGCGTGATCTGGCACGCAAA
TATGGCTCGCTGATGCATCTGCAACTGGGTGAAGTCCCGACCATTGTGGTTAGCTCTCCGAA
ATGGGCGAAAGAAATCCTGACCACCTATGATATTACCTTTGCCAACCGCCCGGAAACCCTGA
CGGGCGAAATCGTGCTGTACCACAATACGGATGTGGTGCTGGCGCCGTATGGTGAATACTGG
CGTCAACTGCGTAAAATTTGCACCCTGGAACTGCTGAGTGTGAAAAAAGTTAAATCTTTCCA
GAGCCTGCGTGAAGAAGAATGTTGGAACCTGGTTCAAGAAATTAAAGCATCGGGCAGCGGTC
GCCCGGTTAACCTGAGTGAAAATGTCTTTAAACTGATTGCTACCATCCTGTCCCGTGCGGCC
TTCGGCAAAGGTATCAAAGATCAGAAAGAACTGACCGAAATTGTCAAAGAAATCCTGCGCCA
AACGGGCGGTTTTGATGTGGCGGACATTTTTCCGTCGAAAAAATTCCTGCATCACCTGAGCG
GTAAACGTGCCCGCCTGACCAGCCTGCGTAAGAAAATTGATAACCTGATCGACAATCTGGTC
GCGGAACATACCGTGAACACGAGTTCCAAAACCAATGAAACGCTGCTGGATGTGCTGCTGCG
CCTGAAAGACTCCGCCGAATTTCCGCTGACCTCAGATAATATCAAAGCGATTATCCTGGATA
TGTTCGGTGCAGGCACCGATACCAGCAGCAGCACCATTGAATGGGCAATCTCAGAACTGATT
AAATGCCCGAAAGCTATGGAAAAAGTCCAGGCAGAACTGCGCAAAGCTCTGAACGGCAAAGA
AAAAATCCATGAAGAAGATATTCAAGAACTGTCTTACCTGAACATGGTTATCAAAGAAACCC
TGCGTCTGCACCCGCCGCTGCCGCTGGTGCTGCCGCGTGAATGTCGCCAGCCGGTTAACCTG
GCAGGCTATAACATCCCGAATAAAACGAAACTGATCGTTAACGTCTTTGCTATTAACCGTGA

Figure 4G

CCCGGAATACTGGAAAGACGCGGAAGCCTTTATCCCGGAACGCTTTGAAAACAGCAGCGCGA
CCGTGATGGGTGCCGAATATGAATACCTGCCGTTTGGCGCGGGTCGTCGCATGTGTCCGGGC
GCAGCTCTGGGTCTGGCAAACGTGCAACTGCCGCTGGCTAATATCCTGTATCACTTCAACTG
GAAACTGCCGAATGGCGTTAGCTACGATCAAATTGACATGACCGAAAGCTCAGGTGCCACGA
TGCAACGCAAAACCGAACTGCTGCTGGTGCCGTCCTTC (SEQ ID NO: 33)

>AtKO [Arabidopsis thaliana]

MAFFSMISILLGFVISSFIFIFFFKKLLSFSRKNMSEVSTLPSVPVVPGFPVIGNLLQLKEK
KPHKTFTRWSEIYGPIYSIKMGSSSLIVLNSTETAKEAMVTRFSSISTRKLSNALTVLTCDK
SMVATSDYDDFHKLVKRCLLNGLLGANAQKRKRHYRDALIENVSSKLHAHARDHPQEPVNFR
AIFEHELFGVALKQAFGKDVESIYVKELGVTLSKDEIFKVLVHDMMEGAIDVDWRDFFPYLK
WIPNKSFEARIQQKHKRRLAVMNALIQDRLKQNGSESDDDCYLNFLMSEAKTLTKEQIAILV
WETIIETADTTLVTTEWAIYELAKHPSVQDRLCKEIQNVCGGEKFKEEQLSQVPYLNGVFHE
TLRKYSPAPLVPIRYAHEDTQIGGYHVPAGSEIAINIYGCNMDKKRWERPEDWWPERFLDDG
KYETSDLHKTMAFGAGKRVCAGALQASLMAGIAIGRLVQEFEWKLRDGEEENVDTYGLTSQK
LYPLMAIINPRRS (SEQ ID NO: 34 | Wild Type)

MALLLAVFSMISILLGFVISSFIFIFFFKKLLSF*SR*KNMSEVSTLPSVPVVPGFPVIGNLLQ
LKEKKPHKTFTRWSEIYGPIYSIKMGSSSLIVLNSTETAKEAMVTRFSSISTRKLSNALTVL
TCDKSMVATSDYDDFHKLVKRCLLNGLLGANAQKRKRHYRDALIENVSSKLHAHARDHPQEP
VNFRAIFEHELFGVALKQAFGKDVESIYVKELGVTLSKDEIFKVLVHDMMEGAIDVDWRDFF
PYLKWIPNKSFEARIQQKHKRRLAVMNALIQDRLKQNGSESDDDCYLNFLMSEAKTLTKEQI
AILVWETIIETADTTLVTTEWAIYELAKHPSVQDRLCKEIQNVCGGEKFKEEQLSQVPYLNG
VFHETLRKYSPAPLVPIRYAHEDTQIGGYHVPAGSEIAINIYGCNMDKKRWERPEDWWPERF
LDDGKYETSDLHKTMAFGAGKRVCAGALQASLMAGIAIGRLVQEFEWKLRDGEEENVDTYGL
TSQKLYPLMAIINPRRS (SEQ ID NO: 35)

ATGGCTCTGTTATTAGCAGTTTTTTCGATGATTTCTATCCTGCTGGGCTTTGTTATCTCGTC
CTTTATCTTTATCTTCTTCTTCAAAAAACTGCTGTCGTTTTCTCGTAAAAACATGTCCGAAG
TTTCAACCCTGCCGAGTGTCCCGGTGGTTCCGGGTTTTCCGGTTATCGGTAATCTGCTGCAG
CTGAAAGAAAAGAAACCGCATAAGACCTTCACGCGCTGGTCCGAAATCTATGGCCCGATCTA
CTCAATTAAAATGGGTAGCTCTAGTCTGATTGTGCTGAACTCTACCGAAACGGCAAAAGAAG
CTATGGTTACCCGTTTTTCCTCAATTTCGACGCGCAAGCTGAGCAATGCGCTGACCGTCCTG
ACGTGCGACAAATCTATGGTGGCCACCAGTGATTACGATGACTTCCATAAACTGGTTAAGCG
TTGTCTGCTGAACGGCCTGCTGGGTGCGAATGCCCAGAAGCGTAAGCGCCACTATCGCGACG
CCCTGATTGAAAACGTGTCGAGCAAACTGCATGCACACGCTCGTGATCATCCGCAGGAACCG
GTCAATTTTCGCGCAATCTTCGAACACGAACTGTTTGGCGTGGCGCTGAAACAAGCCTTCGG
CAAGGATGTTGAATCGATTTACGTCAAAGAACTGGGCGTGACCCTGAGCAAAGACGAAATCT
TTAAGGTCCTGGTGCATGATATGATGGAAGGTGCAATTGACGTTGATTGGCGTGATTTCTTT
CCGTATCTGAAATGGATTCCGAACAAGTCATTCGAAGCTCGCATTCAGCAAAAACACAAGCG
TCGCCTGGCAGTGATGAACGCTCTGATTCAGGATCGTCTGAAACAAAATGGCTCTGAAAGTG
ATGACGATTGCTATCTGAATTTTCTGATGTCCGAAGCAAAAACCCTGACGAAGGAACAGATT
GCTATCCTGGTTTGGGAAACCATTATCGAAACGGCGGACACCACGCTGGTCACCACGGAATG
GGCGATCTACGAACTGGCCAAGCATCCGAGCGTTCAGGATCGCCTGTGCAAAGAAATTCAAA
ACGTCTGTGGCGGTGAAAAATTTAAGGAAGAACAGCTGTCGCAAGTGCCGTATCTGAATGGT
GTTTTCCACGAAACCCTGCGTAAATATAGCCCGGCACCGCTGGTCCCGATCCGTTACGCCCA
TGAAGATACCCAGATTGGCGGTTATCACGTGCCGGCAGGCAGTGAAATTGCTATCAACATTT

Figure 4H

ACGGTTGCAATATGGACAAAAAGCGTTGGGAACGCCCGGAAGATTGGTGGCCGGAACGTTTT
CTGGACGATGGCAAATATGAAACCTCTGATCTGCATAAGACGATGGCGTTCGGTGCAGGTAA
ACGTGTGTGTGCAGGTGCACTGCAAGCAAGTCTGATGGCAGGCATCGCTATTGGTCGTCTGG
TGCAAGAATTTGAATGGAAACTGCGCGACGGCGAAGAAGAAAACGTTGATACCTATGGTCTG
ACGTCCCAGAAACTGTACCCGCTGATGGCCATTATCAATCCGCGTCGCTCA (SEQ ID
NO: 36)

**>*Sr*KO [Stevia rebaudiana]**

MDAVTGLLTVPATAITIGGTAVALAVALIFWYLKSYTSARRSQSNHLPRVPEVPGVPLLGNL
LQLKEKKPYMTFTRWAATYGPIYSIKTGATSMVVVSSNEIAKEALVTRFQSISTRNLSKALK
VLTADKTMVAMSDYDDYHKTVKRHILTAVLGPNAQKKHRIHRDIMMDNISTQLHEFVKNNPE
QEEVDLRKIFQSELFGLAMRQALGKDVESLYVEDLKITMNRDEIFQVLVVDPMMGAIDVDWR
DFFPYLKWVPNKKFENTIQQMYIRREAVMKSLIKEHKKRIASGEKLNSYIDYLLSEAQTLTD
QQLLMSLWEPIIESSDTTMVTTEWAMYELAKNPKLQDRLYRDIKSVCGSEKITEEHLSQLPY
ITAIFHETLRRHSPVPIIPLRHVHEDTVLGGYHVPAGTELAVNIYGCNMDKNVWENPEEWNP
ERFMKENETIDFQKTMAFGGGKRVCAGSLQALLTASIGIGRMVQEFEWKLKDMTQEEVNTIG
LTTQMLRPLRAIIKPRI (SEQ ID NO: 37 | Wild Type)

MALLLAVFAVALAVALIFWYLKSYTSARRSQSNHLPRVPEVPGVPLLGNLLQLKEKKPYMTF
TRWAATYGPIYSIKTGATSMVVVSSNEIAKEALVTRFQSISTRNLSKALKVLTADKTMVAMS
DYDDYHKTVKRHILTAVLGPNAQKKHRIHRDIMMDNISTQLHEFVKNNPEQEEVDLRKIFQS
ELFGLAMRQALGKDVESLYVEDLKITMNRDEIFQVLVVDPMMGAIDVDWRDFFPYLKWVPNK
KFENTIQQMYIRREAVMKSLIKEHKKRIASGEKLNSYIDYLLSEAQTLTDQQLLMSLWEPII
ESSDTTMVTTEWAMYELAKNPKLQDRLYRDIKSVCGSEKITEEHLSQLPYITAIFHETLRRH
SPVPIIPLRHVHEDTVLGGYHVPAGTELAVNIYGCNMDKNVWENPEEWNPERFMKENETIDF
QKTMAFGGGKRVCAGSLQALLTASIGIGRMVQEFEWKLKDMTQEEVNTIGLTTQMLRPLRAI
IKPRI (SEQ ID NO: 38)

ATGGCTCTGTTATTAGCAGTTTTTGCCGTCGCTCTGGCGGTAGCACTGATCTTCTGGTATCT
GAAATCTTACACTAGCGCGCGCCGCTCTCAGTCCAACCACCTGCCGCGTGTGCCGGAAGTTC
CGGGTGTGCCACTGCTGGGCAACCTGCTGCAACTGAAAGAAAAGAAACCGTACATGACCTTT
ACCCGCTGGGCAGCGACTTATGGTCCTATCTACAGCATTAAAACCGGCGCTACGTCTATGGT
TGTGGTTTCTTCCAACGAAATCGCGAAAGAAGCCCTGGTGACTCGTTTCCAGTCCATTAGCA
CCCGCAACCTGTCCAAAGCGCTGAAGGTTCTGACGGCTGACAAGACTATGGTGGCTATGAGC
GACTATGATGACTACCACAAAACCGTTAAACGTCACATCCTGACCGCAGTACTGGGTCCGAA
CGCACAGAAAAAACATCGCATCCACCGCGACATTATGATGGATAACATCTCCACGCAGCTGC
ATGAGTTCGTTAAGAACAATCCAGAACAGGAAGAGGTAGATCTGCGTAAAATTTTTCAGTCC
GAACTGTTCGGTCTGGCTATGCGTCAGGCGCTGGGCAAAGACGTTGAAAGCCTGTATGTCGA
AGACCTGAAAATTACCATGAACCGTGATGAGATCTTCCAGGTTCTGGTTGTAGATCCGATGA
TGGGCGCCATCGACGTGGATTGGCGTGACTTCTTTCCGTACCTGAAATGGGTCCCGAACAAG
AAGTTCGAAAACACCATCCAGCAAATGTACATCCGTCGTGAAGCGGTGATGAAAAGCCTGAT
CAAAGAACACAAAAAGCGTATTGCTTCTGGTGAGAAACTGAACTCCTACATCGATTATCTGC
TGTCCGAAGCGCAGACCCTGACCGACCAACAGCTGCTGATGTCTCTGTGGGAACCGATTATC
GAAAGCAGCGACACCACTATGGTCACTACCGAATGGGCAATGTATGAGCTGGCCAAAAACCC
GAAACTGCAGGATCGTCTGTACCGTGACATCAAAAGCGTTTGCGGCTCCGAGAAAATCACTG
AAGAACACCTGTCTCAGCTGCCGTACATCACTGCTATTTTCCACGAAACCCTGCGTCGCCAT
TCTCCGGTTCCGATCATTCCGCTGCGTCACGTTCACGAAGATACTGTGCTGGGTGGTTACCA

Figure 4I

TGTACCGGCAGGCACTGAACTGGCTGTCAACATCTACGGCTGTAACATGGATAAAAACGTTT
GGGAGAATCCTGAAGAATGGAACCCGGAACGCTTCATGAAAGAGAACGAAACCATCGACTTC
CAGAAAACGATGGCTTTCGGCGGTGGTAAACGTGTGTGCGCAGGTTCTCTGCAGGCGCTGCT
GACGGCGTCCATTGGTATCGGTCGCATGGTACAGGAATTTGAATGGAAGCTGAAAGACATGA
CCCAAGAAGAGGTGAATACCATTGGTCTGACTACCCAGATGCTGCGTCCACTGCGTGCAATC
ATCAAACCTCGTATT (SEQ ID NO: 39)

>PpKO [Physcomitrella patens]

MAKHLATQLLQQWNEALKTMPPGFRTAGKILVWEELASNKVLITIALAWVLLFVARTCLRNK
KRLPPAIPGGLPVLGNLLQLTEKKPHRTFTAWSKEHGPIFTIKVGSVPQAVVNNSEIAKEVL
VTKFASISKRQMPMALRVLTRDKTMVAMSDYGEEHRMLKKLVMTNLLGPTTQNKNRSLRDDA
LIGMIEGVLAELKASPTSPKVVNVRDYVQRSLFPFALQQVFGYIPDQVEVLELGTCVSTWDM
FDALVVAPLSAVINVDWRDFFPALRWIPNRSVEDLVRTVDFKRNSIMKALIRAQRMRLANLK
EPPRCYADIALTEATHLTEKQLEMSLWEPIIESADTTLVTSEWAMYEIAKNPDCQDRLYREI
VSVAGTERMVTEDDLPNMPYLGAIIKETLRKYTPVPLIP*SRF*VEEDITLGGYDIPKGYQILV
NLFAIANDPAVWSNPEKWDPERMLANKKVDMGFRDFSLMPFGAGKRMCAGITQAMFIIPMNV
AALVQHCEWRLSPQEISNINNKIEDVVYLTTHKLSPLSCEATPRISHRLP (SEQ ID NO:
40 | Wild Type)

MALLLAVFTQLLQQWNEALKTMPPGFRTAGKILVWEELASNKVLITIALAWVLLFVARTCLR
NKKRLPPAIPGGLPVLGNLLQLTEKKPHRTFTAWSKEHGPIFTIKVGSVPQAVVNNSEIAKE
VLVTKFASISKRQMPMALRVLTRDKTMVAMSDYGEEHRMLKKLVMTNLLGPTTQNKNRSLRD
DALIGMIEGVLAELKASPTSPKVVNVRDYVQRSLFPFALQQVFGYIPDQVEVLELGTCVSTW
DMFDALVVAPLSAVINVDWRDFFPALRWIPNRSVEDLVRTVDFKRNSIMKALIRAQRMRLAN
LKEPPRCYADIALTEATHLTEKQLEMSLWEPIIESADTTLVTSEWAMYEIAKNPDCQDRLYR
EIVSVAGTERMVTEDDLPNMPYLGAIIKETLRKYTPVPLIP*SRF*VEEDITLGGYDIPKGYQI
LVNLFAIANDPAVWSNPEKWDPERMLANKKVDMGFRDFSLMPFGAGKRMCAGITQAMFIIPM
NVAALVQHCEWRLSPQEISNINNKIEDVVYLTTHKLSPLSCEATPRISHRLP (SEQ ID
NO: 41)

ATGGCTCTGTTATTAGCAGTTTTTACGCAACTGCTGCAACAATGGAATGAAGCTCTGAAGA
CGATGCCGCCGGGTTTTCGCACCGCTGGCAAAATTCTGGTGTGGGAAGAACTGGCAAGCAA
TAAAGTTCTGATTACGATCGCACTGGCTTGGGTCCTGCTGTTTGTGGCTCGTACCTGCCTG
CGCAATAAAAAGCGTCTGCCGCCGGCAATCCCGGGCGGTCTGCCGGTGCTGGGCAACCTGC
TGCAGCTGACGGAAAAGAAACCGCATCGTACCTTTACGGCGTGGAGCAAGGAACACGGCCC
GATTTTCACCATCAAAGTCGGTTCGGTGCCGCAGGCTGTGGTTAACAATAGCGAAATTGCG
AAAGAAGTCCTGGTGACCAAGTTCGCCAGCATCTCTAAACGTCAAATGCCGATGGCACTGC
GCGTCCTGACGCGTGATAAAACGATGGTGGCTATGTCTGACTATGGCGAAGAACATCGCAT
GCTGAAAAAGCTGGTGATGACGAATCTGCTGGGTCCGACCACGCAGAACAAAAATCGTAGT
CTGCGCGATGACGCACTGATTGGCATGATCGAAGGTGTTCTGGCGGAACTGAAGGCCAGTC
CGACCTCCCCGAAAGTCGTGAACGTTCGCGATTATGTCCAGCGTTCTCTGTTTCCGTTCGC
GCTGCAGCAAGTGTTTGGCTACATTCCGGATCAAGTTGAAGTCCTGGAACTGGGCACGTGT
GTTTCTACCTGGGATATGTTCGACGCACTGGTTGTCGCTCCGCTGAGTGCGGTTATTAACG
TCGATTGGCGTGACTTTTTCCCGGCCCTGCGCTGGATTCCGAATCGTTCCGTGGAAGATCT
GGTGCGCACCGTTGACTTTAAGCGTAACTCAATTATGAAAGCCCTGATCCGTGCACAGCGT
ATGCGCCTGGCTAACCTGAAGGAACCGCCGCGCTGCTACGCAGATATTGCTCTGACCGAAG
CGACGCACCTGACCGAAAAACAACTGGAAATGAGTCTGTGGGAACCGATTATCGAATCCGC

Figure 4J

CGATACCACGCTGGTGACCTCAGAATGGGCTATGTATGAAATTGCGAAAAATCCGGATTGT
CAGGACCGTCTGTACCGCGAAATCGTGTCCGTTGCCGGCACGGAACGCATGGTTACCGAAG
ATGACCTGCCGAACATGCCGTATCTGGGTGCAATTATCAAAGAAACGCTGCGCAAGTACAC
CCCGGTTCCGCTGATTCCGAGTCGTTTTGTCGAAGAAGATATCACCCTGGGCGGTTATGAC
ATTCCGAAAGGTTACCAGATCCTGGTCAACCTGTTCGCGATTGCCAATGATCCGGCCGTTT
GGTCGAACCCGGAAAAATGGGACCCGGAACGCATGCTGGCAAATAAAAAGGTGGATATGGG
CTTTCGTGACTTCAGCCTGATGCCGTTTGGCGCCGGTAAACGCATGTGCGCCGGTATCACC
CAAGCAATGTTCATTATCCCGATGAATGTGGCGGCCCTGGTTCAGCATTGTGAATGGCGCC
TGAGCCCGCAAGAAATCTCTAACATCAACAACAAGATCGAAGATGTGGTTTACCTGACCAC
GCATAAACTGTCACCGCTGTCGTGCGAAGCAACCCCGCGTATCAGCCACCGTCTGCCG
(SEQ ID NO: 42)

>BmVO [Bacillus megaterium]

MTIKEMPQPKTFGELKNLPLLNTDKPVQALMKIADELGEIFKFEAPGRVTRYLSSQRLIKEA
CDE*SR*FDKNLSQALKFVRDFAGDGLATSWTHEKNWKKAHNILLPSFSQQAMKGYHAMMVDIA
VQLVQKWERLNADEHIEVPEDMTRLTLDTIGLCGFNYRFNSFYRDQPHPFITSMVRALDEAM
NKLQRANPDDPAYDENKRQFQEDIKVMNDLVDKIIADRKASGEQSDDLLTHMLNGKDPETGE
PLDDENIRYQIITFLIAGHETTSGLLSFALYFLVKNPHVLQKAAEEAARVLVDPVPSYKQVK
QLKYVGMVLNEALRLWPTIPAFSLYAKEDTVLGGEYPLEKGDELMVLIPQLHRDKTIWGDDV
EEFRPERFENPSAIPQHAFKPFGNGQRACIGQQFALHEATLVLGMMLKHFDFEDHTNYELDI
KETLTLKPEGFVVKAKSKKIPLGGIPSPSTEQSAKKVRKKAENAHNTPLLVLYGSNMGTAEG
TARDLADIAMSKGFAPQVATLDSHAGNLPREGAVLIVTASYNGHPPDNAKQFVDWLDQASAD
EVKGVRYSVFGCGDKNWATTYQKVPAFIDETLAAKGAENIADRGEADASDDFEGTYEEWREH
MWSDVAAYFNLDIENSEDNKSTLSLQFVDSAADMPLAKMHGAFSTNVVASKELQQPGSARST
RHLEIELPKEASYQEGDHLGVIPRNYEGIVNRVTARFGLDASQQIRLEAEEEKLAHLPLAKT
VSVEELLQYVELQDPVTRTQLRAMAAKTVCPPHKVELEALLEKQAYKEQVLAKRLTMLELLE
KYPACEMKFSEFIALLPSIRPRYYSISSSPRVDEKQASITVSVVSGEAWSGYGEYKGIASNY
LAELQEGDTITCFISTPQSEFTLPKDPETPLIMVGPGTGVAPFRGFVQARKQLKEQGQSLGE
AHLYFGCRSPHEDYLYQEELENAQSEGIITLHTAF*SR*MPNQPKTYVQHVMEQDGKKLIELLD
QGAHFYICGDGSQMAPAVEATLMKSYADVHQVSEADARLWLQQLEEKGRYAKDVWAG (SEQ
ID NO: 43)

ATGACGATTAAAGAAATGCCGCAACCGAAGACGTTTGGCGAACTGAAGAACCTGCCGCTGCT
GAACACGGATAAGCCGGTGCAAGCCCTGATGAAGATTGCTGATGAACTGGGCGAAATCTTTA
AATTCGAAGCGCCGGGTCGTGTGACCCGTTATCTGAGCAGCCAGCGTCTGATTAAAGAAGCC
TGCGATGAATCGCGCTTTGACAAGAACCTGAGCCAGGCACTGAAATTTGTTCGTGATTTCGC
AGGTGACGGTCTGGCCACCAGCTGGACGCATGAAAAGAACTGGAAAAAGGCCCACAATATTC
TGCTGCCGTCGTTCAGCCAGCAAGCAATGAAAGGCTACCATGCTATGATGGTCGATATCGCG
GTTCAGCTGGTCCAAAAATGGGAACGTCTGAATGCGGACGAACACATTGAAGTGCCGGAAGA
TATGACCCGCCTGACGCTGGACACCATCGGTCTGTGTGGCTTTAACTATCGTTTTAATTCGT
TCTACCGCGATCAGCCGCATCCGTTCATTACCAGCATGGTGCGTGCGCTGGACGAAGCCATG
AACAAACTGCAGCGTGCAAACCCGGATGACCCGGCGTATGATGAAAACAAGCGTCAGTTTCA
AGAAGACATCAAAGTGATGAATGATCTGGTTGACAAGATTATCGCAGATCGCAAAGCGAGCG
GCGAACAGTCAGATGACCTGCTGACGCACATGCTGAACGGCAAAGACCCGGAAACCGGTGAA
CCGCTGGATGACGAAAACATCCGTTATCAGATCATCACCTTTCTGATCGCAGGCCATGAAAC
CACGTCGGGTCTGCTGAGCTTTGCGCTGTACTTCCTGGTCAAGAACCCGCACGTGCTGCAGA

Figure 4K

AAGCGGCCGAAGAAGCAGCTCGTGTGCTGGTTGATCCGGTTCCGTCGTATAAACAGGTCAAG
CAACTGAAATACGTGGGTATGGTTCTGAATGAAGCGCTGCGCCTGTGGCCGACGATTCCGGC
ATTTAGCCTGTATGCTAAGGAAGATACCGTTCTGGGCGGTGAATACCCGCTGGAAAAAGGCG
ATGAACTGATGGTCCTGATTCCGCAGCTGCATCGCGACAAAACCATCTGGGGTGATGACGTG
GAAGAATTTCGCCCGGAACGCTTCGAAAACCCGAGCGCGATTCCGCAGCATGCCTTTAAACC
GTTCGGCAATGGTCAACGTGCGTGCATCGGCCAGCAATTTGCGCTGCACGAAGCCACGCTGG
TTCTGGGTATGATGCTGAAACATTTTGATTTCGAAGACCACACCAACTATGAACTGGATATT
AAGGAAACCCTGACGCTGAAACCGGAAGGCTTCGTGGTTAAAGCGAAGTCTAAAAAGATTCC
GCTGGGCGGTATCCCGTCTCCGAGTACGGAACAGAGTGCCAAAAAGGTCCGTAAAAAGGCGG
AAAACGCCCATAATACCCCGCTGCTGGTGCTGTATGGTTCTAACATGGGCACGGCAGAAGGC
ACCGCTCGCGATCTGGCAGACATTGCTATGTCTAAAGGTTTTGCGCCGCAGGTGGCCACGCT
GGATAGTCATGCAGGCAATCTGCCGCGTGAAGGTGCTGTCCTGATCGTGACCGCAAGCTACA
ACGGTCACCCGCCGGATAATGCGAAGCAGTTCGTTGATTGGCTGGACCAAGCGTCGGCCGAT
GAAGTTAAAGGTGTCCGCTATAGCGTGTTTGGCTGTGGTGACAAGAACTGGGCTACCACGTA
CCAGAAAGTTCCGGCGTTCATTGATGAAACGCTGGCGGCCAAAGGCGCAGAAAATATCGCTG
ATCGTGGTGAAGCAGACGCTTCCGATGACTTTGAAGGCACCTATGAAGAATGGCGCGAACAC
ATGTGGTCGGATGTGGCAGCTTACTTCAACCTGGATATTGAAAACAGCGAAGACAATAAATC
CACCCTGTCACTGCAGTTTGTTGATAGTGCGGCCGACATGCCGCTGGCAAAGATGCACGGCG
CTTTCTCCACGAATGTCGTGGCTTCAAAAGAACTGCAGCAACCGGGTTCGGCACGTAGCACC
CGCCATCTGGAAATTGAACTGCCGAAAGAAGCCAGCTATCAGGAAGGCGATCACCTGGGTGT
GATTCCGCGTAACTACGAAGGCATCGTGAATCGTGTTACGGCCCGCTTTGGTCTGGATGCAT
CCCAGCAAATCCGCCTGGAAGCGGAAGAAGAAAAGCTGGCGCATCTGCCGCTGGCCAAAACC
GTCTCAGTGGAAGAACTGCTGCAGTATGTGGAACTGCAAGATCCGGTTACCCGTACGCAGCT
GCGTGCGATGGCGGCTAAGACCGTCTGCCCGCCGCACAAAGTGGAACTGGAAGCTCTGCTGG
AAAAGCAGGCGTATAAAGAACAAGTGCTGGCGAAACGCCTGACCATGCTGGAACTGCTGGAA
AAGTACCCGGCCTGTGAAATGAAGTTCTCTGAATTTATCGCACTGCTGCCGTCTATCCGTCC
GCGTTATTACAGTATTAGTTCCTCACCGCGTGTGGATGAAAAACAGGCCAGTATCACCGTTT
CTGTTGTCAGTGGCGAAGCATGGTCTGGCTATGGTGAATACAAGGGTATCGCAAGTAACTAC
CTGGCTGAACTGCAGGAAGGCGATACCATTACGTGCTTTATCTCTACGCCGCAAAGTGAATT
TACCCTGCCGAAAGACCCGGAAACGCCGCTGATCATGGTTGGCCCGGGCACCGGTGTCGCAC
CGTTTCGTGGTTTCGTGCAGGCACGCAAGCAACTGAAAGAACAGGGCCAATCCCTGGGTGAA
GCGCATCTGTATTTTGGCTGTCGCTCACCGCACGAAGATTATCTGTACCAGGAAGAACTGGA
AAACGCGCAATCCGAAGGTATTATCACGCTGCATACCGCCTTCTCACGTATGCCGAATCAGC
CGAAAACCTACGTCCAGCACGTGATGGAACAAGATGGCAAAAAGCTGATTGAACTGCTGGAC
CAGGGTGCGCATTTTTATATCTGCGGTGATGGCAGCCAAATGGCACCGGCAGTGGAAGCAAC
CCTGATGAAATCCTACGCAGATGTTCACCAGGTCTCAGAAGCAGACGCTCGTCTGTGGCTGC
AGCAACTGGAAGAAAAGGGCCGCTATGCGAAAGATGTTTGGGCCGGTTAA (SEQ ID NO: 44)

>PsVO {Pleurotus sapidus}

MRYGCAAVALFYLTAMGKLHPLAIIPDYKGSMAASVTIFNKRTNPLDISVNQANDWPWRYAKT
CVLSSDWALHEMIIHLNNTHLVEEAVIVAAQRKLSPSHIVFRLLEPHWVVTLSLNALARSVLI
PEVIVPIAGFSAPHIFQFIRESFTNFDWKSLYVPADLESRGFPVDQLNSPKFHNYAYARDIND
MWTTLKKFVSSVLQDAQYYPDDASVAGDTQIQAWCDEMRSGMGAGMTNFPESITTVDDLVNMV
TMCIHIAAPQHTAVNYLQQYYQTFVSNKPSALFSPLPTSIAQLQKYTESDLMAALPLNAKRQW
LLMAQIPYLLSMQVQEDENIVTYAANASTDKDPIIASAGRQLAADLKKLAAVFLVNSAQLDDQ
NTPYDVLAPEQLANAIVI (SEQ ID NO: 45)

Figure 4L

ATGCGTTATGGCTGTGCTGCTGTGGCTCTGTTCTATCTGACCGCTATGGGCAAACTGCACCCG
CTGGCTATTATCCCGGACTACAAGGGTAGCATGGCGGCCTCTGTCACCATTTTTAACAAACGT
ACGAATCCGCTGGATATCAGCGTTAACCAGGCAAATGACTGGCCGTGGCGCTATGCTAAGACG
TGCGTGCTGAGCAGCGATTGGGCGCTGCATGAAATGATTATCCACCTGAACAATACCCATCTG
GTGGAAGAAGCCGTCATTGTGGCAGCTCAGCGTAAACTGTCACCGTCGCACATCGTTTTTCGC
CTGCTGGAACCGCATTGGGTGGTTACCCTGTCGCTGAACGCACTGGCTCGTAGCGTGCTGATC
CCGGAAGTTATTGTCCCGATCGCGGGTTTCTCTGCCCCGCACATTTTTCAGTTCATCCGCGAA
TCTTTTACCAATTTCGATTGGAAAAGTCTGTACGTCCCGGCGGACCTGGAATCGCGTGGCTTT
CCGGTGGATCAGCTGAACAGCCCGAAGTTCCATAATTATGCGTACGCCCGCGATATCAACGAC
ATGTGGACCACGCTGAAAAAGTTTGTGAGTTCCGTTCTGCAGGATGCCCAATATTACCCGGAT
GACGCAAGTGTGGCTGGTGATACGCAGATTCAAGCATGGTGCGACGAAATGCGTTCCGGCATG
GGTGCGGGCATGACCAACTTCCCGGAATCAATCACCACGGTTGATGACCTGGTCAATATGGTG
ACCATGTGTATTCACATCGCGGCCCCGCAGCATACGGCGGTTAACTATCTGCAGCAATACTAC
CAAACCTTCGTCAGTAACAAGCCGTCCGCACTGTTCTCACCGCTGCCGACCTCTATTGCTCAG
CTGCAAAAATACACGGAAAGTGATCTGATGGCAGCTCTGCCGCTGAACGCGAAGCGTCAGTGG
CTGCTGATGGCCCAAATTCCGTATCTGCTGTCGATGCAGGTGCAAGAAGATGAAAACATCGTT
ACCTACGCGGCCAATGCGTCCACGGATAAAGACCCGATTATCGCATCAGCTGGCCGCCAGCTG
GCAGCTGACCTGAAAAAGCTGGCGGCCGTTTTTCTGGTCAACTCAGCCCAGCTGGATGACCAA
AATACCCCGTATGATGTGCTGGCACCGGAACAGCTGGCGAATGCCATTGTTATCTAA (SEQ ID NO: 46)

>PoLO [Pleurotus ostreatus]

MAPTMSL*SRS*ALKNVHLPYMVQHPEPTDCSTAMKHAAEGYDRARQMIAFLFDILDYESSVPQK
FTPEEKKEKYTWSHSDKFPPHLAIIPEDIDVPAYIIFSIVRLVQTLSIMSGIQCNERLAPGPE
QNTMEKLTKWNAERHKNQGWVKDMFNEPNIGLRNDWYTDAVFAQQFFTGPNPTTITLASDTWM
KAFTEEAASQGKRDLISLFRSAPPNSFYVQDFSDFRARMGAKPDEELCATSDGGVTRYGCAAV
ALFYLPPTGELHPLAIVPDYKGSMAASITLFNKRVDPSDASVDQANDWPWRYAKTCVLSADWV
LHEMIIHLNNTHLVQEAVIVAVQRTLPDSHIVFRLLKPHWVVTLSLNAQARSVLIPEVIVPIA
GFSELRIFQFVGHAFTNFDWKALYVPTDLEFRGFPLDRLDDDKFHNYAYAKDIKDMWMALRKF
VSSVLKDGKYYPDDSAVAADAQIQDWCDEMRSEKGAGMKKFPESISTLDDLIDMVTMCIHIAA
PQHTAVNYLQQYYQTFVPNKPSALFSPLPTLLSQLESYTESDLMAALPLGAKQEWLLMAQVPY
LLSKEVEQDGNIVTYAGTASNNEDPIIAAAGKELSADLVILAGVFLKNSEKLDDQNTAYNVLA
PDQLANAIVI (SEQ ID NO: 47)

ATGGCCCCGACGATGTCACTGTCTCGCTCCGCACTGAAGAATGTCCACCTGCCGTATATGGT
CCAACACCCGGAACCGACCGATTGCAGCACCGCGATGAAACACGCGGCCGAAGGTTATGATC
GTGCTCGCCAGATGATTGCGTTTCTGTTCGACATCCTGGATTACGAAAGCTCTGTTCCGCAA
AAATTTACCCCGGAAGAAAAGAAAGAAAAATATACGTGGTCACACTCGGATAAGTTCCCGCC
GCATCTGGCCATTATCCCGGAAGACATTGATGTGCCGGCATACATTATCTTTAGCATCGTTC
GTCTGGTCCAGACCCTGAGTATTATGTCCGGCATCCAATGCAACGAACGTCTGGCACCGGGG
CCGGAACAGAATACGATGGAAAAACTGACGAAGTGGAACGCGGAACGTCATAAAAATCAAGG
CTGGGTCAAGGATATGTTTAACGAACCGAATATTGGTCTGCGCAACGACTGGTATACCGATG
CTGTGTTCGCGCAGCAATTTTTCACGGGTCCGAATCCGACCACGATTACCCTGGCCTCTGAT
ACGTGGATGAAAGCATTTACCGAAGAAGCAGCTAGTCAGGGCAAGCGTGACCTGATCAGCCT
GTTTCGCTCTGCCCCGCCGAACTCCTTCTACGTTCAGGACTTTTCAGATTTCCGTGCTCGCA
TGGGCGCGAAACCGGACGAAGAACTGTGCGCGACCTCTGATGGCGGTGTTACCCGTTATGGC
TGTGCAGCAGTCGCACTGTTTTACCTGCCGCCGACCGGTGAACTGCATCCGCTGGCCATTGT

Figure 4M

GCCGGATTATAAAGGCAGTATGGCAGCTTCCATCACGCTGTTCAACAAGCGTGTGGACCCGT
CAGATGCCTCGGTTGACCAGGCAAATGATTGGCCGTGGCGCTACGCTAAAACCTGTGTTCTG
TCCGCGGATTGGGTCCTGCATGAAATGATTATCCACCTGAACAATACCCATCTGGTGCAGGA
AGCCGTCATTGTGGCAGTTCAACGTACGCTGCCGGATTCACACATCGTTTTTCGCCTGCTGA
AACCGCATTGGGTGGTTACCCTGTCGCTGAATGCCCAGGCACGTAGCGTTCTGATCCCGGAA
GTCATTGTGCCGATCGCGGGCTTCAGTGAACTGCGCATCTTTCAGTTCGTTGGTCACGCCTT
TACCAACTTCGACTGGAAAGCACTGTATGTCCCGACGGATCTGGAATTTCGTGGTTTCCCGC
TGGACCGCCTGGATGACGATAAGTTCCATAACTATGCTTACGCGAAGGACATTAAGGATATG
TGGATGGCCCTGCGTAAGTTCGTGAGTTCCGTTCTGAAAGATGGCAAGTATTACCCGGACGA
TTCGGCTGTTGCAGCAGACGCGCAGATTCAAGACTGGTGCGATGAAATGCGCAGCGAAAAAG
GCGCGGGTATGAAAAAGTTCCCGGAAAGCATTTCTACCCTGGACGATCTGATCGATATGGTG
ACGATGTGTATTCACATCGCAGCTCCGCAGCATACCGCCGTGAACTATCTGCAGCAATATTA
CCAAACGTTTGTTCCGAATAAACCGTCAGCACTGTTCTCGCCGCTGCCGACCCTGCTGAGCC
AGCTGGAATCTTACACGGAAAGTGATCTGATGGCGGCCCTGCCGCTGGGTGCTAAACAGGAA
TGGCTGCTGATGGCGCAAGTGCCGTATCTGCTGTCTAAGGAAGTCGAACAGGATGGCAACAT
TGTGACCTACGCCGGTACGGCAAGTAACAATGAAGATCCGATTATCGCAGCTGCGGGCAAAG
AACTGTCCGCTGACCTGGTCATCCTGGCGGGTGTGTTTCTGAAAAACTCAGAAAAGCTGGAC
GATCAGAACACCGCCTATAATGTCCTGGCACCGGATCAACTGGCCAATGCAATTGTGATCTA
A (SEQ ID NO: 48)

>CiVO [Cichorium intybus]

MEISIPTTLGLAVIIFIIFKLLTRTTSKKNLLPEPWRLPIIGHMHHLIGTMPHRGVMELARK
HGSLMHLQLGEVSTIVVSSPRWAKEVLTTYDITFANRPETLTGEIVAYHNTDIVLAPYGEYW
RQLRKLCTLELLSNKKVKSFQSLREEECWNLVKDIRSTGQGSPINLSENIFKMIATILSRAA
FGKGIKDQMKFTELVKEILRLTGGFDVADIFPSKKLLHHLSGKRAKLTNIHNKLDNLINNII
AEHPGNRTSSSQETLLDVLLRLKESAEFPLTADNVKAVILDMFGAGTDTSSATIEWAISELI
RCPRAMEKVQTELRQALNGKERIQEEDLQELNYLKLVIKETLRLHPPLPLVMPRECREPCVL
GGYDIPSKTKLIVNVFAINRDPEYWKDAETFMPERFENSPITVMGSEYEYLPFGAGRRMCPG
AALGLANVELPLAHILYFNWKLPNGKTFEDLDMTESFGATVQRKTELLLVPTDFQTLTAST
(SEQ ID NO: 49 | Wild Type)

MALLLAVFLAVIIFIIFKLLTRTTSKKNLLPEPWRLPIIGHMHHLIGTMPHRGVMELARKHG
SLMHLQLGEVSTIVVSSPRWAKEVLTTYDITFANRPETLTGEIVAYHNTDIVLAPYGEYWRQ
LRKLCTLELLSNKKVKSFQSLREEECWNLVKDIRSTGQGSPINLSENIFKMIATIL*SR*AAFG
KGIKDQMKFTELVKEILRLTGGFDVADIFPSKKLLHHLSGKRAKLTNIHNKLDNLINNIIAE
HPGNRTSSSQETLLDVLLRLKESAEFPLTADNVKAVILDMFGAGTDTSSATIEWAISELIRC
PRAMEKVQTELRQALNGKERIQEEDLQELNYLKLVIKETLRLHPPLPLVMPRECREPCVLGG
YDIPSKTKLIVNVFAINRDPEYWKDAETFMPERFENSPITVMGSEYEYLPFGAGRRMCPGAA
LGLANVELPLAHILYFNWKLPNGKTFEDLDMTESFGATVQRKTELLLVPTDFQTLTAST
(SEQ ID NO: 50)

ATGGCTCTGTTATTAGCAGTTTTTCTGGCTGTCATTATCTTTATCATCTTCAAACTGCTGAC
CCGCACCACCTCGAAGAAAAACCTGCTGCCGGAACCGTGGCGTCTGCCGATTATCGGCCACA
TGCATCACCTGATTGGCACCATGCCGCACCGTGGTGTGATGGAACTGGCGCGCAAACATGGC
TCACTGATGCACCTGCAGCTGGGTGAAGTGAGCACCATCGTGGTTAGCTCTCCGCGTTGGGC
GAAAGAAGTTCTGACCACGTATGATATTACCTTTGCCAACCGCCCGGAAACCCTGACGGGCG

Figure 4N

AAATCGTGGCATACCATAATACGGACATTGTTCTGGCTCCGTATGGTGAATACTGGCGTCAG
CTGCGCAAACTGTGCACCCTGGAACTGCTGAGTAACAAAAAGTCAAATCTTTTCAAAGTCT
GCGTGAAGAAGAATGTTGGAATCTGGTGAAAGATATCCGCTCCACCGGCCAGGGTTCACCGA
TCAACCTGTCGGAAAACATCTTCAAAATGATCGCGACGATCCTGTCTCGTGCGGCCTTTGGC
AAAGGTATTAAAGACCAAATGAAATTCACCGAACTGGTTAAAGAAATCCTGCGCCTGACGGG
CGGTTTTGATGTCGCAGACATTTTCCCGAGTAAAAAACTGCTGCATCACCTGTCCGGCAAAC
GTGCTAAACTGACCAACATCCATAACAAACTGGATAACCTGATCAACAACATTATCGCCGAA
CACCCGGGTAATCGTACCAGTTCCTCACAGGAAACGCTGCTGGATGTTCTGCTGCGCCTGAA
AGAAAGCGCAGAATTTCCGCTGACCGCGGACAATGTTAAAGCCGTCATTCTGGATATGTTCG
GTGCAGGCACCGACACGTCGAGCGCAACCATTGAATGGGCTATCTCTGAACTGATTCGTTGC
CCGCGCGCGATGGAAAAAGTGCAGACGGAACTGCGTCAAGCCCTGAACGGCAAAGAACGCAT
CCAGGAAGAAGATCTGCAAGAACTGAACTACCTGAAACTGGTTATCAAAGAAACCCTGCGCC
TGCATCCGCCGCTGCCGCTGGTCATGCCGCGTGAATGCCGCGAACCGTGTGTGCTGGGCGGT
TATGATATCCCGAGCAAAACCAAACTGATCGTCAACGTGTTTGCAATTAATCGTGACCCGGA
ATACTGGAAAGACGCTGAAACCTTTATGCCGGAACGCTTCGAAAACAGCCCGATTACGGTTA
TGGGTTCTGAATATGAATACCTGCCGTTTGGTGCAGGTCGTCGCATGTGTCCGGGTGCAGCT
CTGGGTCTGGCGAATGTCGAACTGCCGCTGGCCCACATCCTGTATTACTTCAACTGGAAACT
GCCGAATGGCAAAACCTTTGAAGATCTGGACATGACCGAATCCTTCGGTGCAACGGTGCAAC
GCAAAACCGAACTGCTGCTGGTGCCGACGGATTTCCAAACGCTGACCGCATCAACG (SEQ ID NO: 51)

>HaGAO |Helianthus annuus|

MEVSLTTSIALATIVFFLYKLLTRPTSSKNRLPEPWRLPIIGHMHHLIGTMPHRGVMDLARK
YGSLMHLQLGEVSAIVVSSPKWAKEILTTYDIPFANRPETLTGEIIAYHNTDIVLAPYGEYW
RQLRKLCTLELLSVKKVKSFQSLREEECWNLVQEIKASGSGTPFNLSEGIFKVIATVL*SR*AA
FGKGIKDQKQFTEIVKEILRETGGFDVADIFPSKKFLHHLSGKRGRLTSIHNKLDSLINNLV
AEHTVSKSSKVNETLLDVLLRLKNSEEFPLTADNVKAIILDMFGAGTDTSSATVEWAISELI
RCPRAMEKVQAELRQALNGKERIKEEEIQDLPYLNLVIRETLRLHPPLPLVMPRECRQAMNL
AGYDVANKTKLIVNVFAINRDPEYWKDAESFNPERFENSNTTIMGADYEYLPFGAGRRMCPG
SALGLANVQLPLANILYYFKWKLPNGASHDQLDMTESFGATVQRKTELMLVPSF (SEQ ID NO: 52 | Wild Type)

MALLLAVFIALATIVFFLYKLLTRPTSSKNRLPEPWRLPIIGHMHHLIGTMPHRGVMDLARKY
GSLMHLQLGEVSAIVVSSPKWAKEILTTYDIPFANRPETLTGEIIAYHNTDIVLAPYGEYWRQ
LRKLCTLELLSVKKVKSFQSLREEECWNLVQEIKASGSGTPFNLSEGIFKVIATVL*SR*AAFGK
GIKDQKQFTEIVKEILRETGGFDVADIFPSKKFLHHLSGKRGRLTSIHNKLDSLINNLVAEHT
VSKSSKVNETLLDVLLRLKNSEEFPLTADNVKAIILDMFGAGTDTSSATVEWAISELIRCPRA
MEKVQAELRQALNGKERIKEEEIQDLPYLNLVIRETLRLHPPLPLVMPRECRQAMNLAGYDVA
NKTKLIVNVFAINRDPEYWKDAESFNPERFENSNTTIMGADYEYLPFGAGRRMCPGSALGLAN
VQLPLANILYYFKWKLPNGASHDQLDMTESFGATVQRKTELMLVPSF (SEQ ID NO: 53)

ATGGCTCTGTTATTAGCAGTTTTCATCGCCCTGGCAACCATTGTCTTTTTCCTGTATAAACTG
CTGACCCGTCCGACCTCATCTAAAAACCGTCTGCCGGAACCGTGGCGCCTGCCGATTATCGGC
CACATGCATCACCTGATTGGCACCATGCCGCACCGTGGTGTCATGGATCTGGCACGCAAATAT
GGCAGCCTGATGCATCTGCAACTGGGTGAAGTTTCTGCGATTGTGGTTAGCTCTCCGAAATGG
GCCAAAGAAATTCTGACCACCTATGATATTCCGTTTGCGAACCGCCCGGAAACCCTGACGGGC
GAAATTATCGCATACCACAATACCGACATTGTGCTGGCTCCGTATGGTGAATACTGGCGTCAA

Figure 4O

CTGCGTAAACTGTGCACGCTGGAACTGCTGAGTGTTAAAAAAGTCAAAAGTTTCCAGAGCCTG
CGTGAAGAAGAATGTTGGAACCTGGTTCAAGAAATTAAAGCGAGCGGCAGCGGCACCCCGTTT
AATCTGAGTGAAGGTATTTTCAAAGTGATTGCGACCGTGCTGAGCCGTGCGGCATTTGGTAAA
GGTATCAAAGATCAGAAACAATTCACCGAAATTGTCAAAGAAATCCTGCGCGAAACGGGCGGT
TTTGATGTGGCGGACATCTTTCCGAGCAAAAAATTCCTGCATCACCTGTCTGGCAAACGTGGT
CGCCTGACCTCAATTCATAACAAACTGGATTCGCTGATCAACAATCTGGTCGCCGAACATACC
GTGAGCAAAAGCAGCAAAGTGAATGAAACGCTGCTGGATGTCCTGCTGCGTCTGAAAAACTCG
GAAGAATTTCCGCTGACCGCAGACAATGTGAAAGCTATTATCCTGGATATGTTCGGTGCAGGC
ACCGATACCAGCAGCGCAACGGTGGAATGGGCCATTAGCGAACTGATCCGTTGCCCGCGCGCA
ATGGAAAAAGTTCAGGCAGAACTGCGTCAAGCTCTGAACGGCAAAGAACGCATTAAAGAAGAA
GAAATCCAGGATCTGCCGTATCTGAATCTGGTTATTCGTGAAACCCTGCGTCTGCATCCGCCG
CTGCCGCTGGTCATGCCGCGTGAATGTCGCCAAGCAATGAACCTGGCTGGCTATGACGTGGCA
AATAAAACCAAACTGATCGTCAATGTGTTTGCGATTAACCGTGACCCGGAATACTGGAAAGAC
GCGGAAAGTTTTAACCCGGAACGCTTTGAAAACAGCAACACCACGATTATGGGTGCGGATTAT
GAATACCTGCCGTTTGGCGCCGGTCGTCGCATGTGTCCGGGCAGCGCGCTGGGTCTGGCCAAC
GTTCAACTGCCGCTGGCCAATATCCTGTATTACTTCAAATGGAAACTGCCGAATGGCGCCTCA
CACGATCAACTGGACATGACCGAATCGTTTGGTGCAACCGTGCAACGCAAAACGGAACTGATG
CTGGTTCCGTCTTTC (SEQ ID NO: 54)

Figure 4P

Figure 4Q

>n20yhcB-t29SrKO
MAWEYALIGLVVGIIIGAVAAWYLKSYTSARRSQSNHLPRVPEVPGVPLLGNLLQLKEKKPYM
TFTRWAATYGPIYSIKTGATSMVVVSSNEIAKEALVTRFQSISTRNLSKALKVLTADKTMVAM
SDYDDYHKTVKRHILTAVLGPNAQKKHRIHRDIMMDNISTQLHEFVKNNPEQEEVDLRKIFQS
ELFGLAMRQALGKDVESLYVEDLKITMNRDEIFQVLVVDPMMGAIDVDWRDFFPYLKWVPNKK
FENTIQQMYIRREAVMKSLIKEHKKRIASGEKLNSYIDYLLSEAQTLTDQQLLMSLWEPIIES
SDTTMVTTEWAMYELAKNPKLQDRLYRDIKSVCGSEKITEEHLSQLPYITAIFHETLRRHSPV
PIIPLRHVHEDTVLGGYHVPAGTELAVNIYGCNMDKNVWENPEEWNPERFMKENETIDFQKTM
AFGGGKRVCAGSLQALLTASIGIGRMVQEFEWKLKDMTQEEVNTIGLTTQMLRPLRAIIKPRI
(SEQ ID NO: 55)

>n22yhcB-t30VO1c9
MAWEYALIGLVVGIIIGAVAMRWYLKSYTSARRSQSNHLPRVPEVPGVPLLGNLLQLKEKKPY
MTFTRWAATYGPIYSIKTGATSVVVVSSNEIAKEAMVTRFQSISTRNLSKALKVLTADKTMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 56)

>n22yhcB-t30VO1c12
MAWEYALIGLVVGIIIGAVAMRWYLKSYTSARRSQSNHLPRVPEVPGVPLLGNLLQLKEKKPY
MTFTKWAATYGPIYSIKTGATSMVVVSSNEIAKEAMVTRFQSISTRNLSKALKVLTADKQMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 57)

>n22yhcB-t30VO1b4
MAWEYALIGLVVGIIIGAVAMRWYLKSYTSARRSQSNHLPRVPEVPGVPLLGNLLQLKEKKPY
MTFTRWAATYGPIYSIKTGATSVVVVSSNEIAKEAMVTRFQSISTRNLSKALKVLTADKQMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 58)

>n20yhcB-t29VO1c11

MAWEYALIGLVVGIIIGAVAAWYLKSYTSARRSQSNHLPRVPEVPGVPLLGNLLQLKEKKPYM
TFTKWAATYGPIYSIKTGATSMVVVSSNEIAKEAMVTRFQSISTRNLSKALKVLTADKQMVAM
SDYDDYHKTVKRHILTAVLGPNAQKKHRIHRDIMMDNISTQLHEFVKNNPEQEEVDLRKIFQS
ELFGLAMRQALGKDVESLYVEDLKITMNRDEILQVLVVDPMMGAIDVDWRDFFPYLKWVPNKK
FENTIQQMYIRREAVMKSLIKEHKKRIASGEKLNSYIDYLLSEAQTLTDQQLLMSLWEPIIES
SDTTMVTTEWAMYELAKNPKLQDRLYRDIKSVCGSEKITEEHLSQLPYITAIFHETLRKHSPV
PILPLRHVHEDTVLGGYHVPAGTELAVNIYGCNMDKNVWENPEEWNPERFMKENETIDFQKTM
AFGGGKRVCAGSLQALLIASIGIGRMVQEFEWKLKDMTQEEVNTIGLTNQMLRPLRAIIKPRI
(SEQ ID NO: 59)

>n22yhcB-t30VO1b6
MAWEYALIGLVVGIIIGAVAMRWYLKSYTSARRSQSNHLPRVPEVPGVPLLGNLLQLKEKKPY
MTFTKWAATYGPIYSIKTGATSVVVVSSNEIAKEAMVTRFQSISTRNLSKALKVLTADKTMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPIIPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 60)

>n22yhcB-t30VO1c6 (VO2)

MAWEYALIGLVVGIIIGAVAMRWYLKSYTSARRSQSNHLPRVPEVPGVPLLGNLLQLKEKKPY
MTFTKWAATYGPIYSIKTGATSVVVVSSNEIAKEALVTRFQSISTRNLSKALKVLTADKQMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEQKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 61)

Figure 4R

Figure 6A

**>*Sr*CPR [Stevia rebaudiana]**

MQSDSVKVSPFDLVSAAMNGKAMEKLNASESEDPTTLPALKMLVENRELLTLFTTSFAVLIGC
LVFLMWRRSSSKKLVQDPVPQVIVVKKKEKESEVDDGKKKVSIFYGTQTGTAEGFAKALVEEA
KVRYEKTSFKVIDLDDYAADDDEYEEKLKKESLAFFFLATYGDGEPTDNAANFYKWFTEGDDK
GEWLKKLQYGVFGLGNRQYEHFNKIAIVVDDKLTEMGAKRLVPVGLGDDDQCIEDDFTAWKEL
VWPELDQLLRDEDDTSVTTPYTAAVLEYRVVYHDKPADSYAEDQTHTNGHVVHDAQHP*SR*SNV
AFKKELHTSQSDRSCTHLEFDISHTGLSYETGDHVGVYSENLSEVVDEALKLLGLSPDTYFSV
HADKEDGTPIGGASLPPPFPPCTLRDALTRYADVLSSPKKVALLALAAHASDPSEADRLKFLA
SPAGKDEYAQWIVANQRSLLEVMQSFPSAKPPLGVFFAAVAPRLQPRYYSISSSPKMSPNRIH
VTCALVYETTPAGRIHRGLCSTWMKNAVPLTESPDCSQASIFVRTSNFRLPVDPKVPVIMIGP
GTGLAPFRGFLQERLALKESGTELGSSIFFFGCRNRKVDFIYEDELNNFVETGALSELIVAF*S*
*R*EGTAKEYVQHKMSQKASDIWKLLSEGAYLYVCGDAKGMAKDVHRTLHTIVQEQGSLDSSKAE
LYVKNLQMSGRYLRDVW (SEQ ID NO: 62)

ATGCAGAGCGATTCTGTTAAAGTATCCCCGTTCGACCTGGTCTCTGCGGCTATGAACGGCAAA
GCAATGGAGAAACTGAACGCGAGCGAATCTGAAGATCCAACCACCCTGCCGGCACTGAAAATG
CTGGTAGAAAACCGTGAACTGCTGACTCTGTTCACCACCTCCTTCGCCGTTCTGATTGGTTGC
CTGGTCTTCCTGATGTGGCGCCGTTCCTCTTCCAAGAAGCTGGTACAGGACCCGGTTCCTCAG
GTGATCGTCGTTAAAAAGAAAGAGAAGGAAAGCGAAGTCGATGACGGCAAAAAGAAGGTTTCC
ATTTTCTACGGTACTCAGACCGGCACCGCTGAGGGTTTTGCCAAAGCACTGGTTGAAGAGGCA
AAAGTGCGTTACGAAAAAACTTCCTTCAAAGTGATTGACCTGGACGACTATGCTGCGGATGAT
GATGAATACGAGGAAAAACTGAAAAAAGAAAGCCTGGCCTTCTTCTTCCTGGCAACCTATGGC
GATGGTGAACCGACCGACAACGCGGCGAACTTCTACAAATGGTTTACCGAAGGCGACGACAAA
GGTGAATGGCTGAAGAAACTGCAGTATGGTGTTTTCGGTCTGGGCAATCGCCAGTACGAACAT
TTTAACAAAATCGCAATCGTTGTTGATGACAAACTGACTGAAATGGGTGCGAAACGTCTGGTG
CCGGTTGGCCTGGGTGACGATGATCAATGCATCGAAGATGACTTCACCGCATGGAAAGAACTG
GTTTGGCCGGAACTGGATCAGCTGCTGCGCGACGAAGACGACACTTCCGTGACCACCCCGTAT
ACCGCTGCAGTGCTGGAGTACCGTGTTGTTTACCACGATAAACCGGCGGACTCTTACGCCGAA
GATCAGACTCACACTAACGGTCACGTCGTACATGACGCACAGCACCCGTCTCGTAGCAATGTT
GCGTTTAAGAAAGAGCTGCACACGAGCCAGTCCGACCGCTCTTGTACGCACCTGGAGTTCGAT
ATCTCCCACACCGGTCTGTCCTATGAAACCGGTGACCATGTTGGCGTTTACAGCGAAAACCTG
AGCGAGGTAGTTGATGAAGCGCTGAAACTGCTGGGCCTGTCTCCAGACACCTACTTTAGCGTG
CATGCTGACAAGGAAGATGGTACTCCGATTGGCGGCGCTTCCCTGCCGCCACCGTTTCCACCT
TGCACTCTGCGTGATGCTCTGACTCGTTACGCTGATGTTCTGTCTAGCCCGAAAAAGGTTGCG
CTGCTGGCGCTGGCCGCACATGCTTCTGACCCGTCTGAAGCTGACCGTCTGAAATTCCTGGCG
TCTCCGGCCGGCAAAGACGAATACGCGCAGTGGATTGTCGCTAACCAGCGCTCTCTGCTGGAA
GTGATGCAGTCCTTCCCGTCTGCCAAACCGCCACTGGGCGTGTTTTTCGCAGCTGTGGCTCCG
CGCCTGCAGCCGCGCTACTATTCTATCTCTAGCTCCCCGAAAATGAGCCCGAACCGCATCCAC
GTTACTTGTGCTCTGGTTTACGAAACCACCCCTGCGGGCCGTATCCACCGTGGTCTGTGCTCT
ACGTGGATGAAAAATGCCGTGCCGCTGACCGAATCCCCGGACTGCTCTCAGGCGTCCATCTTC
GTGCGTACCTCTAACTTCCGTCTGCCGGTGGACCCGAAAGTTCCTGTTATCATGATCGGTCCT
GGCACGGGTCTGGCCCCGTTTCGTGGTTTTCTGCAGGAGCGTCTGGCTCTGAAAGAATCCGGT
ACTGAGCTGGGCTCTTCCATCTTTTTCTTCGGTTGTCGTAACCGCAAAGTCGATTTCATCTAT

GAAGACGAACTGAACAACTTCGTAGAGACTGGTGCACTGTCCGAACTGATTGTGGCATTCTCT
CGTGAAGGCACGGCGAAAGAATACGTTCAACACAAAATGTCTCAGAAAGCGAGCGATATCTGG
AAACTGCTGTCCGAGGGTGCGTATCTGTATGTTTGTGGCGACGCGAAAGGCATGGCTAAAGAT
GTACACCGCACCCTGCACACCATTGTACAAGAACAAGGCTCTCTGGATAGCTCCAAGGCAGAA
CTGTACGTGAAAAACCTGCAGATGTCTGGCCGTTACCTGCGTGATGTATGGTAA (SEQ ID
NO: 63)

>AtCPR [Arabidopsis thaliana]

MTSALYASDLFKQLKSIMGTDSLSDDVVLVIATTSLALVAGFVVLLWKKTTADRSGELKPLMI
PKSLMAKDEDDDLDLGSGKTRVSIFFGTQTGTAEGFAKALSEEIKARYEKAAVKVIDLDDYAA
DDDQYEEKLKKETLAFFCVATYGDGEPTDNAARFSKWFTEENERDIKLQQLAYGVFALGNRQY
EHFNKIGIVLDEELCKKGAKRLIEVGLGDDDQSIEDDFNAWKESLWSELDKLLKDEDDKSVAT
PYTAVIPEYRVVTHDPRFTTQKSMESNVANGNTTIDIHHPCRVDVAVQKELHTHESDRSCIHL
EFDI*SR*TGITYETGDHVGVYAENHVEIVEEAGKLLGHSLDLVFSIHADKEDGSPLESAVPPPF
PGPCTLGTGLARYADLLNPPRKSALVALAAYATEPSEAEKLKHLTSPDGKDEYSQWIVASQRS
LLEVMAAFPSAKPPLGVFFAAIAPRLQPRYYSISSCQDWAP*SR*VHVTSALVYGPTPTGRIHKG
VCSTWMKNAVPAEKSHECSGAPIFIRASNFKLPSNPSTPIVMVGPGTGLAPFRGFLQERMALK
EDGEELGSSLLFFGCRNRQMDFIYEDELNNFVDQGVISELIMAF*SR*EGAQKEYVQHKMMEKAA
QVWDLIKEEGYLYVCGDAKGMARDVHRTLHTIVQEQEGVSSSEAEAIVKKLQTEGRYLRDVW
(SEQ ID NO: 64)

ATGACCAGCGCACTGTACGCAAGCGACCTGTTTAAGCAACTGAAGAGCATTATGGGCACCGAT
AGCCTGAGCGATGATGTTGTCCTGGTCATTGCGACCACGAGCCTGGCACTGGTGGCTGGTTTT
GTGGTTCTGCTGTGGAAAAAGACCACGGCCGATCGTTCTGGCGAACTGAAACCGCTGATGATT
CCGAAAAGTCTGATGGCAAAGGACGAAGATGACGATCTGGATCTGGGCTCCGGTAAAACCCGT
GTGTCAATCTTTTTCGGTACCCAGACGGGCACCGCAGAAGGTTTCGCAAAAGCTCTGTCTGAA
GAAATTAAGGCGCGCTATGAAAAAGCGGCCGTTAAGGTCATCGATCTGGACGATTATGCAGCT
GACGATGACCAGTACGAAGAAAAACTGAAAAAGGAAACCCTGGCGTTTTTCTGCGTTGCCACC
TACGGCGACGGTGAACCGACGGATAACGCGGCCCGTTTTAGTAAATGGTTCACCGAAGAAAAT
GAACGCGACATTAAGCTGCAGCAACTGGCGTATGGCGTGTTTGCTCTGGGTAACCGTCAGTAC
GAACATTTCAACAAGATCGGTATCGTCCTGGATGAAGAACTGTGTAAAAAGGGCGCGAAGCGC
CTGATTGAAGTGGGCCTGGGTGATGACGATCAATCCATCGAAGACGATTTTAACGCCTGGAAA
GAATCTCTGTGGAGTGAACTGGACAAACTGCTGAAGGATGAAGACGATAAGAGCGTGGCGACG
CCGTATACCGCCGTTATTCCGGAATACCGTGTCGTGACCCATGATCCGCGCTTCACCACGCAG
AAAAGCATGGAATCAAATGTTGCGAACGGTAATACCACGATTGACATCCATCACCCGTGCCGT
GTGGATGTTGCCGTCCAAAAAGAACTGCATACCCACGAATCGGACCGTAGCTGTATCCACCTG
GAATTTGATATTAGCCGCACGGGCATCACCTATGAAACGGGCGACCATGTGGGTGTTTACGCA
GAAAACCACGTGGAAATTGTTGAAGAAGCTGGCAAACTGCTGGGTCATTCGCTGGATCTGGTT
TTTAGCATCCACGCGGACAAGGAAGATGGTTCGCCGCTGGAAAGCGCAGTGCCGCCGCCGTTC
CCGGGTCCGTGCACCCTGGGTACGGGTCTGGCACGTTATGCAGATCTGCTGAATCCGCCGCGC
AAATCCGCACTGGTGGCTCTGGCAGCTTACGCAACCGAACCGTCAGAAGCTGAAAAACTGAAG
CATCTGACGTCGCCGGACGGTAAAGATGAATATAGCCAGTGGATTGTTGCGTCTCAACGCAGT
CTGCTGGAAGTCATGGCAGCATTTCCGTCGGCAAAACCGCCGCTGGGCGTGTTTTTCGCAGCT
ATTGCACCGCGTCTGCAGCCGCGCTATTACAGCATCAGCTCTTGTCAAGATTGGGCGCCGTCT
CGTGTCCATGTGACCAGTGCACTGGTGTATGGTCCGACGCCGACCGGTCGCATTCACAAAGGC
GTGTGCTCTACCTGGATGAAAAACGCGGTTCCGGCCGAAAAGTCTCACGAATGTAGTGGTGCG
CCGATTTTTATCCGTGCCAGTAACTTCAAACTGCCGTCCAATCCGTCAACCCCGATCGTTATG

Figure 6B

GTCGGTCCGGGTACGGGTCTGGCACCGTTTCGTGGTTTCCTGCAGGAACGCATGGCTCTGAAA
GAAGATGGCGAAGAACTGGGTAGTTCCCTGCTGTTTTTCGGCTGCCGTAATCGCCAGATGGAC
TTCATCTACGAAGATGAACTGAACAACTTCGTCGATCAAGGTGTGATTTCCGAACTGATCATG
GCATTTTCACGCGAAGGCGCTCAGAAAGAATACGTCCAACATAAAATGATGGAAAAGGCGGCC
CAAGTGTGGGATCTGATCAAAGAAGAAGGCTATCTGTACGTTTGTGGCGACGCAAAGGGTATG
GCTCGTGATGTCCATCGCACCCTGCACACGATTGTTCAGGAACAAGAAGGTGTCTCATCGAGC
GAAGCGGAAGCCATCGTGAAAAAGCTGCAGACCGAAGGCCGTTATCTGCGCGATGTTTGGTAA
(SEQ ID NO: 65)

>TcCPR [Taxus cuspidata]

MQANSNTVEGASQGKSLLDI*SR*LDHIFALLLNGKGGDLGAMTGSALILTENSQNLMILTTALA
VLVACVFFFVWRRGGSDTQKPAVRPTPLVKEEDEEEEDDSAKKKVTIFFGTQTGTAEGFAKAL
AEEAKARYEKAVFKVVDLDNYAADDEQYEEKLKKEKLAFFMLATYGDGEPTDNAARFYKWFLE
GKEREPWLSDLTYGVFGLGNRQYEHFNKVAKAVDEVLIEQGAKRLVPVGLGDDDQCIEDDFTA
WREQVWPELDQLLRDEDDEPTSATPYTAAIPEYRVEIYDSVVSVYEETHALKQNGQAVYDIHH
PCRSNVAVRRELHTPLSDRSCIHLEFDISDTGLIYETGDHVGVHTENSIETVEEAAKLLGYQL
DTIFSVHGDKEDGTPLGGSSLPPPFPGPCTLRTALARYADLLNPPRKAAFLALAAHASDPAEA
ERLKFLSSPAGKDEYSQWVTASQRSLLEIMAEFPSAKPPLGVFFAAIAPRLQPRYYSISSSPR
FAP*SR*IHVTCALVYGPSPTGRIHKGVCSNWMKNSLPSEETHDCSWAPVFVRQSNFKLPADSTT
PIVMVGPGTGFAPFRGFLQERAKLQEAGEKLGPAVLFFGCRNRQMDYIYEDELKGYVEKGILT
NLIVAF*SR*EGATKEYVQHKMLEKASDTWSLIAQGGYLYVCGDAKGMARDVHRTLHTIVQEQES
VDSSKAEFLVKKLQMDGRYLRDIW (SEQ ID NO: 66)

ATGCAGGCTAATTCCAACACGGTGGAAGGTGCCTCCCAGGGGAAGAGCCTGCTGGACATATCT
CGGCTGGACCATATTTTTGCGCTGCTGTTGAACGGCAAGGGAGGAGATCTGGGAGCCATGACC
GGCTCGGCTTTGATTTTGACAGAGAATTCGCAGAATTTGATGATTTTGACCACGGCTTTGGCT
GTTTTGGTCGCGTGTGTTTTCTTCTTCGTTTGGAGGAGGGGAGGATCGGATACGCAGAAGCCG
GCGGTGAGACCGACGCCTCTGGTGAAGGAGGAAGATGAGGAGGAAGAAGACGATTCTGCAAAG
AAGAAAGTCACGATTTTCTTTGGGACACAGACTGGGACGGCCGAGGGATTTGCCAAGGCTCTA
GCAGAAGAGGCAAAGGCAAGATATGAGAAAGCTGTGTTTAAAGTCGTAGATTTGGACAACTAT
GCAGCAGATGATGAGCAGTATGAAGAAAAATTGAAAAAGGAAAAATTAGCATTTTTTATGCTA
GCAACGTATGGAGATGGGGAGCCCACTGACAATGCAGCAAGATTTTATAAGTGGTTTCTTGAG
GGCAAGGAGAGGGAGCCATGGCTTTCTGATCTCACTTATGGGGTGTTTGGATTAGGCAACAGA
CAATATGAACATTTTAATAAGGTGGCTAAAGCAGTAGATGAAGTCTTAATTGAACAAGGTGCA
AAGCGACTTGTTCCAGTGGGCCTTGGTGATGATGACCAATGCATTGAAGATGACTTTACTGCT
TGGCGAGAGCAGGTTTGGCCTGAACTGGATCAGTTACTCCGGGATGAAGATGATGAGCCCACA
AGTGCTACACCTTATACAGCTGCCATACCTGAGTATAGGGTTGAAATTTATGATTCCGTGGTT
TCAGTGTACGAGGAAACTCATGCTCTCAAGCAAAATGGCCAAGCTGTTTATGATATCCATCAC
CCCTGCAGATCTAATGTGGCAGTGAGAAGAGAGCTTCATACACCTTTGTCTGACCGCTCTTGC
ATCCATTTGGAATTTGATATATCAGACACTGGCCTTATATATGAGACAGGAGATCATGTTGGT
GTCCATACAGAAAACAGCATTGAAACTGTGGAGGAAGCAGCAAAGCTACTAGGCTACCAATTG
GACACTATATTCTCAGTCCACGGTGACAAAGAAGATGGCACGCCACTTGGAGGGTCTTCTTTG
CCACCACCTTTCCCTGGTCCATGCACCCTACGAACTGCTCTTGCTCGTTATGCTGATTTGCTG
AATCCTCCTCGGAAGGCCGCCTTTCTTGCATTGGCAGCTCATGCATCTGATCCAGCAGAGGCA
GAGCGGTTGAAGTTCCTCTCATCACCAGCTGGAAAGGATGAATATTCTCAATGGGTCACTGCA
AGTCAGAGAAGTCTTTTAGAAATAATGGCAGAATTTCCATCAGCAAAACCACCCCTTGGTGTT

Figure 6C

TTCTTTGCAGCAATAGCCCCTCGTCTGCAACCCCGATATTATTCTATTTCTTCCTCTCCCAGG
TTTGCACCCTCAAGAATACATGTGACATGTGCTCTTGTTTACGGGCCCAGTCCAACCGGTAGA
ATTCACAAAGGTGTTTGTTCTAACTGGATGAAGAATTCGCTACCCTCAGAAGAAACCCATGAC
TGTAGCTGGGCTCCAGTCTTTGTCAGGCAATCAAATTTTAAATTGCCAGCAGATTCTACTACT
CCTATTGTCATGGTGGGTCCTGGAACTGGTTTTGCACCTTTTAGAGGTTTTTTGCAGGAAAGA
GCAAAACTTCAAGAAGCTGGTGAGAAGCTCGGTCCGGCTGTTTTATTTTTTGGGTGCAGGAAT
CGCCAAATGGACTACATTTATGAAGATGAGCTGAAGGGCTATGTGGAGAAAGGAATACTGACC
AATCTCATTGTTGCTTTCTCTCGTGAAGGAGCAACCAAAGAGTATGTCCAGCACAAGATGCTG
GAAAAGGCATCCGATACCTGGAGTCTCATTGCTCAGGGTGGGTATCTTTATGTATGTGGTGAT
GCCAAGGGTATGGCTAGGGATGTACACAGGACACTGCACACTATTGTCCAAGAGCAGGAATCT
GTGGATAGCAGCAAAGCAGAGTTTCTAGTGAAGAAATTACAGATGGATGGAAGATACTTACGA
GATATATGGTGA (SEQ ID NO: 67)

>AaCPR [Artemisia annua]
MAQSTTSVKLSPFDLMTALLNGKVSFDTSNTSDTNIPLAVFMENRELLMILTTSVAVLIGCVV
VLVWRRSSSAAKKAAESPVIVVPKKVTEDEVDDGRKKVTVFFGTQTGTAEGFAKALVEEAKAR
YEKAVFKVIDLDDYAAEDDEYEEKLKKESLAFFFLATYGDGEPTDNAARFYKWFTEGEEKGEW
LDKLQYAVFGLGNRQYEHFNKIAKVVDEKLVEQGAKRLVPVGMGDDDQCIEDDFTAWKELVWP
ELDQLLRDEDDTSVATPYTAAVAEYRVVFHDKPETYDQDQLTNGHAVHDAQHPCRSNVAVKKE
LHSPLSDRSCTHLEFDISNTGLSYETGDHVGVYVENLSEVVDEAEKLIGLPPHTYFSVHADNE
DGTPLGGASLPPPFPPCTLRKALASYADVLSSPKKSALLALAAHATDSTEADRLKFLASPAGK
DEYAQWIVASHRSLLEVMEAFPSAKPPLGVFFASVAPRLQPRYYSISSSPRFAPNRIHVTCAL
VYEQTPSGRVHKGVCSTWMKNAVPMTESQDCSWAPIYVRTSNFRLPSDPKVPVIMIGPGTGLA
PFRGFLQERLAQKEAGTELGTAILFFGCRNRKVDFIYEDELNNFVETGALSELVTAFSREGAT
KEYVQHKMTQKASDIWNLLSEGAYLYVCGDAKGMAKDVHRTLHTIVQEQGSLDSSKAELYVKN
LQMAGRYLRDVW (SEQ ID NO: 68)

ATGGCGCAGTCTACCACCAGCGTGAAATTGTCCCCTTTTGATCTCATGACCGCTCTGCTGAAT
GGGAAAGTCTCATTCGATACAAGCAACACAAGTGATACCAACATCCCTTTGGCGGTTTTTATG
GAGAATAGAGAGTTACTCATGATTTTAACGACTTCCGTGGCCGTGCTCATTGGGTGCGTCGTC
GTACTTGTCTGGCGCCGGTCAAGTAGCGCAGCAAAGAAGGCGGCGGAGTCCCCGGTTATCGTC
GTCCCAAAGAAGGTTACAGAGGACGAGGTGGACGACGGACGCAAAAAAGTGACGGTATTCTTT
GGTACACAGACCGGAACCGCGGAAGGATTTGCTAAAGCGCTGGTGGAAGAAGCTAAAGCCCGT
TACGAAAAAGCGGTATTCAAAGTGATAGACCTGGATGACTATGCGGCAGAGGACGACGAGTAC
GAGGAAAAATTGAAAAAAGAATCTCTTGCGTTCTTTTTTCTCGCCACTTACGGCGATGGAGAA
CCTACTGATAATGCGGCTCGGTTTTATAAGTGGTTCACTGAGGGTGAAGAAAAAGGTGAATGG
CTGGACAAATTGCAGTACGCAGTATTTGGACTCGGGAATCGTCAATATGAACATTTTAACAAA
ATTGCTAAGGTCGTCGATGAAAAACTGGTTGAGCAGGGTGCGAAACGTCTGGTCCCGGTTGGA
ATGGGCGATGACGACCAGTGCATTGAAGACGACTTTACAGCATGGAAGGAACTGGTGTGGCCG
GAACTGGACCAACTTTTGCGTGACGAGGATGACACATCTGTAGCTACGCCGTACACTGCTGCG
GTAGCCGAGTATAGGGTCGTTTTTCACGATAAACCGGAAACCTACGACCAAGACCAGCTCACA
AATGGTCATGCAGTACATGATGCGCAACATCCTTGCAGGTCAAATGTGGCGGTGAAGAAAGAG
CTGCACAGTCCTCTGTCAGATCGTTCTTGCACCCACCTGGAATTTGACATATCCAATACGGGC
CTTTCGTATGAAACCGGAGATCACGTTGGTGTCTATGTTGAAAATCTGTCGGAAGTGGTTGAT
GAGGCGGAAAAACTTATCGGTCTGCCGCCTCATACGTACTTTTCAGTCCACGCTGATAATGAA
GACGGAACCCCGCTGGGTGGCGCATCGTTACCCCCACCCTTTCCACCATGCACTCTGCGTAAG
GCGCTTGCCAGTTATGCTGATGTTTTGTCTAGTCCCAAAAAGAGTGCACTTCTCGCACTGGCG

Figure 6D

GCCCATGCCACTGATAGTACAGAGGCCGACAGGCTGAAATTTCTGGCGTCACCAGCGGGAAAA
GACGAATACGCCCAATGGATCGTTGCCAGTCATCGGTCTTTACTGGAAGTGATGGAAGCGTTC
CCTTCCGCTAAGCCACCTCTGGGGGTCTTTTTCGCTAGTGTGGCACCCCGTCTACAGCCCCGG
TATTACTCAATATCTAGCTCACCCAGATTTGCTCCGAATAGAATACACGTAACATGCGCGCTG
GTCTATGAGCAGACCCCAAGTGGACGGGTGCATAAAGGGGTTTGTTCTACCTGGATGAAGAAC
GCCGTCCCAATGACCGAGTCTCAGGATTGTTCCTGGGCACCTATATATGTTAGAACATCAAAC
TTTCGACTGCCAAGTGACCCGAAAGTTCCGGTAATTATGATAGGTCCAGGAACAGGGCTGGCT
CCCTTTCGCGGGTTCCTCCAGGAACGTCTGGCGCAGAAGGAGGCGGGAACTGAACTGGGGACG
GCGATTTTATTTTTCGGGTGTAGAAATCGTAAAGTCGATTTTATATATGAAGATGAGTTGAAC
AATTTCGTGGAAACCGGGGCATTATCGGAATTAGTTACGGCTTTTAGCAGGGAGGGGGCGACT
AAAGAGTATGTCCAGCACAAGATGACTCAGAAAGCCTCAGATATATGGAACCTGCTGTCGGAG
GGAGCCTATCTTTATGTTTGCGGTGATGCAAAAGGAATGGCCAAAGATGTCCACCGGACCCTC
CACACTATTGTGCAGGAACAGGGTTCATTAGACTCAAGTAAAGCCGAACTTTACGTAAAAAAT
CTACAGATGGCGGGCCGTTACCTCCGTGACGTTTGGTAA (SEQ ID NO: 69)

>AtCPR1 [Arabidopsis thaliana]
MATSALYASDLFKQLKSIMGTDSLSDDVVLVIATTSLALVAGFVVLLWKKTTADRSGELKPLM
IPKSLMAKDEDDDLDLGSGKTRVSIFFGTQTGTAEGFAKALSEEIKARYEKAAVKVIDLDDYA
ADDDQYEEKLKKETLAFFCVATYGDGEPTDNAARFYKWFTEENERDIKLQQLAYGVFALGNRQ
YEHFNKIGIVLDEELCKKGAKRLIEVGLGDDDQSIEDDFNAWKESLWSELDKLLKDEDDKSVA
TPYTAVIPEYRVVTHDPRFTTQKSMESNVANGNTTIDIHHPCRVDVAVQKELHTHESDRSCIH
LEFDISRTGITYETGDHVGVYAENHVEIVEEAGKLLGHSLDLVFSIHADKEDGSPLESAVPPP
FPGPCTLGTGLARYADLLNPPRKSALVALAAYATEPSEAEKLKHLTSPDGKDEYSQWIVASQR
SLLEVMAAFPSAKPPLGVFFAAIAPRLQPRYYSISSSPRLAPSRVHVTSALVYGPTPTGRIHK
GVCSTWMKNAVPAEKSHECSGAPIFIRASNFKLPSNPSTPIVMVGPGTGLAPFRGFLQERMAL
KEDGEELGSSLLFFGCRNRQMDFIYEDELNNFVDQGVISELIMAFSREGAQKEYVQHKMMEKA
AQVWDLIKEEGYLYVCGDAKGMARDVHRTLHTIVQEQEGVSSSEAEAIVKKLQTEGRYLRDVW
(SEQ ID NO: 70)

ATGGCGACCAGCGCTCTGTATGCTAGTGACCTTTTTAAACAGCTCAAAAGCATCATGGGCACT
GATAGCCTGTCCGACGATGTTGTCCTGGTAATCGCAACCACTTCCCTTGCGCTTGTTGCGGGC
TTTGTGGTGTTACTGTGGAAGAAGACTACCGCAGATAGGAGTGGTGAATTGAAACCGCTGATG
ATCCCAAAAAGTCTGATGGCCAAAGATGAGGATGATGATCTGGATCTTGGATCAGGGAAGACG
CGAGTCAGTATTTTTTTCGGGACCCAGACGGGCACCGCGGAGGGCTTCGCCAAAGCTCTGTCC
GAGGAAATAAAGGCCAGATACGAGAAAGCCGCCGTAAAGGTTATAGACCTAGATGATTACGCC
GCTGATGACGATCAGTATGAGGAGAAACTTAAAAAGGAGACTCTGGCGTTTTTTGCGTGGCA
ACTTACGGAGACGGCGAGCCCACCGATAATGCAGCTAGGTTTTACAAGTGGTTTACCGAGGAG
AACGAACGAGATATAAAGTTACAGCAGTTGGCCTATGGCGTGTTTGCCCTGGGTAATCGGCAA
TATGAGCATTTCAACAAAATTGGCATCGTTCTGGATGAGGAATTGTGCAAAAAGGGTGCAAAA
CGGCTGATAGAGGTGGGTCTAGGTGACGATGATCAATCTATAGAAGACGATTTTAATGCGTGG
AAAGAGAGCTTATGGAGTGAACTGGATAAGCTCTTGAAAGATGAAGACGACAAGTCAGTGGCG
ACCCCTTATACCGCGGTAATCCCGGAATACCGCGTCGTGACACACGATCCGAGGTTTACAACC
CAAAAATCTATGGAGTCTAATGTCGCCAATGGCAACACAACGATTGATATTCACCACCCCTGT
CGTGTTGACGTGGCTGTTCAAAAAGAACTTCATACACACGAAAGTGACCGAAGTTGCATACAC
TTGGAATTTGACATTAGTCGCACCGGAATTACGTATGAAACTGGTGATCACGTGGGTGTATAC
GCAGAAAATCATGTCGAAATAGTAGAAGAAGCTGGCAAACTGCTGGGACATTCACTCGATCTA
GTGTTTAGTATACATGCCGATAAAGAGGATGGCAGCCCATTGGAAAGTGCCGTCCCTCCGCCG

Figure 6E

TTTCCTGGACCGTGTACTCTGGGGACGGGACTCGCCCGCTATGCTGACCTGTTAAACCCCCCT
CGTAAAAGCGCCCTTGTGGCCCTGGCGGCATACGCAACTGAACCGAGCGAAGCGGAGAAGCTG
AAACATCTGACATCACCGGATGGCAAAGACGAGTATAGTCAGTGGATAGTAGCCTCTCAGCGC
TCTCTGCTGGAAGTGATGGCCGCATTTCCGTCCGCCAAACCACCTTTGGGAGTATTTTTCGCT
GCTATCGCACCTCGGCTCCAGCCGCGCTATTACAGCATATCTTCAAGTCCCCGCTTAGCACCG
TCTCGTGTCCATGTCACTTCTGCGTTGGTTTATGGTCCGACTCCAACAGGTCGCATCCACAAA
GGTGTCTGTTCAACCTGGATGAAAAACGCGGTGCCCGCGGAGAAATCTCATGAGTGCAGTGGT
GCACCTATTTTTATCCGCGCAAGTAACTTCAAACTCCCTTCTAATCCGAGCACGCCCATTGTG
ATGGTTGGCCCAGGCACTGGCCTTGCTCCGTTTCGCGGTTTTCTACAGGAGCGGATGGCCCTT
AAAGAAGATGGGGAAGAATTGGGATCATCGTTGCTCTTTTTTGGCTGCCGAAATCGCCAGATG
GATTTTATCTACGAAGACGAGTTGAATAACTTTGTCGATCAAGGAGTAATTTCGGAGTTGATT
ATGGCATTTTCACGCGAAGGGGCTCAGAAAGAGTATGTCCAACACAAGATGATGGAAAAAGCG
GCACAAGTGTGGGATCTTATTAAAGAAGAAGGCTATCTTTATGTATGTGGGGATGCGAAAGGT
ATGGCCCGTGATGTCCATCGCACCCTGCACACGATTGTACAGGAACAGGAAGGTGTGTCCTCG
TCCGAAGCAGAAGCAATCGTTAAAAAACTGCAAACAGAGGGTCGTTACCTTCGCGACGTGTGG
TAA (SEQ ID NO: 71)

>AtCPR2 [Arabidopsis thaliana]
MASSSSSSSTSMIDLMAAIIKGEPVIVSDPANASAYESVAAELSSMLIENRQFAMIVTTSIAV
LIGCIVMLVWRRSGSGNSKRVEPLKPLVIKPREEEIDDGRKKVTIFFGTQTGTAEGFAKALGE
EAKARYEKTRFKIVDLDDYAADDDEYEEKLKKEDVAFFFLATYGDGEPTDNAARFYKWFTEGN
DRGEWLKNLKYGVFGLGNRQYEHFNKVAKVVDDILVEQGAQRLVQVGLGDDDQCIEDDFTAWR
EALWPELDTILREEGDTAVATPYTAAVLEYRVSIHDSEDAKFNDINMANGNGYTVFDAQHPYK
ANVAVKRELHTPESDRSCIHLEFDIAGSGLTYETGDHVGVLCDNLSETVDEALRLLDMSPDTY
FSLHAEKEDGTPISSSLPPPFPPCNLRTALTRYACLLSSPKKSALVALAAHASDPTEAERLKH
LASPAGKDEYSKWVVESQRSLLEVMAEFPSAKPPLGVFFAGVAPRLQPRFYSISSSPKIAETR
IHVTCALVYEKMPTGRIHKGVCSTWMKNAVPYEKSENCSSAPIFVRQSNFKLPSDSKVPIIMI
GPGTGLAPFRGFLQERLALVESGVELGPSVLFFGCRNRRMDFIYEEELQRFVESGALAELSVA
FSREGPTKEYVQHKMMDKASDIWNMISQGAYLYVCGDAKGMARDVHRSLHTIAQEQGSMDSTK
AEGFVKNLQTSGRYLRDVW (SEQ ID NO: 72)

ATGGCGTCCAGCAGTTCATCGAGTTCTACAAGCATGATCGATCTGATGGCCGCTATTATCAAA
GGGGAACCCGTAATTGTCTCTGATCCAGCAAATGCCTCGGCATACGAGTCGGTGGCTGCCGAA
TTATCATCTATGTTAATTGAAAATAGACAATTTGCCATGATTGTGACAACTTCTATTGCTGTG
CTGATAGGTTGCATCGTCATGCTCGTGTGGCGCCGTAGCGGATCAGGCAACTCAAAGCGCGTC
GAGCCTTTGAAACCCCTGGTTATCAAACCGCGAGAGGAGGAAATCGATGATGGCAGAAAAAAG
GTTACTATCTTTTTTGGCACACAGACGGGGACAGCGGAAGGTTTCGCGAAAGCACTCGGAGAG
GAAGCGAAAGCCCGATACGAGAAAACACGGTTCAAAATTGTGGATCTGGATGACTATGCGGCT
GATGATGATGAGTATGAAGAAAAACTGAAAAAAGAAGATGTGGCGTTTTTTTTTCTTGCCACT
TATGGCGACGGAGAGCCCACCGATAATGCAGCGCGGTTTTACAAGTGGTTCACCGAAGGAAAT
GATCGGGGAGAATGGTTAAAAAATCTGAAATACGGTGTGTTCGGTCTTGGCAATCGCCAATAT
GAGCATTTTAATAAAGTCGCGAAAGTGGTCGATGATATATTGGTAGAACAGGGCGCTCAGCGC
CTCGTCCAGGTGGGGCTTGGCGACGATGATCAGTGCATAGAAGATGATTTTACTGCATGGCGT
GAAGCGCTGTGGCCGGAGCTGGACACCATTTTACGTGAAGAGGGCGATACAGCAGTGGCAACC
CCGTACACGGCTGCCGTCTTAGAGTATCGTGTGTCCATTCATGATAGCGAGGATGCCAAATTC
AATGACATCAATATGGCGAATGGAAATGGGTACACCGTGTTTGACGCGCAGCACCCGTATAAG

Figure 6F

GCAAACGTTGCAGTCAAGAGGGAACTGCATACTCCTGAAAGTGATCGCAGTTGCATCCACCTG
GAGTTCGATATTGCGGGATCAGGTTTAACGTACGAAACGGGCGACCACGTAGGTGTGCTGTGC
GACAATCTTTCAGAGACAGTGGACGAAGCTCTGCGCCTGCTGGATATGAGCCCGGATACCTAT
TTTAGCTTGCACGCTGAGAAAGAAGATGGGACTCCAATTAGCAGTAGCTTACCTCCACCCTTT
CCGCCGTGTAATTTGCGTACCGCCCTTACGCGCTATGCGTGTCTGCTGAGTTCGCCAAAGAAG
TCGGCCCTTGTGGCACTGGCGGCACATGCAAGTGACCCGACCGAGGCGGAGAGGCTGAAACAT
CTGGCTTCTCCAGCGGGCAAAGATGAATACAGCAAATGGGTGGTAGAATCACAGCGTTCCCTA
CTAGAAGTAATGGCCGAATTTCCCTCAGCTAAACCACCGCTGGGAGTGTTCTTTGCGGGCGTT
GCTCCCCGCTTGCAACCACGCTTTTATTCAATTAGCTCAAGTCCTAAGATAGCGGAAACACGG
ATACATGTAACTTGCGCATTGGTTTATGAAAAAATGCCAACCGGGAGGATACATAAAGGCGTA
TGTTCAACCTGGATGAAAAATGCTGTGCCATACGAAAAGTCGGAGAATTGCTCCTCTGCCCCA
ATTTTCGTGCGTCAAAGCAACTTTAAACTGCCGAGTGATTCAAAGGTGCCTATTATTATGATA
GGCCCTGGTACAGGACTCGCCCCGTTTCGTGGTTTTCTTCAAGAAAGACTGGCTCTGGTCGAA
TCAGGCGTGGAATTAGGACCCTCCGTGTTATTTTTGGCTGCCGCAACCGTCGAATGGACTTC
ATCTATGAAGAAGAATTGCAACGTTTTGTGGAGTCAGGCGCTCTGGCGGAACTATCCGTCGCC
TTTAGTAGAGAAGGCCCAACCAAAGAATACGTACAGCATAAGATGATGGATAAAGCGAGCGAC
ATTTGGAATATGATCTCACAAGGGGCGTACCTGTACGTATGTGGAGATGCCAAAGGAATGGCA
CGAGACGTACATAGATCGTTGCATACTATTGCTCAAGAACAGGGAAGCATGGATTCGACTAAA
GCAGAAGGCTTTGTTAAAAATCTACAGACATCTGGTCGCTATCTGCGTGACGTGTGGTAA
(SEQ ID NO: 73)

>ATR2 [Arabidopsis thaliana]
MASSSSSSSTSMIDLMAAIIKGEPVIVSDPANASAYESVAAELSSMLIENRQFAMIVTTSIAV
LIGCIVMLVWRRSGSGNSKRVEPLKPLVIKPREEEIDDGRKKVTIFFGTQTGTAEGFAKALGE
EAKARYEKTRFKIVDLDDYAADDDEYEEKLKKEDVAFFFLATYGDGEPTDNAARFYKWFTEGN
DRGEWLKNLKYGVFGLGNRQYEHFNKVAKVVDDILVEQGAQRLVQVGLGDDDQCIEDDFTAWR
EALWPELDTILREEGDTAVATPYTAAVLEYRVSIHDSEDAKFNDITLANGNGYTVFDAQHPYK
ANVAVKRELHTPESDRSCIHLEFDIAGSGLTMKLGDHVGVLCDNLSETVDEALRLLDMSPDTY
FSLHAEKEDGTPISSSLPPPFPPCNLRTALTRYACLLSSPKKSALVALAAHASDPTEAERLKH
LASPAGKDEYSKWVVESQRSLLEVMAEFPSAKPPLGVFFAGVAPRLQPRFYSISSSPKIAETR
IHVTCALVYEKMPTGRIHKGVCSTWMKNAVPYEKSEKLFLGRPIFVRQSNFKLPSDSKVPIIM
IGPGTGLAPFRGFLQERLALVESGVELGPSVLFFGCRNRRMDFIYEEELQRFVESGALAELSV
AFSREGPTKEYVQHKMMDKASDIWNMISQGAYLYVCGDAKGMARDVHRSLHTIAQEQGSMDST
KAEGFVKNLQTSGRYLRDVW (SEQ ID NO: 74)

ATGGCGAGCAGTTCGTCCTCCTCTTCTACCAGTATGATCGATCTGATGGCCGCTATTATAAAA
GGAGAACCAGTCATTGTGTCTGATCCTGCAAACGCATCAGCCTACGAATCTGTGGCTGCTGAA
CTGTCCTCGATGCTGATCGAAAATCGCCAATTTGCAATGATTGTTACAACCAGCATCGCTGTT
CTTATCGGGTGTATTGTCATGCTGGTTTGGCGGCGGAGTGGCAGCGGCAATTCTAAAAGAGTG
GAGCCACTGAAGCCTCTGGTAATCAAACCCCGCGAAGAAGAAATCGATGATGGACGTAAGAAA
GTTACAATTTTTTTTGGTACACAGACAGGTACAGCAGAGGGCTTTGCCAAAGCTCTTGGAGAA
GAAGCAAAAGCTCGATATGAGAAAACACGCTTCAAGATCGTCGATCTGGATGACTACGCGGCA
GACGACGATGAGTACGAAGAAAAACTCAAAAAAGAGGATGTGGCTTTTTTTTTCCTGGCAACT
TATGGGGACGGCGAGCCTACCGACAATGCAGCGCGGTTTTACAAATGGTTTACCGAAGGCAAT
GATAGAGGGGAGTGGCTCAAAAATCTCAAATACGGAGTTTTCGGATTGGGGAATAGACAATAC
GAACACTTTAATAAGGTTGCGAAAGTGGTAGATGATATTCTGGTCGAGCAGGGCGCGCAACGT
TTAGTACAGGTCGGCCTGGGTGATGACGACCAGTGCATCGAAGATGACTTTACGGCCTGGCGA

Figure 6G

GAAGCGCTCTGGCCGGAATTAGATACAATCCTTCGGGAAGAGGGGGACACTGCTGTCGCTACC
CCGTACACTGCCGCAGTGCTGGAATATCGTGTTTCAATACATGATTCGGAAGATGCCAAGTTT
AATGACATCACCCTGGCAAACGGCAACGGATATACCGTATTTGACGCTCAACATCCGTATAAG
GCCAATGTAGCAGTAAAGCGGGAACTCCATACTCCCGAAAGTGACAGAAGTTGCATCCATCTG
GAGTTCGATATAGCGGGAAGCGGACTGACTATGAAACTGGGAGATCATGTAGGGGTCCTGTGC
GATAATTTGAGCGAAACCGTTGACGAAGCGCTCCGGCTTTTAGATATGTCCCCTGATACTTAT
TTCTCTTTGCACGCCGAGAAGGAAGATGGTACACCTATATCCTCCTCGCTGCCGCCGCCTTTT
CCACCATGTAATCTGCGTACGGCCTTGACTAGGTATGCATGTCTTCTTAGCTCCCCGAAAAAG
TCCGCACTGGTAGCGTTGGCAGCTCATGCCAGCGATCCCACGGAGGCAGAGCGTTTAAAACAC
CTGGCGAGTCCTGCTGGCAAAGATGAATACAGCAAATGGGTGGTTGAGTCGCAGAGGTCCCTG
CTGGAAGTCATGGCTGAATTTCCGTCTGCGAAACCGCCTCTGGGAGTTTTCTTCGCAGGAGTA
GCCCCACGTTTACAACCGCGTTTCTATTCTATTTCTTCCTCCCCCAAGATCGCGGAAACTCGA
ATACACGTAACGTGCGCATTGGTGTATGAAAAGATGCCAACTGGTCGTATCCACAAGGGAGTG
TGCTCAACCTGGATGAAAAACGCCGTTCCGTATGAAAAATCGGAAAAATTGTTTTGGGTAGA
CCCATATTCGTTCGGCAGTCAAACTTTAAACTACCTTCTGATAGCAAGGTTCCGATTATTATG
ATTGGACCGGGTACTGGCCTGGCGCCGTTCCGTGGTTTCCTGCAAGAACGGTTGGCGCTGGTG
GAATCCGGCGTGGAACTTGGGCCATCGGTTTTGTTTTTCGGGTGCCGCAATCGTCGCATGGAC
TTCATCTACGAGGAAGAACTCCAGCGTTTTGTCGAAAGCGGTGCCCTTGCTGAATTGTCCGTT
GCATTCAGCCGCGAAGGTCCAACTAAGGAGTATGTGCAGCACAAAATGATGGACAAAGCGAGC
GATATTTGGAATATGATTAGCCAGGGCGCATACCTTTATGTGTGCGGTGATGCTAAGGGAATG
GCGCGCGATGTCCATAGATCTTTACATACCATTGCACAGGAGCAGGGCTCTATGGATTCAACA
AAAGCTGAAGGTTTTGTGAAAAACCTTCAGACCAGCGGGCGGTATCTTCGCGATGTTTGGTAA
(SEQ ID NO: 75)

>SrCPR1 [Stevia rebaudiana]
MAQSDSVKVSPFDLVSAAMNGKAMEKLNASESEDPTTLPALKMLVENRELLTLFTTSFAVLIG
CLVFLMWRRSSSKKLVQDPVPQVIVVKKKEKESEVDDGKKKVSIFYGTQTGTAEGFAKALVEE
AKVRYEKTSFKVIDLDDYAADDDEYEEKLKKESLAFFFLATYGDGEPTDNAANFYKWFTEGDD
KGELLKKLQYGVFGLGNRQYEHFNKIAIVVDDKLTEMGAKRLVPVGLGDDDQCIEDDFTAWKE
LVWPELDQLLRDEDDTSVTTPYTAAVLEYRVVYHDKPADSYAEDQTHTNGHVVHDAQHPSRSN
VAFKKELHTSQSDRSCTHLEFDISHTGLSYETGDHVGVYSENLSEVVDEALKLLGLSPDTYFS
VHADKEDGTPIGGASLPPPFPPCTLRDALTRYADVLSSPKKVALLALAAHASDPSEADRLKFL
ASPAGKDEYAQWIVANQRSLLEVMQSFPSAKPPLGVFFAAVAPRLQPRYYSISSSPKMSPNRI
HVTCALVYETTPAGRIHRGLCSTWMKNAVPLTESPDCSQASIFVRTSNFRLPVDPKVPVIMIG
PGTGLAPFRGFLQERLALKESGTELGSSIFFFGCRNRKVDFIYEDELNNFVETGALSELIVAF
SREGTAKEYVQHKMSQKASDIWKLLSEGAYLYVCGDAKGMAKDVHRTLHTIVQEQGSLDSSKA
ELYVKNLQMSGRYLRDVW (SEQ ID NO: 76)

ATGGCTCAGAGCGATTCTGTTAAAGTATCCCCGTTCGACCTGGTCTCTGCGGCTATGAACGGC
AAAGCAATGGAGAAACTGAACGCGAGCGAATCTGAAGATCCAACCACCCTGCCGGCACTGAAA
ATGCTGGTAGAAAACCGTGAACTGCTGACTCTGTTCACCACCTCCTTCGCCGTTCTGATTGGT
TGCCTGGTCTTCCTGATGTGGCGCCGTTCCTCTTCCAAGAAGCTGGTACAGGACCCGGTTCCT
CAGGTGATCGTCGTTAAAAAGAAAGAGAAGGAAAGCGAAGTCGATGACGGCAAAAAGAAGGTT
TCCATTTTCTACGGTACTCAGACCGGCACCGCTGAGGGTTTTGCCAAAGCACTGGTTGAAGAG
GCAAAAGTGCGTTACGAAAAAACTTCCTTCAAAGTGATTGACCTGGACGACTATGCTGCGGAT
GATGATGAATACGAGGAAAAACTGAAAAAAGAAAGCCTGGCCTTCTTCTTCCTGGCAACCTAT
GGCGATGGTGAACCGACCGACAACGCGGCGAACTTCTACAAATGGTTTACCGAAGGCGACGAC

Figure 6H

AAAGGTGAATTGCTGAAGAAACTGCAGTATGGTGTTTTCGGTCTGGGCAATCGCCAGTACGAA
CATTTTAACAAAATCGCAATCGTTGTTGATGACAAACTGACTGAAATGGGTGCGAAACGTCTG
GTGCCGGTTGGCCTGGGTGACGATGATCAATGCATCGAAGATGACTTCACCGCATGGAAAGAA
CTGGTTTGGCCGGAACTGGATCAGCTGCTGCGCGACGAAGACGACACTTCCGTGACCACCCCG
TATACCGCTGCAGTGCTGGAGTACCGTGTTGTTTACCACGATAAACCGGCGGACTCTTACGCC
GAAGATCAGACTCACACTAACGGTCACGTCGTACATGACGCACAGCACCCGTCTCGTAGCAAT
GTTGCGTTTAAGAAAGAGCTGCACACGAGCCAGTCCGACCGCTCTTGTACGCACCTGGAGTTC
GATATCTCCCACACCGGTCTGTCCTATGAAACCGGTGACCATGTTGGCGTTTACAGCGAAAAC
CTGAGCGAGGTAGTTGATGAAGCGCTGAAACTGCTGGGCCTGTCTCCAGACACCTACTTTAGC
GTGCATGCTGACAAGGAAGATGGTACTCCGATTGGCGGCGCTTCCCTGCCGCCACCGTTTCCA
CCTTGCACTCTGCGTGATGCTCTGACTCGTTACGCTGATGTTCTGTCTAGCCCGAAAAAGGTT
GCGCTGCTGGCGCTGGCCGCACATGCTTCTGACCCGTCTGAAGCTGACCGTCTGAAATTCCTG
GCGTCTCCGGCCGGCAAAGACGAATACGCGCAGTGGATTGTCGCTAACCAGCGCTCTCTGCTG
GAAGTGATGCAGTCCTTCCCGTCTGCCAAACCGCCACTGGGCGTGTTTTTCGCAGCTGTGGCT
CCGCGCCTGCAGCCGCGCTACTATTCTATCTCTAGCTCCCCGAAAATGAGCCCGAACCGCATC
CACGTTACTTGTGCTCTGGTTTACGAAACCACCCCTGCGGGCCGTATCCACCGTGGTCTGTGC
TCTACGTGGATGAAAAATGCCGTGCCGCTGACCGAATCCCCGGACTGCTCTCAGGCGTCCATC
TTCGTGCGTACCTCTAACTTCCGTCTGCCGGTGGACCCGAAAGTTCCTGTTATCATGATCGGT
CCTGGCACGGGTCTGGCCCCGTTTCGTGGTTTTCTGCAGGAGCGTCTGGCTCTGAAAGAATCC
GGTACTGAGCTGGGCTCTTCCATCTTTTTCTTCGGTTGTCGTAACCGCAAAGTCGATTTCATC
TATGAAGACGAACTGAACAACTTCGTAGAGACTGGTGCACTGTCCGAACTGATTGTGGCATTC
TCTCGTGAAGGCACGGCGAAAGAATACGTTCAACACAAAATGTCTCAGAAAGCGAGCGATATC
TGGAAACTGCTGTCCGAGGGTGCGTATCTGTATGTTTGTGGCGACGCGAAAGGCATGGCTAAA
GATGTACACCGCACCCTGCACACCATTGTACAAGAACAAGGCTCTCTGGATAGCTCCAAGGCA
GAACTGTACGTGAAAAACCTGCAGATGTCTGGCCGTTACCTGCGTGATGTATGGTAA (SEQ ID NO: 77)

>SrCPR2 [Stevia rebaudiana]

MAQSESVEASTIDLMTAVLKDTVIDTANASDNGDSKMPPALAMMFEIRDLLLILTTSVAVLV
GCFVVLVWKRSSGKKSGKELEPPKIVVPKRRLEQEVDDGKKKVTIFFGTQTGTAEGFAKALF
EEAKARYEKAAFKVIDLDDYAADLDEYAEKLKKETYAFFFLATYGDGEPTDNAAKFYKWFTE
GDEKGVWLQKLQYGVFGLGNRQYEHFNKIGIVVDDGLTEQGAKRIVPVGLGDDDQSIEDDFS
AWKELVWPELDLLLRDEDDKAAATPYTAAIPEYRVVFHDKPDAFSDDHTQTNGHAVHDAQHP
CRSNVAVKKELHTPESDRSCTHLEFDISHTGLSYETGDHVGVYCENLIEVVEEAGKLLGLST
DTYFSLHIDNEDGSPLGGPSLQPPFPPCTLRKALTNYADLLSSPKKSTLLALAAHASDPTEA
DRLRFLASREGKDEYAEWVVANQRSLLEVMEAFPSARPPLGVFFAAVAPRLQPRYYSISSSP
KMEPNRIHVTCALVYEKTPAGRIHKGICSTWMKNAVPLTESQDCSWAPIFVRTSNFRLPIDP
KVPVIMIGPGTGLAPFRGFLQERLALKESGTELGSSILFFGCRNRKVDYIYENELNNFVENG
ALSELDVAFSRDGPTKEYVQHKMTQKASEIWNMLSEGAYLYVCGDAKGMAKDVHRTLHTIVQ
EQGSLDSSKAELYVKNLQMSGRYLRDVW (SEQ ID NO: 78)

ATGGCGCAATCTGAAAGTGTTGAGGCCAGTACCATCGACCTTATGACGGCAGTGTTGAAGGA
TACAGTTATTGACACTGCAAATGCTTCAGATAACGGCGATTCTAAAATGCCTCCTGCGCTTG
CGATGATGTTCGAGATCCGCGATCTTCTGCTGATCCTTACCACATCAGTAGCGGTGCTGGTG
GGATGCTTTGTGGTACTCGTGTGGAAACGTTCGTCGGGCAAAAAATCAGGTAAGGAGCTGGA

Figure 6I

ACCGCCTAAGATTGTCGTACCGAAACGCCGACTGGAACAAGAAGTTGATGATGGCAAAAAAA
AAGTGACTATATTTTTTGGGACACAGACAGGCACAGCGGAGGGATTTGCGAAAGCCTTATTC
GAGGAGGCGAAGGCACGTTACGAGAAAGCAGCTTTTAAAGTCATTGATCTGGATGACTATGC
AGCAGACCTAGATGAATACGCAGAGAAACTGAAAAAAGAAACTTATGCGTTTTTCTTCCTGG
CCACATACGGAGACGGTGAACCGACGGACAATGCCGCCAAGTTTTATAAGTGGTTCACTGAA
GGGGATGAGAAAGGTGTATGGCTTCAGAAATTGCAATACGGAGTGTTCGGACTAGGAAATCG
GCAATATGAGCACTTTAATAAAATAGGCATAGTAGTAGACGATGGGCTAACCGAGCAGGGGG
CCAAACGGATTGTACCCGTGGGCCTGGGGGACGATGATCAGTCTATTGAGGATGATTTTAGT
GCTTGGAAAGAGCTTGTTTGGCCTGAACTGGACTTACTCCTGCGTGATGAAGACGATAAAGC
GGCAGCGACTCCATACACGGCAGCAATCCCCGAGTATAGAGTCGTATTCCATGATAAACCGG
ATGCTTTCTCTGATGACCATACCCAAACTAATGGTCATGCGGTCCATGATGCACAACATCCC
TGCCGCAGCAATGTAGCGGTGAAAAAGGAGCTGCATACGCCTGAAAGTGATCGCTCATGTAC
GCATCTGGAGTTTGATATTTCACACACAGGTCTTAGCTACGAGACTGGAGATCACGTCGGAG
TCTATTGCGAAAATCTGATCGAAGTGGTTGAAGAGGCCGGGAAACTGTTGGGACTAAGTACA
GATACTTATTTTTCTTTACATATAGATAACGAGGATGGTTCCCCACTTGGCGGTCCATCTCT
TCAGCCTCCATTCCCACCATGTACCTTACGCAAAGCGCTGACTAACTACGCAGATCTGCTGT
CTAGCCCAAAGAAATCAACGCTTCTGGCGTTGGCTGCTCATGCCTCAGATCCGACCGAAGCT
GATCGCCTTCGTTTTCTGGCATCCCGAGAAGGTAAAGATGAATATGCAGAATGGGTGGTAGC
GAATCAGCGTTCTTTGCTGGAAGTCATGGAGGCATTCCCCAGCGCGCGCCCTCCGCTGGGTG
TTTTCTTCGCAGCGGTGGCCCCGCGGCTCCAGCCGCGTTATTATTCAATTAGCAGTTCTCCT
AAGATGGAACCTAATCGAATCCATGTAACATGTGCATTGGTCTATGAGAAAACGCCGGCTGG
CCGCATCCATAAAGGTATATGTAGCACATGGATGAAAAATGCAGTACCCCTCACGGAGTCCC
AGGATTGTAGTTGGGCGCCGATATTTGTTCGGACGAGCAATTTTAGACTTCCTATAGACCCA
AAGGTTCCAGTTATTATGATTGGTCCTGGCACCGGACTTGCGCCATTCCGGGGGTTTCTGCA
AGAAAGACTGGCTCTGAAAGAAAGCGGTACAGAACTCGGCTCCAGTATATTGTTTTTCGGCT
GTCGCAACCGGAAAGTAGATTATATATATGAAAACGAGCTGAATAACTTCGTTGAAAATGGT
GCCCTGTCTGAACTCGATGTCGCTTTTTCGCGAGATGGCCCGACAAAAGAATACGTGCAGCA
TAAAATGACCCAGAAAGCAAGTGAAATCTGGAATATGCTGTCAGAAGGGGCATATCTGTATG
TGTGCGGAGATGCAAAGGGCATGGCCAAAGACGTTCACAGAACCTTGCATACCATAGTACAA
GAGCAGGGCTCTCTGGATAGCTCAAAAGCCGAGCTGTACGTGAAAAATCTCCAGATGAGTGG
ACGCTACCTGAGGGATGTTTGGTAA (SEQ ID NO: 79)

>SrCPR3 [Stevia rebaudiana]

MAQSNSVKISPLDLVTALFSGKVLDTSNASESGESAMLPTIAMIMENRELLMILTTSVAVLI
GCVVVLVWRRSSTKKSALEPPVIVVPKRVQEEEVDDGKKKVTVFFGTQTGTAEGFAKALVEE
AKARYEKAVFKVIDLDDYAADDDEYEEKLKKESLAFFFLATYGDGEPTDNAARFYKWFTEGD
AKGEWLNKLQYGVFGLGNRQYEHFNKIAKVVDDGLVEQGAKRLVPVGLGDDDQCIEDDFTAW
KELVWPELDQLLRDEDDTTVATPYTAAVAEYRVVFHEKPDALSEDYSYTNGHAVHDAQHPCR
SNVAVKKELHSPESDRSCTHLEFDISNTGLSYETGDHVGVYCENLSEVVNDAERLVGLPPDT
YFSIHTDSEDGSPLGGASLPPPFPPCTLRKALTCYADVLSSPKKSALLALAAHATDPSEADR
LKFLASPAGKDEYSQWIVASQRSLLEVMEAFPSAKPSLGVFFASVAPRLQPRYYSISSSPKM
APDRIHVTCALVYEKTPAGRIHKGVCSTWMKNAVPMTESQDCSWAPIYVRTSNFRLPSDPKV
PVIMIGPGTGLAPFRGFLQERLALKEAGTDLGLSILFFGCRNRKVDFIYENELNNFVETGAL
SELIVAFSREGPTKEYVQHKMSEKASDIWNLLSEGAYLYVCGDAKGMAKDVHRTLHTIVQEQ
GSLDSSKAELYVKNLQMSGRYLRDVW (SEQ ID NO: 80)

Figure 6J

ATGGCGCAATCTAATTCTGTGAAAATCTCTCCATTGGATCTGGTTACAGCACTCTTTAGCGG
GAAGGTACTGGATACAAGTAACGCCAGTGAAAGCGGGGAATCCGCGATGCTGCCAACAATCG
CGATGATCATGGAAAATCGGGAACTGCTAATGATTCTGACAACGTCTGTAGCAGTTTTAATC
GGTTGCGTTGTGGTTCTGGTGTGGCGTCGATCATCCACGAAAAAGAGCGCATTAGAACCGCC
TGTTATCGTAGTACCAAAAAGAGTTCAGGAGGAAGAGGTGGATGATGGGAAAAAAAAAGTCA
CCGTTTTCTTCGGGACCCAAACTGGTACGGCAGAAGGTTTTGCGAAAGCACTGGTCGAAGAG
GCGAAAGCCCGCTATGAGAAGGCGGTTTTTAAGGTTATTGACCTTGATGACTATGCGGCGGA
CGATGATGAATACGAAGAAAAATTAAAGAAAGAATCACTTGCCTTTTTTTTTTTGGCAACAT
ACGGTGATGGCGAGCCGACTGATAACGCGGCACGGTTTTACAAATGGTTTACCGAAGGCGAC
GCGAAGGGGGAGTGGTTGAACAAGTTACAGTACGGTGTGTTCGGCTTGGGGAACCGCCAGTA
CGAGCACTTTAACAAGATAGCTAAAGTTGTCGATGATGGTCTGGTAGAACAGGGAGCGAAGC
GTCTCGTGCCAGTAGGGCTGGGCGATGATGATCAGTGTATAGAAGATGATTTTACGGCTTGG
AAGGAGTTAGTTTGGCCGGAACTGGACCAACTGCTGCGCGATGAGGATGATACAACTGTCGC
TACCCCGTATACAGCAGCGGTAGCTGAATACAGGGTGGTTTTTCACGAGAAACCTGATGCGC
TGAGTGAGGACTATTCGTATACTAACGGCCATGCCGTTCACGATGCACAGCACCCGTGCCGT
TCTAATGTCGCCGTAAAAAAGGAACTGCATAGCCCGGAGTCGGACCGCAGTTGTACCCATCT
GGAGTTTGATATTTCAAATACCGGGCTGAGTTACGAAACGGGCGATCACGTTGGCGTGTACT
GTGAGAATCTAAGCGAGGTTGTTAACGATGCAGAACGACTGGTCGGTTTGCCTCCAGATACT
TATTTCTCGATCCACACTGATAGCGAAGATGGCTCTCCACTCGGGGGGGCGAGTCTGCCGCC
CCCGTTTCCCCCGTGTACGCTGAGAAAGGCCCTTACATGTTATGCAGATGTACTCTCTTCCC
CCAAAAAAAGTGCCTTGCTCGCATTAGCAGCCCACGCTACCGATCCCTCGGAAGCAGATCGT
CTGAAATTCTTGGCATCGCCGGCGGGCAAAGATGAATACAGCCAATGGATAGTTGCAAGTCA
GCGCAGTCTCTTAGAAGTGATGGAAGCGTTTCCGTCCGCAAAGCCGTCCTTAGGTGTGTTTT
TCGCGTCCGTGGCACCGCGTCTTCAGCCTAGATATTACAGCATTAGTTCCTCTCCAAAAATG
GCCCCGGACCGTATTCACGTGACTTGTGCTCTTGTATATGAGAAAACCCCGGCAGGTCGTAT
TCACAAAGGCGTGTGCAGCACCTGGATGAAGAATGCAGTGCCGATGACCGAAAGCCAGGATT
GTTCATGGGCGCCAATCTATGTCAGGACAAGTAATTTCAGACTTCCGTCTGATCCTAAAGTT
CCAGTCATAATGATTGGCCCCGGCACGGGACTGGCTCCTTTTCGTGGTTTCCTGCAAGAGCG
CTTGGCACTGAAAGAAGCAGGCACTGACCTGGGACTGTCCATCCTGTTCTTTGGGTGCCGTA
ATCGTAAGGTCGATTTTATATATGAAAATGAATTGAACAACTTTGTAGAAACAGGCGCATTA
TCCGAACTGATCGTAGCTTTTAGTAGAGAGGGGCCGACGAAAGAATATGTACAACACAAGAT
GTCTGAGAAGGCTTCGGATATATGGAACCTGCTCTCTGAGGGTGCCTATCTGTACGTTTGCG
GTGATGCCAAAGGAATGGCCAAAGATGTGCACCGCACTTTACATACAATCGTCCAAGAGCAG
GGTAGCTTGGACTCATCTAAAGCTGAACTGTATGTGAAGAACTTACAGATGAGCGGGCGCTA
TTTGCGAGATGTTTGGTAA (SEQ ID NO: 81)

>PgCPR [Pelargonium graveolens]

MAQSSSGSMSPFDFMTAIIKGKMEPSNASLGAAGEVTAMILDNRELVMILTTSIAVLIGCVV
VFIWRRSSSQTPTAVQPLKPLLAKETESEVDDGKQKVTIFFGTQTGTAEGFAKALADEAKAR
YDKVTFKVVDLDDYAADDEEYEEKLKKETLAFFFLATYGDGEPTDNAARFYKWFLEGKERGE
WLQNLKFGVFGLGNRQYEHFNKIAIVVDEILAEQGGKRLISVGLGDDDQCIEDDFTAWRESL
WPELDQLLRDEDDTTVSTPYTAAVLEYRVVFHDPADAPTLEKSYSNANGHSVVDAQHPLRAN
VAVRRELHTPASDRSCTHLEFDISGTGIAYETGDHVGVYCENLAETVEEALELLGLSPDTYF
SVHADKEDGTPLSGSSLPPPFPPCTLRTALTLHADLLSSPKKSALLALAAHASDPTEADRLR
HLASPAGKDEYAQWIVASQRSLLEVMAEFPSAKPPLGVFFASVAPRLQPRYYSISSSPRIAP
SRIHVTCALVYEKTPTGRVHKGVCSTWMKNSVPSEKSDECSWAPIFVRQSNFKLPADAKVPI

Figure 6K

IMIGPGTGLAPFRGFLQERLALKEAGTELGPSILFFGCRNSKMDYIYEDELDNFVQNGALSE
LVLAFSREGPTKEYVQHKMMEKASDIWNLISQGAYLYVCGDAKGMARDVHRTLHTIAQEQGS
LDSSKAESMVKNLQMSGRYLRDVW (SEQ ID NO: 82)

ATGGCGCAGTCAAGCAGTGGATCAATGAGCCCTTTCGATTTTATGACCGCTATAATAAAGG
TAAAATGGAGCCAAGTAATGCGTCTTTAGGAGCGGCAGGTGAAGTCACAGCAATGATACTTG
ATAATAGGGAGCTGGTTATGATTCTGACGACCAGCATTGCAGTGCTGATCGGTTGCGTTGTA
GTGTTCATTTGGCGTCGTTCATCATCCCAGACCCCTACCGCGGTGCAGCCATTAAAACCACT
TTTAGCGAAGGAAACAGAGAGCGAAGTAGACGATGGCAAACAGAAAGTAACTATCTTTTTG
GTACTCAAACTGGAACCGCTGAAGGTTTCGCGAAAGCGCTCGCAGACGAGGCCAAAGCACGG
TATGATAAAGTCACTTTTAAAGTGGTTGATCTGGACGATTATGCCGCAGATGACGAAGAATA
TGAAGAAAAGCTGAAGAAGGAAACGTTAGCATTCTTTTTCTTGCGACGTATGGAGATGGTG
AACCTACTGACAATGCTGCAAGGTTTTATAAGTGGTTTCTGGAAGGTAAAGAACGCGGAGAA
TGGCTTCAGAATCTAAAATTTGGTGTGTTTGGTTTAGGCAACCGTCAGTATGAGCATTTCAA
TAAAATTGCCATTGTGGTTGATGAAATCCTTGCAGAACAAGGTGGTAAGCGTCTCATTTCAG
TTGGCCTGGGCGATGATGATCAGTGTATTGAGGATGACTTTACTGCCTGGAGGGAATCGCTG
TGGCCGGAGCTAGATCAGTTATTACGCGATGAGGATGATACTACGGTTTCTACGCCGTATAC
CGCCGCGGTGCTGGAATACAGAGTCGTTTTTCATGATCCGGCAGATGCCCCAACTCTCGAAA
AAAGCTACAGCAACGCTAACGGGCATAGCGTGGTTGATGCGCAACATCCGTTACGGGCAAAT
GTTGCCGTCAGACGGGAGTTGCATACTCCTGCGTCTGACCGCTCATGTACCCATCTGGAATT
TGATATATCTGGTACTGGCATCGCATACGAGACGGGTGATCATGTTGGCGTGTATTGCGAGA
ATCTTGCAGAGACGGTAGAAGAAGCGTTGGAACTTTTAGGTCTTTCCCCGGATACATACTTC
TCCGTACACGCAGATAAAGAGGACGGTACGCCTCTCTCAGGCTCATCTCTCCCGCCGCCATT
TCCACCGTGCACTTTACGTACAGCCCTGACGTTACATGCTGACTTACTGTCTTCCCCAAAGA
AATCTGCATTGCTCGCGCTTGCAGCTCATGCATCAGACCCCACTGAAGCTGATCGATTGCGG
CACCTAGCAAGCCCTGCGGGCAAGGACGAATACGCTCAGTGGATAGTTGCTAGTCAGCGTTC
CTTGCTGGAAGTGATGGCGGAGTTCCCCAGTGCCAAGCCCCCGCTGGGAGTATTCTTCGCAT
CGGTTGCTCCAAGATTGCAGCCCCGGTACTACTCTATTTCTTCTTCCCCAAGAATAGCGCCG
TCTCGCATACACGTGACCTGCGCGTTAGTTTACGAGAAAACACCTACGGGCAGAGTACACAA
AGGAGTTTGCTCCACTTGGATGAAAAACTCAGTGCCCTCTGAAAAGAGTGATGAATGTTCAT
GGGCACCAATTTTCGTACGACAGAGCAACTTTAAACTGCCCGCCGATGCGAAAGTACCCATA
ATTATGATTGGTCCAGGAACGGGTCTGGCACCATTTCGCGGCTTCCTCCAGGAGCGGCTTGC
ATTGAAAGAAGCAGGGACAGAACTGGGACCTTCCATATTATTTTTGGGTGCCGCAACAGCA
AAATGGACTATATATACGAGGATGAACTGGATAATTTTGTACAGAATGGGGCACTCTCTGAA
CTCGTGTTGGCGTTCTCACGTGAAGGTCCTACCAAAGAGTATGTGCAACATAAGATGATGGA
GAAAGCCTCAGATATATGGAACCTTATTTCACAGGGAGCTTATTTGTATGTGTGCGGGGACG
CAAAAGGCATGGCGCGTGATGTGCACCGCACGTTACATACCATCGCTCAGGAGCAGGGGTCA
TTAGATAGCTCAAAAGCAGAGAGTATGGTGAAGAATCTTCAGATGTCAGGCAGATACCTGCG
CGATGTCTGGTAA (SEQ ID NO: 83)

Figure 6L

Figure 6M

```
AtCPR2     MASSSSSSSTSMIDLMAAIIKGE-PVIVSDPANASAYESVAAELSSMLIENRQFAMIVTT 59
ATR2       MASSSSSSSTSMIDLMAAIIKGE-PVIVSDPANASAYESVAAELSSMLIENRQFAMIVTT 59
AaCPR      MAQSTTSVKLSPFDLMTALLNG---KVSFDTSNTSDTN----IPLAVFMENRELLMILTT 53
AtCPR      --MTSALYASDLFKQLKSIMGTDS-------------------------LSDDVVLVIATT 34
AtCPR1     -MATSALYASDLFKQLKSIMGTDS------------------------LSDDVVLVIATT 35
              :::     . :. : :::                             :.:   . :* **

AtCPR2     SIAVLIGCIVMLVWRRSGSGNSKRVE-PLKPLVIKPREEE----IDDGRKKVTIFFGTQT 114
ATR2       SIAVLIGCIVMLVWRRSGSGNSKRVE-PLKPLVIKPREEE----IDDGRKKVTIFFGTQT 114
AaCPR      SVAVLIGCVVVLVWRRSSSAAKKAAESPVIVVPKKVTEDE----VDDGRKKVTVFFGTQT 109
AtCPR      SLALVAG-FVVLLWKKTTADRSGELKPLMIPKSLMAKDEDDDLDLGSGKTRVSIFFGTQT 93
AtCPR1     SLALVAG-FVVLLWKKTTADRSGELKPLMIPKSLMAKDEDDDLDLGSGKTRVSIFFGTQT 94
           *:*:: * .*:*:*::: :  .    :  :        :::    :..*:.:*::******

AtCPR2     GTAEGFAKALGEEAKARYEKTRFKIVDLDDYAADDDEYEEKLKKEDVAFFFLATYGDGEP 174
ATR2       GTAEGFAKALGEEAKARYEKTRFKIVDLDDYAADDDEYEEKLKKEDVAFFFLATYGDGEP 174
AaCPR      GTAEGFAKALVEEAKARYEKAVFKVIDLDDYAAEDDEYEEKLKKESLAFFFLATYGDGEP 169
AtCPR      GTAEGFAKALSEEIKARYEKAAVKVIDLDDYAADDDQYEEKLKKETLAFFCVATYGDGEP 153
AtCPR1     GTAEGFAKALSEEIKARYEKAAVKVIDLDDYAADDDQYEEKLKKETLAFFCVATYGDGEP 154
           ********** ** ******: .*::*******:**:******** :*** :********

AtCPR2     TDNAARFYKWFTEGNDRGEWLKNLKYGVFGLGNRQYEHFNKVAKVVDDILVEQGAQRLVQ 234
ATR2       TDNAARFYKWFTEGNDRGEWLKNLKYGVFGLGNRQYEHFNKVAKVVDDILVEQGAQRLVQ 234
AaCPR      TDNAARFYKWFTEGEEKGEWLDKLQYAVFGLGNRQYEHFNKIAKVVDEKLVEQGAKRLVP 229
AtCPR      TDNAARFSKWFTEENERDIKLQQLAYGVFALGNRQYEHFNKIGIVLDEELCKKGAKRLIE 213
AtCPR1     TDNAARFYKWFTEENERDIKLQQLAYGVFALGNRQYEHFNKIGIVLDEELCKKGAKRLIE 214
           ******* ***** :::.  *.:* *.**.***********:. *:*: * ::**:**:

AtCPR2     VGLGDDDQCIEDDFTAWREALWPELDTILREEGDTAVATPYTAAVLEYRVSIHDSEDAKF 294
ATR2       VGLGDDDQCIEDDFTAWREALWPELDTILREEGDTAVATPYTAAVLEYRVSIHDSEDAKF 294
AaCPR      VGMGDDDQCIEDDFTAWKELVWPELDQLLRDEDDTSVATPYTAAVAEYRVVFHD-KPETY 288
AtCPR      VGLGDDDQSIEDDFNAWKESLWSELDKLLKDEDDKSVATPYTAVIPEYRVVTHDPRFTTQ 273
AtCPR1     VGLGDDDQSIEDDFNAWKESLWSELDKLLKDEDDKSVATPYTAVIPEYRVVTHDPRFTTQ 274
           **:*****.*****.**:* :*.*** :*::*.*.:*******.: ****  ** .   .

AtCPR2     NDINMANGNGYTVFDAQHPYKANVAVKRELHTPESDRSCIHLEFDIAGSGLTYETGDHVG 354
```

```
ATR2      NDITLANGNGYTVFDAQHPYKANVAVKRELHTPESDRSCIHLEFDIAGSGLTMKLGDHVG 354
AaCPR     DQDQLTNG--HAVHDAQHPCRSNVAVKKELHSPLSDRSCTHLEFDISNTGLSYETGDHVG 346
AtCPR     KSMESNVANGNTTIDIHHPCRVDVAVQKELHTHESDRSCIHLEFDISRTGITYETGDHVG 333
AtCPR1    KSMESNVANGNTTIDIHHPCRVDVAVQKELHTHESDRSCIHLEFDISRTGITYETGDHVG 334
          ..      .    :. * :** : :***::***:  ***** ******: :*:: : *****

AtCPR2    VLCDNLSETVDEALRLLDMSPDTYFSLHAEKEDGTPIS-SSLPPPFP-PCNLRTALTRYA 412
ATR2      VLCDNLSETVDEALRLLDMSPDTYFSLHAEKEDGTPIS-SSLPPPFP-PCNLRTALTRYA 412
AaCPR     VYVENLSEVVDEAEKLIGLPPHTYFSVHADNEDGTPLGGASLPPPFP-PCTLRKALASYA 405
AtCPR     VYAENHVEIVEEAGKLLGHSLDLVFSIHADKEDGSPLE-SAVPPPFPGPCTLGTGLARYA 392
AtCPR1    VYAENHVEIVEEAGKLLGHSLDLVFSIHADKEDGSPLE-SAVPPPFPGPCTLGTGLARYA 393
          *  :*  * *:** :*:. . .  **:**::***:*:  :::***** **.* ..*: **

AtCPR2    CLLSSPKKSALVALAAHASDPTEAERLKHLASPAGKDEYSKWVVESQRSLLEVMAEFPSA 472
ATR2      CLLSSPKKSALVALAAHASDPTEAERLKHLASPAGKDEYSKWVVESQRSLLEVMAEFPSA 472
AaCPR     DVLSSPKKSALLALAAHATDSTEADRLKFLASPAGKDEYAQWIVASHRSLLEVMEAFPSA 465
AtCPR     DLLNPPRKSALVALAAYATEPSEAEKLKHLTSPDGKDEYSQWIVASQRSLLEVMAAFPSA 452
AtCPR1    DLLNPPRKSALVALAAYATEPSEAEKLKHLTSPDGKDEYSQWIVASQRSLLEVMAAFPSA 453
           :*..*:****:****:*::.:**::**.*:** *****::*:* *:*******  ****

AtCPR2    KPPLGVFFAGVAPRLQPRFYSISSSPKIAETRIHVTCALVYEKMPTGRIHKGVCSTWMKN 532
ATR2      KPPLGVFFAGVAPRLQPRFYSISSSPKIAETRIHVTCALVYEKMPTGRIHKGVCSTWMKN 532
AaCPR     KPPLGVFFASVAPRLQPRYYSISSSPRFAPNRIHVTCALVYEQTPSGRVHKGVCSTWMKN 525
AtCPR     KPPLGVFFAAIAPRLQPRYYSISSCQDWAPSRVHVTSALVYGPTPTGRIHKGVCSTWMKN 512
AtCPR1    KPPLGVFFAAIAPRLQPRYYSISSSPRLAPSRVHVTSALVYGPTPTGRIHKGVCSTWMKN 513
          *********.:*******:*****.    * .*:***.****    *:**:***********

AtCPR2    AVPYEKSENCSS-APIFVRQSNFKLPSDSKVPIIMIGPGTGLAPFRGFLQERLALVESGV 591
ATR2      AVPYEKSEKLFLGRPIFVRQSNFKLPSDSKVPIIMIGPGTGLAPFRGFLQERLALVESGV 592
AaCPR     AVPMTESQDCSW-APIYVRTSNFRLPSDPKVPVIMIGPGTGLAPFRGFLQERLAQKEAGT 584
AtCPR     AVPAEKSHECSG-APIFIRASNFKLPSNPSTPIVMVGPGTGLAPFRGFLQERMALKEDGE 571
AtCPR1    AVPAEKSHECSG-APIFIRASNFKLPSNPSTPIVMVGPGTGLAPFRGFLQERMALKEDGE 572
          ***   :*..      **::* ***:***:...*::*:****************:*   * *

AtCPR2    ELGPSVLFFGCRNRRMDFIYEEELQRFVESGALAELSVAFSREGPTKEYVQHKMMDKASD 651
ATR2      ELGPSVLFFGCRNRRMDFIYEEELQRFVESGALAELSVAFSREGPTKEYVQHKMMDKASD 652
AaCPR     ELGTAILFFGCRNRKVDFIYEDELNNFVETGALSELVTAFSREGATKEYVQHKMTQKASD 644
AtCPR     ELGSSLLFFGCRNRQMDFIYEDELNNFVDQGVISELIMAFSREGAQKEYVQHKMMEKAAQ 631
```

Figure 6N

```
AtCPR1          ELGSSLLFFGCRNRQMDFIYEDELNNFVDQGVISELIMAFSREGAQKEYVQHKMMEKAAQ 632
                ***.::********::*****:**:.**: *.::**  ******. ******** :**::

AtCPR2          IWNMISQGAYLYVCGDAKGMARDVHRSLHTIAQEQGSMDSTKAEGFVKNLQTSGRYLRDVW 712
ATR2            IWNMISQGAYLYVCGDAKGMARDVHRSLHTIAQEQGSMDSTKAEGFVKNLQTSGRYLRDVW 713
AaCPR           IWNLLSEGAYLYVCGDAKGMAKDVHRTLHTIVQEQGSLDSSKAELYVKNLQMAGRYLRDVW 705
AtCPR           VWDLIKEEGYLYVCGDAKGMARDVHRTLHTIVQEQEGVSSSEAEAIVKKLQTEGRYLRDVW 692
AtCPR1          VWDLIKEEGYLYVCGDAKGMARDVHRTLHTIVQEQEGVSSSEAEAIVKKLQTEGRYLRDVW 693
                :*:::.: .************:****:****.*** .:.*::**  **:**  *******
```

Figure 6O

Figure 6P

```
SrCPR2    MAQSESVEASTIDLMTAVLKDTVIDTANASDNGDSKMPPALAMMFEIRDLLLILTTSVAV 60
SrCPR3    MAQSNSVKISPLDLVTALFSGKVLDTSNASESGESAMLPTIAMIMENRELLMILTTSVAV 60
SrCPR     -MQSDSVKVSPFDLVSAAMNGKAMEKLNASESEDPTTLPALKMLVENRELLTLFTTSFAV 59
SrCPR1    MAQSDSVKVSPFDLVSAAMNGKAMEKLNASESEDPTTLPALKMLVENRELLTLFTTSFAV 60
            **:**: *.:**::* :....::. ***:. :.   *:: *:.* *:** ::***.**

SrCPR2    LVGCFVVLVWKRSSGKKSGKELEPPKIVVPKRRLEQEVDDGKKKVTIFFGTQTGTAEGFA 120
SrCPR3    LIGCVVVLVWRRSSTKKS--ALEPPVIVVPKRVQEEEVDDGKKKVTVFFGTQTGTAEGFA 118
SrCPR     LIGCLVFLMWRRSSSKKLVQDPVPQVIVVKKKEKESEVDDGKKKVSIFYGTQTGTAEGFA 119
SrCPR1    LIGCLVFLMWRRSSSKKLVQDPVPQVIVVKKKEKESEVDDGKKKVSIFYGTQTGTAEGFA 120
          *:**.*.*:*:*** **       *  *** *:  *.*********::*:**********

SrCPR2    KALFEEAKARYEKAAFKVIDLDDYAADLDEYAEKLKKETYAFFFLATYGDGEPTDNAAKF 180
SrCPR3    KALVEEAKARYEKAVFKVIDLDDYAADDDEYEEKLKKESLAFFFLATYGDGEPTDNAARF 178
SrCPR     KALVEEAKVRYEKTSFKVIDLDDYAADDDEYEEKLKKESLAFFFLATYGDGEPTDNAANF 179
SrCPR1    KALVEEAKVRYEKTSFKVIDLDDYAADDDEYEEKLKKESLAFFFLATYGDGEPTDNAANF 180
          ***.****.****: *********** *** ******: *****************.*

SrCPR2    YKWFTEGDEKGVWLQKLQYGVFGLGNRQYEHFNKIGIVVDDGLTEQGAKRIVPVGLGDDD 240
SrCPR3    YKWFTEGDAKGEWLNKLQYGVFGLGNRQYEHFNKIAKVVDDGLVEQGAKRLVPVGLGDDD 238
SrCPR     YKWFTEGDDKGEWLKKLQYGVFGLGNRQYEHFNKIAIVVDDKLTEMGAKRLVPVGLGDDD 239
SrCPR1    YKWFTEGDDKGELLKKLQYGVFGLGNRQYEHFNKIAIVVDDKLTEMGAKRLVPVGLGDDD 240
          ******** **  *:*******************. **** *.* ****:*********

SrCPR2    QSIEDDFSAWKELVWPELDLLLRDEDDKAAATPYTAAIPEYRVVFHDKP-DAFSDDHTQT 299
SrCPR3    QCIEDDFTAWKELVWPELDQLLRDEDDTTVATPYTAAVAEYRVVFHEKP-DALSEDYSYT 297
SrCPR     QCIEDDFTAWKELVWPELDQLLRDEDDTSVTTPYTAAVLEYRVVYHDKPADSYAEDQTHT 299
SrCPR1    QCIEDDFTAWKELVWPELDQLLRDEDDTSVTTPYTAAVLEYRVVYHDKPADSYAEDQTHT 300
          *.*****:*********** *******.:.:******: *****:*:** *: ::* : *

SrCPR2    NGHAVHDAQHPCRSNVAVKKELHTPESDRSCTHLEFDISHTGLSYETGDHVGVYCENLIE 359
SrCPR3    NGHAVHDAQHPCRSNVAVKKELHSPESDRSCTHLEFDISNTGLSYETGDHVGVYCENLSE 357
SrCPR     NGHVVHDAQHPSRSNVAFKKELHTSQSDRSCTHLEFDISHTGLSYETGDHVGVYSENLSE 359
SrCPR1    NGHVVHDAQHPSRSNVAFKKELHTSQSDRSCTHLEFDISHTGLSYETGDHVGVYSENLSE 360
          ***.*******.*****.*****:.:************:*************.*** *
```

```
SrCPR2          VVEEAGKLLGLSTDTYFSLHIDNEDGSPLGGPSLQPPFPPCTLRKALTNYADLLSSPKKS 419
SrCPR3          VVNDAERLVGLPPDTYFSIHTDSEDGSPLGGASLPPPFPPCTLRKALTCYADVLSSPKKS 417
SrCPR           VVDEALKLLGLSPDTYFSVHADKEDGTPIGGASLPPPFPPCTLRDALTRYADVLSSPKKV 419
SrCPR1          VVDEALKLLGLSPDTYFSVHADKEDGTPIGGASLPPPFPPCTLRDALTRYADVLSSPKKV 420
                **::* :*:**..*****:* *.***:*:**.** *********.*** ***:******

SrCPR2          TLLALAAHASDPTEADRLRFLASREGKDEYAEWVVANQRSLLEVMEAFPSARPPLGVFFA 479
SrCPR3          ALLALAAHATDPSEADRLKFLASPAGKDEYSQWIVASQRSLLEVMEAFPSAKPSLGVFFA 477
SrCPR           ALLALAAHASDPSEADRLKFLASPAGKDEYAQWIVANQRSLLEVMQSFPSAKPPLGVFFA 479
SrCPR1          ALLALAAHASDPSEADRLKFLASPAGKDEYAQWIVANQRSLLEVMQSFPSAKPPLGVFFA 480
                :********:**:*****:****  *****::*:**.********::****:*.******

SrCPR2          AVAPRLQPRYYSISSSPKMEPNRIHVTCALVYEKTPAGRIHKGICSTWMKNAVPLTESQD 539
SrCPR3          SVAPRLQPRYYSISSSPKMAPDRIHVTCALVYEKTPAGRIHKGVCSTWMKNAVPMTESQD 537
SrCPR           AVAPRLQPRYYSISSSPKMSPNRIHVTCALVYETTPAGRIHRGLCSTWMKNAVPLTESPD 539
SrCPR1          AVAPRLQPRYYSISSSPKMSPNRIHVTCALVYETTPAGRIHRGLCSTWMKNAVPLTESPD 540
                :****************** *:***********.*******:*:**********:*** *

SrCPR2          CSWAPIFVRTSNFRLPIDPKVPVIMIGPGTGLAPFRGFLQERLALKESGTELGSSILFFG 599
SrCPR3          CSWAPIYVRTSNFRLPSDPKVPVIMIGPGTGLAPFRGFLQERLALKEAGTDLGLSILFFG 597
SrCPR           CSQASIFVRTSNFRLPVDPKVPVIMIGPGTGLAPFRGFLQERLALKESGTELGSSIFFFG 599
SrCPR1          CSQASIFVRTSNFRLPVDPKVPVIMIGPGTGLAPFRGFLQERLALKESGTELGSSIFFFG 600
                ** *.*:********* ******************************:**:** **:***

SrCPR2          CRNRKVDYIYENELNNFVENGALSELDVAFSRDGPTKEYVQHKMTQKASEIWNMLSEGAY 659
SrCPR3          CRNRKVDFIYENELNNFVETGALSELIVAFSREGPTKEYVQHKMSEKASDIWNLLSEGAY 657
SrCPR           CRNRKVDFIYEDELNNFVETGALSELIVAFSREGTAKEYVQHKMSQKASDIWKLLSEGAY 659
SrCPR1          CRNRKVDFIYEDELNNFVETGALSELIVAFSREGTAKEYVQHKMSQKASDIWKLLSEGAY 660
                *******:***:*******.****** *****:*.:********::***:**::******

SrCPR2          LYVCGDAKGMAKDVHRTLHTIVQEQGSLDSSKAELYVKNLQMSGRYLRDVW 710
SrCPR3          LYVCGDAKGMAKDVHRTLHTIVQEQGSLDSSKAELYVKNLQMSGRYLRDVW 708
SrCPR           LYVCGDAKGMAKDVHRTLHTIVQEQGSLDSSKAELYVKNLQMSGRYLRDVW 710
SrCPR1          LYVCGDAKGMAKDVHRTLHTIVQEQGSLDSSKAELYVKNLQMSGRYLRDVW 711
                ***************************************************
```

Figure 6Q

```
ATR2      MASSSSSSSTSMIDLMAAIIKGEPVIVSDPANASAYESVAAELSSMLIENRQFAMIVTTS 60
AtCPR2    MASSSSSSSTSMIDLMAAIIKGEPVIVSDPANASAYESVAAELSSMLIENRQFAMIVTTS 60
PgCPR     MAQSSSGS-MSPFDFMTAIIKG----KMEPSNAS--LGAAGEVTAMILDNRELVMILTTS 53
AaCPR     MAQSTTSVKLSPFDLMTALLNGKVS-FDTSNTSDTN-----IP-LAVFMENRELLMILTTS 54
SrCPR3    MAQSN-SVKISPLDLVTALFSGKV--LDTSNASESGESAMLPTIAMIMENRELLMILTTS 57
SrCPR     MAQSD-SVKVSPFDLVSAAMNGKA--MEKLNASESEDPTTLPALKMLVENRELLTLFTTS 57
SrCPR2    MAQSE-SVEASTIDLMTAVLKDTV--IDTANASDNGDSKMPPALAMMFEIRDLLLILTTS 57
AtCPR1    MATSALYASDLFKQLKSIMGTDS-------------------------LSDDVVLVIATTS 36
          ** *         :: :   ..                         ..   .  : ***

ATR2      IAVLIGCIVMLVWRRSGSGNSKRVEPLKP--LVIKPR---EEEIDDGRKKVTIFFGTQTG 115
AtCPR2    IAVLIGCIVMLVWRRSGSGNSKRVEPLKP--LVIKPR---EEEIDDGRKKVTIFFGTQTG 115
PgCPR     IAVLIGCVVVFIWRRSSSQTPTAVQPLKP--LLAKET---ESEVDDGKQKVTIFFGTQTG 108
AaCPR     VAVLIGCVVVLVWRRSSSAAKKAAESP-----VIVVPKKVTEDEVDDGRKKVTVFFGTQTG 110
SrCPR3    VAVLIGCVVVLVWRRSS-TKKSALEPP-----VIVVPKRVQEEEVDDGKKKVTVFFGTQTG 112
SrCPR     FAVLIGCLVFLMWRRSS-SKKLVQDPVPQ--VIVVKKKEKESEVDDGKKKVSIFYGTQTG 114
SrCPR2    VAVLVGCFVVLVWKRSS-GKKSGKELEPP--KIVVPKRRLEQEVDDGKKKVTIFFGTQTG 114
AtCPR1    LALVAG-FVVLLWKKTTADRSGELKPLMIPKSLMAKDEDDDLDLGSGKTRVSIFFGTQTG 95
          .*:: * .*.::*:::        .       :       : ::..*: :*::*:*****

ATR2      TAEGFAKALGEEAKARYEKTRFKIVDLDDYAADDDEYEEKLKKEDVAFFFLATYGDGEPT 175
AtCPR2    TAEGFAKALGEEAKARYEKTRFKIVDLDDYAADDDEYEEKLKKEDVAFFFLATYGDGEPT 175
PgCPR     TAEGFAKALADEAKARYDKVTFKVVDLDDYAADDEEYEEKLKKETLAFFFLATYGDGEPT 168
AaCPR     TAEGFAKALVEEAKARYEKAVFKVIDLDDYAAEDDEYEEKLKKESLAFFFLATYGDGEPT 170
SrCPR3    TAEGFAKALVEEAKARYEKAVFKVIDLDDYAADDDEYEEKLKKESLAFFFLATYGDGEPT 172
SrCPR     TAEGFAKALVEEAKVRYEKTSFKVIDLDDYAADDDEYEEKLKKESLAFFFLATYGDGEPT 174
SrCPR2    TAEGFAKALFEEAKARYEKAAFKVIDLDDYAADLDEYAEKLKKETYAFFFLATYGDGEPT 174
AtCPR1    TAEGFAKALSEEIKARYEKAAVKVIDLDDYAADDDQYEEKLKKETLAFFCVATYGDGEPT 155
          ********* :* *.**:*. .*::*******: ::* ******  *** :*********

ATR2      DNAARFYKWFTEGNDRGEWLKNLKYGVFGLGNRQYEHFNKVAKVVDDILVEQGAQRLVQV 235
AtCPR2    DNAARFYKWFTEGNDRGEWLKNLKYGVFGLGNRQYEHFNKVAKVVDDILVEQGAQRLVQV 235
PgCPR     DNAARFYKWFLEGKERGEWLQNLKFGVFGLGNRQYEHFNKIAIVVDEILAEQGGKRLISV 228
AaCPR     DNAARFYKWFTEGEEKGEWLDKLQYAVFGLGNRQYEHFNKIAKVVDEKLVEQGAKRLVPV 230
SrCPR3    DNAARFYKWFTEGDAKGEWLNKLQYGVFGLGNRQYEHFNKIAKVVDDGLVEQGAKRLVPV 232
SrCPR     DNAANFYKWFTEGDDKGELLKKLQYGVFGLGNRQYEHFNKIAIVVDDKLTEMGAKRLVPV 234
SrCPR2    DNAAKFYKWFTEGDEKGVWLQKLQYGVFGLGNRQYEHFNKIGIVVDDGLTEQGAKRIVPV 234
AtCPR1    DNAARFYKWFTEENERDIKLQQLAYGVFALGNRQYEHFNKIGIVLDEELCKKGAKRLIEV 215
          ****.***** *  . :.  *.:* :.**.**********:. *:*: * : *.:*:: *
```

Figure 6R

```
ATR2      GLGDDDQCIEDDFTAWREALWPELDTILREEGDTAVATPYTAAVLEYRVSIHDSE--DAK 293
AtCPR2    GLGDDDQCIEDDFTAWREALWPELDTILREEGDTAVATPYTAAVLEYRVSIHDSE--DAK 293
PgCPR     GLGDDDQCIEDDFTAWRESLWPELDQLLRDEDDTTVSTPYTAAVLEYRVVFHDPA--DAP 286
AaCPR     GMGDDDQCIEDDFTAWKELVWPELDQLLRDEDDTSVATPYTAAVAEYRVVFHDKP--ETY 288
SrCPR3    GLGDDDQCIEDDFTAWKELVWPELDQLLRDEDDTTVATPYTAAVAEYRVVFHEKP--DAL 290
SrCPR     GLGDDDQCIEDDFTAWKELVWPELDQLLRDEDDTSVTTPYTAAVLEYRVVYHDKPA-DSY 293
SrCPR2    GLGDDDQSIEDDFSAWKELVWPELDLLLRDEDDKAAATPYTAAIPEYRVVFHDKP--DAF 292
AtCPR1    GLGDDDQSIEDDFNAWKESLWSELDKLLKDEDDKSVATPYTAVIPEYRVVTHDPRFTTQK 275
          *:*****.*****.**:* :*.*** :*::*.*.:.:*****.: ****  *:

ATR2      FNDITLANGNGYTVFDAQHPYKANVAVKRELHTPESDRSCIHLEFDIAGSGLTMKLGDHV 353
AtCPR2    FNDINMANGNGYTVFDAQHPYKANVAVKRELHTPESDRSCIHLEFDIAGSGLTYETGDHV 353
PgCPR     TLEKSYSNANGHSVVDAQHPLRANVAVRRELHTPASDRSCTHLEFDISGTGIAYETGDHV 346
AaCPR     DQDQ-LTN--GHAVHDAQHPCRSNVAVKKELHSPLSDRSCTHLEFDISNTGLSYETGDHV 345
SrCPR3    SEDYSYTN--GHAVHDAQHPCRSNVAVKKELHSPESDRSCTHLEFDISNTGLSYETGDHV 348
SrCPR     AEDQTHTN--GHVVHDAQHPSRSNVAFKKELHTSQSDRSCTHLEFDISHTGLSYETGDHV 351
SrCPR2    SDDHTQTN--GHAVHDAQHPCRSNVAVKKELHTPESDRSCTHLEFDISHTGLSYETGDHV 350
AtCPR1    SMESNVAN--GNTTIDIHHPCRVDVAVQKELHTHESDRSCIHLEFDISRTGITYETGDHV 333
            :    :*  *   . * :** : :**.::***:  ***** ******: :*:: : ****

ATR2      GVLCDNLSETVDEALRLLDMSPDTYFSLHAEKEDGTPIS-SSLPPPFP-PCNLRTALTRY 411
AtCPR2    GVLCDNLSETVDEALRLLDMSPDTYFSLHAEKEDGTPIS-SSLPPPFP-PCNLRTALTRY 411
PgCPR     GVYCENLAETVEEALELLGLSPDTYFSVHADKEDGTPLSGSSLPPPFP-PCTLRTALTLH 405
AaCPR     GVYVENLSEVVDEAEKLIGLPPHTYFSVHADNEDGTPLGGASLPPPFP-PCTLRKALASY 404
SrCPR3    GVYCENLSEVVNDAERLVGLPPDTYFSIHTDSEDGSPLGGASLPPPFP-PCTLRKALTCY 407
SrCPR     GVYSENLSEVVDEALKLLGLSPDTYFSVHADKEDGTPIGGASLPPPFP-PCTLRDALTRY 410
SrCPR2    GVYCENLIEVVEEAGKLLGLSTDTYFSLHIDNEDGSPLGGPSLQPPFP-PCTLRKALTNY 409
AtCPR1    GVYAENHVEIVEEAGKLLGHSLDLVFSIHADKEDGSPLE-SAVPPPFPGPCTLGTGLARY 392
          **  :*   * *::* .*:. . .  **:* :.***:*:  .:: **** **.*  .*: :

ATR2      ACLLSSPKKSALVALAAHASDPTEAERLKHLASPAGKDEYSKWVVESQRSLLEVMAEFPS 471
AtCPR2    ACLLSSPKKSALVALAAHASDPTEAERLKHLASPAGKDEYSKWVVESQRSLLEVMAEFPS 471
PgCPR     ADLLSSPKKSALLALAAHASDPTEADRLRHLASPAGKDEYAQWIVASQRSLLEVMAEFPS 465
AaCPR     ADVLSSPKKSALLALAAHATDSTEADRLKFLASPAGKDEYAQWIVASHRSLLEVMEAFPS 464
SrCPR3    ADVLSSPKKSALLALAAHATDPSEADRLKFLASPAGKDEYSQWIVASQRSLLEVMEAFPS 467
SrCPR     ADVLSSPKKVALLALAAHASDPSEADRLKFLASPAGKDEYAQWIVANQRSLLEVMQSFPS 470
SrCPR2    ADLLSSPKKSTLLALAAHASDPTEADRLRFLASREGKDEYAEWVVANQRSLLEVMEAFPS 469
AtCPR1    ADLLNPPRKSALVALAAYATEPSEAEKLKHLTSPDGKDEYSQWIVASQRSLLEVMAAFPS 452
          * :*..*:* :*:****:*::.:**::*:.*:*  *****::*:* .:*******  ***

ATR2      AKPPLGVFFAGVAPRLQPRFYSISSSPKIAETRIHVTCALVYEKMPTGRIHKGVCSTWMK 531
AtCPR2    AKPPLGVFFAGVAPRLQPRFYSISSSPKIAETRIHVTCALVYEKMPTGRIHKGVCSTWMK 531
```

Figure 6S

```
PgCPR      AKPPLGVFFASVAPRLQPRYYSISSSPRIAPSRIHVTCALVYEKTPTGRVHKGVCSTWMK 525
AaCPR      AKPPLGVFFASVAPRLQPRYYSISSSPRFAPNRIHVTCALVYEQTPSGRVHKGVCSTWMK 524
SrCPR3     AKPSLGVFFASVAPRLQPRYYSISSSPKMAPDRIHVTCALVYEKTPAGRIHKGVCSTWMK 527
SrCPR      AKPPLGVFFAAVAPRLQPRYYSISSSPKMSPNRIHVTCALVYETTPAGRIHRGLCSTWMK 530
SrCPR2     ARPPLGVFFAAVAPRLQPRYYSISSSPKMEPNRIHVTCALVYEKTPAGRIHKGICSTWMK 529
AtCPR1     AKPPLGVFFAAIAPRLQPRYYSISSSPRLAPSRVHVTSALVYGPTPTGRIHKGVCSTWMK 512
           *:*.******.:*******:*******::   *:***.****   *:**:*:*:******

ATR2       NAVPYEKSEKLFLGRPIFVRQSNFKLPSDSKVPIIMIGPGTGLAPFRGFLQERLALVESG 591
AtCPR2     NAVPYEKSENCSS-APIFVRQSNFKLPSDSKVPIIMIGPGTGLAPFRGFLQERLALVESG 590
PgCPR      NSVPSEKSDECSW-APIFVRQSNFKLPADAKVPIIMIGPGTGLAPFRGFLQERLALKEAG 584
AaCPR      NAVPMTESQDCSW-APIYVRTSNFRLPSDPKVPVIMIGPGTGLAPFRGFLQERLAQKEAG 583
SrCPR3     NAVPMTESQDCSW-APIYVRTSNFRLPSDPKVPVIMIGPGTGLAPFRGFLQERLALKEAG 586
SrCPR      NAVPLTESPDCSQ-ASIFVRTSNFRLPVDPKVPVIMIGPGTGLAPFRGFLQERLALKESG 589
SrCPR2     NAVPLTESQDCSW-APIFVRTSNFRLPIDPKVPVIMIGPGTGLAPFRGFLQERLALKESG 588
AtCPR1     NAVPAEKSHECSG-APIFIRASNFKLPSNPSTPIVMVGPGTGLAPFRGFLQERMALKEDG 571
           *:**  :* .      .*::* ***:** :...*::*:***************:*  * *

ATR2       VELGPSVLFFGCRNRRMDFIYEEELQRFVESGALAELSVAFSREGPTKEYVQHKMMDKAS 651
AtCPR2     VELGPSVLFFGCRNRRMDFIYEEELQRFVESGALAELSVAFSREGPTKEYVQHKMMDKAS 650
PgCPR      TELGPSILFFGCRNSKMDYIYEDELDNFVQNGALSELVLAFSREGPTKEYVQHKMMEKAS 644
AaCPR      TELGTAILFFGCRNRKVDFIYEDELNNFVETGALSELVTAFSREGATKEYVQHKMTQKAS 643
SrCPR3     TDLGLSILFFGCRNRKVDFIYENELNNFVETGALSELIVAFSREGPTKEYVQHKMSEKAS 646
SrCPR      TELGSSIFFFGCRNRKVDFIYEDELNNFVETGALSELIVAFSREGTAKEYVQHKMSQKAS 649
SrCPR2     TELGSSILFFGCRNRKVDYIYENELNNFVENGALSELDVAFSRDGPTKEYVQHKMTQKAS 648
AtCPR1     EELGSSLLFFGCRNRQMDFIYEDELNNFVDQGVISELIMAFSREGAQKEYVQHKMMEKAA 631
            :** :::****** ::*:***:**:.**: *.::**  ****:*. ******** :**:

ATR2       DIWNMISQGAYLYVCGDAKGMARDVHRSLHTIAQEQGSMDSTKAEGFVKNLQTSGRYLRDVW 713
AtCPR2     DIWNMISQGAYLYVCGDAKGMARDVHRSLHTIAQEQGSMDSTKAEGFVKNLQTSGRYLRDVW 712
PgCPR      DIWNLISQGAYLYVCGDAKGMARDVHRTLHTIAQEQGSLDSSKAESMVKNLQMSGRYLRDVW 706
AaCPR      DIWNLLSEGAYLYVCGDAKGMAKDVHRTLHTIVQEQGSLDSSKAELYVKNLQMAGRYLRDVW 705
SrCPR3     DIWNLLSEGAYLYVCGDAKGMAKDVHRTLHTIVQEQGSLDSSKAELYVKNLQMSGRYLRDVW 708
SrCPR      DIWKLLSEGAYLYVCGDAKGMAKDVHRTLHTIVQEQGSLDSSKAELYVKNLQMSGRYLRDVW 711
SrCPR2     EIWNMLSEGAYLYVCGDAKGMAKDVHRTLHTIVQEQGSLDSSKAELYVKNLQMSGRYLRDVW 710
AtCPR1     QVWDLIKEEGYLYVCGDAKGMARDVHRTLHTIVQEQEGVSSSEAEAIVKKLQTEGRYLRDVW 693
           ::*.::.: .***********:****:****.*** .:.*::**  **:**  ********
```

Figure 6T

| | n20yhcB | n21yhcB | n22yhcB | n23yhcB | n24yhcB |
|---|---|---|---|---|---|
| t28VO1 | n20yhcB_t28VO1 | n21yhcB_t28VO1 | n22yhcB_t28VO1 | n23yhcB_t28VO1 | n24yhcB_t28VO1 |
| t29VO1 | n20yhcB_t29VO1 | n21yhcB_t29VO1 | n22yhcB_t29VO1 | n23yhcB_t29VO1 | n24yhcB_t29VO1 |
| t30VO1 | n20yhcB_t30VO1 | n21yhcB_t30VO1 | Current | n23yhcB_t30VO1 | n24yhcB_t30VO1 |
| t31VO1 | n20yhcB_t31VO1 | n21yhcB_t31VO1 | n22yhcB_t31VO1 | n23yhcB_t31VO1 | n24yhcB_t31VO1 |
| t32VO1 | n20yhcB_t32VO1 | n21yhcB_t32VO1 | n22yhcB_t32VO1 | n23yhcB_t32VO1 | n24yhcB_t32VO1 |

| # | (+)-nootkatone Downstream Pathway Enzymes |
|---|---|
| 1 | Valencene synthase (VS) |
| 2 | Valencene oxygenase (VO) |
| 3 | P450 reductase (CPR) |
| 4 | Alcohol dehydrogenase (ADH) |

Oxygenation capacity = (α-nootkatol + β-nootkatol + 2 * (+)-nootkatone)

Oxygenation capacity = (α-nootkatol + β-nootkatol + 2 * (+)-nootkatone)

Figure 22A

>ReCDH [Rhodococcus erythropolis]

MARVEGQVALITGAARGQGRSHAIKLAEEGADVILVDVPNDVVDIGYPLGTADELDQTAKDVENLG
RKAIVIHADVRDLESLTAEVDRAVSTLGRLDIVSANAGIASVPFLSHDIPDNTWRQMIDINLTGVW
HTAKVAVPHILAGERGGSIVLTSSAAGLKGYAQISHYSAAKHGVVGLMRSLALELAPHRVRVNSLH
PTQVNTPMIQNEGTYRIFSPDLENPTREDFEIASTTTNALPIPWVESVDVSNALLFLVSEDARYIT
GAAIPVDAGTTLK (SEQ ID NO: 84)

ATGGCCCGTGTGGAAGGTCAAGTGGCTCTGATTACCGGCGCTGCTCGTGGTCAAGGTCGTAGTCAT
GCGATTAAACTGGCGGAAGAAGGCGCGGATGTGATTCTGGTTGACGTCCCGAATGATGTGGTTGAC
ATCGGCTATCCGCTGGGTACGGCAGATGAACTGGACCAGACCGCTAAAGATGTTGAAAACCTGGGT
CGTAAGGCGATTGTCATCCATGCCGATGTGCGCGACCTGGAATCACTGACGGCAGAAGTGGATCGT
GCTGTTAGTACCCTGGGCCGCCTGGACATTGTTTCCGCAAATGCTGGTATCGCCAGCGTCCCGTTT
CTGTCTCACGATATTCCGGACAACACCTGGCGTCAGATGATTGATATCAATCTGACGGGCGTCTGG
CATACCGCGAAAGTGGCCGTTCCGCACATTCTGGCCGGTGAACGCGGCGGTTCCATCGTTCTGACC
AGCTCTGCGGCCGGCCTGAAAGGTTATGCACAAATTAGTCATTACTCCGCAGCTAAGCACGGCGTC
GTGGGTCTGATGCGTTCACTGGCACTGGAACTGGCTCCGCATCGTGTCCGCGTGAACTCGCTGCAC
CCGACGCAGGTGAACACCCCGATGATTCAAAATGAAGGCACGTATCGTATCTTTAGCCCGGATCTG
GAAAACCCGACCCGCGAAGACTTCGAAATTGCGTCTACCACGACCAATGCCCTGCCGATCCCGTGG
GTGGAATCAGTTGATGTCTCGAACGCACTGCTGTTCCTGGTTAGCGAAGACGCACGTTACATTACC
GGTGCAGCAATCCCGGTGGATGCCGGTACGACCCTGAAGTAA (SEQ ID NO: 85)

>CsDH [Citrus sinensis]

MATPPISSLISQRLLGKVALVTGGASGIGEGIVRLFHRHGAKVCFVDVQDELGYRLQESLVGDKDS
NIFYSHCDVTVEDDVRRAVDLTVTKFGTLDIMVNNAGISGTPSSDIRNVDVSEFEKVFDINVKGVF
MGMKYAASVMIPRKQGSIISLGSVGSVIGGIGPHHYISSKHAVVGLTRSIAAELGQHGIRVNCVSP
YAVPTNLAVAHLPEDERTEDMFTGFREFAKKNANLQGVELTVEDVANAVLFLASEDARYISGDNLI
VDGGFTRVNHSFRVFR (SEQ ID NO: 86)

ATGGCAACGCCGCCGATTTCATCCCTGATTTCACAACGCCTGCTGGGTAAAGTCGCCCTGGTCACG
GGTGGTGCTTCTGGTATTGGTGAAGGCATCGTGCGTCTGTTTCACCGTCATGGCGCGAAAGTGTGC
TTTGTTGATGTGCAGGATGAACTGGGCTACCGTCTGCAAGAATCTCTGGTGGGCGACAAAGATTCA
AACATCTTTTATAGCCACTGTGATGTCACCGTGGAAGACGATGTGCGCCGCGCTGTGGATCTGACC
GTGACGAAATTCGGTACGCTGGATATTATGGTCAATAACGCGGGTATTAGTGGCACCCCGTCCAGC
GATATTCGTAATGTTGATGTGAGCGAATTTGAAAAAGTGTTTGATATTAACGTCAAAGGCGTGTTT
ATGGGCATGAAATATGCCGCGAGCGTGATGATCCCGCGCAAACAGGGTAGCATCATCTCCCTGGGT
TCTGTTGGCAGCGTGATCGGTGGCATTGGCCCGCACCATTATATCAGCTCGAAACATGCGGTTGTG
GGCCTGACCCGCAGCATTGCAGCGGAACTGGGTCAGCATGGCATTCGTGTGAACTGTGTGTCTCCG
TATGCGGTTCCGACCAATCTGGCGGTTGCACACCTGCCGGAAGATGAACGTACCGAAGATATGTTT
ACGGGCTTCCGTGAATTTGCGAAAAAGAATGCCAACCTGCAAGGTGTTGAACTGACCGTCGAAGAT
GTGGCCAATGCGGTGCTGTTTCTGGCCAGCGAAGATGCACGCTACATTAGCGGTGATAATCTGATC
GTTGATGGCGGCTTTACCCGTGTGAACCACTCATTTCGTGTTTTCCGTTAA (SEQ ID NO: 87)

>CsDH1 [Citrus sinensis]

MSKPRLQGKVAIIMGAASGIGEATAKLFAEHGAFVIIADIQDELGNQVVSSIGPEKASYRHCDVRD
EKQVEETVAYAIEKYGSLDIMYSNAGVAGPVGTILDLDMAQFDRTIATNLAGSVMAVKYAARVMVA

NKIRGSIICTTSTASTVGGSGPHAYTISKHGLLGLVRSAASELGKHGIRVNCVSPFGVATPFSAGT
INDVEGFVCKVANLKGIVLKAKHVAEAALFLASDESAYVSGHDLVVDGGFTAVTNVMSMLEGHG
(SEQ ID NO: 88)

ATGTCAAAACCGCGTCTGCAAGGCAAAGTGGCTATTATTATGGGTGCTGCGTCTGGCATCGGTGAA
GCTACGGCTAAACTGTTCGCTGAACATGGCGCATTTGTGATTATCGCTGATATTCAGGACGAACTG
GGCAACCAGGTGGTTAGCTCTATCGGCCCGGAAAAAGCGTCTTATCGTCACTGCGATGTGCGTGAT
GAAAAACAGGTTGAAGAAACCGTCGCGTATGCGATTGAAAAATACGGCAGCCTGGATATTATGTAC
TCCAATGCGGGCGTGGCCGGTCCGGTTGGCACGATTCTGGATCTGGACATGGCCCAATTCGACCGT
ACCATCGCAACGAACCTGGCTGGTAGTGTTATGGCAGTCAAATATGCGGCCCGTGTCATGGTGGCG
AATAAAATTCGCGGTAGCATTATCTGTACCACGAGTACCGCCTCCACGGTGGGCGGCAGCGGCCCG
CACGCCTATACCATTAGCAAACACGGTCTGCTGGGCCTGGTTCGTTCAGCAGCTTCGGAACTGGGT
AAACATGGCATCCGCGTGAACTGCGTTAGCCCGTTTGGTGTTGCGACCCCGTTCTCTGCCGGTACG
ATTAACGATGTCGAAGGCTTTGTCTGTAAAGTGGCGAATCTGAAAGGCATCGTCCTGAAAGCGAAG
CATGTGGCCGAAGCGGCCCTGTTCCTGGCAAGCGATGAATCTGCTTATGTGAGCGGTCACGACCTG
GTGGTGGATGGTGGCTTTACGGCAGTTACGAATGTCATGTCAATGCTGGAAGGTCACGGCTAA
(SEQ ID NO: 89)

>CsDH2 [Citrus sinensis]

MSNPRMEGKVALITGAASGIGEAAVRLFAEHGAFVVAADVQDELGHQVAASVGTDQVCYHHCDVRD
EKQVEETVRYTLEKYGKLDVLFSNAGIMGPLTGILELDLTGFGNTMATNVCGVAATIKHAARAMVD
KNIRGSIICTTSVASSLGGTAPHAYTTSKHALVGLVRTACSELGAYGIRVNCISPFGVATPLSCTA
YNLRPDEVEANSCALANLKGIVLKAKHIAEAALFLASDESAYISGHNLAVDGGFTVVNHSSSSAT
(SEQ ID NO: 90)

ATGTCAAACCCGCGTATGGAAGGCAAAGTCGCACTGATTACGGGCGCAGCATCTGGTATCGGTGAA
GCAGCAGTCCGTCTGTTCGCTGAACATGGTGCGTTTGTCGTGGCGGCAGATGTGCAAGACGAACTG
GGTCATCAGGTGGCGGCATCTGTGGGTACGGACCAGGTGTGCTACCATCACTGCGATGTGCGCGAT
GAAAAACAAGTGGAAGAAACCGTGCGTTATACCCTGGAAAAATACGGCAAACTGGATGTCCTGTTT
TCAAACGCGGGCATCATGGGTCCGCTGACCGGCATTCTGGAACTGGATCTGACCGGCTTCGGTAAC
ACGATGGCAACCAATGTGTGCGGTGTTGCCGCGACCATTAAACACGCGGCACGCGCAATGGTGGAC
AAAAACATTCGCGGTAGCATTATCTGCACCACCAGCGTGGCTTCATCGCTGGGTGGCACCGCGCCG
CACGCATACACCACGAGCAAACACGCACTGGTGGGCCTGGTTCGTACGGCATGTTCGGAACTGGGT
GCGTATGGCATTCGTGTGAACTGTATCAGCCCGTTTGGTGTTGCAACGCCGCTGTCTTGCACGGCC
TATAACCTGCGCCCGGATGAAGTGGAAGCAAACTCATGCGCACTGGCGAACCTGAAAGGTATTGTG
CTGAAAGCGAAACACATTGCGGAAGCAGCGCTGTTCCTGGCGAGCGATGAAAGCGCGTATATTAGC
GGTCATAATCTGGCGGTGGATGGTGGTTTCACGGTGGTTAATCATTCAAGTTCGTCGGCGACGTAA
(SEQ ID NO: 91)

>CsDH3 [Citrus sinensis]

MTTAGSRDSPLVAQRLLGKVALVTGGATGIGESIVRLFHKHGAKVCVVDINDDLGQHLCQTLGPTT
RFIHGDVAIEDDVSRAVDFTVANFGTLDIMVNNAGMGGPPCPDIREFPISTFEKVFDINTKGTFIG
MKHAARVMIPSKKGSIVSISSVTSAIGGAGPHAYTASKHAVLGLTKSVAAELGQHGIRVNCVSPYA
ILTNLALAHLHEDERTDDARAGFRAFIGKNANLQGVDLVEDDVANAVLFLASDDARYISGDNLFVD
GGFTCTNHSLRVFR (SEQ ID NO: 92)

Figure 22B

ATGACGACGGCTGGTTCGCGTGACAGTCCGCTGGTCGCTCAACGCCTGCTGGGCAAAGTGGCCCTG
GTTACGGGTGGTGCTACCGGCATTGGTGAAAGTATCGTGCGTCTGTTTCATAAACACGGCGCGAAA
GTTTGCGTGGTTGATATTAACGATGACCTGGGCCAGCATCTGTGTCAAACCCTGGGTCCGACCACC
CGTTTCATTCACGGCGATGTTGCAATCGAAGATGATGTGAGCCGTGCGGTTGATTTTACCGTCGCC
AACTTCGGTACGCTGGACATTATGGTGAACAATGCCGGTATGGGCGGTCCGCCGTGCCCGGATATT
CGTGAATTTCCGATCTCGACCTTTGAAAAAGTCTTCGACATTAACACCAAAGGCACGTTCATCGGT
ATGAAACATGCGGCCCGCGTGATGATTCCGAGTAAAAAAGGTAGTATTGTCAGCATTAGCAGCGTG
ACCAGCGCGATTGGCGGCGCGGGTCCGCACGCCTATACCGCGAGCAAACATGCGGTGCTGGGCCTG
ACGAAATCTGTCGCGGCGGAACTGGGCCAGCACGGTATTCGTGTCAACTGTGTGTCTCCGTACGCC
ATCCTGACCAATCTGGCGCTGGCCCATCTGCACGAAGATGAACGTACGGATGACGCGCGTGCGGGT
TTTCGTGCATTCATTGGTAAAAACGCTAATCTGCAAGGTGTTGATCTGGTCGAAGATGACGTGGCG
AATGCCGTTCTGTTTCTGGCATCAGATGACGCTCGCTATATCTCGGGCGATAACCTGTTCGTGGAT
GGCGGCTTCACCTGTACCAATCACTCCCTGCGTGTGTTCCGTTAA (SEQ ID NO: 93)

>VvDH [Vitis vinifera]

MAATSIDNSPLPSQRLLGKVALVTGGATGIGESIVRLFLKQGAKVCIVDVQDDLGQKLCDTLGGDP
NVSFFHCDVTIEDDVCHAVDFTVTKFGTLDIMVNNAGMAGPPCSDIRNVEVSMFEKVFDVNVKGVF
LGMKHAARIMIPLKKGTIISLCSVSSAIAGVGPHAYTGSKCAVAGLTQSVAAEMGGHGIRVNCISP
YAIATGLALAHLPEDERTEDAMAGFRAFVGKNANLQGVELTVDDVAHAAVFLASDEARYISGLNLM
LDGGFSCTNHSLRVFR (SEQ ID NO: 94)

ATGGCCGCAACGAGCATTGATAATTCTCCGCTGCCGAGTCAACGTCTGCTGGGTAAAGTCGCACTG
GTCACGGGTGGCGCTACGGGTATTGGCGAAAGCATCGTGCGTCTGTTTCTGAAACAGGGTGCTAAA
GTGTGCATTGTGGACGTGCAAGATGACCTGGGCCAGAAACTGTGCGATACCCTGGGTGGCGATCCG
AACGTTAGCTTTTTCCATTGCGATGTGACCATCGAAGATGATGTGTGCCATGCAGTTGATTTTACC
GTCACGAAATTCGGCACCCTGGATATTATGGTGAACAATGCGGGTATGGCAGGTCCGCCGTGCTCG
GACATCCGCAACGTGGAAGTCAGCATGTTTGAAAAAGTGTTTGATGTGAATGTGAAAGGTGTTTTC
CTGGGCATGAAACATGCAGCCCGCATTATGATTCCGCTGAAAAAAGGCACCATTATCAGCCTGTGT
TCAGTTTCCAGCGCTATCGCGGGCGTTGGTCCGCACGCATATACGGGTAGCAAATGCGCAGTGGCG
GGTCTGACGCAATCGGTCGCAGCAGAAATGGGTGGTCATGGCATTCGCGTGAACTGTATCAGCCCG
TATGCAATCGCAACGGGTCTGGCGCTGGCACATCTGCCGGAAGATGAACGCACGGAAGATGCAATG
GCGGGTTTCCGTGCGTTTGTGGGTAAAAATGCGAATCTGCAAGGTGTTGAACTGACCGTGGATGAT
GTGGCGCACGCAGCGGTGTTTCTGGCAAGCGATGAAGCACGTTACATCTCTGGTCTGAATCTGATG
CTGGACGGCGGCTTTTCGTGTACCAACCACTCGCTGCGTGTCTTTCGCTAA (SEQ ID NO: 95)

>VvDH1 [Vitis vinifera]

MSTASSGDVSLLSQRLVGKVALITGGATGIGESIARLFYRHGAKVCIVDIQDNPGQNLCRELGTDD
ACFFHCDVSIEIDVIRAVDFVVNRFGKLDIMVNNAGIADPPCPDIRNTDLSIFEKVFDVNVKGTFQ
CMKHAARVMVPQKKGSIISLTSVASVIGGAGPHAYTGSKHAVLGLTKSVAAELGLHGIRVNCVSPY
AVPTGMPLAHLPESEKTEDAMMGMRAFVGRNANLQGIELTVDDVANSVVFLASDEARYVSGLNLML
DGGFSCVNHSLRVFR (SEQ ID NO: 96)

ATGTCAACGGCTTCCTCGGGTGATGTGTCGCTGCTGTCGCAACGCCTGGTCGGTAAAGTCGCTCTG
ATTACGGGTGGTGCAACGGGCATTGGTGAATCGATTGCGCGTCTGTTTTACCGTCATGGTGCGAAA
GTGTGCATCGTTGACATTCAGGATAATCCGGGTCAAAACCTGTGCCGTGAACTGGGCACCGACGAT
GCGTGCTTCTTTCACTGCGATGTGAGCATTGAAATCGATGTGATTCGTGCTGTTGACTTTGTGGTT
AACCGCTTTGGTAAACTGGACATTATGGTTAATAACGCGGGCATCGCAGATCCGCCGTGCCCGGAT

Figure 22C

ATTCGCAACACCGATCTGAGCATTTTTGAAAAAGTGTTCGATGTGAACGTGAAAGGCACCTTTCAG
TGTATGAAACACGCAGCGCGCGTTATGGTGCCGCAGAAAAAAGGTAGCATTATCAGCCTGACCTCG
GTGGCGAGCGTGATTGGTGGCGCGGGTCCGCACGCCTATACGGGTAGCAAACACGCGGTTCTGGGT
CTGACGAAAAGCGTTGCGGCAGAACTGGGTCTGCATGGTATTCGCGTGAACTGTGTGAGTCCGTAT
GCAGTTCCGACGGGTATGCCGCTGGCACATCTGCCGGAATCGGAAAAAACCGAAGATGCGATGATG
GGTATGCGTGCATTTGTGGGTCGTAATGCCAACCTGCAAGGTATTGAACTGACCGTGGACGATGTC
GCAAATAGCGTCGTGTTTCTGGCGTCGGATGAAGCGCGTTATGTTAGCGGTCTGAACCTGATGCTG
GACGGCGGCTTCTCGTGTGTCAACCACTCGCTGCGTGTGTTTCGCTAA (SEQ ID NO: 97)

>CsABA2 [Citrus sinensis]

MSNSNSTDSSPAVQRLVGRVALITGGATGIGESTVRLFHKHGAKVCIADVQDNLGQQVCQSLGGEP
DTFFCHCDVTKEEDVCSAVDLTVEKFGTLDIMVNNAGISGAPCPDIREADLSEFEKVFDINVKGVF
HGMKHAARIMIPQTKGTIISICSVAGAIGGLGPHAYTGSKHAVLGLNKNVAAELGKYGIRVNCVSP
YAVATGLALAHLPEEERTEDAMVGFRNFVARNANMQGTELTANDVANAVLFLASDEARYISGTNLM
VDGGFTSVNHSLRVFR (SEQ ID NO: 98)

ATGTCCAATAGCAACTCTACGGATTCGTCGCCGGCAGTCCAACGCCTGGTCGGTCGTGTCGCCCTG
ATTACGGGTGGTGCAACGGGTATTGGCGAAAGCACGGTGCGCCTGTTTCATAAACATGGCGCGAAA
GTGTGTATTGCCGACGTTCAGGATAACCTGGGTCAGCAAGTGTGTCAGAGTCTGGGTGGCGAACCG
GATACCTTTTTCTGCCATTGTGATGTGACGAAAGAAGAAGATGTGTGTAGCGCAGTTGATCTGACC
GTGGAAAAATTTGGCACCCTGGACATTATGGTGAACAATGCGGGTATTAGCGGCGCACCGTGCCCG
GACATTCGTGAAGCCGATCTGAGCGAATTTGAAAAAGTTTTCGACATCAACGTGAAAGGCGTGTTT
CACGGCATGAAACATGCAGCGCGTATTATGATCCCGCAAACCAAAGGCACCATTATCAGCATTTGC
TCCGTGGCTGGTGCGATTGGTGGCCTGGGTCCGCACGCATATACCGGCTCCAAACATGCAGTCCTG
GGCCTGAACAAAAACGTGGCCGCGGAACTGGGCAAATACGGTATCCGTGTGAATTGCGTCAGCCCG
TATGCTGTTGCCACCGGCCTGGCTCTGGCACACCTGCCGGAAGAAGAACGTACCGAAGATGCAATG
GTGGGCTTTCGTAATTTTGTGGCACGCAACGCGAATATGCAAGGCACCGAACTGACGGCGAATGAT
GTGGCAAACGCGGTCCTGTTTCTGGCCTCTGATGAAGCCCGTTATATCAGCGGCACGAATCTGATG
GTGGATGGCGGTTTTACCTCGGTCAATCACTCGCTGCGTGTCTTCCGTTAA (SEQ ID NO: 99)

>BdDH [Brachypodium distachyon]

MSAAAAVSSSSSPRLEGKVALVTGGASGIGEAIVRLFRQHGAKVCIADVQDEAGQQVRDSLGDDAG
TDVLFVHCDVTVEEDVSRAVDAAAEKFGTLDIMVNNAGITGDKVTDIRNLDFAEVRKVFDINVHGM
LLGMKHAARVMIPGKKGSIVSLASVASVMGGMGPHAYTASKHAVVGLTKSVALELGKHGIRVNCVS
PYAVPTALSMPHLPQGEHKGDAVRDFLAFVGGEANLKGVDLLPKDVAQAVLYLASDEARYISALNL
VVDGGFTSVNPNLKAFED (SEQ ID NO: 100)

ATGTCCGCTGCTGCCGCCGTGTCCTCCTCATCGTCGCCGCGTCTGGAAGGCAAAGTCGCTCTGGTT
ACGGGTGGTGCGTCAGGTATCGGCGAAGCCATTGTGCGCCTGTTCCGTCAACATGGTGCCAAAGTG
TGTATCGCGGATGTCCAAGACGAAGCGGGCCAACAGGTCCGTGATAGCCTGGGTGACGATGCCGGT
ACGGATGTGCTGTTTGTGCATTGCGACGTTACCGTGGAAGAAGATGTGTCACGCGCGGTGGATGCC
GCTGCGGAAAAATTCGGCACCCTGGACATTATGGTGAACAACGCAGGTATTACGGGCGACAAAGTG
ACGGACATTCGCAACCTGGATTTCGCTGAAGTCCGTAAAGTGTTCGACATCAATGTGCACGGTATG
CTGCTGGGCATGAAACATGCGGCCCGCGTGATGATTCCGGGTAAAAAAGGCTCGATTGTGAGCCTG
GCATCGGTCGCAAGCGTTATGGGTGGTATGGGTCCGCACGCATATACCGCAAGCAAACACGCGGTT
GTGGGTCTGACGAAAAGCGTTGCACTGGAACTGGGCAAACATGGTATTCGTGTCAACTGTGTGAGC
CCGTATGCAGTTCCGACCGCACTGTCAATGCCGCACCTGCCGCAGGGCGAACATAAAGGTGATGCG

Figure 22D

GTGCGTGATTTCCTGGCGTTTGTTGGCGGTGAAGCGAATCTGAAAGGTGTCGATCTGCTGCCGAAA
GATGTTGCACAGGCGGTTCTGTATCTGGCAAGCGACGAAGCGCGCTATATTTCTGCGCTGAATCTG
GTGGTTGATGGCGGTTTTACGAGCGTGAATCCGAATCTGAAAGCATTTGAAGACTAA (SEQ ID NO: 101)

>ZzSDR [Zingiber zerumbet]

MRLEGKVALVTGGASGIGESIARLFIEHGAKICIVDVQDELGQQVSQRLGGDPHACYFHCDVTVED
DVRRAVDFTAEKYGTIDIMVNNAGITGDKVIDIRDADFNEFKKVFDINVNGVFLGMKHAARIMIPK
MKGSIVSLASVSSVIAGAGPHGYTGAKHAVVGLTKSVAAELGRHGIRVNCVSPYAVPTRLSMPYLP
ESEMQEDALRGFLTFVRSNANLKGVDLMPNDVAEAVLYLATEESKYVSGLNLVIDGGFSIANHTLQ
VFE (SEQ ID NO: 102)

ATGCGTCTGGAAGGCAAAGTGGCTCTGGTCACGGGCGGTGCGTCGGGTATTGGCGAATCTATTGCT
CGTCTGTTTATTGAACACGGTGCAAAAATTTGCATCGTGGATGTCCAGGATGAACTGGGTCAACAG
GTCTCTCAGCGTCTGGGTGGCGATCCGCACGCCTGTTATTTCCACTGTGATGTGACCGTGGAAGAT
GACGTTCGTCGCGCGGTGGATTTTACGGCGGAAAAATATGGCACCATTGACATTATGGTTAACAAT
GCGGGCATTACGGGCGATAAAGTGATCGATATTCGTGATGCGGATTTCAACGAATTTAAAAAAGTG
TTCGACATTAACGTGAATGGTGTCTTTCTGGGCATGAAACACGCAGCGCGTATTATGATCCCGAAA
ATGAAAGGCTCCATCGTTTCGCTGGCGTCCGTTAGCTCGGTGATTGCTGGTGCAGGTCCGCATGGC
TATACCGGCGCAAAACATGCGGTTGTGGGTCTGACCAAAAGCGTTGCAGCCGAACTGGGTCGTCAT
GGTATTCGCGTGAACTGCGTTTCGCCGTATGCGGTGCCGACGCGCCTGTCAATGCCGTATCTGCCG
GAATCGGAAATGCAGGAAGATGCACTGCGCGGCTTTCTGACCTTTGTGCGTAGCAATGCGAACCTG
AAAGGCGTTGATCTGATGCCGAATGATGTGGCGGAAGCTGTTCTGTATCTGGCGACCGAAGAAAGC
AAATATGTTTCAGGTCTGAATCTGGTTATTGACGGCGGCTTCTCCATCGCTAATCATACCCTGCAA
GTGTTTGAATAA (SEQ ID NO: 103)

Figure 22E

```
CsDH3     MTTAGSRDSPLVAQRLLGKVALVTGGATGIGESIVRLFHKHGAKVCVVDIN--------- 51
VvDH      MAATSIDNSPLPSQRLLGKVALVTGGATGIGESIVRLFLKQGAKVCIVDVQ--------- 51
VvDH1     MSTASSGDVSLLSQRLVGKVALITGGATGIGESIARLFYRHGAKVCIVDIQ--------- 51
CsABA2    MSNSNSTDSSPAVQRLVGRVALITGGATGIGESTVRLFHKHGAKVCIADVQ--------- 51
CsDH      MATPPIS--SLISQRLLGKVALVTGGASGIGEGIVRLFHRHGAKVCFVDVQ--------- 49
BdDH      -MSAAAAVSSSSSPRLEGKVALVTGGASGIGEAIVRLFRQHGAKVCIADVQ--------- 50
ZzSDR     -------------MRLEGKVALVTGGASGIGESIARLFIEHGAKICIVDVQ--------- 38
CsDH1     ----------MSKPRLQGKVAIIMGAASGIGEATAKLFAEHGAFVIIADIQ--------- 41
CsDH2     ----------MSNPRMEGKVALITGAASGIGEAAVRLFAEHGAFVVAADVQ--------- 41
ReCDH     ------------MARVEGQVALITGAARGQGRSHAIKLAEEGADVILVDVPNDVVDIGYP 48
                        *: *:**:: *.* * *.. .  : ..** :  .*:

CsDH3     ----DDLGQHLCQTLG----PTTRFIHGDVAIEDDVSRAVDFTVANFGTLDIMVNNAGMG 103
VvDH      ----DDLGQKLCDTLGG--DPNVSFFHCDVTIEDDVCHAVDFTVTKFGTLDIMVNNAGMA 105
VvDH1     ----DNPGQNLCRELG---TDDACFFHCDVSIEIDVIRAVDFVVNRFGKLDIMVNNAGIA 104
CsABA2    ----DNLGQQVCQSLGG--EPDTFFCHCDVTKEEDVCSAVDLTVEKFGTLDIMVNNAGIS 105
CsDH      ----DELGYRLQESLVGDKDSNIFYSHCDVTVEDDVRRAVDLTVTKFGTLDIMVNNAGIS 105
BdDH      ----DEAGQQVRDSLGDDAGTDVLFVHCDVTVEEDVSRAVDAAAEKFGTLDIMVNNAGIT 106
ZzSDR     ----DELGQQVSQRLGGDP--HACYFHCDVTVEDDVRRAVDFTAEKYGTIDIMVNNAGIT 92
CsDH1     ----DELGNQVVSSIGP---EKASYRHCDVRDEKQVEETVAYAIEKYGSLDIMYSNAGVA 94
CsDH2     ----DELGHQVAASVGT---DQVCYHHCDVRDEKQVEETVRYTLEKYGKLDVLFSNAGIM 94
ReCDH     LGTADELDQTAKDVENLG--RKAIVIHADVRDLESLTAEVDRAVSTLGRLDIVSANAGIA 106
              *: .                  * **     .:   *  .    * :*::  ***:

CsDH3     GPPCPDIREFPISTFEKVFDINTKGTFIGMKHAARVMIPS-KKGSIVSISSVTSAIGGAG 162
VvDH      GPPCSDIRNVEVSMFEKVFDVNVKGVFLGMKHAARIMIPL-KKGTIISLCSVSSAIAGVG 164
VvDH1     DPPCPDIRNTDLSIFEKVFDVNVKGTFQCMKHAARVMVPQ-KKGSIISLTSVASVIGGAG 163
CsABA2    GAPCPDIREADLSEFEKVFDINVKGVFHGMKHAARIMIPQ-TKGTIISICSVAGAIGGLG 164
CsDH      GTPSSDIRNVDVSEFEKVFDINVKGVFMGMKYAASVMIPR-KQGSIISLGSVGSVIGGIG 164
BdDH      GDKVTDIRNLDFAEVRKVFDINVHGMLLGMKHAARVMIPG-KKGSIVSLASVASVMGGMG 165
ZzSDR     GDKVIDIRDADFNEFKKVFDINVNGVFLGMKHAARIMIPK-MKGSIVSLASVSSVIAGAG 151
CsDH1     G-PVGTILDLDMAQFDRTIATNLAGSVMAVKYAARVMVANKIRGSIICTTSTASTVGGSG 153
CsDH2     G-PLTGILELDLTGFGNTMATNVCGVAATIKHAARAMVDKNIRGSIICTTSVASSLGGTA 153
ReCDH     SVPFLSH-DIPDNTWRQMIDINLTGVWHTAKVAVPHILAGERGGSIVLTSSAAGLKGYAQ 165
```

Figure 22F

```
                .       :       . :  *  *     * *.  ::     *:*:   *. .  .

CsDH3           PHAYTASKHAVLGLTKSVAAELGQHGIRVNCVSPYAILTNLA----LAHLHEDERTDDAR 218
VvDH            PHAYTGSKCAVAGLTQSVAAEMGGHGIRVNCISPYAIATGLA----LAHLPEDERTEDAM 220
VvDH1           PHAYTGSKHAVLGLTKSVAAELGLHGIRVNCVSPYAVPTGMP----LAHLPESEKTEDAM 219
CsABA2          PHAYTGSKHAVLGLNKNVAAELGKYGIRVNCVSPYAVATGLA----LAHLPEEERTEDAM 220
CsDH            PHHYISSKHAVVGLTRSIAAELGQHGIRVNCVSPYAVPTNLA----VAHLPEDERTEDMF 220
BdDH            PHAYTASKHAVVGLTKSVALELGKHGIRVNCVSPYAVPTALS----MPHLPQGEHKGDAV 221
ZzSDR           PHGYTGAKHAVVGLTKSVAAELGRHGIRVNCVSPYAVPTRLS----MPYLPESEMQEDAL 207
CsDH1           PHAYTISKHGLLGLVRSAASELGKHGIRVNCVSPFGVATPFS----AGTIN--------- 200
CsDH2           PHAYTTSKHALVGLVRTACSELGAYGIRVNCISPFGVATPLS----CTAYNLRP------ 203
ReCDH           ISHYSAAKHGVVGLMRSLALELAPHRVRVNSLHPTQVNTPMIQNEGTYRIFSPDLENPTR 225
                   *  :* .: ** :. . *:. : :***.: *  : * :

CsDH3           AGFRAFIGKNANLQGVDLVEDDVANAVLFLASDDARYISGDNLFVDGGFTCTNHSLRVFR--- 278
VvDH            AGFRAFVGKNANLQGVELTVDDVAHAAVFLASDEARYISGLNLMLDGGFSCTNHSLRVFR--- 280
VvDH1           MGMRAFVGRNANLQGIELTVDDVANSVVFLASDEARYVSGLNLMLDGGFSCVNHSLRVFR--- 279
CsABA2          VGFRNFVARNANMQGTELTANDVANAVLFLASDEARYISGTNLMVDGGFTSVNHSLRVFR--- 280
CsDH            TGFREFAKKNANLQGVELTVEDVANAVLFLASEDARYISGDNLIVDGGFTRVNHSFRVFR--- 280
BdDH            RDFLAFVGGEANLKGVDLLPKDVAQAVLYLASDEARYISALNLVVDGGFTSVNPNLKAFED-- 282
ZzSDR           RGFLTFVRSNANLKGVDLMPNDVAEAVLYLATEESKYVSGLNLVIDGGFSIANHTLQVFE--- 267
CsDH1           -DVEGFVCKVANLKGIVLKAKHVAEAALFLASDESAYVSGHDLVVDGGFTAVTNVMSMLEGHG 262
CsDH2           DEVEANSCALANLKGIVLKAKHIAEAALFLASDESAYISGHNLAVDGGFTVVNHSSSSAT--- 263
ReCDH           EDFEIASTTTNALPIPWVESVDVSNALLFLVSEDARYITGAAIPVDAGTTLK----------- 277
                  .         :    :   .::.: ::*.:::: *::.  : :*.* :
```

Figure 22G

Figure 23A

```
8rp-t20SrKO        ----MALLLAVFAVALAVALIFWYLKSYTSARRSQSNHLPRVPEVPGVPLLGNLLQLKEK
8rp-t20VO0         ----MALLLAVFAVALAVALIFWYLKSYTSARRSQSNHLPRVPEVPGVPLLGNLLQLKEK
n22yhcB-t30VO1     MAWEYALIGLVVGIIIGAVAMRWYLKSYTSARRSQSNRLPRVPEVPGVPLLGNLLQLKEK
n22yhcB-t30VO2     MAWEYALIGLVVGIIIGAVAMRWYLKSYTSARRSQSNHLPRVPEVPGVPLLGNLLQLKEK
                        **:  *..: :... : ***************:**********************

8rp-t20SrKO        KPYMTFTRWAATYGPIYSIKTGATSMVVVSSNEIAKEALVTRFQSISTRNLSKALKVLTA
8rp-t20VO0         KPYMTFTRWAATYGPIYSIKTGATSMVVVSSNEIAKEALVTRFQSISTRNLSKALKVLTA
n22yhcB-t30VO1     KPYMTFTRWAATYGPIYSIKTGATSMVVVSSNEIAKEALVTRFQSISTRNLSKALKVLTA
n22yhcB-t30VO2     KPYMTFTKWAATYGPIYSIKTGATSVVVVSSNEIAKEALVTRFQSISTRNLSKALKVLTA
                   *******:*****************:**********************************

8rp-t20SrKO        DKTMVAMSDYDDYHKTVKRHILTAVLGPNAQKKHRIHRDIMMDNISTQLHEFVKNNPEQE
8rp-t20VO0         DKTMVAMSDYDDYHKTVKRHILTAVLGPNAQKKHRIHRDIMMDNISTQLHEFVKNNPEQE
n22yhcB-t30VO1     DKTMVAMSDYDDYHKTVKRHILTAVLGPNAQKKHRIHRDIMMDNISTQLHEFVKNNPEQE
n22yhcB-t30VO2     DKQMVAMSDYDDYHKTVKRHILTAVLGPNAQKKHRIHRDIMMDNISTQLHEFVKNNPEQE
                   ** *********************************************************

8rp-t20SrKO        EVDLRKIFQSELFGLAMRQALGKDVESLYVEDLKITMNRDEIFQVLVVDPMMGAIDVDWR
8rp-t20VO0         EVDLRKIFQSELFGLAMRQALGKDVESLYVEDLKITMNRDEIFQVLVVDPMMGAIDVDWR
n22yhcB-t30VO1     EVDLRKIFQSELFGLAMRQALGKDVESLYVEDLKITMNRDEILQVLVVDPMMGAIDVDWR
n22yhcB-t30VO2     EVDLRKIFQSELFGLAMRQALGKDVESLYVEDLKITMNRDEILQVLVVDPMMGAIDVDWR
                   ******************************************:*****************

8rp-t20SrKO        DFFPYLKWVPNKKFENTIQQMYIRREAVMKSLIKEHKKRIASGEKLNSYIDYLLSEAQTL
8rp-t20VO0         DFFPYLKWVPNKKFENTIQQMYIRREAVMKSLIKEHKKRIASGEKLNSYIDYLLSEAQTL
n22yhcB-t30VO1     DFFPYLKWVPNKKFENTIQQMYIRREAVMKSLIKEQKKRIASGEKLNSYIDYLLSEAQTL
n22yhcB-t30VO2     DFFPYLKWVPNKKFENTIQQMYIRREAVMKSLIKEQKKRIASGEKLNSYIDYLLSEAQTL
                   ***********************************:************************

8rp-t20SrKO        TDQQLLMSLWEPIIESSDTTMVTTEWAMYELAKNPKLQDRLYRDIKSVCGSEKITEEHLS
8rp-t20VO0         TDQQLLMSLWEPIIESSDTTMVTTEWAMYELAKNPKLQDRLYRDIKSVCGSEKITEEHLS
n22yhcB-t30VO1     TDQQLLMSLWEPIIESSDTTMVTTEWAMYELAKNPKLQDRLYRDIKSVCGSEKITEEHLS
```

```
n22yhcB-t30VO2      TDQQLLMSLWEPIIESSDTTMVTTEWAMYELAKNPKLQDRLYRDIKSVCGSEKITEEHLS
                    ************************************************************

8rp-t20SrKO         QLPYITAIFHETLRRHSPVPIIPLRHVHEDTVLGGYHVPAGTELAVNIYGCNMDKNVWEN
8rp-t20VO0          QLPYITAIFHETLRRHSPVPIIPLRHVHEDTVLGGYHVPAGTELAVNIYGCNMDKNVWEN
n22yhcB-t30VO1      QLPYITAIFHETLRKHSPVPIIPLRHVHEDTQLGGYHVPAGTELAVNIYGCNMDKNVWEN
n22yhcB-t30VO2      QLPYITAIFHETLRKHSPVPILPLRHVHEDTVLGGYHVPAGTELAVNIYGCNMDKNVWEN
                    **************:******:********* ****************************

8rp-t20SrKO         PEEWNPERFMKENETIDFQKTMAFGGGKRVCAGSLQALLTASIGIGRMVQEFEWKLKDMT
8rp-t20VO0          PEEWNPERFMKENETIDFQKTMAFGGGKRVCAGSLQALLTASIGIGRMVQEFEWKLKDMT
n22yhcB-t30VO1      PEEWNPERFMKENETADFQKTMAFGGGKRVCAGSLQALLTASIGIGRMVQEFEWKLKDMD
n22yhcB-t30VO2      PEEWNPERFMKENETIDFQKTMAFGGGKRVCAGSLQALLIASIGIGRMVQEFEWKLKDMT
                    *************** *********************** *******************

8rp-t20SrKO         QEEVNTIGLTTQMLRPLRAIIKPRI (SEQ ID NO: 106)
8rp-t20VO0          QEEVNTIGLTNQMLRPLRAIIKPRI (SEQ ID NO: 107)
n22yhcB-t30VO1      QEEVNTIGLTNQMLRPLRAIIKPRI (SEQ ID NO: 104)
n22yhcB-t30VO2      QEEVNTIGLTNQMLRPLRAIIKPRI (SEQ ID NO: 105)
                    **********.**************
```

Figure 23B

~~Figure 23B~~

```
VO2     MDAVTGLLTVPATAITIGGTAVALAVALIFWYLKSYTSARRSQSNHLPRVPEVPGVPLLG
VO1     MDAVTGLLTVPATAITIGGTAVALAVALIFWYLKSYTSARRSQSNRLPRVPEVPGVPLLG
SrKO    MDAVTGLLTVPATAITIGGTAVALAVALIFWYLKSYTSARRSQSNHLPRVPEVPGVPLLG
VO0     MDAVTGLLTVPATAITIGGTAVALAVALIFWYLKSYTSARRSQSNHLPRVPEVPGVPLLG
        *********************************************:**************

VO2     NLLQLKEKKPYMTFTKWAATYGPIYSIKTGATSVVVVSSNEIAKEALVTRFQSISTRNLS
VO1     NLLQLKEKKPYMTFTRWAATYGPIYSIKTGATSMVVVSSNEIAKEALVTRFQSISTRNLS
SrKO    NLLQLKEKKPYMTFTRWAATYGPIYSIKTGATSMVVVSSNEIAKEALVTRFQSISTRNLS
VO0     NLLQLKEKKPYMTFTRWAATYGPIYSIKTGATSMVVVSSNEIAKEALVTRFQSISTRNLS
        ***************:*****************:**************************

VO2     KALKVLTADKQMVAMSDYDDYHKTVKRHILTAVLGPNAQKKHRIHRDIMMDNISTQLHEF
VO1     KALKVLTADKTMVAMSDYDDYHKTVKRHILTAVLGPNAQKKHRIHRDIMMDNISTQLHEF
SrKO    KALKVLTADKTMVAMSDYDDYHKTVKRHILTAVLGPNAQKKHRIHRDIMMDNISTQLHEF
VO0     KALKVLTADKTMVAMSDYDDYHKTVKRHILTAVLGPNAQKKHRIHRDIMMDNISTQLHEF
        ********** *************************************************

VO2     VKNNPEQEEVDLRKIFQSELFGLAMRQALGKDVESLYVEDLKITMNRDEILQVLVVDPMM
VO1     VKNNPEQEEVDLRKIFQSELFGLAMRQALGKDVESLYVEDLKITMNRDEILQVLVVDPMM
SrKO    VKNNPEQEEVDLRKIFQSELFGLAMRQALGKDVESLYVEDLKITMNRDEIFQVLVVDPMM
VO0     VKNNPEQEEVDLRKIFQSELFGLAMRQALGKDVESLYVEDLKITMNRDEIFQVLVVDPMM
        **************************************************:*********

VO2     GAIDVDWRDFFPYLKWVPNKKFENTIQQMYIRREAVMKSLIKEQKKRIASGEKLNSYIDY
VO1     GAIDVDWRDFFPYLKWVPNKKFENTIQQMYIRREAVMKSLIKEQKKRIASGEKLNSYIDY
SrKO    GAIDVDWRDFFPYLKWVPNKKFENTIQQMYIRREAVMKSLIKEHKKRIASGEKLNSYIDY
VO0     GAIDVDWRDFFPYLKWVPNKKFENTIQQMYIRREAVMKSLIKEHKKRIASGEKLNSYIDY
        *******************************************:****************

VO2     LLSEAQTLTDQQLLMSLWEPIIESSDTTMVTTEWAMYELAKNPKLQDRLYRDIKSVCGSE
VO1     LLSEAQTLTDQQLLMSLWEPIIESSDTTMVTTEWAMYELAKNPKLQDRLYRDIKSVCGSE
SrKO    LLSEAQTLTDQQLLMSLWEPIIESSDTTMVTTEWAMYELAKNPKLQDRLYRDIKSVCGSE
```

Figure 23C

```
VO0     LLSEAQTLTDQQLLMSLWEPIIESSDTTMVTTEWAMYELAKNPKLQDRLYRDIKSVCGSE
        ************************************************************

VO2     KITEEHLSQLPYITAIFHETLRKHSPVPILPLRHVHEDTVLGGYHVPAGTELAVNIYGCN
VO1     KITEEHLSQLPYITAIFHETLRKHSPVPIIPLRHVHEDTQLGGYHVPAGTELAVNIYGCN
SrKO    KITEEHLSQLPYITAIFHETLRRHSPVPIIPLRHVHEDTVLGGYHVPAGTELAVNIYGCN
VO0     KITEEHLSQLPYITAIFHETLRRHSPVPIIPLRHVHEDTVLGGYHVPAGTELAVNIYGCN
        **********************:******:********* ********************

VO2     MDKNVWENPEEWNPERFMKENETIDFQKTMAFGGGKRVCAGSLQALLIASIGIGRMVQEF
VO1     MDKNVWENPEEWNPERFMKENETADFQKTMAFGGGKRVCAGSLQALLTASIGIGRMVQEF
SrKO    MDKNVWENPEEWNPERFMKENETIDFQKTMAFGGGKRVCAGSLQALLTASIGIGRMVQEF
VO0     MDKNVWENPEEWNPERFMKENETIDFQKTMAFGGGKRVCAGSLQALLTASIGIGRMVQEF
        *********************** *********************** ************

VO2     EWKLKDMTQEEVNTIGLTNQMLRPLRAIIKPRI (SEQ ID NO: 111)
VO1     EWKLKDMDQEEVNTIGLTNQMLRPLRAIIKPRI (SEQ ID NO: 110)
SrKO    EWKLKDMTQEEVNTIGLTTQMLRPLRAIIKPRI (SEQ ID NO: 108)
VO0     EWKLKDMTQEEVNTIGLTNQMLRPLRAIIKPRI (SEQ ID NO: 109)
        ******* **********.**************
```

Figure 23D

SEQUENCE LISTING

```
Sequence total quantity: 132
SEQ ID NO: 1            moltype = AA  length = 556
FEATURE                 Location/Qualifiers
source                  1..556
                        mol_type = protein
                        organism = Vitis vinifera
```

-continued

```
SEQUENCE: 1
MSTQVSASSL AQIPQPKNRP VANFHPNIWG DQFITYTPED KVTRACKEEQ IEDLKKEVKR  60
KLTAAAVANP SQLLNFIDAV QRLGVAYHFE QEIEEALQHI CNSFHDCNDM DGDLYNIALG  120
FRLLRQQGYT ISCDIFNKFT DERGRFKEAL ISDVRGMLGL YEAAHLRVHG EDILAKALAF  180
TTTHLKAMVE SLGYHLAEQV AHALNRPIRK GLERLEARWY ISVYQDEAFH DKTLLELAKL  240
DFNLVQSLHK EELSNLARWW KELDFATKLP FARDRLVEGY FWMHGVYFEP QYLRGRRILT  300
KVIAMTSILD DIHDAYGTPE ELKLFIEAIE RWDINSINQL PEYMKLCYVA LLDVYKEIEE  360
EMEKEGNQYR VHYAKEVMKN QVRAYFAEAK WLHEEHVPAF EEYMRVALAS SGYCLLATTS  420
FVGMGEIATK EAFDWVTSDP KIMSSSNFIT RLMDDIKSHK FEQKRGHVTS AVECYMKQYG  480
VSEEQVYSEF QKQIENAWLD INQECLKPTA VSMPLLARLL NFTRTMDVIY KEQDSYTHVG  540
KVMRDNIASV FINAVI                                                  556

SEQ ID NO: 2           moltype = DNA  length = 1671
FEATURE                Location/Qualifiers
source                 1..1671
                       mol_type = other DNA
                       organism = Vitis vinifera
SEQUENCE: 2
atggctacgc aggtctcagc ctcgtcactg gcacaaatcc cgcagccgaa aaatcgtccg  60
gtggcgaact tccatccgaa tatctggggt gaccagttta tcacgtatac cccggaagat  120
aaagtgaccc gtgcgtgcaa ggaagaacaa attgaagacc tgaaaaagga agtcaaacgc  180
aagctgaccg cagcagcagt ggcaaacccg tctcagctgc tgaattttat cgatgcggtt  240
caacgtctgg gcgtcgccta tcatttcgaa caggaaattg aagaagcact gcaacatatc  300
tgcaacagct ttcacgattg taatgatatg gacggcgatc tgtataacat tgctctgggt  360
ttccgtctgc tgcgccagca aggctacacg atttcctgtg acatctttaa taaattcacc  420
gatgaacgtg gtcgctttaa ggaagcgctg atctcagacg ttcgtggcat gctgggtctg  480
tatgaagctg cgcatctgcg cgtccacggc gaagatattc tggccaaagc actggctttc  540
accacgaccc acctgaaggc gatggtcgaa tctctgggtt accatctggc agaacaggtg  600
gcacacgccc tgaaccgtcc gatccgcaaa ggcctggaac gtctggaagc gcgctggtat  660
attagtgtgt accaggacga agcatttcat gataaaaccc tgctggaact ggctaagctg  720
gatttcaacc tggttcaatc tctgcacaaa gaagaactga gtaatctggc ccgttggtgg  780
aaagaactgg actttgcgac caagctgccg ttcgcccgtg atcgcctggt tgaaggctat  840
ttttggatgc atggtgtcta tttcgaaccg cagtacctgc gcggtcgtcg cattctgacg  900
aaagtgatcg caatgacctc gattctggat gacatccacg acgcttacgg caccccggaa  960
gaactgaaac tgtttattga agcgatcgaa cgttgggata ttaacagcat caatcagctg  1020
ccggaatata tgaaactgtg ctacgtggcc ctgctggatg tttacaagga aatcgaagaa  1080
gaaatggaaa aggaaggtaa ccagtatcgt gttcattacg cgaaagaagt catgaagaat  1140
caagtgcgcg cctactttgc agaagctaaa tggctgcatg aagaacacgt gccggcgttc  1200
gaagaatata tgcgcgttgc gctggccagc tctggctact gtctgctggc cacgacctct  1260
tttgtgggca tgggtgaaat tgcaacgaaa gaagcgtttg actgggttac cagtgatccg  1320
aagattatga gttcctcaaa ctttatcacc cgtctgatgg atgacattaa atcccataag  1380
ttcgaacaga aacgcggtca cgtcacctca gccgtggaat gctatatgaa acagtacggc  1440
gtttcggaag aacaagtcta tagcgaattt cagaaacaaa tcgaaaacgc atggctggat  1500
attaatcagg aatgtctgaa accgacggca gtctccatgc cgctgctggc tcgtctgctg  1560
aattttacgc gcacgatgga tgtgatctat aaagaacagg attcgtacac ccatgtgggc  1620
aaggttatgc gcgataacat tgcaagcgtg ttcattaatg ctgttatcta a           1671

SEQ ID NO: 3           moltype = AA  length = 556
FEATURE                Location/Qualifiers
REGION                 1..556
                       note = Synthetic - Engineered valencene synthase
source                 1..556
                       mol_type = protein
                       organism = synthetic construct
SEQUENCE: 3
MATQVSASSL AQIPQPKNRP VANFHPNIWG DQFITYTPED KVTRACKEEQ IEDLKKEVKR  60
KLTAAAVANP SQLLNFIDAV QRLGVAYHFE QEIEEALQHI CNSFHDCNDM DGDLYNIALG  120
FRLLRQQGYT ISCDIFNKFT DERGRFKEAL ISDVRGMLGL YEAAHLRVHG EDILAKALAF  180
TTTHLKAMVE SLGYHLAEQV AHALNRPIRK GLERLEARWY ISVYQDEAFH DKTLLELAKL  240
DFNLVQSLHK EELSNLARWW KELDFATKLP FARDRLVEGY FWMHGVYFEP QYLRGRRILT  300
KVIAMTSILD DIHDAYGSPE ELKLFIEAIE KWDESSINQL PEYMKLCFVA LIDVYNEIEE  360
EMEKEGNQYR IHYLKEVMKN QVRAYFAEAK WLHDEHVPAF EEYMRVALAS SGYCLLAVTS  420
FVGMGEIVTK EAFDWVTSDP KLMSSSNFIT RLMDDIKSHK FEQKRGHVTS AVECYMKQYG  480
VTEEQVYSEF KKQIENAWLD INQECLKPTA VPMPLLARLL NFTRTMDVIY KEQDSYTHVG  540
KVMRDNIASV FINPVI                                                  556

SEQ ID NO: 4           moltype = DNA  length = 1671
FEATURE                Location/Qualifiers
misc_feature           1..1671
                       note = Synthetic - Engineered valencene synthase
source                 1..1671
                       mol_type = other DNA
                       organism = synthetic construct
SEQUENCE: 4
atggcaaccc aggtgagtgc aagcagcctg gcccaaatcc ctcagccgaa aaaccgcccg  60
gttgcaaact tccaccctaa tatctggggc gatcagttca tcacctatac cccggaagat  120
aaagtgacaa gggcctgcaa agaggagcag atcgaggacc tgaaaaaaga ggtgaagcgc  180
aagctgaccg cagccgcagt ggcaaacccg agccaactgt taaacttcat cgatgccgtg  240
cagcgcctgg gcgttgccta tcacttcgag caggaaatcg aagaagccct acagcacatc  300
```

```
tgtaacagct tccacgattg taacgacatg gatggcgact tatacaacat agcattaggt  360
ttccgcttac tgcgtcagca gggctacacc ataagctgcg acatctttaa caagtttacc  420
gacgagcgcg gtcgttttaa agaggcgctg attagcgacg ttcgcggcat gttaggtctg  480
tacgaagccg cacatctgcg cgtgcacggc gaagacattc tggcgaaggc gctggcattc  540
acaaccacac acctgaaggc aatggtggaa agtctgggct accacttagc cgagcaggtt  600
gcccatgcac tgaatcgccc gattcgtaag ggcctggaac gcctggaagc ccgctggtac  660
atcagtgttt atcaggatga agcctttcat gataagaccc tgctggagct ggcaaagctg  720
gatttcaacc tggttcagag cctgcataag gaagagctga gcaacctggc ccgttggtgg  780
aaggagctgg atttcgcaac caagctgccg ttcgccaggg acaggttagt tgaaggctac  840
ttctggatgc acggcgttta cttcgagccg caatacctgc gtggccgccg catcctgacg  900
aaggtgatcg ccatgaccag cattctggac gacatccacg atgcgtacgg gagccctgag  960
gagttaaagc tgttcatcga ggcaatcgag aagtgggatg agagtagcat caaccaactg  1020
ccggagtata tgaaactgtg cttcgtggcc ctgattgatg tttacaatga gattgaagag  1080
gagatggaga aagaggggaa ccagtaccgc atccactacc tgaaagaggt gatgaagaat  1140
caggtgcgcg catacttcgc agaggccaaa tggctgcatg atgagcatgt tcctgccttc  1200
gaggagtaca tgcgcgtggc attagccagc agtggttact gtctgttagc cgttacgagc  1260
ttcgtgggta tgggcgagat cgtgaccaaa gaggcattcg actgggtgac gagcgacccg  1320
aagctgatga gcagcagcaa cttcatcacc cgtctgatgg acgacatcaa gagccacaag  1380
ttcgagcaga aacgcggtca cgttaccagc gccgtggagt gctacatgaa gcagtacggc  1440
gtgacagagg agcaagtgta cagcgagttc aagaaacaaa tcgagaacgc ctggctggac  1500
atcaaccaag agtgcctgaa accgaccgca gtgccgatgc ctctgttagc ccgtctgctg  1560
aatttcacac gcacgatgga cgttatctac aaggagcagg atagctacac ccacgttggt  1620
aaggtgatgc gcgacaacat cgccagtgtg ttcatcaacc cggtgatcta a           1671

SEQ ID NO: 5            moltype = AA  length = 556
FEATURE                 Location/Qualifiers
REGION                  1..556
                        note = Synthetic - Engineered valencene synthase
source                  1..556
                        mol_type = protein
                        organism = synthetic construct
SEQUENCE: 5
MATQVSASSL AQIPQPKNRP VANFHPNIWG DQFITYTPED KVTRACKEEQ IEDLKKEVKR  60
KLTAAAVANP SQLLNFIDAV QRLGVAYHFE QEIEEALQHI CNSFHDCNDM DGDLYNIALG  120
FRLLRQQGYT ISCDIFNKFT DERGRFKEAL ISDVRGMLGL YEAAHLRVHG EDILAKALAF  180
TTTHLKAMVE SLGYHLAEQV AHALNRPIRK GLERLEARWY ISVYQDEAFH DKTLLELAKL  240
DFNLVQSLHK EELSNLARWW KELDFATKLP FARDRLVEGY FWMHGVYFEP QYLRGRRILT  300
KVIALTSILD DIHDAYGTPE ELKLFIEAIE KWDESSINQL PEYMKLCYVA LLDVYNEIEE  360
EMEKEGNQYR IHYLKEVMKN QVRAYFAEAK WLHDEHVPAF EEYMRVALAS SGYCLLAVTS  420
FVGMGEIVTK EAFDWVTSDP RIMSSSNFIT RLMDDIKSHK FEQKRGHVTS AVECYMKQYA  480
VTEEQVYSEF KKQIENAWLD INQECLKPTA VPMPLLARLL NFTRTMDVIY KEQDSYTHVG  540
KTMRDNIASV FINPVI                                                556

SEQ ID NO: 6            moltype = DNA  length = 1671
FEATURE                 Location/Qualifiers
misc_feature            1..1671
                        note = Synthetic - Engineered valencene synthase
source                  1..1671
                        mol_type = other DNA
                        organism = synthetic construct
SEQUENCE: 6
atggcaaccc aggtgagtgc aagcagcctg gcccaaatcc ctcagccgaa aaaccgcccg  60
gttgcaaact tccaccctaa tatctggggc gatcagttca tcacctatac cccggaagat  120
aaagtgacaa gggcctgcaa agaggagcag atcgaggacc tgaaaaaaga ggtgaagcgc  180
aagctgaccg cagccgcagt ggcaaacccg agccaactgt taaacttcat cgatgccgtg  240
cagcgcctgg gcgttgccta tcacttcgag caggaaatcg aagaagccct acagcacatc  300
tgtaacagct tccacgattg taacgacatg gatggcgact tatacaacat agcattaggt  360
ttccgcttac tgcgtcagca gggctacacc ataagctgcg acatctttaa caagtttacc  420
gacgagcgcg gtcgttttaa agaggcgctg attagcgacg ttcgcggcat gttaggtctg  480
tacgaagccg cacatctgcg cgtgcacggc gaagacattc tggcgaaggc gctggcattc  540
acaaccacac acctgaaggc aatggtggaa agtctgggct accacttagc cgagcaggtt  600
gcccatgcac tgaatcgccc gattcgtaag ggcctggaac gcctggaagc ccgctggtac  660
atcagtgttt atcaggatga agcctttcat gataagaccc tgctggagct ggcaaagctg  720
gatttcaacc tggttcagag cctgcataag gaagagctga gcaacctggc ccgttggtgg  780
aaggagctgg atttcgcaac caagctgccg ttcgccaggg acaggttagt tgaaggctac  840
ttctggatgc acggcgttta cttcgagccg caatacctgc gtggccgccg catcctgacg  900
aaggtgatcg ccctgaccag cattctggac gacatccacg atgcgtacgg gacccctgag  960
gagttaaagc tgttcatcga ggcaatcgag aagtgggatg agagtagcat caaccaactg  1020
ccggagtata tgaaactgtg ctatgtggcc ctgctggatg tttacaatga gattgaagag  1080
gagatggaga aagaggggaa ccagtaccgc atccactacc tgaaagaggt gatgaagaat  1140
caggtgcgcg catacttcgc agaggccaaa tggctgcatg atgagcatgt tcctgccttc  1200
gaggagtaca tgcgcgtggc attagccagc agtggttact gtctgttagc cgttacgagc  1260
ttcgtgggta tgggcgagat cgtgaccaaa gaggcattcg actgggtgac gagcgacccg  1320
cgtattatga gcagcagcaa cttcatcacc cgtctgatgg acgacatcaa gagccacaag  1380
ttcgagcaga aacgcggtca cgttaccagc gccgtggagt gctacatgaa gcagtacgca  1440
gtgacagagg agcaagtgta cagcgagttc aagaaacaaa tcgagaacgc ctggctggac  1500
atcaaccaag agtgcctgaa accgaccgca gtgccgatgc ctctgttagc ccgtctgctg  1560
aatttcacac gcacgatgga cgttatctac aaggagcagg atagctacac ccacgttggt  1620
aagaccatgc gcgacaacat cgccagtgtg ttcatcaacc cggtgatcta a           1671
```

```
SEQ ID NO: 7            moltype = AA  length = 556
FEATURE                 Location/Qualifiers
REGION                  1..556
                        note = Synthetic - Engineered valencene synthase
source                  1..556
                        mol_type = protein
                        organism = synthetic construct
SEQUENCE: 7
MATQVSASSL AQIPQPKNRP VANFHPNIWG DQFITYTPED KVTRAKKEEQ IEDLKKEVKR  60
KLTAAAVANP SQLLNFIDAV QRLGVAYHFE QEIEEALQHI CNSFHDCNDM DGDLYNIALG  120
FRLLRQQGYT ISCDIFNKFT DERGRFKEAL ISDVRGMLGL YEAAHLRVHG EDILAKALAF  180
TTTHLKAMVE SLGYHLAEQV AHALNRPIRK GLERLEARWY ISVYQDEAFH DKTLLELAKL  240
DFNLVQSLHK EELSNLARWW KELDFATKLP FARDRLVEGY FWMMGVYFEP QYLRGRRILT  300
KVIAMTSILD DIHDAYGSPE ELKLFIEAIE KWDESSINQL PEYMKLCFVA LIDVYNEIEE  360
EMEKEGNQYR IHYLKEVMKN QVRAYFAEAK WLHDEHVPAF EEYMRVALAS SGYCLLAVTS  420
FVGMGEIVTK EAFDWVTSDP KLMSSSNTIT RLMDDIKSHK FEQKRGHVTS AVECYMKQYG  480
VTEEQVYSEF KKQIENAWLD INQECLKPTA VPMPLLARLL NFTRTMDVIY KEEDSYTHVG  540
KVMRDNIASV FINPVI                                                 556

SEQ ID NO: 8            moltype = DNA  length = 1671
FEATURE                 Location/Qualifiers
misc_feature            1..1671
                        note = Synthetic - Engineered valencene synthase
source                  1..1671
                        mol_type = other DNA
                        organism = synthetic construct
SEQUENCE: 8
atggcaaccc aggtgagtgc aagcagcctg gcccaaatcc ctcagccgaa aaaccgcccg  60
gttgcaaact tccaccctaa tatctggggc gatcagttca tcacctatac cccggaagat  120
aaagtgacaa gggccaaaaa agaggagcag atcgaggacc tgaaaaaaga ggtgaagcgc  180
aagctgaccg cagccgcagt ggcaaacccg agccaactgt taaacttcat cgatgccgtg  240
cagcgcctgg gcgttgccta tcacttcgag caggaaatcg aagaagccct acagcacatc  300
tgtaacagct tccacgattg taacgacatg gatggcgact tatacaacat agcattaggt  360
ttccgcttac tgcgtcagca gggctacacc ataagctgcg acatctttaa caagtttacc  420
gacgagcgcg gtcgttttaa agaggcgctg attagcgacg ttcgcggcat gttaggtctg  480
tacgaagccg cacatctgcg cgtgcacggc gaagacattc tggcgaaggc gctggcattc  540
acaaccacac acctgaaggc aatggtggaa agtctgggct accacttagc cgagcaggtt  600
gcccatgcac tgaatcgccc gattcgtaag ggcctggaac gcctggaagc ccgctggtac  660
atcagtgttt atcaggatga agcctttcat gataagaccc tgctggagct ggcaaagctg  720
gatttcaacc tggttcagag cctgcataag gaagagctga gcaacctggc ccgttggtgg  780
aaggagctgg atttcgcaac caagctgccg ttcgccaggg acaggttagt tgaaggctac  840
ttctggatga tgggcgttta cttcgagccg caatacctgc gtggccgccg catcctgacg  900
aaggtgatcg ccatgaccag cattctggac gacatccacg atgcgtacgg gagccctgag  960
gagttaaagc tgttcatcga ggcaatcgag aagtgggatg agagtagcat caaccaactg  1020
ccggagtata tgaaactgtg cttcgtggcc ctgattgatg tttacaatga gattgaagag  1080
gagatggaga aagaggggaa ccagtaccgc atccactacc tgaaagaggt gatgaagaat  1140
caggtgcgcg catacttcgc agaggccaaa tggctgcatg atgagcatgt tcctgccttc  1200
gaggagtaca tgcgcgtggc attagccagc agtggttact gtctgttagc cgttacgagc  1260
ttcgtgggta tgggcgagat cgtgaccaaa gaggcattcg actgggtgac gagcgacccg  1320
aagctgatga gcagcagcaa caccatcacc cgtctgatgg acgacatcaa gagccacaag  1380
ttcgagcaga aacgcggtca cgttaccagc gccgtggagt gctacatgaa gcagtacggc  1440
gtgacagagg agcaagtgta cagcgagttc aagaaacaaa tcgagaacgc ctggctggac  1500
atcaaccaag agtgcctgaa accgaccgca gtgccgatgc ctctgttagc ccgtctgctg  1560
aatttcacac gcacgatgga cgttatctac aaggaggaag atagctacac ccacgttggt  1620
aaggtgatgc gcgacaacat cgccagtgtg ttcatcaacc cggtgatcta a          1671

SEQ ID NO: 9            moltype = AA  length = 556
FEATURE                 Location/Qualifiers
REGION                  1..556
                        note = Synthetic - Engineered valencene synthase
source                  1..556
                        mol_type = protein
                        organism = synthetic construct
SEQUENCE: 9
MATQVSASSL AQIPQPKNRP VANFHPNIWG DQFITYTPED KVTRAKKEEQ IEDLKKEVKR  60
KLTAAAVANP SQLLNFIDAV QRLGVAYHFE QEIEEALQHI CNSFHDCNDM DGDLYNIALG  120
FRLLRQQGYT ISCDIFNKFT DERGRFKEAL ISDVRGMLGL YEAAHLRVHG EDILAKALAF  180
TTTHLKAMVE SLGYHLAEQV AHALNRPIRK GLERLEARWY ISVYQDEAFH DKTLLELAKL  240
DFNLVQSLHK EELSNLARWW KELDFATKLP FARDRLVEGY FWMMGVYFEP QYLRGRRILT  300
KVIALTSILD DIHDAYGTPE ELKLFIEAIE KWDESSINQL PEYMKLCYVA LLDVYNEIEE  360
EMEKEGNQYR IHYLKEVMKN QVRAYFAEAK WLHDEHVPAF EEYMRVALAS SGYCLLAVTS  420
FVGMGEIVTK EAFDWVTSDP RIMSSSNTIT RLMDDIKSHK FEQKRGHVTS AVECYMKQYA  480
VTEEQVYSEF KKQIENAWLD INQECLKPTA VPMPLLARLL NFTRTMDVIY KEEDSYTHVG  540
KTMRDNIASV FINPVI                                                 556

SEQ ID NO: 10           moltype = DNA  length = 1671
FEATURE                 Location/Qualifiers
misc_feature            1..1671
```

```
                        note = Synthetic - Engineered valencene synthase
source                  1..1671
                        mol_type = other DNA
                        organism = synthetic construct
SEQUENCE: 10
atggcaaccc aggtgagtgc aagcagcctg gcccaaatcc ctcagccgaa aaaccgcccg  60
gttgcaaact tccaccctaa tatctggggc gatcagttca tcacctatac cccggaagat  120
aaagtgacaa gggccaaaaa agaggagcag atcgaggacc tgaaaaaaga ggtgaagcgc  180
aagctgaccg cagccgcagt ggcaaacccg agccaactgt taaacttcat cgatgccgtg  240
cagcgcctgg gcgttgccta tcacttcgag caggaaatcg aagaagccct acagcacatc  300
tgtaacagct tccacgattg taacgacatg gatggcgact tatacaacat agcattaggt  360
ttccgcttac tgcgtcagca gggctacacc ataagctgcg acatctttaa caagtttacc  420
gacgagcgcg gtcgttttaa agaggcgctg attagcgacg ttcgcggcat gttaggtctg  480
tacgaagccg cacatctgcg cgtgcacggc gaagacattc tggcgaaggc gctggcattc  540
acaaccacac acctgaaggc aatggtggaa agtctgggct accacttagc cgagcaggtt  600
gcccatgcac tgaatcgccc gattcgtaag ggcctggaac gcctggaagc ccgctggtac  660
atcagtgttt atcaggatga agcctttcat gataagaccc tgctggagct ggcaaagctg  720
gatttcaacc tggttcagag cctgcataag gaagagctga gcaacctggc ccgttggtgg  780
aaggagctgg atttcgcaac caagctgccg ttcgccaggg acaggttagt tgaaggctac  840
ttctggatga tgggcgttta cttcgagccg caatacctgc gtggccgccg catcctgacg  900
aaggtgatcg ccctgaccag cattctggac gacatccacg atgcgtacgg gacccctgag  960
gagttaaagc tgttcatcga ggcaatcgag aagtgggatg agagtagcat caaccaactg  1020
ccggagtata tgaaactgtg ctatgtggcc ctgctggatg tttacaatga gattgaagag  1080
gagatggaga aagaggggaa ccagtaccgc atccactacc tgaaagaggt gatgaagaat  1140
caggtgcgcg catacttcgc agaggccaaa tggctgcatg atgagcatgt tcctgccttc  1200
gaggagtaca tgcgcgtggc attagccagc agtggttact gtctgttagc cgttacgagc  1260
ttcgtgggta tgggcgagat cgtgaccaaa gaggcattcg actgggtgac gagcgacccg  1320
cgtattatga gcagcagcaa caccatcacc cgtctgatgg acgacatcaa gagccacaag  1380
ttcgagcaga aacgcggtca cgttaccagc gccgtggagt gctacatgaa gcagtacgca  1440
gtgacagagg agcaagtgta cagcgagttc aagaaacaaa tcgagaacgc ctggctggac  1500
atcaaccaag agtgcctgaa accgaccgca gtgccgatgc ctctgttagc ccgtctgctg  1560
aatttcacac gcacgatgga cgttatctac aaggaggaag atagctacac ccacgttggt  1620
aagaccatgc gcgacaacat cgccagtgtg ttcatcaacc cggtgatcta a           1671

SEQ ID NO: 11           moltype = AA  length = 556
FEATURE                 Location/Qualifiers
REGION                  1..556
                        note = Synthetic - Engineered valencene synthase
source                  1..556
                        mol_type = protein
                        organism = synthetic construct
SEQUENCE: 11
MATQVSASSL AQIPQPKNRP VANFHPNIWG DQFITYTPED KVTRAKKEEQ IEDLKKEVKR  60
KLTAAAVANP SQLLNFIDAV QRLGVAYHFE QEIEEALQHI CNSFHDCNDM DGDLYNIALG  120
FRLLRQQGYT ISCDIFNKFT DERGRFKEAL ISDVRGMLGL YEAAHLRVHG EDILAKALAF  180
TTTHLKAMVE SLGYHLAEQV AHALNRPIRK GLERLEARWY ISVYQDEAFH DKTLLELAKL  240
DFNLVQSLHK EELSNLARWW KELDFATKLP FARDRLVEGY FWMMGVYFEP QYLRGRRILT  300
KVIALTSILD DIHDAYGTPE ELKLFIEAIE KWDESSINQL PEYMKLCYVA LLDVYNEIEE  360
EMEKEGNQYR IHYLKEVMKN QVRAYFAEAK WLHDEHVPAF EEYMRVALAS SGYCLLAVTS  420
FVGMGEIVTK EAFDWVTSDP RIMSSSNTIT RLMDDIKSHK FEQKRGHVTS AVECYMKQYA  480
VTEEQVYSEF KKQIENAWLD INQECLKPTA VPMPLLARLL NFTRTMDVIY KEEDSYTHVG  540
KTMRDNIASV FINPVI                                                  556

SEQ ID NO: 12           moltype = AA  length = 548
FEATURE                 Location/Qualifiers
source                  1..548
                        mol_type = protein
                        organism = Citrus sinensis
SEQUENCE: 12
MASGETFRPT ADFHPSLWRN HFLKGASDFK TVDHTATQER HEALKEEVRR MITDAEDKPV  60
QKLRLIDEVQ RLGVAYHFEK EIGDAIQKLC PIYIDSNRAD LHTVSLHFRL LRQQGIKISC  120
DVFEKFKDDE GRFKSSLIND VQGMLSLYEA AYMAVRGEHI LDEAIAFTTT HLKSLVAQDH  180
VTPKLAEQIN HALYRPLRKT LPRLEARYFM SMINSTSDHL CNKTLLNFAK LDFNILLELH  240
KEELNELTKW WKDLDFTTKL PYARDRLVEL YFWDLGTYFE PQYAFGRKIM TQLNYILSII  300
DDTYDAYGTL EELSLFTEAV QRWNIEAVDM LPEYMKLIYR TLLDAFNEIE EDMAKQGRSH  360
CVRYAKEENQ KVIGAYSVQA KWFSEGYVPT IEEYMPIALT SCAYTFVITN SFLGMGDFAT  420
KEVFEWISNN PKVVKAASVI CRLMDDMQGH EFEQKRGHVA SAIECYTKQH GVSKEEAIKM  480
FEEEVANAWK DINEELMMKP TVVARPLLGT ILNLARAIDF IYKEDDGYTH SYLIKDQIAS  540
VLGDHVPF                                                           548

SEQ ID NO: 13           moltype = AA  length = 513
FEATURE                 Location/Qualifiers
source                  1..513
                        mol_type = protein
                        organism = Zingiber zerumbet
SEQUENCE: 13
MEAISLFSPF FFITLFLGFF ITLLIKRSSR SSVHKQQVLL ASLPPSPPRL PLIGNIHQLV  60
GGNPHRILLQ LARTHGPLIC LRLGQVDQVV ASSVEAVEEI IKRHDLKFAD RPRDLTFSRI  120
FFYDGNAVVM TPYGGEWKQM RKIYAMELLN SRRVKSFAAI REDVARKLTG EIAHKAFAQT  180
```

```
PVINLSEMVM SMINAIVIRV AFGDKCKQQA YFLHLVKEAM SYVSSFSVAD MYPSLKFLDT  240
LTGLKSKLEG VHGKLDKVFD EIIAQRQAAL AAEQAEEDLI IDVLLKLKDE GNQEFPITYT  300
SVKAIVMEIF LAGTETSSSV IDWVMSELIK NPKAMEKVQK EMREAMQGKT KLEESDIPKF  360
SYLNLVIKET LRLHPPGPLL FPRECRETCE VMGYRVPAGA RLLINAFALS RDEKYWGSDA  420
ESFKPERFEG ISVDFKGSNF EFMPFGAGRR ICPGMTFGIS SVEVALAHLL FHFDWQLPQG  480
MKIEDLDMME VSGMSATRRS PLLVLAKLII PLP                              513

SEQ ID NO: 14          moltype = AA  length = 512
FEATURE                Location/Qualifiers
source                 1..512
                       mol_type = protein
                       organism = Zingiber zerumbet
SEQUENCE: 14
MALLLAVFFF FITLFLGFFI TLLIKRSSRS SVHKQQVLLA SLPPSPPRLP LIGNIHQLVG  60
GNPHRILLQL ARTHGPLICL RLGQVDQVVA SSVEAVEEII KRHDLKFADR PRDLTFSRIF  120
FYDGNAVVMT PYGGEWKQMR KIYAMELLNS RRVKSFAAIR EDVARKLTGE IAHKAFAQTP  180
VINLSEMVMS MINAIVIRVA FGDKCKQQAY FLHLVKEAMS YVSSFSVADM YPSLKFLDTL  240
TGLKSKLEGV HGKLDKVFDE IIAQRQAALA AEQAEEDLII DVLLKLKDEG NQEFPITYTS  300
VKAIVMEIFL AGTETSSSVI DWVMSELIKN PKAMEKVQKE MREAMQGKTK LEESDIPKFS  360
YLNLVIKETL RLHPPGPLLF PRECRETCEV MGYRVPAGAR LLINAFALSR DEKYWGSDAE  420
SFKPERFEGI SVDFKGSNFE FMPFGAGRRI CPGMTFGISS VEVALAHLLF HFDWQLPQGM  480
KIEDLDMMEV SGMSATRRSP LLVLAKLIIP LP                               512

SEQ ID NO: 15          moltype = DNA  length = 1536
FEATURE                Location/Qualifiers
source                 1..1536
                       mol_type = other DNA
                       organism = Zingiber zerumbet
SEQUENCE: 15
atggctctgt tattagcagt gttcttcttt ttcattacgc tgtttctggg tttctttatt  60
acgctgctga ttaaacgctc gtcccgtagc tctgtccata aacagcaagt gctgctggcc  120
tctctgccgc cgagtccgcc gcgcctgccg ctgattggca acatccatca actggtgggc  180
ggcaacccgc atcgtattct gctgcaactg gcgcgtaccc acggcccgct gatctgcctg  240
cgtctgggtc aggttgatca agtggttgca agttccgtgg aagctgttga agaaattatc  300
aaacgtcacg acctgaaatt tgcagatcgt ccgcgcgacc tgacctttag ccgtattttc  360
ttttatgatg gtaacgctgt cgtgatgacg ccgtacggcg gtgaatggaa acagatgcgt  420
aaaatctatg caatggaact gctgaacagc cgtcgtgtga aatcttttgc ggccattcgt  480
gaagacgttg cacgcaaact gaccggcgaa atcgctcaca aagcattcgc tcagacgccg  540
gtcattaacc tgtctgaaat ggtgatgagt atgatcaatg cgattgtcat ccgcgtggcc  600
tttggtgata aatgtaaaca gcaagcatac ttcctgcatc tggtgaaaga agctatgtcc  660
tatgtttcat cgttttcagt cgcggatatg tacccgtccc tgaaattcct ggacaccctg  720
acgggcctga aagcaaact ggaaggcgtt cacggtaaac tggataaagt cttcgacgaa  780
atcatcgcac agcgtcaagc agcgctggcg gcggaacagg ctgaagaaga tctgattatc  840
gacgtgctgc tgaaactgaa agatgaaggc aaccaggaat ttccgattac ctatacgtca  900
gttaaagcga ttgtcatgga aatcttcctg gccggcaccg aaaccagcag cagcgtgatt  960
gactgggtta tgagtgaact gatcaaaaac ccgaaagcga tggaaaaagt gcagaaagaa  1020
atgcgtgaag ccatgcaagg caaaaccaaa ctggaagaat cggatattcc gaaatttagc  1080
tacctgaatc tggttatcaa agaaaccctg cgtctgcatc cgccgggtcc gctgctgttc  1140
ccgcgtgaat gccgcgaaac ctgcgaagtg atgggctatc gtgttccggc gggtgcccgc  1200
ctgctgatta acgcatttgc tctgtctcgt gatgaaaaat actggggttc cgacgccgaa  1260
tcatttaaac cggaacgctt tgaaggcatc tctgtggatt tcaaaggtag taattttgaa  1320
tttatgccgt tcggcgcggg ccgtcgtatt tgtccgggca tgacctttgg tatctcctca  1380
gttgaagtcg cgctggccca tctgctgttt cacttcgatt ggcaactgcc gcaaggcatg  1440
aaaattgaag atctggacat gatggaagtc tcgggtatga gcgcaacccg tcgtagcccg  1500
ctgctggttc tggccaaact gattatcccg ctgccg                           1536

SEQ ID NO: 16          moltype = AA  length = 496
FEATURE                Location/Qualifiers
source                 1..496
                       mol_type = protein
                       organism = Barnadesia spinosa
SEQUENCE: 16
MELTLTTSLG LAVFVFILFK LLTGSKSTKN SLPEAWRLPI IGHMHHLVGT LPHRGVTDMA  60
RKYGSLMHLQ LGEVSTIVVS SPRWAKEVLT TYDITFANRP ETLTGEIVAY HNTDIVLSPY  120
GEYWRQLRKL CTLELLSAKK VKSFQSLREE ECWNLVKEVR SSGSGSPVDL SESIFKLIAT  180
ILSRAAFGKG IKDQREFTEI VKEILRLTGG FDVADIFPSK KILHHLSGKR AKLTNIHNKL  240
DSLINNIVSE HPGSRTSSSQ ESLLDVLLRL KDSAELPLTS DNVKAVILDM FGAGTDTSSA  300
TIEWAISELI RCPRAMEKVQ TELRQALNGK ERIQEEDIQE LSYLKLVIKE TLRLHPPLPL  360
VMPRECREPC VLAGYEIPTK TKLIVNVFAI NRDPEYWKDA ETFMPERFEN SPINIMGSEY  420
EYLPFGAGRR MCPGAALGLA NVELPLAHIL YYFNWKLPNG ARLDELDMSE CFGATVQRKS  480
ELLLVPTAYK TANNSA                                                 496

SEQ ID NO: 17          moltype = AA  length = 496
FEATURE                Location/Qualifiers
source                 1..496
                       mol_type = protein
                       organism = Barnadesia spinosa
SEQUENCE: 17
MALLLAVFLG LAVFVFILFK LLTGSKSTKN SLPEAWRLPI IGHMHHLVGT LPHRGVTDMA  60
```

```
RKYGSLMHLQ LGEVSTIVVS SPRWAKEVLT TYDITFANRP ETLTGEIVAY HNTDIVLSPY  120
GEYWRQLRKL CTLELLSAKK VKSFQSLREE ECWNLVKEVR SSGSGSPVDL SESIFKLIAT  180
ILSRAAFGKG IKDQREFTEI VKEILRLTGG FDVADIFPSK KILHHLSGKR AKLTNIHNKL  240
DSLINNIVSE HPGSRTSSSQ ESLLDVLLRL KDSAELPLTS DNVKAVILDM FGAGTDTSSA  300
TIEWAISELI RCPRAMEKVQ TELRQALNGK ERIQEEDIQE LSYLKLVIKE TLRLHPPLPL  360
VMPRECREPC VLAGYEIPTK TKLIVNVFAI NRDPEYWKDA ETFMPERFEN SPINIMGSEY  420
EYLPFGAGRR MCPGAALGLA NVELPLAHIL YYFNWKLPNG ARLDELDMSE CFGATVQRKS  480
ELLLVPTAYK TANNSA                                                 496

SEQ ID NO: 18          moltype = DNA  length = 1488
FEATURE                Location/Qualifiers
source                 1..1488
                       mol_type = other DNA
                       organism = Barnadesia spinosa
SEQUENCE: 18
atggctctgt tattagcagt tttcctgggc ctggctgtct tcgtctttat cctgttcaaa  60
ctgctgaccg gctcaaaatc aaccaaaaat tcactgccgg aagcatggcg tctgccgatc  120
attggccaca tgcatcacct ggttggcacg ctgccgcatc gcggtgtgac cgacatggcg  180
cgtaaatacg gcagcctgat gcatctgcaa ctgggcgaag tgagcaccat tgtcgtctca  240
tcgccgcgtt gggcaaaaga agtgctgacg acgtatgata ttacctttgc gaatcgcccg  300
gaaaccctga ccggcgaaat tgttgcgtac cacaacacgg atattgtgct gtcaccgtat  360
ggcgaatact ggcgccaact gcgtaaactg tgcacgctgg aactgctgag cgccaaaaaa  420
gtgaaaagtt ttcagtcgct gcgtgaagaa gaatgctgga atctggtgaa agaagtgcgt  480
tcgagcggct caggttcccc ggtcgatctg tcggaatcca tctttaaact gattgcaacc  540
attctgagcc gcgcagcgtt tggcaaaggt atcaaagatc agcgtgaatt taccgaaatt  600
gtgaaagaaa tcctgcgcct gacgggcggt tttgatgtgg cggatatttt cccgtccaaa  660
aagatcctgc accacctgag cggcaaacgt gcgaaactga ccaacatcca caacaaactg  720
gattccctga ttaataacat tgtttctgaa catccgggtt cgcgtacctc gtcgagccag  780
gaaagcctgc tggatgtgct gctgcgcctg aaagattccg cggaactgcc gctgacctcg  840
gacaatgtta aagccgtgat cctggatatg ttcggtgcgg gcacggatac gtcgagcgcc  900
acgattgaat gggcgatcag cgaactgatc cgctgcccgc gtgcaatgga aaaagtgcaa  960
acggaactgc gtcaagcgct gaatggtaaa gaacgcattc aggaagaaga tattcaggaa  1020
ctgtcctatc tgaaactggt cattaaagaa accctgcgcc tgcatccgcc gctgccgctg  1080
gtgatgccgc gtgaatgtcg tgaaccgtgt gtcctggcgg gttacgaaat cccgaccaaa  1140
acgaaactga ttgtgaatgt ctttgccatc aatcgtgacc cggaatactg gaaagatgca  1200
gaaaccttca tgccggaacg ctttgaaaac agcccgatta acatcatggg tagtgaatat  1260
gaatacctgc cgtttggcgc aggccgccgt atgtgtccgg gtgcagctct gggtctggcg  1320
aatgtggaac tgccgctggc gcacatcctg tattatttta actggaaact gccgaatggc  1380
gctcgcctgg atgaactgga tatgtcggaa tgctttggcg cgacggtcca acgcaaaagc  1440
gaactgctgc tggtcccgac ggcatacaaa acggcaaaca actccgca              1488

SEQ ID NO: 19          moltype = AA  length = 502
FEATURE                Location/Qualifiers
source                 1..502
                       mol_type = protein
                       organism = Hyoscyamus muticus
SEQUENCE: 19
MQFFSLVSIF LFLSFLFLLR KWKNSNSQSK KLPPGPWKLP LLGSMLHMVG GLPHHVLRDL  60
AKKYGPLMHL QLGEVSAVVV TSPDMAKEVL KTHDIAFASR PKLLAPEIVC YNRSDIAFCP  120
YGDYWRQMRK ICVLEVLSAK NVRSFSSIRR DEVLRLVNFV RSSTSEPVNF TERLFLFTSS  180
MTCRSAFGKV FKEQETFIQL IKEVIGLAGG FDVADIFPSL KFLHVLTGME GKIMKAHHKV  240
DAIVEDVINE HKKNLAMGKT NGALGGEDLI DVLLRLMNDG GLQFPITNDN IKAIIFDMFA  300
AGTETSSSTL VWAMVQMMRN PTILAKAQAE VREAFKGKET FDENDVEELK YLKLVIKETL  360
RLHPPVPLLV PRECREETEI NGYTIPVKTK VMVNVWALGR DPKYWDDADN FKPERFEQCS  420
VDFIGNNFEY LPFGGGRRIC PGISFGLANV YLPLAQLLYH FDWKLPTGME PKDLDLTELV  480
GVTAARKSDL MLVATPYQPS RE                                          502

SEQ ID NO: 20          moltype = AA  length = 508
FEATURE                Location/Qualifiers
source                 1..508
                       mol_type = protein
                       organism = Hyoscyamus muticus
SEQUENCE: 20
MALLLAVFFF SLVSIFLFLS FLFLLRKWKN SNSQSKKLPP GPWKLPLLGS MLHMVGGLPH  60
HVLRDLAKKY GPLMHLQLGE VSAVVVTSPD MAKEVLKTHD IAFASRPKLL APEIVCYNRS  120
DIAFCPYGDY WRQMRKICVL EVLSAKNVRS FSSIRRDEVL RLVNFVRSST SEPVNFTERL  180
FLFTSSMTCR SAFGKVFKEQ ETFIQLIKEV IGLAGGFDVA DIFPSLKFLH VLTGMEGKIM  240
KAHHKVDAIV EDVINEHKKN LAMGKTNGAL GGEDLIDVLL RLMNDGGLQF PITNDNIKAI  300
IFDMFAAGTE TSSSTLVWAM VQMMRNPTIL AKAQAEVREA FKGKETFDEN DVEELKYLKL  360
VIKETLRLHP PVPLLVPREC REETEINGYT IPVKTKVMVN VWALGRDPKY WDDADNFKPE  420
RFEQCSVDFI GNNFEYLPFG GGRRICPGIS FGLANVYLPL AQLLYHFDWK LPTGMEPKDL  480
DLTELVGVTA ARKSDLMLVA TPYQPSRE                                    508

SEQ ID NO: 21          moltype = DNA  length = 1524
FEATURE                Location/Qualifiers
source                 1..1524
                       mol_type = other DNA
                       organism = Hyoscyamus muticus
SEQUENCE: 21
```

```
atggctctgt tattagcagt tttcttcttc tccctggtct caatctttct gttcctgtcc  60
tttctgttcc tgctgcgtaa atggaaaaac tcaaactccc aatcgaaaaa actgccgccg  120
ggtccgtgga aactgccgct gctgggctct atgctgcaca tggttggcgg cctgccgcat  180
cacgttctgc gtgatctggc gaaaaaatat ggtccgctga tgcatctgca actgggcgaa  240
gtctccgccg tggttgtcac ctcaccggat atggcaaaag aagtgctgaa aacgcatgac  300
attgcgttcg cctcccgtcc gaaactgctg gccccggaaa ttgtgtgcta caaccgctca  360
gatattgcat tttgtccgta tggtgactac tggcgtcaaa tgcgcaaaat ttgcgtcctg  420
gaagtgctgt cggccaaaaa tgtgcgcagc tttagctcta ttcgtcgtga tgaagttctg  480
cgtctggtta acttcgtccg cagttccacc tcggagccgg tgaattttac ggaacgtctg  540
tttctgttca cctcatcgat gacctgccgt agcgcatttg gtaaagtttt caaagaacag  600
gaaaccttca ttcaactgat caaagaagtc attggcctgg ccggcggttt tgatgtggca  660
gacatctttc cgagtctgaa attcctgcat gttctgaccg gcatggaagg caaaattatg  720
aaagctcatc acaaagtcga tgcgattgtg gaagacgtta tcaacgaaca caagaaaaac  780
ctggcgatgg gcaaaacgaa cggcgcactg ggcggtgaag atctgatcga cgttctgctg  840
cgtctgatga atgatggcgg cctgcaattt ccgatcacca acgataatat caaagctatt  900
atctttgata tgtttgcggc gggcaccgaa accagcagca gcaccctggt gtgggcgatg  960
gtgcagatga tgcgtaaccc gacgattctg gcaaaagctc aagcggaagt gcgcgaagcc  1020
ttcaaaggca aagaaacctt tgatgaaaat gacgttgaag aactgaaata tctgaaactg  1080
gtcatcaaag aaacgctgcg tctgcatccg ccggttccgc tgctggtccc gcgtgaatgc  1140
cgcgaagaaa ccgaaattaa cggttatacc atcccggtta aaacgaaagt gatggttaat  1200
gtctgggctc tgggccgtga tccgaaatac tgggatgacg cggacaactt taaaccggaa  1260
cgctttgaac agtgctctgt ggatttcatc ggcaacaact ttgaatatct gccgtttggc  1320
ggtggccgtc gcatttgtcc gggtatcagc ttcggcctgg ctaatgttta tctgccgctg  1380
gcgcaactgc tgtaccactt tgattggaaa ctgccgaccg gcatggaacc gaaagatctg  1440
gacctgaccg aactggtggg cgttacggca gctcgtaaat ctgatctgat gctggttgcg  1500
accccgtacc agccgagccg tgaa                                          1524
```

```
SEQ ID NO: 22          moltype = AA  length = 488
FEATURE                Location/Qualifiers
source                 1..488
                       mol_type = protein
                       organism = Lactuca sativa
SEQUENCE: 22
MELSITTSIA LATIVFFLYK LATRPKSTKK QLPEASRLPI IGHMHHLIGT MPHRGVMDLA  60
RKHGSLMHLQ LGEVSTIVVS SPKWAKEILT TYDITFANRP ETLTGEIIAY HNTDIVLAPY  120
GEYWRQLRKL CTLELLSVKK VKSFQSIREE ECWNLVKEVK ESGSGKPINL SESIFTMIAT  180
ILSRAAFGKG IKDQREFTEI VKEILRQTGG FDVADIFPSK KFLHHLSGKR ARLTSIHKKL  240
DNLINNIVAE HHVSTSSKAN ETLLDVLLRL KDSAEFPLTA DNVKAIILDM FGAGTDTSSA  300
TVEWAISELI RCPRAMEKVQ AELRQALNGK EKIQEEDIQD LAYLNLVIRE TLRLHPPLPL  360
VMPRECREPV NLAGYEIANK TKLIVNVFAI NRDPEYWKDA EAFIPERFEN NPNNIMGADY  420
EYLPFGAGRR MCPGAALGLA NVQLPLANIL YHFNWKLPNG ASHDQLDMTE SFGATVQRKT  480
ELLLVPSF                                                            488
```

```
SEQ ID NO: 23          moltype = AA  length = 488
FEATURE                Location/Qualifiers
source                 1..488
                       mol_type = protein
                       organism = Lactuca sativa
SEQUENCE: 23
MALLLAVFIA LATIVFFLYK LATRPKSTKK QLPEASRLPI IGHMHHLIGT MPHRGVMDLA  60
RKHGSLMHLQ LGEVSTIVVS SPKWAKEILT TYDITFANRP ETLTGEIIAY HNTDIVLAPY  120
GEYWRQLRKL CTLELLSVKK VKSFQSIREE ECWNLVKEVK ESGSGKPINL SESIFTMIAT  180
ILSRAAFGKG IKDQREFTEI VKEILRQTGG FDVADIFPSK KFLHHLSGKR ARLTSIHKKL  240
DNLINNIVAE HHVSTSSKAN ETLLDVLLRL KDSAEFPLTA DNVKAIILDM FGAGTDTSSA  300
TVEWAISELI RCPRAMEKVQ AELRQALNGK EKIQEEDIQD LAYLNLVIRE TLRLHPPLPL  360
VMPRECREPV NLAGYEIANK TKLIVNVFAI NRDPEYWKDA EAFIPERFEN NPNNIMGADY  420
EYLPFGAGRR MCPGAALGLA NVQLPLANIL YHFNWKLPNG ASHDQLDMTE SFGATVQRKT  480
ELLLVPSF                                                            488
```

```
SEQ ID NO: 24          moltype = DNA  length = 1464
FEATURE                Location/Qualifiers
source                 1..1464
                       mol_type = other DNA
                       organism = Lactuca sativa
SEQUENCE: 24
atggctctgt tattagcagt tttcatcgca ctggctacca tcgtcttctt cctgtataaa  60
ctggcaacgc gcccgaaatc taccaaaaaa caactgccgg aagcgagccg tctgccgatt  120
atcggccaca tgcatcacct gattggcacc atgccgcacc gtggtgtcat ggatctggcc  180
cgcaaacatg gctcgctgat gcatctgcaa ctgggcgaag tgagcaccat tgtggttagc  240
tctccgaaat gggcaaaaga aattctgacc acctatgata ttacctttgc taaccgcccg  300
gaaaccctga cgggcgaaat tatcgcgtac cataatacgg acattgtgct ggccccgtat  360
ggtgaatact ggcgtcaact gcgtaaactg tgcaccctgg aactgctgtc cgttaaaaaa  420
gtcaaatcat ttcaatcgat tcgtgaagaa gaatgttgga acctggtgaa agaagttaaa  480
gaaagcggct ctggtaaacc gattaatctg agtgaatcca tcttcaccat gattgcgacg  540
atcctgagtc gtgcggcctt tggcaaaggt attaaagatc agcgcgaatt taccgaaatt  600
gtcaaagaaa tcctgcgtca aacgggcggt ttcgatgtgg cagacatttt tccgagcaaa  660
aaattcctgc atcacctgtc tggcaaacgt gctcgcctga ccagtatcca taaaaaactg  720
gataacctga tcaacaatat cgtcgcggaa catcatgtga gcaccagcag caaagcgaat  780
gaaacgctgc tggatgttct gctgcgcctg aaagacagtg ccgaatttcc gctgaccgca  840
```

```
gacaacgtca aagctattat cctggatatg ttcggtgcag gcaccgatac cagcagcgca  900
acggtggaat gggccattag cgaactgatc cgttgcccgc gcgcaatgga aaaagttcag  960
gcagaactgc gtcaagctct gaacggtaaa gaaaaaatcc aggaagaaga tattcaagac  1020
ctggcctatc tgaatctggt gattcgtgaa accctgcgtc tgcacccgcc gctgccgctg  1080
gttatgccgc gtgaatgccg tgagccggtg aacctggcgg gctatgaaat cgccaataaa  1140
accaaactga tcgtcaatgt gtttgcgatt aaccgtgacc cggaatactg gaaagacgcg  1200
gaagccttta tcccggaacg ttttgaaaac aatccgaaca atatcatggg tgcagattat  1260
gaatacctgc cgtttggcgc tggtcgtcgc atgtgtccgg gcgcagctct gggtctggca  1320
aacgttcaac tgccgctggc gaacattctg taccatttca actggaaact gccgaatggc  1380
gcgtcccacg atcaactgga catgaccgaa tcatttggtg ccaccgtgca acgtaaaacg  1440
gaactgctgc tggttccgag cttc                                        1464
```

```
SEQ ID NO: 25          moltype = AA  length = 504
FEATURE                Location/Qualifiers
source                 1..504
                       mol_type = protein
                       organism = Nicotiani tabacum
SEQUENCE: 25
MQFFSLVSIF LFLSFLFLLR KWKNSNSQSK KLPPGPWKIP ILGSMLHMIG GEPHHVLRDL  60
AKKYGPLMHL QLGEISAVVV TSRDMAKEVL KTHDVVFASR PKIVAMDIIC YNQSDIAFSP  120
YGDHWRQMRK ICVMELLNAK NVRSFSSIRR DEVVRLIDSI RSDSSSGELV NFTQRIIWFA  180
SSMTCRSAFG QVLKGQDIFA KKIREVIGLA EGFDVVDIFP TYKFLHVLSG MKRKLLNAHL  240
KVDAIVEDVI NEHKKNLAAG KSNGALGGED LIDVLLRLMN DTSLQFPITN DNIKAVIVDM  300
FAAGTETSST TTVWAMAEMM KNPSVFTKAQ AEVREAFRDK VSFDENDVEE LKYLKLVIKE  360
TLRLHPPSPL LVPRECREDT DINGYTIPAK TKVMVNVWAL GRDPKYWDDA ESFKPERFEQ  420
CSVDFFGNNF EFLPFGGGRR ICPGMSFGLA NLYLPLAQLL YHFDWKLPTG IMPRDLDLTE  480
LSGITIARKG GLYLNATPYQ PSRE                                        504
```

```
SEQ ID NO: 26          moltype = AA  length = 510
FEATURE                Location/Qualifiers
source                 1..510
                       mol_type = protein
                       organism = Nicotiani tabacum
SEQUENCE: 26
MALLLAVFFF SLVSIFLFLS FLFLLRKWKN SNSQSKKLPP GPWKIPILGS MLHMIGGEPH  60
HVLRDLAKKY GPLMHLQLGE ISAVVVTSRD MAKEVLKTHD VVFASRPKIV AMDIICYNQS  120
DIAFSPYGDH WRQMRKICVM ELLNAKNVRS FSSIRRDEVV RLIDSIRSDS SSGELVNFTQ  180
RIIWFASSMT CRSAFGQVLK GQDIFAKKIR EVIGLAEGFD VVDIFPTYKF LHVLSGMKRK  240
LLNAHLKVDA IVEDVINEHK KNLAAGKSNG ALGGEDLIDV LLRLMNDTSL QFPITNDNIK  300
AVIVDMFAAG TETSSTTTVW AMAEMMKNPS VFTKAQAEVR EAFRDKVSFD ENDVEELKYL  360
KLVIKETLRL HPPSPLLVPR ECREDTDING YTIPAKTKVM VNVWALGRDP KYWDDAESFK  420
PERFEQCSVD FFGNNFEFLP FGGGRRICPG MSFGLANLYL PLAQLLYHFD WKLPTGIMPR  480
DLDLTELSGI TIARKGGLYL NATPYQPSRE                                  510
```

```
SEQ ID NO: 27          moltype = DNA  length = 1530
FEATURE                Location/Qualifiers
source                 1..1530
                       mol_type = other DNA
                       organism = Nicotiani tabacum
SEQUENCE: 27
atggctctgt tattagcagt tttcttcttc tccctggtct caatcttcct gttcctgtcc  60
tttctgttcc tgctgcgtaa atggaaaaac tctaatagcc aatccaaaaa actgccgccg  120
ggtccgtgga aaattccgat cctgggctct atgctgcaca tgattggcgg tgaaccgcat  180
catgtgctgc gtgatctggc gaaaaaatat ggtccgctga tgcatctgca actgggcgaa  240
atctctgcgg tggttgtcac gagtcgtgac atggccaaag aagtgctgaa aacccatgat  300
gtggtttttg catctcgccc gaaaatcgtt gctatggata ttatctgcta taaccagtcg  360
gacatcgcgt tcagcccgta cggtgatcac tggcgtcaaa tgcgcaaaat ttgtgtcatg  420
gaactgctga acgccaaaaa tgtgcgcagt tttagctcta ttcgtcgtga tgaagtcgtg  480
cgtctgattg attccatccg ctcagacagt tcctcaggcg aactggtgaa ttttacgcag  540
cgtattatct ggttcgcatc gagcatgacc tgccgctcgg cttttggtca ggttctgaaa  600
ggccaagata tttttgcgaa gaaaattcgt gaagtgatcg gtctggccga aggcttcgat  660
gttgtggata tttttccgac ctataaattc ctgcatgtcc tgagcggtat gaaacgcaaa  720
ctgctgaacg cgcacctgaa agttgatgcc attgtcgaag acgtgatcaa cgaacataag  780
aaaaacctgg cggcgggtaa atccaacggc gcactgggcg gtgaagatct gattgacgtg  840
ctgctgcgtc tgatgaatga taccagcctg caatttccga tcaccaacga caacattaaa  900
gcggtgatcg ttgatatgtt cgcggcgggc accgaaacct ctagtaccac gaccgtttgg  960
gcgatggccg aaatgatgaa aaacccgtcg gtgtttacca aagcacaagc ggaagtgcgt  1020
gaagcgtttc gtgataaagt tagcttcgat gaaaatgatg tggaagaact gaaatacctg  1080
aaactggtga ttaaagaaac gctgcgtctg catccgccga gcccgctgct ggttccgcgt  1140
gaatgccgtg aagataccga cattaacggt tatacgatcc cggcaaaaac caaagtcatg  1200
gtgaatgttt gggctctggg ccgtgacccg aaatactggg atgacgcaga atcctttaaa  1260
ccggaacgct ttgaacagtg ctcagtggat ttctttggta acaactttga atttctgccg  1320
tttggcggtg gccgtcgcat ttgtccgggt atgtccttcg gcctggcgaa cctgtatctg  1380
ccgctggccc aactgctgta ccactttgat tggaaactgc cgacgggtat tatgccgcgt  1440
gatctggacc tgacggaact gtctggcatt accatcgcac gcaaaggtgg cctgtatctg  1500
aatgctaccc cgtaccagcc gagtcgtgaa                                  1530
```

```
SEQ ID NO: 28          moltype = AA  length = 522
FEATURE                Location/Qualifiers
```

```
source                  1..522
                        mol_type = protein
                        organism = Citrus x paradisi
SEQUENCE: 28
MELPLKSIAL TIVIVTVLTW AWRVLNWVWL RPKKLEKFLR QQGLKGNSYR LLFGDLKENS  60
IELKEAKARP LSLDDDIAIR VNPFLHKLVN DYGKNSFMWF GPTPRVNIMN PDQIKAIFTK  120
INDFQKVNSI PLARLLIVGL ATLEGEKWAK HRKLINPAFH QEKLKLMLPA FYLSCIEIIT  180
KWEKQMSVEG SSELDVWPYL ANLTSDVISR TAFGSSYEEG RRIFQLQAEL AELTMQVFRS  240
VHIPGWRFLP TKRNRRMKEI DKEIRASLMG IIKNREKAMR AGEAANNDLL GILMETSFRE  300
IEEHGNNKNV GFSMNDVIEE CKLFYFAGQE TTSVLLNWTM VLLSKHQDWQ ERARQEVLQV  360
FGNNKPDYDG LNHLKIVQMI LYEVLRLYPP VTVLSRAVFK ETKLGNLTLP AGVQIGLPMI  420
LVHQDPELWG DDAVEFKPER FAEGISKAAK NQVSYFPFAL GPRICVGQNF ALVEAKMATA  480
MILQNYSFEL SPSYVHAPTA VPTLHPELGT QLILRKLWCK NN                    522

SEQ ID NO: 29           moltype = AA  length = 523
FEATURE                 Location/Qualifiers
source                  1..523
                        mol_type = protein
                        organism = Citrus x paradisi
SEQUENCE: 29
MALLLAVFIA LTIVIVTVLT WAWRVLNWVW LRPKKLEKFL RQQGLKGNSY RLLFGDLKEN  60
SIELKEAKAR PLSLDDDIAI RVNPFLHKLV NDYGKNSFMW FGPTPRVNIM NPDQIKAIFT  120
KINDFQKVNS IPLARLLIVG LATLEGEKWA KHRKLINPAF HQEKLKLMLP AFYLSCIEII  180
TKWEKQMSVE GSSELDVWPY LANLTSDVIS RTAFGSSYEE GRRIFQLQAE LAELTMQVFR  240
SVHIPGWRFL PTKRNRRMKE IDKEIRASLM GIIKNREKAM RAGEAANNDL LGILMETSFR  300
EIEEHGNNKN VGFSMNDVIE ECKLFYFAGQ ETTSVLLNWT MVLLSKHQDW QERARQEVLQ  360
VFGNNKPDYD GLNHLKIVQM ILYEVLRLYP PVTVLSRAVF KETKLGNLTL PAGVQIGLPM  420
ILVHQDPELW GDDAVEFKPE RFAEGISKAA KNQVSYFPFA LGPRICVGQN FALVEAKMAT  480
AMILQNYSFE LSPSYVHAPT AVPTLHPELG TQLILRKLWC KNN                   523

SEQ ID NO: 30           moltype = DNA  length = 1569
FEATURE                 Location/Qualifiers
source                  1..1569
                        mol_type = other DNA
                        organism = Citrus x paradisi
SEQUENCE: 30
atggctctgt tattagcagt tttcattgct ctgacgattg ttattgttac ggtgctgacc  60
tgggcgtggc gtgtgctgaa ctgggtttgg ctgcgtccga aaaaactgga aaaatttctg  120
cgccagcaag gcctgaaggg taacagctat cgtctgctgt tcggcgatct gaaagaaaat  180
tctattgaac tgaaagaagc gaaagcccgt ccgctgagtc tggatgacga tattgcaatc  240
cgcgttaacc cgtttctgca taaactggtc aacgattacg gcaaaaattc ttttatgtgg  300
ttcggtccga ccccgcgcgt gaacattatg aacccggatc agattaaagc gatctttacg  360
aaaatcaacg atttccaaaa agttaatagc attccgctgg cgcgtctgct gatcgtcggc  420
ctggccaccc tggaaggtga aaaatgggca aaacatcgca aactgattaa cccggctttt  480
caccaagaaa aactgaaact gatgctgccg gcgttctatc tgtcctgcat cgaaattatc  540
acgaaatggg aaaaacagat gtcagtggaa ggtagctctg aactggacgt ttggccgtat  600
ctggccaatc tgaccagcga tgttatttct cgtacggcat ttggcagttc ctacgaagaa  660
ggtcgtcgca tcttccagtt acaggcggaa ctggccgaac tgaccatgca ggtttttcgt  720
tctgtccata ttccgggctg gcgtttcctg ccgacgaaac gcaaccgtcg catgaaagaa  780
attgacaaag aaatccgcgc cagtctgatg ggtattatca aaatcgtga aaaagcaatg  840
cgcgctggcg aagcggccaa caatgatctg ctgggtattc tgatggaaac cagctttcgt  900
gaaatcgaag aacacggcaa caataaaaac gtcggtttca gcatgaatga cgtgatcgaa  960
gaatgtaaac tgttttattt cgctggccag gaaaccacgt cagttctgct gaactggacg  1020
atggtgctgc tgtcgaaaca tcaggattgg caagaacgtg cccgccagga agtcctgcaa  1080
gtgtttggca acaataaacc ggactacgat ggtctgaacc acctgaaaat tgtgcagatg  1140
atcctgtatg aagttctgcg tctgtatccg ccggtgacgg tgctgagccg tgcggtgttt  1200
aaagaaacca aactgggtaa tctgacgctg ccggcaggcg tccagattgg tctgccgatg  1260
atcctggtgc accaggaccc ggaactgtgg ggcgacgatg ctgtggaatt taaaccggaa  1320
cgtttcgcgg aaggtattag taaagcagct aaaaatcagg tttcctattt tccgttcgcg  1380
ctgggtccgc gtatttgcgt cggtcaaaac tttgcactgg tggaagctaa aatggcaacc  1440
gctatgatcc tgcaaaatta tagctttgaa ctgtcaccga gctatgttca tgcgccgacc  1500
gccgttccga cgctgcaccc ggaactgggc acgcaactga ttctgcgtaa actgtggtgt  1560
aaaaacaat                                                         1569

SEQ ID NO: 31           moltype = AA  length = 495
FEATURE                 Location/Qualifiers
source                  1..495
                        mol_type = protein
                        organism = Artemesia annua
SEQUENCE: 31
MKSILKAMAL SLTTSIALAT ILLFVYKFAT RSKSTKKSLP EPWRLPIIGH MHHLIGTTPH  60
RGVRDLARKY GSLMHLQLGE VPTIVVSSPK WAKEILTTYD ITFANRPETL TGEIVLYHNT  120
DVVLAPYGEY WRQLRKICTL ELLSVKKVKS FQSLREEECW NLVQEIKASG SGRPVNLSEN  180
VFKLIATILS RAAFGKGIKD QKELTEIVKE ILRQTGGFDV ADIFPSKKFL HHLSGKRARL  240
TSLRKKIDNL IDNLVAEHTV NTSSKTNETL LDVLLRLKDS AEFPLTSDNI KAIILDMFGA  300
GTDTSSSTIE WAISELIKCP KAMEKVQAEL RKALNGKEKI HEEDIQELSY LNMVIKETLR  360
LHPPLPLVLP RECRQPVNLA GYNIPNKTKL IVNVFAINRD PEYWKDAEAF IPERFENSSA  420
TVMGAEYEYL PFGAGRRMCP GAALGLANVQ LPLANILYHF NWKLPNGVSY DQIDMTESSG  480
ATMQRKTELL LVPSF                                                  495
```

```
SEQ ID NO: 32          moltype = AA  length = 488
FEATURE                Location/Qualifiers
source                 1..488
                       mol_type = protein
                       organism = Artemesia annua
SEQUENCE: 32
MALLLAVFIA LATILLFVYK FATRSKSTKK SLPEPWRLPI IGHMHHLIGT TPHRGVRDLA  60
RKYGSLMHLQ LGEVPTIVVS SPKWAKEILT TYDITFANRP ETLTGEIVLY HNTDVVLAPY  120
GEYWRQLRKI CTLELLSVKK VKSFQSLREE ECWNLVQEIK ASGSGRPVNL SENVFKLIAT  180
ILSRAAFGKG IKDQKELTEI VKEILRQTGG FDVADIFPSK KFLHHLSGKR ARLTSLRKKI  240
DNLIDNLVAE HTVNTSSKTN ETLLDVLLRL KDSAEFPLTS DNIKAIILDM FGAGTDTSSS  300
TIEWAISELI KCPKAMEKVQ AELRKALNGK EKIHEEDIQE LSYLNMVIKE TLRLHPPLPL  360
VLPRECRQPV NLAGYNIPNK TKLIVNVFAI NRDPEYWKDA EAFIPERFEN SSATVMGAEY  420
EYLPFGAGRR MCPGAALGLA NVQLPLANIL YHFNWKLPNG VSYDQIDMTE SSGATMQRKT  480
ELLLVPSF                                                          488

SEQ ID NO: 33          moltype = DNA  length = 1464
FEATURE                Location/Qualifiers
source                 1..1464
                       mol_type = other DNA
                       organism = Artemesia annua
SEQUENCE: 33
atggctctgt tattagcagt tttcatcgca ctggcaacca ttctgctgtt tgtgtataaa  60
ttcgctaccc gttccaaatc aacgaaaaaa tcactgccgg aaccgtggcg cctgccgatt  120
atcggtcaca tgcatcacct gatcggcacc accccgcatc gtggcgtgcg tgatctggca  180
cgcaaatatg gctcgctgat gcatctgcaa ctgggtgaag tcccgaccat tgtggttagc  240
tctccgaaat gggcgaaaga aatcctgacc acctatgata ttacctttgc caaccgcccg  300
gaaaccctga cgggcgaaat cgtgctgtac cacaatacgg atgtggtgct ggcgccgtat  360
ggtgaatact ggcgtcaact gcgtaaaatt tgcaccctgg aactgctgag tgtgaaaaaa  420
gttaaatctt tccagagcct gcgtgaagaa gaatgttgga acctggttca agaaattaaa  480
gcatcgggca gcggtcgccc ggttaacctg agtgaaaatg tctttaaact gattgctacc  540
atcctgtccc gtgcggcctt cggcaaaggt atcaaagatc agaaagaact gaccgaaatt  600
gtcaaagaaa tcctgcgcca aacgggcggt tttgatgtgg cggacatttt tccgtcgaaa  660
aaattcctgc atcacctgag cggtaaacgt gcccgcctga ccagcctgcg taagaaaatt  720
gataacctga tcgacaatct ggtcgcggaa cataccgtga acacgagttc caaaaccaat  780
gaaacgctgc tggatgtgct gctgcgcctg aaagactccg ccgaatttcc gctgacctca  840
gataatatca aagcgattat cctggatatg ttcggtgcag gcaccgatac cagcagcagc  900
accattgaat gggcaatctc agaactgatt aaatgcccga aagctatgga aaaagtccag  960
gcagaactgc gcaaagctct gaacggcaaa gaaaaaatcc atgaagaaga tattcaagaa  1020
ctgtcttacc tgaacatggt tatcaaagaa accctgcgtc tgcacccgcc gctgccgctg  1080
gtgctgccgc gtgaatgtcg ccagccggtt aacctggcag gctataacat cccgaataaa  1140
acgaaactga tcgttaacgt ctttgctatt aaccgtgacc cggaatactg gaaagacgcg  1200
gaagccttta tcccggaacg ctttgaaaac agcagcgcga ccgtgatggg tgccgaatat  1260
gaatacctgc cgtttggcgc gggtcgtcgc atgtgtccgg gcgcagctct gggtctggca  1320
aacgtgcaac tgccgctggc taatatcctg tatcacttca actggaaact gccgaatggc  1380
gttagctacg atcaaattga catgaccgaa agctcaggtg ccacgatgca acgcaaaacc  1440
gaactgctgc tggtgccgtc cttc                                        1464

SEQ ID NO: 34          moltype = AA  length = 509
FEATURE                Location/Qualifiers
source                 1..509
                       mol_type = protein
                       organism = Arabidopsis thaliana
SEQUENCE: 34
MAFFSMISIL LGFVISSFIF IFFFKKLLSF SRKNMSEVST LPSVPVVPGF PVIGNLLQLK  60
EKKPHKTFTR WSEIYGPIYS IKMGSSSLIV LNSTETAKEA MVTRFSSIST RKLSNALTVL  120
TCDKSMVATS DYDDFHKLVK RCLLNGLLGA NAQKRKRHYR DALIENVSSK LHAHARDHPQ  180
EPVNFRAIFE HELFGVALKQ AFGKDVESIY VKELGVTLSK DEIFKVLVHD MMEGAIDVDW  240
RDFFPYLKWI PNKSFEARIQ QKHKRRLAVM NALIQDRLKQ NGSESDDDCY LNFLMSEAKT  300
LTKEQIAILV WETIIETADT TLVTTEWAIY ELAKHPSVQD RLCKEIQNVC GGEKFKEEQL  360
SQVPYLNGVF HETLRKYSPA PLVPIRYAHE DTQIGGYHVP AGSEIAINIY GCNMDKKRWE  420
RPEDWWPERF LDDGKYETSD LHKTMAFGAG KRVCAGALQA SLMAGIAIGR LVQEFEWKLR  480
DGEEENVDTY GLTSQKLYPL MAIINPRRS                                   509

SEQ ID NO: 35          moltype = AA  length = 513
FEATURE                Location/Qualifiers
source                 1..513
                       mol_type = protein
                       organism = Arabidopsis thaliana
SEQUENCE: 35
MALLLAVFSM ISILLGFVIS SFIFIFFFKK LLSFSRKNMS EVSTLPSVPV VPGFPVIGNL  60
LQLKEKKPHK TFTRWSEIYG PIYSIKMGSS SLIVLNSTET AKEAMVTRFS SISTRKLSNA  120
LTVLTCDKSM VATSDYDDFH KLVKRCLLNG LLGANAQKRK RHYRDALIEN VSSKLHAHAR  180
DHPQEPVNFR AIFEHELFGV ALKQAFGKDV ESIYVKELGV TLSKDEIFKV LVHDMMEGAI  240
DVDWRDFFPY LKWIPNKSFE ARIQQKHKRR LAVMNALIQD RLKQNGSESD DDCYLNFLMS  300
EAKTLTKEQI AILVWETIIE TADTTLVTTE WAIYELAKHP SVQDRLCKEI QNVCGGEKFK  360
EEQLSQVPYL NGVFHETLRK YSPAPLVPIR YAHEDTQIGG YHVPAGSEIA INIYGCNMDK  420
KRWERPEDWW PERFLDDGKY ETSDLHKTMA FGAGKRVCAG ALQASLMAGI AIGRLVQEFE  480
```

```
WKLRDGEEEN VDTYGLTSQK LYPLMAIINP RRS                         513

SEQ ID NO: 36          moltype = DNA  length = 1539
FEATURE                Location/Qualifiers
source                 1..1539
                       mol_type = other DNA
                       organism = Arabidopsis thaliana
SEQUENCE: 36
atggctctgt tattagcagt tttttcgatg atttctatcc tgctgggctt tgttatctcg  60
tcctttatct ttatcttctt cttcaaaaaa ctgctgtcgt tttctcgtaa aaacatgtcc  120
gaagtttcaa ccctgccgag tgtcccggtg gttccgggtt ttccggttat cggtaatctg  180
ctgcagctga aagaaaagaa accgcataag accttcacgc gctggtccga aatctatggc  240
ccgatctact caattaaaat gggtagctct agtctgattg tgctgaactc taccgaaacg  300
gcaaaagaag ctatggttac ccgtttttcc tcaatttcga cgcgcaagct gagcaatgcg  360
ctgaccgtcc tgacgtgcga caaatctatg gtggccacca gtgattacga tgacttccat  420
aaactggtta agcgttgtct gctgaacggc ctgctgggtg cgaatgccca gaagcgtaag  480
cgccactatc gcgacgccct gattgaaaac gtgtcgagca aactgcatgc acacgctcgt  540
gatcatccgc aggaaccggt caattttcgc gcaatcttcg aacacgaact gtttggcgtg  600
gcgctgaaac aagccttcgg caaggatgtt gaatcgattt acgtcaaaga actgggcgtg  660
accctgagca aagacgaaat ctttaaggtc ctggtgcatg atatgatgga aggtgcaatt  720
gacgttgatt ggcgtgattt ctttccgtat ctgaaatgga ttccgaacaa gtcattcgaa  780
gctcgcattc agcaaaaaca caagcgtcgc ctggcagtga tgaacgctct gattcaggat  840
cgtctgaaac aaaatggctc tgaaagtgat gacgattgct atctgaattt tctgatgtcc  900
gaagcaaaaa ccctgacgaa ggaacagatt gctatcctgg tttgggaaac cattatcgaa  960
acggcggaca ccacgctggt caccacggaa tgggcgatct acgaactggc caagcatccg  1020
agcgttcagg atcgcctgtg caaagaaatt caaaacgtct gtggcggtga aaaatttaag  1080
gaagaacagc tgtcgcaagt gccgtatctg aatggtgttt tccacgaaac cctgcgtaaa  1140
tatagcccgg caccgctggt cccgatccgt tacgcccatg aagataccca gattggcggt  1200
tatcacgtgc cggcaggcag tgaaattgct atcaacattt acggttgcaa tatggacaaa  1260
aagcgttggg aacgcccgga agattggtgg ccggaacgtt ttctggacga tggcaaatat  1320
gaaacctctg atctgcataa gacgatggcg ttcggtgcag gtaaacgtgt gtgtgcaggt  1380
gcactgcaag caagtctgat ggcaggcatc gctattggtc gtctggtgca agaatttgaa  1440
tggaaactgc gcgacggcga agaagaaaac gttgatacct atggtctgac gtcccagaaa  1500
ctgtacccgc tgatggccat tatcaatccg cgtcgctca                        1539

SEQ ID NO: 37          moltype = AA  length = 513
FEATURE                Location/Qualifiers
source                 1..513
                       mol_type = protein
                       organism = Stevia rebaudiana
SEQUENCE: 37
MDAVTGLLTV PATAITIGGT AVALAVALIF WYLKSYTSAR RSQSNHLPRV PEVPGVPLLG  60
NLLQLKEKKP YMTFTRWAAT YGPIYSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI FQVLVVDPMM  240
GAIDVDWRDF FPYLKWVPNK KFENTIQQMY IRREAVMKSL IKEHKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRRHSPVPII PLRHVHEDTV LGGYHVPAGT ELAVNIYGCN  420
MDKNVWENPE EWNPERFMKE NETIDFQKTM AFGGGKRVCA GSLQALLTAS IGIGRMVQEF  480
EWKLKDMTQE EVNTIGLTTQ MLRPLRAIIK PRI                         513

SEQ ID NO: 38          moltype = AA  length = 501
FEATURE                Location/Qualifiers
source                 1..501
                       mol_type = protein
                       organism = Stevia rebaudiana
SEQUENCE: 38
MALLLAVFAV ALAVALIFWY LKSYTSARRS QSNHLPRVPE VPGVPLLGNL LQLKEKKPYM  60
TFTRWAATYG PIYSIKTGAT SMVVVSSNEI AKEALVTRFQ SISTRNLSKA LKVLTADKTM  120
VAMSDYDDYH KTVKRHILTA VLGPNAQKKH RIHRDIMMDN ISTQLHEFVK NNPEQEEVDL  180
RKIFQSELFG LAMRQALGKD VESLYVEDLK ITMNRDEIFQ VLVVDPMMGA IDVDWRDFFP  240
YLKWVPNKKF ENTIQQMYIR REAVMKSLIK EHKKRIASGE KLNSYIDYLL SEAQTLTDQQ  300
LLMSLWEPII ESSDTTMVTT EWAMYELAKN PKLQDRLYRD IKSVCGSEKI TEEHLSQLPY  360
ITAIFHETLR RHSPVPIIPL RHVHEDTVLG GYHVPAGTEL AVNIYGCNMD KNVWENPEEW  420
NPERFMKENE TIDFQKTMAF GGGKRVCAGS LQALLTASIG IGRMVQEFEW KLKDMTQEEV  480
NTIGLTTQML RPLRAIIKPR I                                      501

SEQ ID NO: 39          moltype = DNA  length = 1503
FEATURE                Location/Qualifiers
source                 1..1503
                       mol_type = other DNA
                       organism = Stevia rebaudiana
SEQUENCE: 39
atggctctgt tattagcagt ttttgccgtc gctctggcgg tagcactgat cttctggtat  60
ctgaaatctt acactagcgc gcgccgctct cagtccaacc acctgccgcg tgtgccggaa  120
gttccgggtg tgccactgct gggcaacctg ctgcaactga aagaaaagaa accgtacatg  180
acctttaccc gctgggcagc gacttatggt cctatctaca gcattaaaac cggcgctacg  240
tctatggttg tggtttcttc caacgaaatc gcgaaagaag ccctggtgac tcgtttccag  300
tccattagca cccgcaacct gtccaaagcg ctgaaggttc tgacggctga caagactatg  360
```

```
gtggctatga gcgactatga tgactaccac aaaaccgtta aacgtcacat cctgaccgca  420
gtactgggtc cgaacgcaca gaaaaaacat cgcatccacc gcgacattat gatggataac  480
atctccacgc agctgcatga gttcgttaag aacaatccag aacaggaaga ggtagatctg  540
cgtaaaattt ttcagtccga actgttcggt ctggctatgc gtcaggcgct gggcaaagac  600
gttgaaagcc tgtatgtcga agacctgaaa attaccatga accgtgatga gatcttccag  660
gttctggttg tagatccgat gatgggcgcc atcgacgtgg attggcgtga cttctttccg  720
tacctgaaat gggtcccgaa caagaagttc gaaaacacca tccagcaaat gtacatccgt  780
cgtgaagcgg tgatgaaaag cctgatcaaa gaacacaaaa agcgtattgc ttctggtgag  840
aaactgaact cctacatcga ttatctgctg tccgaagcgc agaccctgac cgaccaacag  900
ctgctgatgt ctctgtggga accgattatc gaaagcagcg acaccactat ggtcactacc  960
gaatgggcaa tgtatgagct ggccaaaaac ccgaaactgc aggatcgtct gtaccgtgac  1020
atcaaaagcg tttgcggctc cgagaaaatc actgaagaac acctgtctca gctgccgtac  1080
atcactgcta ttttccacga aaccctgcgt cgccattctc cggttccgat cattccgctg  1140
cgtcacgttc acgaagatac tgtgctgggt ggttaccatg taccggcagg cactgaactg  1200
gctgtcaaca tctacggctg taacatggat aaaaacgttt gggagaatcc tgaagaatgg  1260
aaccccggaac gcttcatgaa agagaacgaa accatcgact tccagaaaac gatggctttc  1320
ggcggtggta aacgtgtgtg cgcaggttct ctgcaggcgc tgctgacggc gtccattggt  1380
atcggtcgca tggtacagga atttgaatgg aagctgaaag acatgaccca agaagaggtg  1440
aataccattg gtctgactac ccagatgctg cgtccactgc gtgcaatcat caaacctcgt  1500
att                                                                1503

SEQ ID NO: 40          moltype = AA  length = 546
FEATURE                Location/Qualifiers
source                 1..546
                       mol_type = protein
                       organism = Physcomitrella patens
SEQUENCE: 40
MAKHLATQLL QQWNEALKTM PPGFRTAGKI LVWEELASNK VLITIALAWV LLFVARTCLR  60
NKKRLPPAIP GGLPVLGNLL QLTEKKPHRT FTAWSKEHGP IFTIKVGSVP QAVVNNSEIA  120
KEVLVTKFAS ISKRQMPMAL RVLTRDKTMV AMSDYGEEHR MLKKLVMTNL LGPTTQNKNR  180
SLRDDALIGM IEGVLAELKA SPTSPKVVNV RDYVQRSLFP FALQQVFGYI PDQVEVLELG  240
TCVSTWDMFD ALVVAPLSAV INVDWRDFFP ALRWIPNRSV EDLVRTVDFK RNSIMKALIR  300
AQRMRLANLK EPPRCYADIA LTEATHLTEK QLEMSLWEPI IESADTTLVT SEWAMYEIAK  360
NPDCQDRLYR EIVSVAGTER MVTEDDLPNM PYLGAIIKET LRKYTPVPLI PSRFVEEDIT  420
LGGYDIPKGY QILVNLFAIA NDPAVWSNPE KWDPERMLAN KKVDMGFRDF SLMPFGAGKR  480
MCAGITQAMF IIPMNVAALV QHCEWRLSPQ EISNINNKIE DVVYLTTHKL SPLSCEATPR  540
ISHRLP                                                             546

SEQ ID NO: 41          moltype = AA  length = 548
FEATURE                Location/Qualifiers
source                 1..548
                       mol_type = protein
                       organism = Physcomitrella patens
SEQUENCE: 41
MALLLAVFTQ LLQQWNEALK TMPPGFRTAG KILVWEELAS NKVLITIALA WVLLFVARTC  60
LRNKKRLPPA IPGGLPVLGN LLQLTEKKPH RTFTAWSKEH GPIFTIKVGS VPQAVVNNSE  120
IAKEVLVTKF ASISKRQMPM ALRVLTRDKT MVAMSDYGEE HRMLKKLVMT NLLGPTTQNK  180
NRSLRDDALI GMIEGVLAEL KASPTSPKVV NVRDYVQRSL FPFALQQVFG YIPDQVEVLE  240
LGTCVSTWDM FDALVVAPLS AVINVDWRDF FPALRWIPNR SVEDLVRTVD FKRNSIMKAL  300
IRAQRMRLAN LKEPPRCYAD IALTEATHLT EKQLEMSLWE PIIESADTTL VTSEWAMYEI  360
AKNPDCQDRL YREIVSVAGT ERMVTEDDLP NMPYLGAIIK ETLRKYTPVP LIPSRFVEED  420
ITLGGYDIPK GYQILVNLFA IANDPAVWSN PEKWDPERML ANKKVDMGFR DFSLMPFGAG  480
KRMCAGITQA MFIIPMNVAA LVQHCEWRLS PQEISNINNK IEDVVYLTTH KLSPLSCEAT  540
PRISHRLP                                                           548

SEQ ID NO: 42          moltype = DNA  length = 1644
FEATURE                Location/Qualifiers
source                 1..1644
                       mol_type = other DNA
                       organism = Physcomitrella patens
SEQUENCE: 42
atggctctgt tattagcagt ttttacgcaa ctgctgcaac aatggaatga agctctgaag  60
acgatgccgc cgggttttcg caccgctggc aaaattctgg tgtgggaaga actggcaagc  120
aataaagttc tgattacgat cgcactggct tgggtcctgc tgtttgtggc tcgtacctgc  180
ctgcgcaata aaaagcgtct gccgccggca atcccgggcg gtctgccggt gctgggcaac  240
ctgctgcagc tgacggaaaa gaaaccgcat cgtaccttta cggcgtggag caaggaacac  300
ggcccgattt tcaccatcaa agtcggttcg gtgccgcagg ctgtggttaa caatagcgaa  360
attgcgaaag aagtcctggt gaccaagttc gccagcatct ctaaacgtca aatgccgatg  420
gcactgcgcg tcctgacgcg tgataaaacg atggtggcta tgtctgacta tggcgaagaa  480
catcgcatgc tgaaaaagct ggtgatgacg aatctgctgg gtccgaccac gcagaacaaa  540
aatcgtagtc tgcgcgatga cgcactgatt ggcatgatcg aaggtgttct ggcggaactg  600
aaggccagtc cgacctcccc gaaagtcgtg aacgttcgcg attatgtcca gcgttctctg  660
tttccgttcg cgctgcagca agtgtttggc tacattccgg atcaagttga agtcctggaa  720
ctgggcacgt gtgtttctac ctgggatatg ttcgacgcac tggttgtcgc tccgctgagt  780
gcggttatta acgtcgattg gcgtgacttt ttcccggccc tgcgctggat tccgaatcgt  840
tccgtggaag atctggtgcg caccgttgac tttaagcgta actcaattat gaaagccctg  900
atccgtgcac agcgtatgcg cctggctaac ctgaaggaac cgccgcgctg ctacgcagat  960
attgctctga ccgaagcgac gcacctgacc gaaaaacaac tggaaatgag tctgtgggaa  1020
ccgattatcg aatccgccga taccacgctg gtgacctcag aatgggctat gtatgaaatt  1080
```

```
gcgaaaaatc cggattgtca ggaccgtctg taccgcgaaa tcgtgtccgt tgccggcacg  1140
gaacgcatgg ttaccgaaga tgacctgccg aacatgccgt atctgggtgc aattatcaaa  1200
gaaacgctgc gcaagtacac cccggttccg ctgattccga gtcgttttgt cgaagaagat  1260
atcaccctgg gcggttatga cattccgaaa ggttaccaga tcctggtcaa cctgttcgcg  1320
attgccaatg atccggccgt ttggtcgaac ccggaaaaat gggacccgga acgcatgctg  1380
gcaaataaaa aggtggatat gggctttcgt gacttcagcc tgatgccgtt tggcgccggt  1440
aaacgcatgt gcgccggtat cacccaagca atgttcatta tcccgatgaa tgtggcggcc  1500
ctggttcagc attgtgaatg gcgcctgagc ccgcaagaaa tctctaacat caacaacaag  1560
atcgaagatg tggtttacct gaccacgcat aaactgtcac cgctgtcgtg cgaagcaacc  1620
ccgcgtatca gccaccgtct gccg                                         1644

SEQ ID NO: 43          moltype = AA  length = 1049
FEATURE                Location/Qualifiers
source                 1..1049
                       mol_type = protein
                       organism = Bacillus megaterium
SEQUENCE: 43
MTIKEMPQPK TFGELKNLPL LNTDKPVQAL MKIADELGEI FKFEAPGRVT RYLSSQRLIK  60
EACDESRFDK NLSQALKFVR DFAGDGLATS WTHEKNWKKA HNILLPSFSQ QAMKGYHAMM  120
VDIAVQLVQK WERLNADEHI EVPEDMTRLT LDTIGLCGFN YRFNSFYRDQ PHPFITSMVR  180
ALDEAMNKLQ RANPDDPAYD ENKRQFQEDI KVMNDLVDKI IADRKASGEQ SDDLLTHMLN  240
GKDPETGEPL DDENIRYQII TFLIAGHETT SGLLSFALYF LVKNPHVLQK AAEEAARVLV  300
DPVPSYKQVK QLKYVGMVLN EALRLWPTIP AFSLYAKEDT VLGGEYPLEK GDELMVLIPQ  360
LHRDKTIWGD DVEEFRPERF ENPSAIPQHA FKPFGNGQRA CIGQQFALHE ATLVLGMMLK  420
HFDFEDHTNY ELDIKETLTL KPEGFVVKAK SKKIPLGGIP SPSTEQSAKK VRKKAENAHN  480
TPLLVLYGSN MGTAEGTARD LADIAMSKGF APQVATLDSH AGNLPREGAV LIVTASYNGH  540
PPDNAKQFVD WLDQASADEV KGVRYSVFGC GDKNWATTYQ KVPAFIDETL AAKGAENIAD  600
RGEADASDDF EGTYEEWREH MWSDVAAYFN LDIENSEDNK STLSLQFVDS AADMPLAKMH  660
GAFSTNVVAS KELQQPGSAR STRHLEIELP KEASYQEGDH LGVIPRNYEG IVNRVTARFG  720
LDASQQIRLE AEEEKLAHLP LAKTVSVEEL LQYVELQDPV TRTQLRAMAA KTVCPPHKVE  780
LEALLEKQAY KEQVLAKRLT MLELLEKYPA CEMKFSEFIA LLPSIRPRYY SISSSPRVDE  840
KQASITVSVV SGEAWSGYGE YKGIASNYLA ELQEGDTITC FISTPQSEFT LPKDPETPLI  900
MVGPGTGVAP FRGFVQARKQ LKEQGQSLGE AHLYFGCRSP HEDYLYQEEL ENAQSEGIIT  960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                    1049

SEQ ID NO: 44          moltype = DNA  length = 3150
FEATURE                Location/Qualifiers
source                 1..3150
                       mol_type = other DNA
                       organism = Bacillus megaterium
SEQUENCE: 44
atgacgatta aagaaatgcc gcaaccgaag acgtttggcg aactgaagaa cctgccgctg  60
ctgaacacgg ataagccggt gcaagccctg atgaagattg ctgatgaact gggcgaaatc  120
tttaaattcg aagcgccggg tcgtgtgacc cgttatctga gcagccagcg tctgattaaa  180
gaagcctgcg atgaatcgcg ctttgacaag aacctgagcc aggcactgaa atttgttcgt  240
gatttcgcag gtgacggtct ggccaccagc tggacgcatg aaaagaactg gaaaaaggcc  300
cacaatattc tgctgccgtc gttcagccag caagcaatga aaggctacca tgctatgatg  360
gtcgatatcg cggttcagct ggtccaaaaa tgggaacgtc tgaatgcgga cgaacacatt  420
gaagtgccgg aagatatgac ccgcctgacg ctggacacca tcggtctgtg tggctttaac  480
tatcgtttta attcgttcta ccgcgatcag ccgcatccgt tcattaccag catggtgcgt  540
gcgctggacg aagccatgaa caaactgcag cgtgcaaacc cggatgaccc ggcgtatgat  600
gaaaacaagc gtcagtttca agaagacatc aaagtgatga atgatctggt tgacaagatt  660
atcgcagatc gcaaagcgag cggcgaacag tcagatgacc tgctgacgca catgctgaac  720
ggcaaagacc cggaaaccgg tgaaccgctg gatgacgaaa acatccgtta tcagatcatc  780
acctttctga tcgcaggcca tgaaaccacg tcgggtctgc tgagctttgc gctgtacttc  840
ctggtcaaga acccgcacgt gctgcagaaa gcggccgaag aagcagctcg tgtgctggtt  900
gatccggttc cgtcgtataa acaggtcaag caactgaaat acgtgggtat ggttctgaat  960
gaagcgctgc gcctgtggcc gacgattccg gcatttagcc tgtatgctaa ggaagatacc  1020
gttctgggcg gtgaataccc gctggaaaaa ggcgatgaac tgatggtcct gattccgcag  1080
ctgcatcgcg acaaaaccat ctggggtgat gacgtggaag aatttcgccc ggaacgcttc  1140
gaaaacccga gcgcgattcc gcagcatgcc tttaaaccgt tcggcaatgg tcaacgtgcg  1200
tgcatcggcc agcaatttgc gctgcacgaa gccacgctgg ttctgggtat gatgctgaaa  1260
cattttgatt tcgaagacca caccaactat gaactggata ttaaggaaac cctgacgctg  1320
aaaccggaag gcttcgtggt taaagcgaag tctaaaaaga ttccgctggg cggtatcccg  1380
tctccgagta cggaacagag tgccaaaaag gtccgtaaaa aggcggaaaa cgcccataat  1440
accccgctgc tggtgctgta tggttctaac atgggcacgg cagaaggcac cgctcgcgat  1500
ctggcagaca ttgctatgtc taaaggtttt gcgccgcagg tggccacgct ggatagtcat  1560
gcaggcaatc tgccgcgtga aggtgctgtc ctgatcgtga ccgcaagcta caacggtcac  1620
ccgccggata atgcgaagca gttcgttgat tggctggacc aagcgtcggc cgatgaagtt  1680
aaaggtgtcc gctatagcgt gtttggctgt ggtgacaaga actgggctac cacgtaccag  1740
aaagttccgg cgttcattga tgaaacgctg gcggccaaag gcgcagaaaa tatcgctgat  1800
cgtggtgaag cagacgcttc cgatgacttt gaaggcacct atgaagaatg gcgcgaacac  1860
atgtggtcgg atgtggcagc ttacttcaac ctggatattg aaaacagcga agacaataaa  1920
tccaccctgt cactgcagtt tgttgatagt gcggccgaca tgccgctggc aaagatgcac  1980
ggcgctttct ccacgaatgt cgtggcttca aaagaactgc agcaaccggg ttcggcacgt  2040
agcacccgcc atctggaaat tgaactgccg aaagaagcca gctatcagga aggcgatcac  2100
ctgggtgtga ttccgcgtaa ctacgaaggc atcgtgaatc gtgttacggc ccgctttggt  2160
ctggatgcat cccagcaaat ccgcctggaa gcggaagaag aaaagctggc gcatctgccg  2220
```

-continued

```
ctggccaaaa ccgtctcagt ggaagaactg ctgcagtatg tggaactgca agatccggtt  2280
acccgtacgc agctgcgtgc gatggcggct aagaccgtct gcccgccgca caaagtggaa  2340
ctggaagctc tgctggaaaa gcaggcgtat aaagaacaag tgctggcgaa acgcctgacc  2400
atgctggaac tgctggaaaa gtacccggcc tgtgaaatga agttctctga atttatcgca  2460
ctgctgccgt ctatccgtcc gcgttattac agtattagtt cctcaccgcg tgtggatgaa  2520
aaacaggcca gtatcaccgt ttctgttgtc agtggcgaag catggtctgg ctatggtgaa  2580
tacaagggta tcgcaagtaa ctacctggct gaactgcagg aaggcgatac cattacgtgc  2640
tttatctcta cgccgcaaag tgaatttacc ctgccgaaag acccggaaac gccgctgatc  2700
atggttggcc cgggcaccgg tgtcgcaccg tttcgtggtt tcgtgcaggc acgcaagcaa  2760
ctgaaagaac agggccaatc cctgggtgaa gcgcatctgt attttggctg tcgctcaccg  2820
cacgaagatt atctgtacca ggaagaactg gaaaacgcgc aatccgaagg tattatcacg  2880
ctgcataccg ccttctcacg tatgccgaat cagccgaaaa cctacgtcca gcacgtgatg  2940
gaacaagatg gcaaaaagct gattgaactg ctggaccagg gtgcgcattt ttatatctgc  3000
ggtgatggca gccaaatggc accggcagtg gaagcaaccc tgatgaaatc ctacgcagat  3060
gttcaccagg tctcagaagc agacgctcgt ctgtggctgc agcaactgga agaaaagggc  3120
cgctatgcga aagatgtttg ggccggttaa                                    3150

SEQ ID NO: 45          moltype = AA  length = 396
FEATURE                Location/Qualifiers
source                 1..396
                       mol_type = protein
                       organism = Pleurotus sapidus
SEQUENCE: 45
MRYGCAAVAL FYLTAMGKLH PLAIIPDYKG SMAASVTIFN KRTNPLDISV NQANDWPWRY  60
AKTCVLSSDW ALHEMIIHLN NTHLVEEAVI VAAQRKLSPS HIVFRLLEPH WVVTLSLNAL  120
ARSVLIPEVI VPIAGFSAPH IFQFIRESFT NFDWKSLYVP ADLESRGFPV DQLNSPKFHN  180
YAYARDINDM WTTLKKFVSS VLQDAQYYPD DASVAGDTQI QAWCDEMRSG MGAGMTNFPE  240
SITTVDDLVN MVTMCIHIAA PQHTAVNYLQ QYYQTFVSNK PSALFSPLPT SIAQLQKYTE  300
SDLMAALPLN AKRQWLLMAQ IPYLLSMQVQ EDENIVTYAA NASTDKDPII ASAGRQLAAD  360
LKKLAAVFLV NSAQLDDQNT PYDVLAPEQL ANAIVI                             396

SEQ ID NO: 46          moltype = DNA  length = 1191
FEATURE                Location/Qualifiers
source                 1..1191
                       mol_type = other DNA
                       organism = Pleurotus sapidus
SEQUENCE: 46
atgcgttatg gctgtgctgc tgtggctctg ttctatctga ccgctatggg caaactgcac  60
ccgctggcta ttatcccgga ctacaagggt agcatggcgg cctctgtcac catttttaac  120
aaacgtacga atccgctgga tatcagcgtt aaccaggcaa atgactggcc gtggcgctat  180
gctaagacgt gcgtgctgag cagcgattgg gcgctgcatg aaatgattat ccacctgaac  240
aatacccatc tggtggaaga agccgtcatt gtggcagctc agcgtaaact gtcaccgtcg  300
cacatcgttt ttcgcctgct ggaaccgcat tgggtggtta ccctgtcgct gaacgcactg  360
gctcgtagcg tgctgatccc ggaagttatt gtcccgatcg cgggtttctc tgccccgcac  420
atttttcagt tcatccgcga atcttttacc aatttcgatt ggaaaagtct gtacgtcccg  480
gcggacctgg aatcgcgtgg ctttccggtg gatcagctga acagcccgaa gttccataat  540
tatgcgtacg cccgcgatat caacgacatg tggaccacgc tgaaaaagtt tgtgagttcc  600
gttctgcagg atgcccaata ttacccggat gacgcaagtg tggctggtga tacgcagatt  660
caagcatggt gcgacgaaat gcgttccggc atgggtgcgg gcatgaccaa cttcccggaa  720
tcaatcacca cggttgatga cctggtcaat atggtgacca tgtgtattca catcgcggcc  780
ccgcagcata cggcggttaa ctatctgcag caatactacc aaaccttcgt cagtaacaag  840
ccgtccgcac tgttctcacc gctgccgacc tctattgctc agctgcaaaa atacacggaa  900
agtgatctga tggcagctct gccgctgaac gcgaagcgtc agtggctgct gatggcccaa  960
attccgtatc tgctgtcgat gcaggtgcaa gaagatgaaa acatcgttac ctacgcggcc  1020
aatgcgtcca cggataaaga cccgattatc gcatcagctg gccgccagct ggcagctgac  1080
ctgaaaaagc tggcggccgt tttctggtc aactcagccc agctggatga ccaaaatacc  1140
ccgtatgatg tgctggcacc ggaacagctg gcgaatgcca ttgttatcta a            1191

SEQ ID NO: 47          moltype = AA  length = 640
FEATURE                Location/Qualifiers
source                 1..640
                       mol_type = protein
                       organism = Pleurotus ostreatus
SEQUENCE: 47
MAPTMSLSRS ALKNVHLPYM VQHPEPTDCS TAMKHAAEGY DRARQMIAFL FDILDYESSV  60
PQKFTPEEKK EKYTWSHSDK FPPHLAIIPE DIDVPAYIIF SIVRLVQTLS IMSGIQCNER  120
LAPGPEQNTM EKLTKWNAER HKNQGWVKDM FNEPNIGLRN DWYTDAVFAQ QFFTGPNPTT  180
ITLASDTWMK AFTEEAASQG KRDLISLFRS APPNSFYVQD FSDFRARMGA KPDEELCATS  240
DGGVTRYGCA AVALFYLPPT GELHPLAIVP DYKGSMAASI TLFNKRVDPS DASVDQANDW  300
PWRYAKTCVL SADWVLHEMI IHLNNTHLVQ EAVIVAVQRT LPDSHIVFRL LKPHWVVTLS  360
LNAQARSVLI PEVIVPIAGF SELRIFQFVG HAFTNFDWKA LYVPTDLEFR GFPLDRLDDD  420
KFHNYAYAKD IKDMWMALRK FVSSVLKDGK YYPDDSAVAA DAQIQDWCDE MRSEKGAGMK  480
KFPESISTLD DLIDMVTMCI HIAAPQHTAV NYLQQYYQTF VPNKPSALFS PLPTLLSQLE  540
SYTESDLMAA LPLGAKQEWL LMAQVPYLLS KEVEQDGNIV TYAGTASNNE DPIIAAAGKE  600
LSADLVILAG VFLKNSEKLD DQNTAYNVLA PDQLANAIVI                        640

SEQ ID NO: 48          moltype = DNA  length = 1923
FEATURE                Location/Qualifiers
source                 1..1923
```

```
                         mol_type = other DNA
                         organism = Pleurotus ostreatus
SEQUENCE: 48
atggccccga cgatgtcact gtctcgctcc gcactgaaga atgtccacct gccgtatatg  60
gtccaacacc cggaaccgac cgattgcagc accgcgatga aacacgcggc cgaaggttat  120
gatcgtgctc gccagatgat tgcgtttctg ttcgacatcc tggattacga aagctctgtt  180
ccgcaaaaat ttaccccgga agaaaagaaa gaaaaatata cgtggtcaca ctcggataag  240
ttcccgccgc atctggccat tatcccggaa gacattgatg tgccggcata cattatcttt  300
agcatcgttc gtctggtcca gaccctgagt attatgtccg gcatccaatg caacgaacgt  360
ctggcaccgg ggccggaaca gaatacgatg gaaaaactga cgaagtggaa cgcggaacgt  420
cataaaaatc aaggctgggt caaggatatg tttaacgaac cgaatattgg tctgcgcaac  480
gactggtata ccgatgctgt gttcgcgcag caatttttca cgggtccgaa tccgaccacg  540
attaccctgg cctctgatac gtggatgaaa gcatttaccg aagaagcagc tagtcagggc  600
aagcgtgacc tgatcagcct gtttcgctct gccccgccga actccttcta cgttcaggac  660
ttttcagatt tccgtgctcg catgggcgcg aaaccggacg aagaactgtg cgcgacctct  720
gatggcggtg ttacccgtta tggctgtgca gcagtcgcac tgttttacct gccgccgacc  780
ggtgaactgc atccgctggc cattgtgccg gattataaag gcagtatggc agcttccatc  840
acgctgttca acaagcgtgt ggacccgtca gatgcctcgg ttgaccaggc aaatgattgg  900
ccgtggcgct acgctaaaac ctgtgttctg tccgcggatt gggtcctgca tgaaatgatt  960
atccacctga acaataccca tctggtgcag gaagccgtca ttgtggcagt tcaacgtacg  1020
ctgccggatt cacacatcgt ttttcgcctg ctgaaaccgc attgggtggt taccctgtcg  1080
ctgaatgccc aggcacgtag cgttctgatc ccggaagtca ttgtgccgat cgcgggcttc  1140
agtgaactgc gcatctttca gttcgttggt cacgccttta ccaacttcga ctggaaagca  1200
ctgtatgtcc cgacggatct ggaatttcgt ggtttcccgc tggaccgcct ggatgacgat  1260
aagttccata actatgctta cgcgaaggac attaaggata tgtggatggc cctgcgtaag  1320
ttcgtgagtt ccgttctgaa agatggcaag tattacccgg acgattcggc tgttgcagca  1380
gacgcgcaga ttcaagactg gtgcgatgaa atgcgcagcg aaaaaggcgc gggtatgaaa  1440
aagttcccgg aaagcatttc taccctggac gatctgatcg atatggtgac gatgtgtatt  1500
cacatcgcag ctccgcagca taccgccgtg aactatctgc agcaatatta ccaaacgttt  1560
gttccgaata aaccgtcagc actgttctcg ccgctgccga ccctgctgag ccagctggaa  1620
tcttacacgg aaagtgatct gatggcggcc ctgccgctgg gtgctaaaca ggaatggctg  1680
ctgatggcgc aagtgccgta tctgctgtct aaggaagtcg aacaggatgg caacattgtg  1740
acctacgccg gtacggcaag taacaatgaa gatccgatta tcgcagctgc gggcaaagaa  1800
ctgtccgctg acctggtcat cctggcgggt gtgtttctga aaaactcaga aaagctggac  1860
gatcagaaca ccgcctataa tgtcctggca ccggatcaac tggccaatgc aattgtgatc  1920
taa                                                                1923

SEQ ID NO: 49           moltype = AA  length = 495
FEATURE                 Location/Qualifiers
source                  1..495
                        mol_type = protein
                        organism = Cichorium intybus
SEQUENCE: 49
MEISIPTTLG LAVIIFIIFK LLTRTTSKKN LLPEPWRLPI IGHMHHLIGT MPHRGVMELA  60
RKHGSLMHLQ LGEVSTIVVS SPRWAKEVLT TYDITFANRP ETLTGEIVAY HNTDIVLAPY  120
GEYWRQLRKL CTLELLSNKK VKSFQSLREE ECWNLVKDIR STGQGSPINL SENIFKMIAT  180
ILSRAAFGKG IKDQMKFTEL VKEILRLTGG FDVADIFPSK KLLHHLSGKR AKLTNIHNKL  240
DNLINNIIAE HPGNRTSSSQ ETLLDVLLRL KESAEFPLTA DNVKAVILDM FGAGTDTSSA  300
TIEWAISELI RCPRAMEKVQ TELRQALNGK ERIQEEDLQE LNYLKLVIKE TLRLHPPLPL  360
VMPRECREPC VLGGYDIPSK TKLIVNVFAI NRDPEYWKDA ETFMPERFEN SPITVMGSEY  420
EYLPFGAGRR MCPGAALGLA NVELPLAHIL YFNWKLPNGK TFEDLDMTES FGATVQRKTE  480
LLLVPTDFQT LTAST                                                   495

SEQ ID NO: 50           moltype = AA  length = 493
FEATURE                 Location/Qualifiers
source                  1..493
                        mol_type = protein
                        organism = Cichorium intybus
SEQUENCE: 50
MALLLAVFLA VIIFIIFKLL TRTTSKKNLL PEPWRLPIIG HMHHLIGTMP HRGVMELARK  60
HGSLMHLQLG EVSTIVVSSP RWAKEVLTTY DITFANRPET LTGEIVAYHN TDIVLAPYGE  120
YWRQLRKLCT LELLSNKKVK SFQSLREEEC WNLVKDIRST GQGSPINLSE NIFKMIATIL  180
SRAAFGKGIK DQMKFTELVK EILRLTGGFD VADIFPSKKL LHHLSGKRAK LTNIHNKLDN  240
LINNIIAEHP GNRTSSSQET LLDVLLRLKE SAEFPLTADN VKAVILDMFG AGTDTSSATI  300
EWAISELIRC PRAMEKVQTE LRQALNGKER IQEEDLQELN YLKLVIKETL RLHPPLPLVM  360
PRECREPCVL GGYDIPSKTK LIVNVFAINR DPEYWKDAET FMPERFENSP ITVMGSEYEY  420
LPFGAGRRMC PGAALGLANV ELPLAHILYF NWKLPNGKTF EDLDMTESFG ATVQRKTELL  480
LVPTDFQTLT AST                                                     493

SEQ ID NO: 51           moltype = DNA  length = 1482
FEATURE                 Location/Qualifiers
source                  1..1482
                        mol_type = other DNA
                        organism = Cichorium intybus
SEQUENCE: 51
atggctctgt tattagcagt ttttctggct gtcattatct ttatcatctt caaactgctg  60
acccgcacca cctcgaagaa aaacctgctg ccggaaccgt ggcgtctgcc gattatcggc  120
cacatgcatc acctgattgg caccatgccg caccgtggtg tgatggaact ggcgcgcaaa  180
catggctcac tgatgcacct gcagctgggt gaagtgagca ccatcgtggt tagctctccg  240
```

```
cgttgggcga aagaagttct gaccacgtat gatattacct ttgccaaccg cccggaaacc  300
ctgacgggcg aaatcgtggc ataccataat acggacattg ttctggctcc gtatggtgaa  360
tactggcgtc agctgcgcaa actgtgcacc ctggaactgc tgagtaacaa aaaagtcaaa  420
tcttttcaaa gtctgcgtga agaagaatgt tggaatctgg tgaaagatat ccgctccacc  480
ggccagggtt caccgatcaa cctgtcggaa aacatcttca aaatgatcgc gacgatcctg  540
tctcgtgcgg cctttggcaa aggtattaaa gaccaaatga aattcaccga actggttaaa  600
gaaatcctgc gcctgacggg cggttttgat gtcgcagaca ttttcccgag taaaaaactg  660
ctgcatcacc tgtccggcaa acgtgctaaa ctgaccaaca tccataacaa actggataac  720
ctgatcaaca acattatcgc cgaacacccg ggtaatcgta ccagttcctc acaggaaacg  780
ctgctggatg ttctgctgcg cctgaaagaa agcgcagaat ttccgctgac cgcggacaat  840
gttaaagccg tcattctgga tatgttcggt gcaggcaccg acacgtcgag cgcaaccatt  900
gaatgggcta tctctgaact gattcgttgc ccgcgcgcga tggaaaaagt gcagacggaa  960
ctgcgtcaag ccctgaacgg caaagaacgc atccaggaag aagatctgca agaactgaac  1020
tacctgaaac tggttatcaa agaaaccctg cgcctgcatc cgccgctgcc gctggtcatg  1080
ccgcgtgaat gccgcgaacc gtgtgtgctg ggcggttatg atatcccgag caaaaccaaa  1140
ctgatcgtca acgtgtttgc aattaatcgt gacccggaat actggaaaga cgctgaaacc  1200
tttatgccgg aacgcttcga aaacagcccg attacggtta tgggttctga atatgaatac  1260
ctgccgtttg gtgcaggtcg tcgcatgtgt ccgggtgcag ctctgggtct ggcgaatgtc  1320
gaactgccgc tggcccacat cctgtattac ttcaactgga aactgccgaa tggcaaaacc  1380
tttgaagatc tggacatgac cgaatccttc ggtgcaacgg tgcaacgcaa aaccgaactg  1440
ctgctggtgc cgacggattt ccaaacgctg accgcatcaa cg                    1482

SEQ ID NO: 52          moltype = AA  length = 488
FEATURE                Location/Qualifiers
source                 1..488
                       mol_type = protein
                       organism = Helianthus annuus
SEQUENCE: 52
MEVSLTTSIA LATIVFFLYK LLTRPTSSKN RLPEPWRLPI IGHMHHLIGT MPHRGVMDLA  60
RKYGSLMHLQ LGEVSAIVVS SPKWAKEILT TYDIPFANRP ETLTGEIIAY HNTDIVLAPY  120
GEYWRQLRKL CTLELLSVKK VKSFQSLREE ECWNLVQEIK ASGSGTPFNL SEGIFKVIAT  180
VLSRAAFGKG IKDQKQFTEI VKEILRETGG FDVADIFPSK KFLHHLSGKR GRLTSIHNKL  240
DSLINNLVAE HTVSKSSKVN ETLLDVLLRL KNSEEFPLTA DNVKAIILDM FGAGTDTSSA  300
TVEWAISELI RCPRAMEKVQ AELRQALNGK ERIKEEEIQD LPYLNLVIRE TLRLHPPLPL  360
VMPRECRQAM NLAGYDVANK TKLIVNVFAI NRDPEYWKDA ESFNPERFEN SNTTIMGADY  420
EYLPFGAGRR MCPGSALGLA NVQLPLANIL YYFKWKLPNG ASHDQLDMTE SFGATVQRKT  480
ELMLVPSF                                                          488

SEQ ID NO: 53          moltype = AA  length = 488
FEATURE                Location/Qualifiers
source                 1..488
                       mol_type = protein
                       organism = Helianthus annuus
SEQUENCE: 53
MALLLAVFIA LATIVFFLYK LLTRPTSSKN RLPEPWRLPI IGHMHHLIGT MPHRGVMDLA  60
RKYGSLMHLQ LGEVSAIVVS SPKWAKEILT TYDIPFANRP ETLTGEIIAY HNTDIVLAPY  120
GEYWRQLRKL CTLELLSVKK VKSFQSLREE ECWNLVQEIK ASGSGTPFNL SEGIFKVIAT  180
VLSRAAFGKG IKDQKQFTEI VKEILRETGG FDVADIFPSK KFLHHLSGKR GRLTSIHNKL  240
DSLINNLVAE HTVSKSSKVN ETLLDVLLRL KNSEEFPLTA DNVKAIILDM FGAGTDTSSA  300
TVEWAISELI RCPRAMEKVQ AELRQALNGK ERIKEEEIQD LPYLNLVIRE TLRLHPPLPL  360
VMPRECRQAM NLAGYDVANK TKLIVNVFAI NRDPEYWKDA ESFNPERFEN SNTTIMGADY  420
EYLPFGAGRR MCPGSALGLA NVQLPLANIL YYFKWKLPNG ASHDQLDMTE SFGATVQRKT  480
ELMLVPSF                                                          488

SEQ ID NO: 54          moltype = DNA  length = 1464
FEATURE                Location/Qualifiers
source                 1..1464
                       mol_type = other DNA
                       organism = Helianthus annuus
SEQUENCE: 54
atggctctgt tattagcagt tttcatcgcc ctggcaacca ttgtcttttt cctgtataaa  60
ctgctgaccc gtccgacctc atctaaaaac cgtctgccgg aaccgtggcg cctgccgatt  120
atcggccaca tgcatcacct gattggcacc atgccgcacc gtggtgtcat ggatctggca  180
cgcaaatatg gcagcctgat gcatctgcaa ctgggtgaag tttctgcgat tgtggttagc  240
tctccgaaat gggccaaaga aattctgacc acctatgata ttccgtttgc gaaccgcccg  300
gaaaccctga cgggcgaaat tatcgcatac cacaataccg acattgtgct ggctccgtat  360
ggtgaatact ggcgtcaact gcgtaaactg tgcacgctgg aactgctgag tgttaaaaaa  420
gtcaaaagtt tccagagcct gcgtgaagaa gaatgttgga acctggttca agaaattaaa  480
gcgagcggca gcggcacccc gtttaatctg agtgaaggta ttttcaaagt gattgcgacc  540
gtgctgagcc gtgcggcatt tggtaaaggt atcaaagatc agaaacaatt caccgaaatt  600
gtcaaagaaa tcctgcgcga aacgggcggt tttgatgtgg cggacatctt tccgagcaaa  660
aaattcctgc atcacctgtc tggcaaacgt ggtcgcctga cctcaattca taacaaactg  720
gattcgctga tcaacaatct ggtcgccgaa cataccgtga gcaaaagcag caaagtgaat  780
gaaacgctgc tggatgtcct gctgcgtctg aaaaactcgg aagaatttcc gctgaccgca  840
gacaatgtga aagctattat cctggatatg ttcggtgcag gcaccgatac cagcagcgca  900
acggtggaat gggccattag cgaactgatc cgttgcccgc gcgcaatgga aaaagttcag  960
gcagaactgc gtcaagctct gaacggcaaa gaacgcatta aagaagaaga aatccaggat  1020
ctgccgtatc tgaatctggt tattcgtgaa accctgcgtc tgcatccgcc gctgccgctg  1080
gtcatgccgc gtgaatgtcg ccaagcaatg aacctggctg gctatgacgt ggcaaataaa  1140
```

-continued

```
accaaactga tcgtcaatgt gtttgcgatt aaccgtgacc cggaatactg gaaagacgcg  1200
gaaagtttta acccggaacg ctttgaaaac agcaacacca cgattatggg tgcggattat  1260
gaatacctgc cgtttggcgc cggtcgtcgc atgtgtccgg gcagcgcgct gggtctggcc  1320
aacgttcaac tgccgctggc caatatcctg tattacttca aatggaaact gccgaatggc  1380
gcctcacacg atcaactgga catgaccgaa tcgtttggtg caaccgtgca acgcaaaacg  1440
gaactgatgc tggttccgtc tttc                                          1464

SEQ ID NO: 55          moltype = AA  length = 504
FEATURE                Location/Qualifiers
REGION                 1..504
                       note = Synthetic - Engineered valencene oxidase
source                 1..504
                       mol_type = protein
                       organism = synthetic construct
SEQUENCE: 55
MAWEYALIGL VVGIIIGAVA AWYLKSYTSA RRSQSNHLPR VPEVPGVPLL GNLLQLKEKK  60
PYMTFTRWAA TYGPIYSIKT GATSMVVVSS NEIAKEALVT RFQSISTRNL SKALKVLTAD  120
KTMVAMSDYD DYHKTVKRHI LTAVLGPNAQ KKHRIHRDIM MDNISTQLHE FVKNNPEQEE  180
VDLRKIFQSE LFGLAMRQAL GKDVESLYVE DLKITMNRDE IFQVLVVDPM MGAIDVDWRD  240
FFPYLKWVPN KKFENTIQQM YIRREAVMKS LIKEHKKRIA SGEKLNSYID YLLSEAQTLT  300
DQQLLMSLWE PIIESSDTTM VTTEWAMYEL AKNPKLQDRL YRDIKSVCGS EKITEEHLSQ  360
LPYITAIFHE TLRRHSPVPI IPLRHVHEDT VLGGYHVPAG TELAVNIYGC NMDKNVWENP  420
EEWNPERFMK ENETIDFQKT MAFGGGKRVC AGSLQALLTA SIGIGRMVQE FEWKLKDMTQ  480
EEVNTIGLTT QMLRPLRAII KPRI                                          504

SEQ ID NO: 56          moltype = AA  length = 505
FEATURE                Location/Qualifiers
REGION                 1..505
                       note = Synthetic - Engineered valencene oxidase
source                 1..505
                       mol_type = protein
                       organism = synthetic construct
SEQUENCE: 56
MAWEYALIGL VVGIIIGAVA MRWYLKSYTS ARRSQSNHLP RVPEVPGVPL LGNLLQLKEK  60
KPYMTFTRWA ATYGPIYSIK TGATSVVVVS SNEIAKEAMV TRFQSISTRN LSKALKVLTA  120
DKTMVAMSDY DDYHKTVKRH ILTAVLGPNA QKKHRIHRDI MMDNISTQLH EFVKNNPEQE  180
EVDLRKIFQS ELFGLAMRQA LGKDVESLYV EDLKITMNRD EILQVLVVDP MMGAIDVDWR  240
DFFPYLKWVP NKKFENTIQQ MYIRREAVMK SLIKEHKKRI ASGEKLNSYI DYLLSEAQTL  300
TDQQLLMSLW EPIIESSDTT MVTTEWAMYE LAKNPKLQDR LYRDIKSVCG SEKITEEHLS  360
QLPYITAIFH ETLRKHSPVP ILPLRHVHED TVLGGYHVPA GTELAVNIYG CNMDKNVWEN  420
PEEWNPERFM KENETIDFQK TMAFGGGKRV CAGSLQALLI ASIGIGRMVQ EFEWKLKDMT  480
QEEVNTIGLT NQMLRPLRAI IKPRI                                         505

SEQ ID NO: 57          moltype = AA  length = 505
FEATURE                Location/Qualifiers
REGION                 1..505
                       note = Synthetic - Engineered valencene oxidase
source                 1..505
                       mol_type = protein
                       organism = synthetic construct
SEQUENCE: 57
MAWEYALIGL VVGIIIGAVA MRWYLKSYTS ARRSQSNHLP RVPEVPGVPL LGNLLQLKEK  60
KPYMTFTKWA ATYGPIYSIK TGATSMVVVS SNEIAKEAMV TRFQSISTRN LSKALKVLTA  120
DKQMVAMSDY DDYHKTVKRH ILTAVLGPNA QKKHRIHRDI MMDNISTQLH EFVKNNPEQE  180
EVDLRKIFQS ELFGLAMRQA LGKDVESLYV EDLKITMNRD EILQVLVVDP MMGAIDVDWR  240
DFFPYLKWVP NKKFENTIQQ MYIRREAVMK SLIKEHKKRI ASGEKLNSYI DYLLSEAQTL  300
TDQQLLMSLW EPIIESSDTT MVTTEWAMYE LAKNPKLQDR LYRDIKSVCG SEKITEEHLS  360
QLPYITAIFH ETLRKHSPVP ILPLRHVHED TVLGGYHVPA GTELAVNIYG CNMDKNVWEN  420
PEEWNPERFM KENETIDFQK TMAFGGGKRV CAGSLQALLI ASIGIGRMVQ EFEWKLKDMT  480
QEEVNTIGLT NQMLRPLRAI IKPRI                                         505

SEQ ID NO: 58          moltype = AA  length = 505
FEATURE                Location/Qualifiers
REGION                 1..505
                       note = Synthetic - Engineered valencene oxidase
source                 1..505
                       mol_type = protein
                       organism = synthetic construct
SEQUENCE: 58
MAWEYALIGL VVGIIIGAVA MRWYLKSYTS ARRSQSNHLP RVPEVPGVPL LGNLLQLKEK  60
KPYMTFTRWA ATYGPIYSIK TGATSVVVVS SNEIAKEAMV TRFQSISTRN LSKALKVLTA  120
DKQMVAMSDY DDYHKTVKRH ILTAVLGPNA QKKHRIHRDI MMDNISTQLH EFVKNNPEQE  180
EVDLRKIFQS ELFGLAMRQA LGKDVESLYV EDLKITMNRD EILQVLVVDP MMGAIDVDWR  240
DFFPYLKWVP NKKFENTIQQ MYIRREAVMK SLIKEHKKRI ASGEKLNSYI DYLLSEAQTL  300
TDQQLLMSLW EPIIESSDTT MVTTEWAMYE LAKNPKLQDR LYRDIKSVCG SEKITEEHLS  360
QLPYITAIFH ETLRKHSPVP ILPLRHVHED TVLGGYHVPA GTELAVNIYG CNMDKNVWEN  420
PEEWNPERFM KENETIDFQK TMAFGGGKRV CAGSLQALLI ASIGIGRMVQ EFEWKLKDMT  480
QEEVNTIGLT NQMLRPLRAI IKPRI                                         505
```

```
SEQ ID NO: 59          moltype = AA  length = 504
FEATURE                Location/Qualifiers
REGION                 1..504
                       note = Synthetic - Engineered valencene oxidase
source                 1..504
                       mol_type = protein
                       organism = synthetic construct
SEQUENCE: 59
MAWEYALIGL VVGIIIGAVA AWYLKSYTSA RRSQSNHLPR VPEVPGVPLL GNLLQLKEKK  60
PYMTFTKWAA TYGPIYSIKT GATSMVVVSS NEIAKEAMVT RFQSISTRNL SKALKVLTAD  120
KQMVAMSDYD DYHKTVKRHI LTAVLGPNAQ KKHRIHRDIM MDNISTQLHE FVKNNPEQEE  180
VDLRKIFQSE LFGLAMRQAL GKDVESLYVE DLKITMNRDE ILQVLVVDPM MGAIDVDWRD  240
FFPYLKWVPN KKFENTIQQM YIRREAVMKS LIKEHKKRIA SGEKLNSYID YLLSEAQTLT  300
DQQLLMSLWE PIIESSDTTM VTTEWAMYEL AKNPKLQDRL YRDIKSVCGS EKITEEHLSQ  360
LPYITAIFHE TLRKHSPVPI LPLRHVHEDT VLGGYHVPAG TELAVNIYGC NMDKNVWENP  420
EEWNPERFMK ENETIDFQKT MAFGGGKRVC AGSLQALLIA SIGIGRMVQE FEWKLKDMTQ  480
EEVNTIGLTN QMLRPLRAII KPRI                                       504

SEQ ID NO: 60          moltype = AA  length = 505
FEATURE                Location/Qualifiers
REGION                 1..505
                       note = Synthetic - Engineered valencene oxidase
source                 1..505
                       mol_type = protein
                       organism = synthetic construct
SEQUENCE: 60
MAWEYALIGL VVGIIIGAVA MRWYLKSYTS ARRSQSNHLP RVPEVPGVPL LGNLLQLKEK  60
KPYMTFTKWA ATYGPIYSIK TGATSVVVVS SNEIAKEAMV TRFQSISTRN LSKALKVLTA  120
DKTMVAMSDY DDYHKTVKRH ILTAVLGPNA QKKHRIHRDI MMDNISTQLH EFVKNNPEQE  180
EVDLRKIFQS ELFGLAMRQA LGKDVESLYV EDLKITMNRD EILQVLVVDP MMGAIDVDWR  240
DFFPYLKWVP NKKFENTIQQ MYIRREAVMK SLIKEHKKRI ASGEKLNSYI DYLLSEAQTL  300
TDQQLLMSLW EPIIESSDTT MVTTEWAMYE LAKNPKLQDR LYRDIKSVCG SEKITEEHLS  360
QLPYITAIFH ETLRKHSPVP IIPLRHVHED TVLGGYHVPA GTELAVNIYG CNMDKNVWEN  420
PEEWNPERFM KENETIDFQK TMAFGGGKRV CAGSLQALLI ASIGIGRMVQ EFEWKLKDMT  480
QEEVNTIGLT NQMLRPLRAI IKPRI                                      505

SEQ ID NO: 61          moltype = AA  length = 505
FEATURE                Location/Qualifiers
REGION                 1..505
                       note = Synthetic - Engineered valencene oxidase
source                 1..505
                       mol_type = protein
                       organism = synthetic construct
SEQUENCE: 61
MAWEYALIGL VVGIIIGAVA MRWYLKSYTS ARRSQSNHLP RVPEVPGVPL LGNLLQLKEK  60
KPYMTFTKWA ATYGPIYSIK TGATSVVVVS SNEIAKEALV TRFQSISTRN LSKALKVLTA  120
DKQMVAMSDY DDYHKTVKRH ILTAVLGPNA QKKHRIHRDI MMDNISTQLH EFVKNNPEQE  180
EVDLRKIFQS ELFGLAMRQA LGKDVESLYV EDLKITMNRD EILQVLVVDP MMGAIDVDWR  240
DFFPYLKWVP NKKFENTIQQ MYIRREAVMK SLIKEQKKRI ASGEKLNSYI DYLLSEAQTL  300
TDQQLLMSLW EPIIESSDTT MVTTEWAMYE LAKNPKLQDR LYRDIKSVCG SEKITEEHLS  360
QLPYITAIFH ETLRKHSPVP ILPLRHVHED TVLGGYHVPA GTELAVNIYG CNMDKNVWEN  420
PEEWNPERFM KENETIDFQK TMAFGGGKRV CAGSLQALLI ASIGIGRMVQ EFEWKLKDMT  480
QEEVNTIGLT NQMLRPLRAI IKPRI                                      505

SEQ ID NO: 62          moltype = AA  length = 710
FEATURE                Location/Qualifiers
source                 1..710
                       mol_type = protein
                       organism = Stevia rebaudiana
SEQUENCE: 62
MQSDSVKVSP FDLVSAAMNG KAMEKLNASE SEDPTTLPAL KMLVENRELL TLFTTSFAVL  60
IGCLVFLMWR RSSSKKLVQD PVPQVIVVKK KEKESEVDDG KKKVSIFYGT QTGTAEGFAK  120
ALVEEAKVRY EKTSFKVIDL DDYAADDDEY EEKLKKESLA FFFLATYGDG EPTDNAANFY  180
KWFTEGDDKG EWLKKLQYGV FGLGNRQYEH FNKIAIVVDD KLTEMGAKRL VPVGLGDDDQ  240
CIEDDFTAWK ELVWPELDQL LRDEDDTSVT TPYTAAVLEY RVVYHDKPAD SYAEDQTHTN  300
GHVVHDAQHP SRSNVAFKKE LHTSQSDRSC THLEFDISHT GLSYETGDHV GVYSENLSEV  360
VDEALKLLGL SPDTYFSVHA DKEDGTPIGG ASLPPPFPPC TLRDALTRYA DVLSSPKKVA  420
LLALAAHASD PSEADRLKFL ASPAGKDEYA QWIVANQRSL LEVMQSFPSA KPPLGVFFAA  480
VAPRLQPRYY SISSSPKMSP NRIHVTCALV YETTPAGRIH RGLCSTWMKN AVPLTESPDC  540
SQASIFVRTS NFRLPVDPKV PVIMIGPGTG LAPFRGFLQE RLALKESGTE LGSSIFFFGC  600
RNRKVDFIYE DELNNFVETG ALSELIVAFS REGTAKEYVQ HKMSQKASDI WKLLSEGAYL  660
YVCGDAKGMA KDVHRTLHTI VQEQGSLDSS KAELYVKNLQ MSGRYLRDVW            710

SEQ ID NO: 63          moltype = DNA  length = 2133
FEATURE                Location/Qualifiers
source                 1..2133
                       mol_type = other DNA
                       organism = Stevia rebaudiana
SEQUENCE: 63
```

```
atgcagagcg attctgttaa agtatccccg ttcgacctgg tctctgcggc tatgaacggc  60
aaagcaatgg agaaactgaa cgcgagcgaa tctgaagatc caaccaccct gccggcactg  120
aaaatgctgg tagaaaaccg tgaactgctg actctgttca ccacctcctt cgccgttctg  180
attggttgcc tggtcttcct gatgtggcgc cgttcctctt ccaagaagct ggtacaggac  240
ccggttcctc aggtgatcgt cgttaaaaag aaagagaagg aaagcgaagt cgatgacggc  300
aaaaagaagg tttccatttt ctacggtact cagaccggca ccgctgaggg ttttgccaaa  360
gcactggttg aagaggcaaa agtgcgttac gaaaaaactt ccttcaaagt gattgacctg  420
gacgactatg ctgcggatga tgatgaatac gaggaaaaac tgaaaaaaga aagcctggcc  480
ttcttcttcc tggcaaccta tggcgatggt gaaccgaccg acaacgcggc gaacttctac  540
aaatggttta ccgaaggcga cgacaaaggt gaatggctga agaaactgca gtatggtgtt  600
ttcggtctgg gcaatcgcca gtacgaacat tttaacaaaa tcgcaatcgt tgttgatgac  660
aaactgactg aaatgggtgc gaaacgtctg gtgccggttg gcctgggtga cgatgatcaa  720
tgcatcgaag atgacttcac cgcatggaaa gaactggttt ggccggaact ggatcagctg  780
ctgcgcgacg aagacgacac ttccgtgacc accccgtata ccgctgcagt gctggagtac  840
cgtgttgttt accacgataa accggcggac tcttacgccg aagatcagac tcacactaac  900
ggtcacgtcg tacatgacgc acagcacccg tctcgtagca atgttgcgtt taagaaagag  960
ctgcacacga gccagtccga ccgctcttgt acgcacctgg agttcgatat ctcccacacc  1020
ggtctgtcct atgaaaccgg tgaccatgtt ggcgtttaca gcgaaaacct gagcgaggta  1080
gttgatgaag cgctgaaact gctgggcctg tctccagaca cctactttag cgtgcatgct  1140
gacaaggaag atggtactcc gattggcggc gcttccctgc cgccaccgtt tccaccttgc  1200
actctgcgtg atgctctgac tcgttacgct gatgttctgt ctagcccgaa aaaggttgcg  1260
ctgctggcgc tggccgcaca tgcttctgac ccgtctgaag ctgaccgtct gaaattcctg  1320
gcgtctccgg ccggcaaaga cgaatacgcg cagtggattg tcgctaacca gcgctctctg  1380
ctggaagtga tgcagtcctt cccgtctgcc aaaccgccac tgggcgtgtt tttcgcagct  1440
gtggctccgc gcctgcagcc gcgctactat tctatctcta gctccccgaa aatgagcccg  1500
aaccgcatcc acgttacttg tgctctggtt tacgaaacca cccctgcggg ccgtatccac  1560
cgtggtctgt gctctacgtg gatgaaaaat gccgtgccgc tgaccgaatc ccccggactgc  1620
tctcaggcgt ccatcttcgt gcgtacctct aacttccgtc tgccggtgga cccgaaagtt  1680
cctgttatca tgatcggtcc tggcacgggt ctggccccgt ttcgtggttt tctgcaggag  1740
cgtctggctc tgaaagaatc cggtactgag ctgggctctt ccatcttttt cttcggttgt  1800
cgtaaccgca aagtcgattt catctatgaa gacgaactga acaacttcgt agagactggt  1860
gcactgtccg aactgattgt ggcattctct cgtgaaggca cggcgaaaga atacgttcaa  1920
cacaaaatgt ctcagaaagc gagcgatatc tggaaactgc tgtccgaggg tgcgtatctg  1980
tatgtttgtg gcgacgcgaa aggcatggct aaagatgtac accgcaccct gcacaccatt  2040
gtacaagaac aaggctctct ggatagctcc aaggcagaac tgtacgtgaa aaacctgcag  2100
atgtctggcc gttacctgcg tgatgtatgg taa                             2133
```

```
SEQ ID NO: 64          moltype = AA  length = 692
FEATURE                Location/Qualifiers
source                 1..692
                       mol_type = protein
                       organism = Arabidopsis thaliana
SEQUENCE: 64
MTSALYASDL FKQLKSIMGT DSLSDDVVLV IATTSLALVA GFVVLLWKKT TADRSGELKP  60
LMIPKSLMAK DEDDDLDLGS GKTRVSIFFG TQTGTAEGFA KALSEEIKAR YEKAAVKVID  120
LDDYAADDDQ YEEKLKKETL AFFCVATYGD GEPTDNAARF SKWFTEENER DIKLQQLAYG  180
VFALGNRQYE HFNKIGIVLD EELCKKGAKR LIEVGLGDDD QSIEDDFNAW KESLWSELDK  240
LLKDEDDKSV ATPYTAVIPE YRVVTHDPRF TTQKSMESNV ANGNTTIDIH HPCRVDVAVQ  300
KELHTHESDR SCIHLEFDIS RTGITYETGD HVGVYAENHV EIVEEAGKLL GHSLDLVFSI  360
HADKEDGSPL ESAVPPPFPG PCTLGTGLAR YADLLNPPRK SALVALAAYA TEPSEAEKLK  420
HLTSPDGKDE YSQWIVASQR SLLEVMAAFP SAKPPLGVFF AAIAPRLQPR YYSISSCQDW  480
APSRVHVTSA LVYGPTPTGR IHKGVCSTWM KNAVPAEKSH ECSGAPIFIR ASNFKLPSNP  540
STPIVMVGPG TGLAPFRGFL QERMALKEDG EELGSSLLFF GCRNRQMDFI YEDELNNFVD  600
QGVISELIMA FSREGAQKEY VQHKMMEKAA QVWDLIKEEG YLYVCGDAKG MARDVHRTLH  660
TIVQEQEGVS SSEAEAIVKK LQTEGRYLRD VW                                692
```

```
SEQ ID NO: 65          moltype = DNA  length = 2079
FEATURE                Location/Qualifiers
source                 1..2079
                       mol_type = other DNA
                       organism = Arabidopsis thaliana
SEQUENCE: 65
atgaccagcg cactgtacgc aagcgacctg tttaagcaac tgaagagcat tatgggcacc  60
gatagcctga gcgatgatgt tgtcctggtc attgcgacca cgagcctggc actggtggct  120
ggttttgtgg ttctgctgtg gaaaaagacc acggccgatc gttctggcga actgaaaccg  180
ctgatgattc cgaaaagtct gatggcaaag gacgaagatg acgatctgga tctgggctcc  240
ggtaaaaccc gtgtgtcaat ctttttcggt acccagacgg gcaccgcaga aggtttcgca  300
aaagctctgt ctgaagaaat taaggcgcgc tatgaaaaag cggccgttaa ggtcatcgat  360
ctggacgatt atgcagctga cgatgaccag tacgaagaaa aactgaaaaa ggaaaccctg  420
gcgtttttct gcgttgccac ctacggcgac ggtgaaccga cggataacgc ggcccgtttt  480
agtaaatggt tcaccgaaga aaatgaacgc gacattaagc tgcagcaact ggcgtatggc  540
gtgtttgctc tgggtaaccg tcagtacgaa catttcaaca agatcggtat cgtcctggat  600
gaagaactgt gtaaaaaggg cgcgaagcgc ctgattgaag tgggcctggg tgatgacgat  660
caatccatcg aagacgattt taacgcctgg aaagaatctc tgtggagtga actggacaaa  720
ctgctgaagg atgaagacga taagagcgtg gcgacgccgt ataccgccgt tattccggaa  780
taccgtgtcg tgacccatga tccgcgcttc accacgcaga aaagcatgga atcaaatgtt  840
gcgaacggta ataccacgat tgacatccat cacccgtgcc gtgtggatgt tgccgtccaa  900
aaagaactgc atacccacga atcggaccgt agctgtatcc acctggaatt tgatattagc  960
cgcacgggca tcacctatga aacgggcgac catgtgggtg tttacgcaga aaaccacgtg  1020
```

```
gaaattgttg aagaagctgg caaactgctg ggtcattcgc tggatctggt ttttagcatc  1080
cacgcggaca aggaagatgg ttcgccgctg gaaagcgcag tgccgccgcc gttcccgggt  1140
ccgtgcaccc tgggtacggg tctggcacgt tatgcagatc tgctgaatcc gccgcgcaaa  1200
tccgcactgg tggctctggc agcttacgca accgaaccgt cagaagctga aaaactgaag  1260
catctgacgt cgccggacgg taaagatgaa tatagccagt ggattgttgc gtctcaacgc  1320
agtctgctgg aagtcatggc agcatttccg tcggcaaaac cgccgctggg cgtgtttttc  1380
gcagctattg caccgcgtct gcagccgcgc tattacagca tcagctcttg tcaagattgg  1440
gcgccgtctc gtgtccatgt gaccagtgca ctggtgtatg gtccgacgcc gaccggtcgc  1500
attcacaaag gcgtgtgctc tacctggatg aaaaacgcgg ttccggccga aaagtctcac  1560
gaatgtagtg gtgcgccgat ttttatccgt gccagtaact tcaaactgcc gtccaatccg  1620
tcaaccccga tcgttatggt cggtccgggt acgggtctgg caccgtttcg tggtttcctg  1680
caggaacgca tggctctgaa agaagatggc gaagaactgg gtagttccct gctgtttttc  1740
ggctgccgta atcgccagat ggacttcatc tacgaagatg aactgaacaa cttcgtcgat  1800
caaggtgtga tttccgaact gatcatggca ttttcacgcg aaggcgctca gaaagaatac  1860
gtccaacata aaatgatgga aaaggcggcc caagtgtggg atctgatcaa agaagaaggc  1920
tatctgtacg tttgtggcga cgcaaagggt atggctcgtg atgtccatcg caccctgcac  1980
acgattgttc aggaacaaga aggtgtctca tcgagcgaag cggaagccat cgtgaaaaag  2040
ctgcagaccg aaggccgtta tctgcgcgat gtttggtaa                         2079

SEQ ID NO: 66           moltype = AA  length = 717
FEATURE                 Location/Qualifiers
source                  1..717
                        mol_type = protein
                        organism = Taxus cuspidata
SEQUENCE: 66
MQANSNTVEG ASQGKSLLDI SRLDHIFALL LNGKGGDLGA MTGSALILTE NSQNLMILTT  60
ALAVLVACVF FFVWRRGGSD TQKPAVRPTP LVKEEDEEEE DDSAKKKVTI FFGTQTGTAE  120
GFAKALAEEA KARYEKAVFK VVDLDNYAAD DEQYEEKLKK EKLAFFMLAT YGDGEPTDNA  180
ARFYKWFLEG KEREPWLSDL TYGVFGLGNR QYEHFNKVAK AVDEVLIEQG AKRLVPVGLG  240
DDDQCIEDDF TAWREQVWPE LDQLLRDEDD EPTSATPYTA AIPEYRVEIY DSVVSVYEET  300
HALKQNGQAV YDIHHPCRSN VAVRRELHTP LSDRSCIHLE FDISDTGLIY ETGDHVGVHT  360
ENSIETVEEA AKLLGYQLDT IFSVHGDKED GTPLGGSSLP PPFPGPCTLR TALARYADLL  420
NPPRKAAFLA LAAHASDPAE AERLKFLSSP AGKDEYSQWV TASQRSLLEI MAEFPSAKPP  480
LGVFFAAIAP RLQPRYYSIS SSPRFAPSRI HVTCALVYGP SPTGRIHKGV CSNWMKNSLP  540
SEETHDCSWA PVFVRQSNFK LPADSTTPIV MVGPGTGFAP FRGFLQERAK LQEAGEKLGP  600
AVLFFGCRNR QMDYIYEDEL KGYVEKGILT NLIVAFSREG ATKEYVQHKM LEKASDTWSL  660
IAQGGYLYVC GDAKGMARDV HRTLHTIVQE QESVDSSKAE FLVKKLQMDG RYLRDIW     717

SEQ ID NO: 67           moltype = DNA  length = 2154
FEATURE                 Location/Qualifiers
source                  1..2154
                        mol_type = genomic DNA
                        organism = Taxus cuspidata
SEQUENCE: 67
atgcaggcta attccaacac ggtggaaggt gcctcccagg ggaagagcct gctggacata  60
tctcggctgg accatatttt tgcgctgctg ttgaacggca agggaggaga tctgggagcc  120
atgaccggct cggctttgat tttgacagag aattcgcaga atttgatgat tttgaccacg  180
gctttggctg ttttggtcgc gtgtgttttc ttcttcgttt ggaggagggg aggatcggat  240
acgcagaagc cggcggtgag accgacgcct ctggtgaagg aggaagatga ggaggaagaa  300
gacgattctg caaagaagaa agtcacgatt ttctttggga cacagactgg gacggccgag  360
ggatttgcca aggctctagc agaagaggca aaggcaagat atgagaaagc tgtgtttaaa  420
gtcgtagatt tggacaacta tgcagcagat gatgagcagt atgaagaaaa attgaaaaag  480
gaaaaattag cattttttat gctagcaacg tatggagatg gggagcccac tgacaatgca  540
gcaagatttt ataagtggtt tcttgagggc aaggagaggg agccatggct ttctgatctc  600
acttatgggg tgtttggatt aggcaacaga caatatgaac attttaataa ggtggctaaa  660
gcagtagatg aagtcttaat tgaacaaggt gcaaagcgac ttgttccagt gggccttggt  720
gatgatgacc aatgcattga agatgacttt actgcttggc gagagcaggt ttggcctgaa  780
ctggatcagt tactccggga tgaagatgat gagcccacaa gtgctacacc ttatacagct  840
gccatacctg agtatagggt tgaaatttat gattccgtgg tttcagtgta cgaggaaact  900
catgctctca agcaaaatgg ccaagctgtt tatgatatcc atcacccctg cagatctaat  960
gtggcagtga gaagagagct tcatacacct ttgtctgacc gctcttgcat ccatttggaa  1020
tttgatatat cagacactgg ccttatatat gagacaggag atcatgttgg tgtccataca  1080
gaaaacagca ttgaaactgt ggaggaagca gcaaagctac taggctacca attggacact  1140
atattctcag tccacggtga caaagaagat ggcacgccac ttggagggtc ttctttgcca  1200
ccacctttcc ctggtccatg caccctacga actgctcttg ctcgttatgc tgatttgctg  1260
aatcctcctc ggaaggccgc ctttcttgca ttggcagctc atgcatctga tccagcagag  1320
gcagagcggt tgaagttcct ctcatcacca gctggaaagg atgaatattc tcaatgggtc  1380
actgcaagtc agagaagtct tttagaaata atggcagaat ttccatcagc aaaaccaccc  1440
cttggtgttt tctttgcagc aatagcccct cgtctgcaac cccgatatta ttctatttct  1500
tcctctccca ggtttgcacc ctcaagaata catgtgacat gtgctcttgt ttacgggccc  1560
agtccaaccg gtagaattca caaaggtgtt tgttctaact ggatgaagaa ttcgctaccc  1620
tcagaagaaa cccatgactg tagctgggct ccagtctttg tcaggcaatc aaattttaaa  1680
ttgccagcag attctactac tcctattgtc atggtgggtc ctggaactgg ttttgcacct  1740
tttagaggtt ttttgcagga aagagcaaaa cttcaagaag ctggtgagaa gctcggtccg  1800
gctgttttat tttttgggtg caggaatcgc caaatggact acatttatga agatgagctg  1860
aagggctatg tggagaaagg aatactgacc aatctcattg ttgctttctc tcgtgaagga  1920
gcaaccaaag agtatgtcca gcacaagatg ctggaaaagg catccgatac ctggagtctc  1980
attgctcagg gtgggtatct ttatgtatgt ggtgatgcca agggtatggc tagggatgta  2040
cacaggacac tgcacactat tgtccaagag caggaatctg tggatagcag caaagcagag  2100
```

```
tttctagtga agaaattaca gatggatgga agatacttac gagatatatg gtga       2154

SEQ ID NO: 68          moltype = AA  length = 705
FEATURE                Location/Qualifiers
source                 1..705
                       mol_type = protein
                       organism = Artemisia annua
SEQUENCE: 68
MAQSTTSVKL SPFDLMTALL NGKVSFDTSN TSDTNIPLAV FMENRELLMI LTTSVAVLIG  60
CVVVLVWRRS SSAAKKAAES PVIVVPKKVT EDEVDDGRKK VTVFFGTQTG TAEGFAKALV  120
EEAKARYEKA VFKVIDLDDY AAEDDEYEEK LKKESLAFFF LATYGDGEPT DNAARFYKWF  180
TEGEEKGEWL DKLQYAVFGL GNRQYEHFNK IAKVVDEKLV EQGAKRLVPV GMGDDDQCIE  240
DDFTAWKELV WPELDQLLRD EDDTSVATPY TAAVAEYRVV FHDKPETYDQ DQLTNGHAVH  300
DAQHPCRSNV AVKKELHSPL SDRSCTHLEF DISNTGLSYE TGDHVGVYVE NLSEVVDEAE  360
KLIGLPPHTY FSVHADNEDG TPLGGASLPP PFPPCTLRKA LASYADVLSS PKKSALLALA  420
AHATDSTEAD RLKFLASPAG KDEYAQWIVA SHRSLLEVME AFPSAKPPLG VFFASVAPRL  480
QPRYYSISSS PRFAPNRIHV TCALVYEQTP SGRVHKGVCS TWMKNAVPMT ESQDCSWAPI  540
YVRTSNFRLP SDPKVPVIMI GPGTGLAPFR GFLQERLAQK EAGTELGTAI LFFGCRNRKV  600
DFIYEDELNN FVETGALSEL VTAFSREGAT KEYVQHKMTQ KASDIWNLLS EGAYLYVCGD  660
AKGMAKDVHR TLHTIVQEQG SLDSSKAELY VKNLQMAGRY LRDVW                 705

SEQ ID NO: 69          moltype = DNA  length = 2118
FEATURE                Location/Qualifiers
source                 1..2118
                       mol_type = other DNA
                       organism = Artemisia annua
SEQUENCE: 69
atggcgcagt ctaccaccag cgtgaaattg tccccttttg atctcatgac cgctctgctg  60
aatgggaaag tctcattcga tacaagcaac acaagtgata ccaacatccc tttggcggtt  120
tttatggaga atagagagtt actcatgatt ttaacgactt ccgtggccgt gctcattggg  180
tgcgtcgtcg tacttgtctg gcgccggtca agtagcgcag caaagaaggc ggcggagtcc  240
ccggttatcg tcgtcccaaa gaaggttaca gaggacgagg tggacgacgg acgcaaaaaa  300
gtgacggtat tctttggtac acagaccgga accgcggaag gatttgctaa agcgctggtg  360
gaagaagcta aagcccgtta cgaaaaagcg gtattcaaag tgatagacct ggatgactat  420
gcggcagagg acgacgagta cgaggaaaaa ttgaaaaaag aatctcttgc gttctttttt  480
ctcgccactt acggcgatgg agaacctact gataatgcgg ctcggtttta taagtggttc  540
actgagggtg aagaaaaagg tgaatggctg gacaaattgc agtacgcagt atttggactc  600
gggaatcgtc aatatgaaca ttttaacaaa attgctaagg tcgtcgatga aaaactggtt  660
gagcagggtg cgaaacgtct ggtcccggtt ggaatgggcg atgacgacca gtgcattgaa  720
gacgacttta cagcatggaa ggaactggtg tggccggaac tggaccaact tttgcgtgac  780
gaggatgaca catctgtagc tacgccgtac actgctgcgg tagccgagta tagggtcgtt  840
tttcacgata aaccggaaac ctacgaccaa gaccagctca caaatggtca tgcagtacat  900
gatgcgcaac atccttgcag gtcaaatgtg gcggtgaaga aagagctgca cagtcctctg  960
tcagatcgtt cttgcaccca cctggaattt gacatatcca atacgggcct ttcgtatgaa  1020
accggagatc acgttggtgt ctatgttgaa aatctgtcgg aagtggttga tgaggcggaa  1080
aaacttatcg gtctgccgcc tcatacgtac ttttcagtcc acgctgataa tgaagacgga  1140
accccgctgg gtggcgcatc gttacccccca ccctttccac catgcactct gcgtaaggcg  1200
cttgccagtt atgctgatgt tttgtctagt cccaaaaaga gtgcacttct cgcactggcg  1260
gcccatgcca ctgatagtac agaggccgac aggctgaaat ttctggcgtc accagcggga  1320
aaagacgaat acgcccaatg gatcgttgcc agtcatcggt ctttactgga agtgatggaa  1380
gcgttccctt ccgctaagcc acctctgggg gtctttttcg ctagtgtggc accccgtcta  1440
cagccccggt attactcaat atctagctca cccagatttg ctccgaatag aatacacgta  1500
acatgcgcgc tggtctatga gcagacccca agtggacggg tgcataaagg ggtttgttct  1560
acctggatga agaacgccgt cccaatgacc gagtctcagg attgttcctg ggcacctata  1620
tatgttagaa catcaaactt tcgactgcca agtgacccga aagttccggt aattatgata  1680
ggtccaggaa cagggctggc tccctttcgc gggttcctcc aggaacgtct ggcgcagaag  1740
gaggcgggaa ctgaactggg gacggcgatt ttatttttcg ggtgtagaaa tcgtaaagtc  1800
gattttatat atgaagatga gttgaacaat ttcgtggaaa ccggggcatt atcggaatta  1860
gttacggctt ttagcaggga gggggcgact aaagagtatg tccagcacaa gatgactcag  1920
aaagcctcag atatatggaa cctgctgtcg gagggagcct atctttatgt ttgcggtgat  1980
gcaaaaggaa tggccaaaga tgtccaccgg accctccaca ctattgtgca ggaacagggt  2040
tcattagact caagtaaagc cgaactttac gtaaaaaatc tacagatggc gggccgttac  2100
ctccgtgacg tttggtaa                                               2118

SEQ ID NO: 70          moltype = AA  length = 693
FEATURE                Location/Qualifiers
source                 1..693
                       mol_type = protein
                       organism = Arabidopsis thaliana
SEQUENCE: 70
MATSALYASD LFKQLKSIMG TDSLSDDVVL VIATTSLALV AGFVVLLWKK TTADRSGELK  60
PLMIPKSLMA KDEDDDLDLG SGKTRVSIFF GTQTGTAEGF AKALSEEIKA RYEKAAVKVI  120
DLDDYAADDD QYEEKLKKET LAFFCVATYG DGEPTDNAAR FYKWFTEENE RDIKLQQLAY  180
GVFALGNRQY EHFNKIGIVL DEELCKKGAK RLIEVGLGDD DQSIEDDFNA WKESLWSELD  240
KLLKDEDDKS VATPYTAVIP EYRVVTHDPR FTTQKSMESN VANGNTTIDI HHPCRVDVAV  300
QKELHTHESD RSCIHLEFDI SRTGITYETG DHVGVYAENH VEIVEEAGKL LGHSLDLVFS  360
IHADKEDGSP LESAVPPPFP GPCTLGTGLA RYADLLNPPR KSALVALAAY ATEPSEAEKL  420
KHLTSPDGKD EYSQWIVASQ RSLLEVMAAF PSAKPPLGVF FAAIAPRLQP RYYSISSSPR  480
LAPSRVHVTS ALVYGPTPTG RIHKGVCSTW MKNAVPAEKS HECSGAPIFI RASNFKLPSN  540
```

```
PSTPIVMVGP GTGLAPFRGF LQERMALKED GEELGSSLLF FGCRNRQMDF IYEDELNNFV  600
DQGVISELIM AFSREGAQKE YVQHKMMEKA AQVWDLIKEE GYLYVCGDAK GMARDVHRTL  660
HTIVQEQEGV SSSEAEAIVK KLQTEGRYLR DVW                              693

SEQ ID NO: 71          moltype = DNA  length = 2082
FEATURE                Location/Qualifiers
source                 1..2082
                       mol_type = other DNA
                       organism = Arabidopsis thaliana
SEQUENCE: 71
atggcgacca gcgctctgta tgctagtgac ctttttaaac agctcaaaag catcatgggc  60
actgatagcc tgtccgacga tgttgtcctg gtaatcgcaa ccacttccct tgcgcttgtt  120
gcgggctttg tggtgttact gtggaagaag actaccgcag ataggagtgg tgaattgaaa  180
ccgctgatga tcccaaaaag tctgatggcc aaagatgagg atgatgatct ggatcttgga  240
tcagggaaga cgcgagtcag tattttttc gggacccaga cgggcaccgc ggagggcttc  300
gccaaagctc tgtccgagga aataaaggcc agatacgaga aagccgccgt aaaggttata  360
gacctagatg attacgccgc tgatgacgat cagtatgagg agaaacttaa aaaggagact  420
ctggcgtttt tttgcgtggc aacttacgga gacggcgagc ccaccgataa tgcagctagg  480
ttttacaagt ggtttaccga ggagaacgaa cgagatataa agttacagca gttggcctat  540
ggcgtgtttg ccctgggtaa tcggcaatat gagcatttca acaaaattgg catcgttctg  600
gatgaggaat tgtgcaaaaa gggtgcaaaa cggctgatag aggtgggtct aggtgacgat  660
gatcaatcta tagaagacga ttttaatgcg tggaaagaga gcttatggag tgaactggat  720
aagctcttga aagatgaaga cgacaagtca gtggcgaccc cttataccgc ggtaatcccg  780
gaataccgcg tcgtgacaca cgatccgagg tttacaaccc aaaaatctat ggagtctaat  840
gtcgccaatg gcaacacaac gattgatatt caccacccct gtcgtgttga cgtggctgtt  900
caaaaagaac ttcatacaca cgaaagtgac cgaagttgca tacacttgga atttgacatt  960
agtcgcaccg gaattacgta tgaaactggt gatcacgtgg gtgtatacgc agaaaatcat  1020
gtcgaaatag tagaagaagc tggcaaactg ctgggacatt cactcgatct agtgtttagt  1080
atacatgccg ataaagagga tggcagccca ttggaaagtg ccgtccctcc gccgtttcct  1140
ggaccgtgta ctctggggac gggactcgcc cgctatgctg acctgttaaa cccccctcgt  1200
aaaagcgccc ttgtggccct ggcggcatac gcaactgaac cgagcgaagc ggagaagctg  1260
aaacatctga catcaccgga tggcaaagac gagtatagtc agtggatagt agcctctcag  1320
cgctctctgc tggaagtgat ggccgcattt ccgtccgcca aaccaccttt gggagtattt  1380
ttcgctgcta tcgcacctcg gctccagccg cgctattaca gcatatcttc aagtccccgc  1440
ttagcaccgt ctcgtgtcca tgtcacttct gcgttggttt atggtccgac tccaacaggt  1500
cgcatccaca aaggtgtctg ttcaacctgg atgaaaaacg cggtgcccgc ggagaaatct  1560
catgagtgca gtggtgcacc tatttttatc cgcgcaagta acttcaaact cccttctaat  1620
ccgagcacgc ccattgtgat ggttggccca ggcactggcc ttgctccgtt tcgcggtttt  1680
ctacaggagc ggatggccct taaagaagat ggggaagaat tgggatcatc gttgctcttt  1740
tttggctgcc gaaatcgcca gatggatttt atctacgaag acgagttgaa taactttgtc  1800
gatcaaggag taatttcgga gttgattatg gcattttcac gcgaaggggc tcagaaagag  1860
tatgtccaac acaagatgat ggaaaaagcg gcacaagtgt gggatcttat taaagaagaa  1920
ggctatcttt atgtatgtgg ggatgcgaaa ggtatggccc gtgatgtcca tcgcaccctg  1980
cacacgattg tacaggaaca ggaaggtgtg tcctcgtccg aagcagaagc aatcgttaaa  2040
aaactgcaaa cagagggtcg ttaccttcgc gacgtgtggt aa                    2082

SEQ ID NO: 72          moltype = AA  length = 712
FEATURE                Location/Qualifiers
source                 1..712
                       mol_type = protein
                       organism = Arabidopsis thaliana
SEQUENCE: 72
MASSSSSSST SMIDLMAAII KGEPVIVSDP ANASAYESVA AELSSMLIEN RQFAMIVTTS  60
IAVLIGCIVM LVWRRSGSGN SKRVEPLKPL VIKPREEEID DGRKKVTIFF GTQTGTAEGF  120
AKALGEEAKA RYEKTRFKIV DLDDYAADDD EYEEKLKKED VAFFFLATYG DGEPTDNAAR  180
FYKWFTEGND RGEWLKNLKY GVFGLGNRQY EHFNKVAKVV DDILVEQGAQ RLVQVGLGDD  240
DQCIEDDFTA WREALWPELD TILREEGDTA VATPYTAAVL EYRVSIHDSE DAKFNDINMA  300
NGNGYTVFDA QHPYKANVAV KRELHTPESD RSCIHLEFDI AGSGLTYETG DHVGVLCDNL  360
SETVDEALRL LDMSPDTYFS LHAEKEDGTP ISSSLPPPFP PCNLRTALTR YACLLSSPKK  420
SALVALAAHA SDPTEAERLK HLASPAGKDE YSKWVVESQR SLLEVMAEFP SAKPPLGVFF  480
AGVAPRLQPR FYSISSSPKI AETRIHVTCA LVYEKMPTGR IHKGVCSTWM KNAVPYEKSE  540
NCSSAPIFVR QSNFKLPSDS KVPIIMIGPG TGLAPFRGFL QERLALVESG VELGPSVLFF  600
GCRNRRMDFI YEEELQRFVE SGALAELSVA FSREGPTKEY VQHKMMDKAS DIWNMISQGA  660
YLYVCGDAKG MARDVHRSLH TIAQEQGSMD STKAEGFVKN LQTSGRYLRD VW            712

SEQ ID NO: 73          moltype = DNA  length = 2139
FEATURE                Location/Qualifiers
source                 1..2139
                       mol_type = other DNA
                       organism = Arabidopsis thaliana
SEQUENCE: 73
atggcgtcca gcagttcatc gagttctaca agcatgatcg atctgatggc cgctattatc  60
aaaggggaac ccgtaattgt ctctgatcca gcaaatgcct cggcatacga gtcggtggct  120
gccgaattat catctatgtt aattgaaaat agacaatttg ccatgattgt gacaacttct  180
attgctgtgc tgataggttg catcgtcatg ctcgtgtggc gccgtagcgg atcaggcaac  240
tcaaagcgcg tcgagccttt gaaacccctg gttatcaaac cgcgagagga ggaaatcgat  300
gatggcagaa aaaaggttac tatctttttt ggcacacaga cggggacagc ggaaggtttc  360
gcgaaagcac tcggagagga agcgaaagcc cgatacgaga aaacacggtt caaaattgtg  420
gatctggatg actatgcggc tgatgatgat gagtatgaag aaaaactgaa aaaagaagat  480
```

```
gtggcgtttt tttttcttgc cacttatggc gacggagagc ccaccgataa tgcagcgcgg  540
ttttacaagt ggttcaccga aggaaatgat cggggagaat ggttaaaaaa tctgaaatac  600
ggtgtgttcg gtcttggcaa tcgccaatat gagcatttta ataaagtcgc gaaagtggtc  660
gatgatatat tggtagaaca gggcgctcag cgcctcgtcc aggtggggct tggcgacgat  720
gatcagtgca tagaagatga ttttactgca tggcgtgaag cgctgtggcc ggagctggac  780
accattttac gtgaagaggg cgatacagca gtggcaaccc cgtacacggc tgccgtctta  840
gagtatcgtg tgtccattca tgatagcgag gatgccaaat tcaatgacat caatatggcg  900
aatggaaatg ggtacaccgt gtttgacgcg cagcacccgt ataaggcaaa cgttgcagtc  960
aagagggaac tgcatactcc tgaaagtgat cgcagttgca tccacctgga gttcgatatt  1020
gcgggatcag gtttaacgta cgaaacgggc gaccacgtag gtgtgctgtg cgacaatctt  1080
tcagagacag tggacgaagc tctgcgcctg ctggatatga gcccggatac ctattttagc  1140
ttgcacgctg agaaagaaga tgggactcca attagcagta gcttacctcc accctttccg  1200
ccgtgtaatt tgcgtaccgc ccttacgcgc tatgcgtgtc tgctgagttc gccaaagaag  1260
tcggcccttg tggcactggc ggcacatgca agtgacccga ccgaggcgga gaggctgaaa  1320
catctggctt ctccagcggg caaagatgaa tacagcaaat gggtggtaga atcacagcgt  1380
tccctactag aagtaatggc cgaatttccc tcagctaaac caccgctggg agtgttcttt  1440
gcgggcgttg ctccccgctt gcaaccacgc ttttattcaa ttagctcaag tcctaagata  1500
gcggaaacac ggatacatgt aacttgcgca ttggtttatg aaaaaatgcc aaccgggagg  1560
atacataaag gcgtatgttc aacctggatg aaaaatgctg tgccatacga aaagtcggag  1620
aattgctcct ctgccccaat tttcgtgcgt caaagcaact ttaaactgcc gagtgattca  1680
aaggtgccta ttattatgat aggccctggt acaggactcg ccccgtttcg tggttttctt  1740
caagaaagac tggctctggt cgaatcaggc gtggaattag gaccctccgt gttatttttt  1800
ggctgccgca accgtcgaat ggacttcatc tatgaagaag aattgcaacg ttttgtggag  1860
tcaggcgctc tggcggaact atccgtcgcc tttagtagag aaggcccaac caaagaatac  1920
gtacagcata agatgatgga taaagcgagc gacatttgga atatgatctc acaaggggcg  1980
tacctgtacg tatgtggaga tgccaaagga atggcacgag acgtacatag atcgttgcat  2040
actattgctc aagaacaggg aagcatggat tcgactaaag cagaaggctt tgttaaaaat  2100
ctacagacat ctggtcgcta tctgcgtgac gtgtggtaa                        2139

SEQ ID NO: 74          moltype = AA  length = 713
FEATURE                Location/Qualifiers
source                 1..713
                       mol_type = protein
                       organism = Arabidopsis thaliana
SEQUENCE: 74
MASSSSSSST SMIDLMAAII KGEPVIVSDP ANASAYESVA AELSSMLIEN RQFAMIVTTS  60
IAVLIGCIVM LVWRRSGSGN SKRVEPLKPL VIKPREEEID DGRKKVTIFF GTQTGTAEGF  120
AKALGEEAKA RYEKTRFKIV DLDDYAADDD EYEEKLKKED VAFFFLATYG DGEPTDNAAR  180
FYKWFTEGND RGEWLKNLKY GVFGLGNRQY EHFNKVAKVV DDILVEQGAQ RLVQVGLGDD  240
DQCIEDDFTA WREALWPELD TILREEGDTA VATPYTAAVL EYRVSIHDSE DAKFNDITLA  300
NGNGYTVFDA QHPYKANVAV KRELHTPESD RSCIHLEFDI AGSGLTMKLG DHVGVLCDNL  360
SETVDEALRL LDMSPDTYFS LHAEKEDGTP ISSSLPPPFP PCNLRTALTR YACLLSSPKK  420
SALVALAAHA SDPTEAERLK HLASPAGKDE YSKWVVESQR SLLEVMAEFP SAKPPLGVFF  480
AGVAPRLQPR FYSISSSPKI AETRIHVTCA LVYEKMPTGR IHKGVCSTWM KNAVPYEKSE  540
KLFLGRPIFV RQSNFKLPSD SKVPIIMIGP GTGLAPFRGF LQERLALVES GVELGPSVLF  600
FGCRNRRMDF IYEEELQRFV ESGALAELSV AFSREGPTKE YVQHKMMDKA SDIWNMISQG  660
AYLYVCGDAK GMARDVHRSL HTIAQEQGSM DSTKAEGFVK NLQTSGRYLR DVW         713

SEQ ID NO: 75          moltype = DNA  length = 2142
FEATURE                Location/Qualifiers
source                 1..2142
                       mol_type = other DNA
                       organism = Arabidopsis thaliana
SEQUENCE: 75
atggcgagca gttcgtcctc ctcttctacc agtatgatcg atctgatggc cgctattata  60
aaaggagaac cagtcattgt gtctgatcct gcaaacgcat cagcctacga atctgtggct  120
gctgaactgt cctcgatgct gatcgaaaat cgccaatttg caatgattgt tacaaccagc  180
atcgctgttc ttatcgggtg tattgtcatg ctggtttggc ggcggagtgg cagcggcaat  240
tctaaaagag tggagccact gaagcctctg gtaatcaaac cccgcgaaga agaaatcgat  300
gatggacgta agaaagttac aatttttttt ggtacacaga caggtacagc agagggcttt  360
gccaaagctc ttggagaaga agcaaaagct cgatatgaga aaacacgctt caagatcgtc  420
gatctggatg actacgcggc agacgacgat gagtacgaag aaaaactcaa aaaagaggat  480
gtggcttttt ttttcctggc aacttatggg gacggcgagc ctaccgacaa tgcagcgcgg  540
ttttacaaat ggtttaccga aggcaatgat agaggggagt ggctcaaaaa tctcaaatac  600
ggagttttcg gattggggaa tagacaatac gaacacttta ataaggttgc gaaagtggta  660
gatgatattc tggtcgagca gggcgcgcaa cgtttagtac aggtcggcct gggtgatgac  720
gaccagtgca tcgaagatga ctttacggcc tggcgagaag cgctctggcc ggaattagat  780
acaatccttc gggaagaggg ggacactgct gtcgctaccc cgtacactgc cgcagtgctg  840
gaatatcgtg tttcaataca tgattcggaa gatgccaagt ttaatgacat caccctggca  900
aacggcaacg gatataccgt atttgacgct caacatccgt ataaggccaa tgtagcagta  960
aagcgggaac tccatactcc cgaaagtgac agaagttgca tccatctgga gttcgatata  1020
gcgggaagcg gactgactat gaaactggga gatcatgtag ggtcctgtg cgataatttg   1080
agcgaaaccg ttgacgaagc gctccggctt ttagatatgt cccctgatac ttatttctct  1140
ttgcacgccg agaaggaaga tggtacacct atatcctcct cgctgccgcc gccttttcca  1200
ccatgtaatc tgcgtacggc cttgactagg tatgcatgtc ttcttagctc cccgaaaaag  1260
tccgcactgg tagcgttggc agctcatgcc agcgatccca cggaggcaga gcgtttaaaa  1320
cacctggcga gtcctgctgg caaagatgaa tacagcaaat gggtggttga gtcgcagagg  1380
tccctgctgg aagtcatggc tgaatttccg tctgcgaaac cgcctctggg agtttcttc   1440
gcaggagtag ccccacgttt acaaccgcgt ttctattcta tttcttcctc ccccaagatc  1500
```

```
gcggaaactc gaatacacgt aacgtgcgca ttggtgtatg aaaagatgcc aactggtcgt  1560
atccacaagg gagtgtgctc aacctggatg aaaaacgccg ttccgtatga aaaatcggaa  1620
aaattgtttt tgggtagacc catattcgtt cggcagtcaa actttaaact accttctgat  1680
agcaaggttc cgattattat gattggaccg ggtactggcc tggcgccgtt ccgtggtttc  1740
ctgcaagaac ggttggcgct ggtggaatcc ggcgtggaac ttgggccatc ggttttgttt  1800
ttcgggtgcc gcaatcgtcg catggacttc atctacgagg aagaactcca gcgttttgtc  1860
gaaagcggtg cccttgctga attgtccgtt gcattcagcc gcgaaggtcc aactaaggag  1920
tatgtgcagc acaaaatgat ggacaaagcg agcgatattt ggaatatgat tagccagggc  1980
gcataccttt atgtgtgcgg tgatgctaag ggaatggcgc gcgatgtcca tagatcttta  2040
cataccattg cacaggagca gggctctatg gattcaacaa aagctgaagg ttttgtgaaa  2100
aaccttcaga ccagcgggcg gtatcttcgc gatgtttggt aa                     2142

SEQ ID NO: 76          moltype = AA  length = 711
FEATURE                Location/Qualifiers
source                 1..711
                       mol_type = protein
                       organism = Stevia rebaudiana
SEQUENCE: 76
MAQSDSVKVS PFDLVSAAMN GKAMEKLNAS ESEDPTTLPA LKMLVENREL LTLFTTSFAV  60
LIGCLVFLMW RRSSSKKLVQ DPVPQVIVVK KKEKESEVDD GKKKVSIFYG TQTGTAEGFA  120
KALVEEAKVR YEKTSFKVID LDDYAADDDE YEEKLKKESL AFFFLATYGD GEPTDNAANF  180
YKWFTEGDDK GELLKKLQYG VFGLGNRQYE HFNKIAIVVD DKLTEMGAKR LVPVGLGDDD  240
QCIEDDFTAW KELVWPELDQ LLRDEDDTSV TTPYTAAVLE YRVVYHDKPA DSYAEDQTHT  300
NGHVVHDAQH PSRSNVAFKK ELHTSQSDRS CTHLEFDISH TGLSYETGDH VGVYSENLSE  360
VVDEALKLLG LSPDTYFSVH ADKEDGTPIG GASLPPPFPP CTLRDALTRY ADVLSSPKKV  420
ALLALAAHAS DPSEADRLKF LASPAGKDEY AQWIVANQRS LLEVMQSFPS AKPPLGVFFA  480
AVAPRLQPRY YSISSSPKMS PNRIHVTCAL VYETTPAGRI HRGLCSTWMK NAVPLTESPD  540
CSQASIFVRT SNFRLPVDPK VPVIMIGPGT GLAPFRGFLQ ERLALKESGT ELGSSIFFFG  600
CRNRKVDFIY EDELNNFVET GALSELIVAF SREGTAKEYV QHKMSQKASD IWKLLSEGAY  660
LYVCGDAKGM AKDVHRTLHT IVQEQGSLDS SKAELYVKNL QMSGRYLRDV W           711

SEQ ID NO: 77          moltype = DNA  length = 2136
FEATURE                Location/Qualifiers
source                 1..2136
                       mol_type = other DNA
                       organism = Stevia rebaudiana
SEQUENCE: 77
atggctcaga gcgattctgt taaagtatcc ccgttcgacc tggtctctgc ggctatgaac  60
ggcaaagcaa tggagaaact gaacgcgagc gaatctgaag atccaaccac cctgccggca  120
ctgaaaatgc tggtagaaaa ccgtgaactg ctgactctgt tcaccacctc cttcgccgtt  180
ctgattggtt gcctggtctt cctgatgtgg cgccgttcct cttccaagaa gctggtacag  240
gacccggttc ctcaggtgat cgtcgttaaa aagaaagaga aggaaagcga agtcgatgac  300
ggcaaaaaga aggtttccat tttctacggt actcagaccg gcaccgctga gggttttgcc  360
aaagcactgg ttgaagaggc aaaagtgcgt tacgaaaaaa cttccttcaa agtgattgac  420
ctggacgact atgctgcgga tgatgatgaa tacgaggaaa aactgaaaaa agaaagcctg  480
gccttcttct tcctggcaac ctatggcgat ggtgaaccga ccgacaacgc ggcgaacttc  540
tacaaatggt ttaccgaagg cgacgacaaa ggtgaattgc tgaagaaact gcagtatggt  600
gttttcggtc tgggcaatcg ccagtacgaa cattttaaca aaatcgcaat cgttgttgat  660
gacaaactga ctgaaatggg tgcgaaacgt ctggtgccgg ttggcctggg tgacgatgat  720
caatgcatcg aagatgactt caccgcatgg aaagaactgg tttggccgga actggatcag  780
ctgctgcgcg acgaagacga cacttccgtg accaccccgt ataccgctgc agtgctggag  840
taccgtgttg tttaccacga taaaccggcg gactcttacg ccgaagatca gactcacact  900
aacggtcacg tcgtacatga cgcacagcac ccgtctcgta gcaatgttgc gtttaagaaa  960
gagctgcaca cgagccagtc cgaccgctct tgtacgcacc tggagttcga tatctcccac  1020
accggtctgt cctatgaaac cggtgaccat gttggcgttt acagcgaaaa cctgagcgag  1080
gtagttgatg aagcgctgaa actgctgggc ctgtctccag acacctactt tagcgtgcat  1140
gctgacaagg aagatggtac tccgattggc ggcgcttccc tgccgccacc gtttccacct  1200
tgcactctgc gtgatgctct gactcgttac gctgatgttc tgtctagccc gaaaaaggtt  1260
gcgctgctgg cgctggccgc acatgcttct gacccgtctg aagctgaccg tctgaaattc  1320
ctggcgtctc cggccggcaa agacgaatac gcgcagtgga ttgtcgctaa ccagcgctct  1380
ctgctggaag tgatgcagtc cttcccgtct gccaaaccgc cactgggcgt gtttttcgca  1440
gctgtggctc cgcgcctgca gccgcgctac tattctatct ctagctcccc gaaaatgagc  1500
ccgaaccgca tccacgttac ttgtgctctg gtttacgaaa ccacccctgc gggccgtatc  1560
caccgtggtc tgtgctctac gtggatgaaa aatgccgtgc cgctgaccga atccccggac  1620
tgctctcagg cgtccatctt cgtgcgtacc tctaacttcc gtctgccggt ggacccgaaa  1680
gttcctgtta tcatgatcgg tcctggcacg ggtctggccc cgtttcgtgg ttttctgcag  1740
gagcgtctgg ctctgaaaga atccggtact gagctgggct cttccatctt tttcttcggt  1800
tgtcgtaacc gcaaagtcga tttcatctat gaagacgaac tgaacaactt cgtagagact  1860
ggtgcactgt ccgaactgat tgtggcattc tctcgtgaag gcacggcgaa agaatacgtt  1920
caacacaaaa tgtctcagaa agcgagcgat atctggaaac tgctgtccga gggtgcgtat  1980
ctgtatgttt gtggcgacgc gaaaggcatg gctaaagatg tacaccgcac cctgcacacc  2040
attgtacaag aacaaggctc tctggatagc tccaaggcag aactgtacgt gaaaaacctg  2100
cagatgtctg gccgttacct gcgtgatgta tggtaa                            2136

SEQ ID NO: 78          moltype = AA  length = 710
FEATURE                Location/Qualifiers
source                 1..710
                       mol_type = protein
                       organism = Stevia rebaudiana
```

```
SEQUENCE: 78
MAQSESVEAS TIDLMTAVLK DTVIDTANAS DNGDSKMPPA LAMMFEIRDL LLILTTSVAV  60
LVGCFVVLVW KRSSGKKSGK ELEPPKIVVP KRRLEQEVDD GKKKVTIFFG TQTGTAEGFA  120
KALFEEAKAR YEKAAFKVID LDDYAADLDE YAEKLKKETY AFFFLATYGD GEPTDNAAKF  180
YKWFTEGDEK GVWLQKLQYG VFGLGNRQYE HFNKIGIVVD DGLTEQGAKR IVPVGLGDDD  240
QSIEDDFSAW KELVWPELDL LLRDEDDKAA ATPYTAAIPE YRVVFHDKPD AFSDDHTQTN  300
GHAVHDAQHP CRSNVAVKKE LHTPESDRSC THLEFDISHT GLSYETGDHV GVYCENLIEV  360
VEEAGKLLGL STDTYFSLHI DNEDGSPLGG PSLQPPFPPC TLRKALTNYA DLLSSPKKST  420
LLALAAHASD PTEADRLRFL ASREGKDEYA EWVVANQRSL LEVMEAFPSA RPPLGVFFAA  480
VAPRLQPRYY SISSSPKMEP NRIHVTCALV YEKTPAGRIH KGICSTWMKN AVPLTESQDC  540
SWAPIFVRTS NFRLPIDPKV PVIMIGPGTG LAPFRGFLQE RLALKESGTE LGSSILFFGC  600
RNRKVDYIYE NELNNFVENG ALSELDVAFS RDGPTKEYVQ HKMTQKASEI WNMLSEGAYL  660
YVCGDAKGMA KDVHRTLHTI VQEQGSLDSS KAELYVKNLQ MSGRYLRDVW             710

SEQ ID NO: 79           moltype = DNA  length = 2133
FEATURE                 Location/Qualifiers
source                  1..2133
                        mol_type = other DNA
                        organism = Stevia rebaudiana
SEQUENCE: 79
atggcgcaat ctgaaagtgt tgaggccagt accatcgacc ttatgacggc agtgttgaag  60
gatacagtta ttgacactgc aaatgcttca gataacggcg attctaaaat gcctcctgcg  120
cttgcgatga tgttcgagat ccgcgatctt ctgctgatcc ttaccacatc agtagcggtg  180
ctggtgggat gctttgtggt actcgtgtgg aaacgttcgt cgggcaaaaa atcaggtaag  240
gagctggaac cgcctaagat tgtcgtaccg aaacgccgac tggaacaaga agttgatgat  300
ggcaaaaaaa aagtgactat attttttggg acacagacag gcacagcgga gggatttgcg  360
aaagccttat tcgaggaggc gaaggcacgt tacgagaaag cagcttttaa agtcattgat  420
ctggatgact atgcagcaga cctagatgaa tacgcagaga aactgaaaaa agaaacttat  480
gcgtttttct tcctggccac atacggagac ggtgaaccga cggacaatgc cgccaagttt  540
tataagtggt tcactgaagg ggatgagaaa ggtgtatggc ttcagaaatt gcaatacgga  600
gtgttcggac taggaaatcg gcaatatgag cactttaata aaataggcat agtagtagac  660
gatgggctaa ccgagcaggg ggccaaacgg attgtacccg tgggcctggg ggacgatgat  720
cagtctattg aggatgattt tagtgcttgg aaagagcttg tttggcctga actggactta  780
ctcctgcgtg atgaagacga taaagcggca gcgactccat acacggcagc aatccccgag  840
tatagagtcg tattccatga taaaccggat gctttctctg atgaccatac ccaaactaat  900
ggtcatgcgg tccatgatgc acaacatccc tgccgcagca atgtagcggt gaaaaaggag  960
ctgcatacgc ctgaaagtga tcgctcatgt acgcatctgg agtttgatat ttcacacaca  1020
ggtcttagct acgagactgg agatcacgtc ggagtctatt gcgaaaatct gatcgaagtg  1080
gttgaagagg ccgggaaact gttgggacta agtacagata cttatttttc tttacatata  1140
gataacgagg atggttcccc acttggcggt ccatctcttc agcctccatt cccaccatgt  1200
accttacgca aagcgctgac taactacgca gatctgctgt ctagcccaaa gaaatcaacg  1260
cttctggcgt tggctgctca tgcctcagat ccgaccgaag ctgatcgcct tcgttttctg  1320
gcatcccgag aaggtaaaga tgaatatgca gaatgggtgg tagcgaatca gcgttctttg  1380
ctggaagtca tggaggcatt ccccagcgcg cgccctccgc tgggtgtttt cttcgcagcg  1440
gtggccccgc ggctccagcc gcgttattat tcaattagca gttctcctaa gatggaacct  1500
aatcgaatcc atgtaacatg tgcattggtc tatgagaaaa cgccggctgg ccgcatccat  1560
aaaggtatat gtagcacatg gatgaaaaat gcagtacccc tcacggagtc ccaggattgt  1620
agttgggcgc cgatatttgt tcggacgagc aattttagac ttcctataga cccaaaggtt  1680
ccagttatta tgattggtcc tggcaccgga cttgcgccat tccgggggtt tctgcaagaa  1740
agactggctc tgaaagaaag cggtacagaa ctcggctcca gtatattgtt tttcggctgt  1800
cgcaaccgga aagtagatta tatatatgaa aacgagctga ataacttcgt tgaaaatggt  1860
gccctgtctg aactcgatgt cgctttttcg cgagatggcc cgacaaaaga atacgtgcag  1920
cataaaatga cccagaaagc aagtgaaatc tggaatatgc tgtcagaagg ggcatatctg  1980
tatgtgtgcg gagatgcaaa gggcatggcc aaagacgttc acagaacctt gcataccata  2040
gtacaagagc agggctctct ggatagctca aaagccgagc tgtacgtgaa aaatctccag  2100
atgagtggac gctacctgag ggatgtttgg taa                              2133

SEQ ID NO: 80           moltype = AA  length = 708
FEATURE                 Location/Qualifiers
source                  1..708
                        mol_type = protein
                        organism = Stevia rebaudiana
SEQUENCE: 80
MAQSNSVKIS PLDLVTALFS GKVLDTSNAS ESGESAMLPT IAMIMENREL LMILTTSVAV  60
LIGCVVVLVW RRSSTKKSAL EPPVIVVPKR VQEEEVDDGK KKVTVFFGTQ TGTAEGFAKA  120
LVEEAKARYE KAVFKVIDLD DYAADDEYE EKLKKESLAF FFLATYGDGE PTDNAARFYK  180
WFTEGDAKGE WLNKLQYGVF GLGNRQYEHF NKIAKVVDDG LVEQGAKRLV PVGLGDDDQC  240
IEDDFTAWKE LVWPELDQLL RDEDDTTVAT PYTAAVAEYR VVFHEKPDAL SEDYSYTNGH  300
AVHDAQHPCR SNVAVKKELH SPESDRSCTH LEFDISNTGL SYETGDHVGV YCENLSEVVN  360
DAERLVGLPP DTYFSIHTDS EDGSPLGGAS LPPPFPPCTL RKALTCYADV LSSPKKSALL  420
ALAAHATDPS EADRLKFLAS PAGKDEYSQW IVASQRSLLE VMEAFPSAKP SLGVFFASVA  480
PRLQPRYYSI SSSPKMAPDR IHVTCALVYE KTPAGRIHKG VCSTWMKNAV PMTESQDCSW  540
APIYVRTSNF RLPSDPKVPV IMIGPGTGLA PFRGFLQERL ALKEAGTDLG LSILFFGCRN  600
RKVDFIYENE LNNFVETGAL SELIVAFSRE GPTKEYVQHK MSEKASDIWN LLSEGAYLYV  660
CGDAKGMAKD VHRTLHTIVQ EQGSLDSSKA ELYVKNLQMS GRYLRDVW               708

SEQ ID NO: 81           moltype = DNA  length = 2127
FEATURE                 Location/Qualifiers
source                  1..2127
```

```
                         mol_type = other DNA
                         organism = Stevia rebaudiana
SEQUENCE: 81
atggcgcaat ctaattctgt gaaaatctct ccattggatc tggttacagc actctttagc  60
gggaaggtac tggatacaag taacgccagt gaaagcgggg aatccgcgat gctgccaaca  120
atcgcgatga tcatggaaaa tcgggaactg ctaatgattc tgacaacgtc tgtagcagtt  180
ttaatcggtt gcgttgtggt tctggtgtgg cgtcgatcat ccacgaaaaa gagcgcatta  240
gaaccgcctg ttatcgtagt accaaaaaga gttcaggagg aagaggtgga tgatgggaaa  300
aaaaaagtca ccgttttctt cgggacccaa actggtacgg cagaaggttt tgcgaaagca  360
ctggtcgaag aggcgaaagc ccgctatgag aaggcggttt ttaaggttat tgaccttgat  420
gactatgcgg cggacgatga tgaatacgaa gaaaaattaa agaaagaatc acttgccttt  480
ttttttttgg caacatacgg tgatggcgag ccgactgata acgcggcacg gttttacaaa  540
tggtttaccg aaggcgacgc gaagggggag tggttgaaca agttacagta cggtgtgttc  600
ggcttgggga accgccagta cgagcacttt aacaagatag ctaaagttgt cgatgatggt  660
ctggtagaac agggagcgaa gcgtctcgtg ccagtagggc tgggcgatga tgatcagtgt  720
atagaagatg attttacggc ttggaaggag ttagtttggc cggaactgga ccaactgctg  780
cgcgatgagg atgatacaac tgtcgctacc ccgtatacag cagcggtagc tgaatacagg  840
gtggtttttc acgagaaacc tgatgcgctg agtgaggact attcgtatac taacggccat  900
gccgttcacg atgcacagca cccgtgccgt tctaatgtcg ccgtaaaaaa ggaactgcat  960
agcccggagt cggaccgcag ttgtacccat ctggagtttg atatttcaaa taccgggctg  1020
agttacgaaa cgggcgatca cgttggcgtg tactgtgaga atctaagcga ggttgttaac  1080
gatgcagaac gactggtcgg tttgcctcca gatacttatt tctcgatcca cactgatagc  1140
gaagatggct ctccactcgg gggggcgagt ctgccgcccc cgtttccccc gtgtacgctg  1200
agaaaggccc ttacatgtta tgcagatgta ctctcttccc ccaaaaaaag tgccttgctc  1260
gcattagcag cccacgctac cgatccctcg gaagcagatc gtctgaaatt cttggcatcg  1320
ccggcgggca aagatgaata cagccaatgg atagttgcaa gtcagcgcag tctcttagaa  1380
gtgatggaag cgtttccgtc cgcaaagccg tccttaggtg tgtttttcgc gtccgtggca  1440
ccgcgtcttc agcctagata ttacagcatt agttcctctc caaaaatggc cccggaccgt  1500
attcacgtga cttgtgctct tgtatatgag aaaaccccgg caggtcgtat tcacaaaggc  1560
gtgtgcagca cctggatgaa gaatgcagtg ccgatgaccg aaagccagga ttgttcatgg  1620
gcgccaatct atgtcaggac aagtaatttc agacttccgt ctgatcctaa agttccagtc  1680
ataatgattg gccccggcac gggactggct ccttttcgtg gtttcctgca agagcgcttg  1740
gcactgaaag aagcaggcac tgacctggga ctgtccatcc tgttctttgg gtgccgtaat  1800
cgtaaggtcg attttatata tgaaaatgaa ttgaacaact ttgtagaaac aggcgcatta  1860
tccgaactga tcgtagcttt tagtagagag gggccgacga aagaatatgt acaacacaag  1920
atgtctgaga aggcttcgga tatatggaac ctgctctctg agggtgccta tctgtacgtt  1980
tgcggtgatg ccaaaggaat ggccaaagat gtgcaccgca ctttacatac aatcgtccaa  2040
gagcagggta gcttggactc atctaaagct gaactgtatg tgaagaactt acagatgagc  2100
gggcgctatt tgcgagatgt ttggtaa                                      2127

SEQ ID NO: 82            moltype = AA  length = 706
FEATURE                  Location/Qualifiers
source                   1..706
                         mol_type = protein
                         organism = Pelargonium graveolens
SEQUENCE: 82
MAQSSSGSMS PFDFMTAIIK GKMEPSNASL GAAGEVTAMI LDNRELVMIL TTSIAVLIGC  60
VVVFIWRRSS SQTPTAVQPL KPLLAKETES EVDDGKQKVT IFFGTQTGTA EGFAKALADE  120
AKARYDKVTF KVVDLDDYAA DDEEYEEKLK KETLAFFFLA TYGDGEPTDN AARFYKWFLE  180
GKERGEWLQN LKFGVFGLGN RQYEHFNKIA IVVDEILAEQ GGKRLISVGL GDDDQCIEDD  240
FTAWRESLWP ELDQLLRDED DTTVSTPYTA AVLEYRVVFH DPADAPTLEK SYSNANGHSV  300
VDAQHPLRAN VAVRRELHTP ASDRSCTHLE FDISGTGIAY ETGDHVGVYC ENLAETVEEA  360
LELLGLSPDT YFSVHADKED GTPLSGSSLP PPFPPCTLRT ALTLHADLLS SPKKSALLAL  420
AAHASDPTEA DRLRHLASPA GKDEYAQWIV ASQRSLLEVM AEFPSAKPPL GVFFASVAPR  480
LQPRYYSISS SPRIAPSRIH VTCALVYEKT PTGRVHKGVC STWMKNSVPS EKSDECSWAP  540
IFVRQSNFKL PADAKVPIIM IGPGTGLAPF RGFLQERLAL KEAGTELGPS ILFFGCRNSK  600
MDYIYEDELD NFVQNGALSE LVLAFSREGP TKEYVQHKMM EKASDIWNLI SQGAYLYVCG  660
DAKGMARDVH RTLHTIAQEQ GSLDSSKKAES MVKNLQMSGR YLRDVW                706

SEQ ID NO: 83            moltype = DNA  length = 2121
FEATURE                  Location/Qualifiers
source                   1..2121
                         mol_type = genomic DNA
                         organism = Pelargonium graveolens
SEQUENCE: 83
atggcgcagt caagcagtgg atcaatgagc cctttcgatt ttatgaccgc tataataaaa  60
ggtaaaatgg agccaagtaa tgcgtcttta ggagcggcag gtgaagtcac agcaatgata  120
cttgataata gggagctggt tatgattctg acgaccagca ttgcagtgct gatcggttgc  180
gttgtagtgt tcatttggcg tcgttcatca tcccagaccc ctaccgcggt gcagccatta  240
aaaccacttt tagcgaagga aacagagagc gaagtagacg atggcaaaca gaaagtaact  300
atctttttg gtactcaaac tggaaccgct gaaggtttcg cgaaagcgct cgcagacgag  360
gccaaagcac ggtatgataa agtcactttt aaagtggttg atctggacga ttatgccgca  420
gatgacgaag aatatgaaga aaagctgaag aaggaaacgt tagcattctt ttttcttgcg  480
acgtatggag atggtgaacc tactgacaat gctgcaaggt tttataagtg gtttctggaa  540
ggtaaagaac gcggagaatg gcttcagaat ctaaaatttg gtgtgtttgg tttaggcaac  600
cgtcagtatg agcatttcaa taaaattgcc attgtggttg atgaaatcct tgcagaacaa  660
ggtggtaagc gtctcatttc agttggcctg ggcgatgatg atcagtgtat tgaggatgac  720
tttactgcct ggagggaatc gctgtggccg gagctagatc agttattacg cgatgaggat  780
gatactacgg tttctacgcc gtataccgcc gcggtgctgg aatacagagt cgtttttcat  840
```

```
gatccggcag atgccccaac tctcgaaaaa agctacagca acgctaacgg gcatagcgtg  900
gttgatgcgc aacatccgtt acgggcaaat gttgccgtca gacgggagtt gcatactcct  960
gcgtctgacc gctcatgtac ccatctggaa tttgatatat ctggtactgg catcgcatac  1020
gagacgggtg atcatgttgg cgtgtattgc gagaatcttg cagagacggt agaagaagcg  1080
ttggaacttt taggtctttc cccggataca tacttctccg tacacgcaga taaagaggac  1140
ggtacgcctc tctcaggctc atctctcccg ccgccatttc caccgtgcac tttacgtaca  1200
gccctgacgt tacatgctga cttactgtct tccccaaaga aatctgcatt gctcgcgctt  1260
gcagctcatg catcagaccc cactgaagct gatcgattgc ggcacctagc aagccctgcg  1320
ggcaaggacg aatacgctca gtggatagtt gctagtcagc gttccttgct ggaagtgatg  1380
gcggagttcc ccagtgccaa gcccccgctg ggagtattct tcgcatcggt tgctccaaga  1440
ttgcagcccc ggtactactc tatttcttct tccccaagaa tagcgccgtc tcgcatacac  1500
gtgacctgcg cgttagttta cgagaaaaca cctacgggca gagtacacaa aggagtttgc  1560
tccacttgga tgaaaaactc agtgccctct gaaaagagtg atgaatgttc atgggcacca  1620
attttcgtac gacagagcaa ctttaaactg cccgccgatg cgaaagtacc cataattatg  1680
attggtccag gaacgggtct ggcaccattt cgcggcttcc tccaggagcg gcttgcattg  1740
aaagaagcag ggacagaact gggaccttcc atattatttt ttgggtgccg caacagcaaa  1800
atggactata tatacgagga tgaactggat aattttgtac agaatggggc actctctgaa  1860
ctcgtgttgg cgttctcacg tgaaggtcct accaaagagt atgtgcaaca taagatgatg  1920
gagaaagcct cagatatatg gaaccttatt tcacagggag cttatttgta tgtgtgcggg  1980
gacgcaaaag gcatggcgcg tgatgtgcac cgcacgttac ataccatcgc tcaggagcag  2040
gggtcattag atagctcaaa agcagagagt atggtgaaga atcttcagat gtcaggcaga  2100
tacctgcgcg atgtctggta a                                            2121

SEQ ID NO: 84          moltype = AA  length = 277
FEATURE                Location/Qualifiers
source                 1..277
                       mol_type = protein
                       organism = Rhodococcus erythropolis
SEQUENCE: 84
MARVEGQVAL ITGAARGQGR SHAIKLAEEG ADVILVDVPN DVVDIGYPLG TADELDQTAK  60
DVENLGRKAI VIHADVRDLE SLTAEVDRAV STLGRLDIVS ANAGIASVPF LSHDIPDNTW  120
RQMIDINLTG VWHTAKVAVP HILAGERGGS IVLTSSAAGL KGYAQISHYS AAKHGVVGLM  180
RSLALELAPH RVRVNSLHPT QVNTPMIQNE GTYRIFSPDL ENPTREDFEI ASTTTNALPI  240
PWVESVDVSN ALLFLVSEDA RYITGAAIPV DAGTTLK                           277

SEQ ID NO: 85          moltype = DNA  length = 834
FEATURE                Location/Qualifiers
source                 1..834
                       mol_type = other DNA
                       organism = Rhodococcus erythropolis
SEQUENCE: 85
atggcccgtg tggaaggtca agtggctctg attaccggcg ctgctcgtgg tcaaggtcgt  60
agtcatgcga ttaaactggc ggaagaaggc gcggatgtga ttctggttga cgtcccgaat  120
gatgtggttg acatcggcta tccgctgggt acggcagatg aactggacca gaccgctaaa  180
gatgttgaaa acctgggtcg taaggcgatt gtcatccatg ccgatgtgcg cgacctggaa  240
tcactgacgg cagaagtgga tcgtgctgtt agtaccctgg gccgcctgga cattgtttcc  300
gcaaatgctg gtatcgccag cgtcccgttt ctgtctcacg atattccgga caacacctgg  360
cgtcagatga ttgatatcaa tctgacgggc gtctggcata ccgcgaaagt ggccgttccg  420
cacattctgg ccggtgaacg cggcggttcc atcgttctga ccagctctgc ggccggcctg  480
aaaggttatg cacaaattag tcattactcc gcagctaagc acggcgtcgt gggtctgatg  540
cgttcactgg cactggaact ggctccgcat cgtgtccgcg tgaactcgct gcacccgacg  600
caggtgaaca ccccgatgat tcaaaatgaa ggcacgtatc gtatctttag cccggatctg  660
gaaaacccga cccgcgaaga cttcgaaatt gcgtctacca cgaccaatgc cctgccgatc  720
ccgtgggtgg aatcagttga tgtctcgaac gcactgctgt tcctggttag cgaagacgca  780
cgttacatta ccggtgcagc aatcccggtg gatgccggta cgaccctgaa gtaa        834

SEQ ID NO: 86          moltype = AA  length = 280
FEATURE                Location/Qualifiers
source                 1..280
                       mol_type = protein
                       organism = Citrus sinensis
SEQUENCE: 86
MATPPISSLI SQRLLGKVAL VTGGASGIGE GIVRLFHRHG AKVCFVDVQD ELGYRLQESL  60
VGDKDSNIFY SHCDVTVEDD VRRAVDLTVT KFGTLDIMVN NAGISGTPSS DIRNVDVSEF  120
EKVFDINVKG VFMGMKYAAS VMIPRKQGSI ISLGSVGSVI GGIGPHHYIS SKHAVVGLTR  180
SIAAELGQHG IRVNCVSPYA VPTNLAVAHL PEDERTEDMF TGFREFAKKN ANLQGVELTV  240
EDVANAVLFL ASEDARYISG DNLIVDGGFT RVNHSFRVFR                        280

SEQ ID NO: 87          moltype = DNA  length = 843
FEATURE                Location/Qualifiers
source                 1..843
                       mol_type = other DNA
                       organism = Citrus sinensis
SEQUENCE: 87
atggcaacgc cgccgatttc atccctgatt tcacaacgcc tgctgggtaa agtcgccctg  60
gtcacgggtg gtgcttctgg tattggtgaa ggcatcgtgc gtctgtttca ccgtcatggc  120
gcgaaagtgt gctttgttga tgtgcaggat gaactgggct accgtctgca agaatctctg  180
gtgggcgaca aagattcaaa catcttttat agccactgtg atgtcaccgt ggaagacgat  240
gtgcgccgcg ctgtggatct gaccgtgacg aaattcggta cgctggatat tatggtcaat  300
```

```
aacgcgggta ttagtggcac cccgtccagc gatattcgta atgttgatgt gagcgaattt  360
gaaaaagtgt ttgatattaa cgtcaaaggc gtgtttatgg gcatgaaata tgccgcgagc  420
gtgatgatcc cgcgcaaaca gggtagcatc atctccctgg gttctgttgg cagcgtgatc  480
ggtggcattg gcccgcacca ttatatcagc tcgaaacatg cggttgtggg cctgacccgc  540
agcattgcag cggaactggg tcagcatggc attcgtgtga actgtgtgtc tccgtatgcg  600
gttccgacca atctggcggt tgcacacctg ccggaagatg aacgtaccga agatatgttt  660
acgggcttcc gtgaatttgc gaaaaagaat gccaacctgc aaggtgttga actgaccgtc  720
gaagatgtgg ccaatgcggt gctgtttctg gccagcgaag atgcacgcta cattagcggt  780
gataatctga tcgttgatgg cggctttacc cgtgtgaacc actcatttcg tgttttccgt  840
taa                                                                843

SEQ ID NO: 88          moltype = AA  length = 262
FEATURE                Location/Qualifiers
source                 1..262
                       mol_type = protein
                       organism = Citrus sinensis
SEQUENCE: 88
MSKPRLQGKV AIIMGAASGI GEATAKLFAE HGAFVIIADI QDELGNQVVS SIGPEKASYR  60
HCDVRDEKQV EETVAYAIEK YGSLDIMYSN AGVAGPVGTI LDLDMAQFDR TIATNLAGSV  120
MAVKYAARVM VANKIRGSII CTTSTASTVG GSGPHAYTIS KHGLLGLVRS AASELGKHGI  180
RVNCVSPFGV ATPFSAGTIN DVEGFVCKVA NLKGIVLKAK HVAEAALFLA SDESAYVSGH  240
DLVVDGGFTA VTNVMSMLEG HG                                           262

SEQ ID NO: 89          moltype = DNA  length = 789
FEATURE                Location/Qualifiers
source                 1..789
                       mol_type = other DNA
                       organism = Citrus sinensis
SEQUENCE: 89
atgtcaaaac cgcgtctgca aggcaaagtg gctattatta tgggtgctgc gtctggcatc  60
ggtgaagcta cggctaaact gttcgctgaa catggcgcat ttgtgattat cgctgatatt  120
caggacgaac tgggcaacca ggtggttagc tctatcggcc cggaaaaagc gtcttatcgt  180
cactgcgatg tgcgtgatga aaaacaggtt gaagaaaccg tcgcgtatgc gattgaaaaa  240
tacggcagcc tggatattat gtactccaat gcgggcgtgg ccggtccggt tggcacgatt  300
ctggatctgg acatggccca attcgaccgt accatcgcaa cgaacctggc tggtagtgtt  360
atggcagtca aatatgcggc ccgtgtcatg gtggcgaata aaattcgcgg tagcattatc  420
tgtaccacga gtaccgcctc cacggtgggc ggcagcggcc cgcacgccta taccattagc  480
aaacacggtc tgctgggcct ggttcgttca gcagcttcgg aactgggtaa acatggcatc  540
cgcgtgaact gcgttagccc gtttggtgtt gcgaccccgt tctctgccgg tacgattaac  600
gatgtcgaag gctttgtctg taaagtggcg aatctgaaag gcatcgtcct gaaagcgaag  660
catgtggccg aagcggccct gttcctggca agcgatgaat ctgcttatgt gagcggtcac  720
gacctggtgg tggatggtgg ctttacggca gttacgaatg tcatgtcaat gctggaaggt  780
cacggctaa                                                          789

SEQ ID NO: 90          moltype = AA  length = 263
FEATURE                Location/Qualifiers
source                 1..263
                       mol_type = protein
                       organism = Citrus sinensis
SEQUENCE: 90
MSNPRMEGKV ALITGAASGI GEAAVRLFAE HGAFVVAADV QDELGHQVAA SVGTDQVCYH  60
HCDVRDEKQV EETVRYTLEK YGKLDVLFSN AGIMGPLTGI LELDLTGFGN TMATNVCGVA  120
ATIKHAARAM VDKNIRGSII CTTSVASSLG GTAPHAYTTS KHALVGLVRT ACSELGAYGI  180
RVNCISPFGV ATPLSCTAYN LRPDEVEANS CALANLKGIV LKAKHIAEAA LFLASDESAY  240
ISGHNLAVDG GFTVVNHSSS SAT                                          263

SEQ ID NO: 91          moltype = DNA  length = 792
FEATURE                Location/Qualifiers
source                 1..792
                       mol_type = other DNA
                       organism = Citrus sinensis
SEQUENCE: 91
atgtcaaacc cgcgtatgga aggcaaagtc gcactgatta cgggcgcagc atctggtatc  60
ggtgaagcag cagtccgtct gttcgctgaa catggtgcgt ttgtcgtggc ggcagatgtg  120
caagacgaac tgggtcatca ggtggcggca tctgtgggta cggaccaggt gtgctaccat  180
cactgcgatg tgcgcgatga aaaacaagtg gaagaaaccg tgcgttatac cctggaaaaa  240
tacggcaaac tggatgtcct gttttcaaac gcgggcatca tgggtccgct gaccggcatt  300
ctggaactgg atctgaccgg cttcggtaac acgatggcaa ccaatgtgtg cggtgttgcc  360
gcgaccatta aacacgcggc acgcgcaatg gtggacaaaa acattcgcgg tagcattatc  420
tgcaccacca gcgtggcttc atcgctgggt ggcaccgcgc cgcacgcata caccacgagc  480
aaacacgcac tggtgggcct ggttcgtacg gcatgttcgg aactgggtgc gtatggcatt  540
cgtgtgaact gtatcagccc gtttggtgtt gcaacgccgc tgtcttgcac ggcctataac  600
ctgcgcccgg atgaagtgga agcaaactca tgcgcactgg cgaacctgaa aggtattgtg  660
ctgaaagcga aacacattgc ggaagcagcg ctgttcctgg cgagcgatga aagcgcgtat  720
attagcggtc ataatctggc ggtggatggt ggtttcacgg tggttaatca ttcaagttcg  780
tcggcgacgt aa                                                      792

SEQ ID NO: 92          moltype = AA  length = 278
FEATURE                Location/Qualifiers
```

```
source                  1..278
                        mol_type = protein
                        organism = Citrus sinensis
SEQUENCE: 92
MTTAGSRDSP LVAQRLLGKV ALVTGGATGI GESIVRLFHK HGAKVCVVDI NDDLGQHLCQ  60
TLGPTTRFIH GDVAIEDDVS RAVDFTVANF GTLDIMVNNA GMGGPPCPDI REFPISTFEK  120
VFDINTKGTF IGMKHAARVM IPSKKGSIVS ISSVTSAIGG AGPHAYTASK HAVLGLTKSV  180
AAELGQHGIR VNCVSPYAIL TNLALAHLHE DERTDDARAG FRAFIGKNAN LQGVDLVEDD  240
VANAVLFLAS DDARYISGDN LFVDGGFTCT NHSLRVFR                          278

SEQ ID NO: 93           moltype = DNA  length = 837
FEATURE                 Location/Qualifiers
source                  1..837
                        mol_type = other DNA
                        organism = Citrus sinensis
SEQUENCE: 93
atgacgacgg ctggttcgcg tgacagtccg ctggtcgctc aacgcctgct gggcaaagtg  60
gccctggtta cgggtggtgc taccggcatt ggtgaaagta tcgtgcgtct gtttcataaa  120
cacggcgcga aagtttgcgt ggttgatatt aacgatgacc tgggccagca tctgtgtcaa  180
accctgggtc cgaccacccg tttcattcac ggcgatgttg caatcgaaga tgatgtgagc  240
cgtgcggttg attttaccgt cgccaacttc ggtacgctgg acattatggt gaacaatgcc  300
ggtatgggcg gtccgccgtg cccggatatt cgtgaatttc cgatctcgac ctttgaaaaa  360
gtcttcgaca ttaacaccaa aggcacgttc atcggtatga aacatgcggc ccgcgtgatg  420
attccgagta aaaaaggtag tattgtcagc attagcagcg tgaccagcgc gattggcggc  480
gcgggtccgc acgcctatac cgcgagcaaa catgcggtgc tgggcctgac gaaatctgtc  540
gcggcggaac tgggccagca cggtattcgt gtcaactgtg tgtctccgta cgccatcctg  600
accaatctgg cgctggccca tctgcacgaa gatgaacgta cggatgacgc gcgtgcgggt  660
tttcgtgcat tcattggtaa aaacgctaat ctgcaaggtg ttgatctggt cgaagatgac  720
gtggcgaatg ccgttctgtt tctggcatca gatgacgctc gctatatctc gggcgataac  780
ctgttcgtgg atggcggctt cacctgtacc aatcactccc tgcgtgtgtt ccgttaa     837

SEQ ID NO: 94           moltype = AA  length = 280
FEATURE                 Location/Qualifiers
source                  1..280
                        mol_type = protein
                        organism = Vitis vinifera
SEQUENCE: 94
MAATSIDNSP LPSQRLLGKV ALVTGGATGI GESIVRLFLK QGAKVCIVDV QDDLGQKLCD  60
TLGGDPNVSF FHCDVTIEDD VCHAVDFTVT KFGTLDIMVN NAGMAGPPCS DIRNVEVSMF  120
EKVFDVNVKG VFLGMKHAAR IMIPLKKGTI ISLCSVSSAI AGVGPHAYTG SKCAVAGLTQ  180
SVAAEMGGHG IRVNCISPYA IATGLALAHL PEDERTEDAM AGFRAFVGKN ANLQGVELTV  240
DDVAHAAVFL ASDEARYISG LNLMLDGGFS CTNHSLRVFR                        280

SEQ ID NO: 95           moltype = DNA  length = 843
FEATURE                 Location/Qualifiers
source                  1..843
                        mol_type = other DNA
                        organism = Vitis vinifera
SEQUENCE: 95
atggccgcaa cgagcattga taattctccg ctgccgagtc aacgtctgct gggtaaagtc  60
gcactggtca cgggtggcgc tacgggtatt ggcgaaagca tcgtgcgtct gtttctgaaa  120
cagggtgcta aagtgtgcat tgtggacgtg caagatgacc tgggccagaa actgtgcgat  180
accctgggtg gcgatccgaa cgttagcttt ttccattgcg atgtgaccat cgaagatgat  240
gtgtgccatg cagttgattt taccgtcacg aaattcggca ccctggatat tatggtgaac  300
aatgcgggta tggcaggtcc gccgtgctcg gacatccgca acgtggaagt cagcatgttt  360
gaaaaagtgt ttgatgtgaa tgtgaaaggt gttttcctgg gcatgaaaca tgcagcccgc  420
attatgattc cgctgaaaaa aggcaccatt atcagcctgt gttcagtttc cagcgctatc  480
gcgggcgttg gtccgcacgc atatacgggt agcaaatgcg cagtggcggg tctgacgcaa  540
tcggtcgcag cagaaatggg tggtcatggc attcgcgtga actgtatcag cccgtatgca  600
atcgcaacgg gtctggcgct ggcacatctg ccggaagatg aacgcacgga agatgcaatg  660
gcgggtttcc gtgcgtttgt gggtaaaaat gcgaatctgc aaggtgttga actgaccgtg  720
gatgatgtgg cgcacgcagc ggtgtttctg gcaagcgatg aagcacgtta catctctggt  780
ctgaatctga tgctggacgg cggcttttcg tgtaccaacc actcgctgcg tgtctttcgc  840
taa                                                                843

SEQ ID NO: 96           moltype = AA  length = 279
FEATURE                 Location/Qualifiers
source                  1..279
                        mol_type = protein
                        organism = Vitis vinifera
SEQUENCE: 96
MSTASSGDVS LLSQRLVGKV ALITGGATGI GESIARLFYR HGAKVCIVDI QDNPGQNLCR  60
ELGTDDACFF HCDVSIEIDV IRAVDFVVNR FGKLDIMVNN AGIADPPCPD IRNTDLSIFE  120
KVFDVNVKGT FQCMKHAARV MVPQKKGSII SLTSVASVIG GAGPHAYTGS KHAVLGLTKS  180
VAAELGLHGI RVNCVSPYAV PTGMPLAHLP ESEKTEDAMM GMRAFVGRNA NLQGIELTVD  240
DVANSVVFLA SDEARYVSGL NLMLDGGFSC VNHSLRVFR                         279

SEQ ID NO: 97           moltype = DNA  length = 840
FEATURE                 Location/Qualifiers
```

```
source                  1..840
                        mol_type = other DNA
                        organism = Vitis vinifera
SEQUENCE: 97
atgtcaacgg cttcctcggg tgatgtgtcg ctgctgtcgc aacgcctggt cggtaaagtc  60
gctctgatta cgggtggtgc aacgggcatt ggtgaatcga ttgcgcgtct gttttaccgt  120
catggtgcga aagtgtgcat cgttgacatt caggataatc cgggtcaaaa cctgtgccgt  180
gaactgggca ccgacgatgc gtgcttcttt cactgcgatg tgagcattga aatcgatgtg  240
attcgtgctg ttgactttgt ggttaaccgc tttggtaaac tggacattat ggttaataac  300
gcgggcatcg cagatccgcc gtgcccggat attcgcaaca ccgatctgag catttttgaa  360
aaagtgttcg atgtgaacgt gaaaggcacc tttcagtgta tgaaacacgc agcgcgcgtt  420
atggtgccgc agaaaaaagg tagcattatc agcctgacct cggtggcgag cgtgattggt  480
ggcgcgggtc cgcacgccta tacgggtagc aaacacgcgg ttctgggtct gacgaaaagc  540
gttgcggcag aactgggtct gcatggtatt cgcgtgaact gtgtgagtcc gtatgcagtt  600
ccgacgggta tgccgctggc acatctgccg gaatcggaaa aaaccgaaga tgcgatgatg  660
ggtatgcgtg catttgtggg tcgtaatgcc aacctgcaag gtattgaact gaccgtggac  720
gatgtcgcaa atagcgtcgt gtttctggcg tcggatgaag cgcgttatgt tagcggtctg  780
aacctgatgc tggacggcgg cttctcgtgt gtcaaccact cgctgcgtgt gtttcgctaa  840

SEQ ID NO: 98           moltype = AA  length = 280
FEATURE                 Location/Qualifiers
source                  1..280
                        mol_type = protein
                        organism = Citrus sinensis
SEQUENCE: 98
MSNSNSTDSS PAVQRLVGRV ALITGGATGI GESTVRLFHK HGAKVCIADV QDNLGQQVCQ  60
SLGGEPDTFF CHCDVTKEED VCSAVDLTVE KFGTLDIMVN NAGISGAPCP DIREADLSEF  120
EKVFDINVKG VFHGMKHAAR IMIPQTKGTI ISICSVAGAI GGLGPHAYTG SKHAVLGLNK  180
NVAAELGKYG IRVNCVSPYA VATGLALAHL PEEERTEDAM VGFRNFVARN ANMQGTELTA  240
NDVANAVLFL ASDEARYISG TNLMVDGGFT SVNHSLRVFR                        280

SEQ ID NO: 99           moltype = DNA  length = 843
FEATURE                 Location/Qualifiers
source                  1..843
                        mol_type = other DNA
                        organism = Citrus sinensis
SEQUENCE: 99
atgtccaata gcaactctac ggattcgtcg ccggcagtcc aacgcctggt cggtcgtgtc  60
gccctgatta cgggtggtgc aacgggtatt ggcgaaagca cggtgcgcct gtttcataaa  120
catggcgcga aagtgtgtat tgccgacgtt caggataacc tgggtcagca agtgtgtcag  180
agtctgggtg gcgaaccgga tacctttttc tgccattgtg atgtgacgaa agaagaagat  240
gtgtgtagcg cagttgatct gaccgtggaa aaatttggca ccctggacat tatggtgaac  300
aatgcgggta ttagcggcgc accgtgcccg gacattcgtg aagccgatct gagcgaattt  360
gaaaaagttt tcgacatcaa cgtgaaaggc gtgtttcacg gcatgaaaca tgcagcgcgt  420
attatgatcc cgcaaaccaa aggcaccatt atcagcattt gctccgtggc tggtgcgatt  480
ggtggcctgg gtccgcacgc atataccggc tccaaacatg cagtcctggg cctgaacaaa  540
aacgtggccg cggaactggg caaatacggt atccgtgtga attgcgtcag cccgtatgct  600
gttgccaccg gcctggctct ggcacacctg ccggaagaag aacgtaccga agatgcaatg  660
gtgggctttc gtaattttgt ggcacgcaac gcgaatatgc aaggcaccga actgacggcg  720
aatgatgtgg caaacgcggt cctgtttctg gcctctgatg aagcccgtta tatcagcggc  780
acgaatctga tggtggatgg cggttttacc tcggtcaatc actcgctgcg tgtcttccgt  840
taa                                                                843

SEQ ID NO: 100          moltype = AA  length = 282
FEATURE                 Location/Qualifiers
source                  1..282
                        mol_type = protein
                        organism = Brachypodium distachyon
SEQUENCE: 100
MSAAAAVSSS SSPRLEGKVA LVTGGASGIG EAIVRLFRQH GAKVCIADVQ DEAGQQVRDS  60
LGDDAGTDVL FVHCDVTVEE DVSRAVDAAA EKFGTLDIMV NNAGITGDKV TDIRNLDFAE  120
VRKVFDINVH GMLLGMKHAA RVMIPGKKGS IVSLASVASV MGGMGPHAYT ASKHAVVGLT  180
KSVALELGKH GIRVNCVSPY AVPTALSMPH LPQGEHKGDA VRDFLAFVGG EANLKGVDLL  240
PKDVAQAVLY LASDEARYIS ALNLVVDGGF TSVNPNLKAF ED                     282

SEQ ID NO: 101          moltype = DNA  length = 849
FEATURE                 Location/Qualifiers
source                  1..849
                        mol_type = other DNA
                        organism = Brachypodium distachyon
SEQUENCE: 101
atgtccgctg ctgccgccgt gtcctcctca tcgtcgccgc gtctggaagg caaagtcgct  60
ctggttacgg gtggtgcgtc aggtatcggc gaagccattg tgcgcctgtt ccgtcaacat  120
ggtgccaaag tgtgtatcgc ggatgtccaa gacgaagcgg gccaacaggt ccgtgatagc  180
ctgggtgacg atgccggtac ggatgtgctg tttgtgcatt gcgacgttac cgtggaagaa  240
gatgtgtcac gcgcggtgga tgccgctgcg gaaaaattcg gcaccctgga cattatggtg  300
aacaacgcag gtattacggg cgacaaagtg acggacattc gcaacctgga tttcgctgaa  360
gtccgtaaag tgttcgacat caatgtgcac ggtatgctgc tgggcatgaa acatgcggcc  420
cgcgtgatga ttccgggtaa aaaaggctcg attgtgagcc tggcatcggt cgcaagcgtt  480
```

```
atgggtggta tgggtccgca cgcatatacc gcaagcaaac acgcggttgt gggtctgacg  540
aaaagcgttg cactggaact gggcaaacat ggtattcgtg tcaactgtgt gagcccgtat  600
gcagttccga ccgcactgtc aatgccgcac ctgccgcagg gcgaacataa aggtgatgcg  660
gtgcgtgatt tcctggcgtt tgttggcggt gaagcgaatc tgaaaggtgt cgatctgctg  720
ccgaaagatg ttgcacaggc ggttctgtat ctggcaagcg acgaagcgcg ctatatttct  780
gcgctgaatc tggtggttga tggcggtttt acgagcgtga atccgaatct gaaagcattt  840
gaagactaa                                                           849

SEQ ID NO: 102          moltype = AA  length = 267
FEATURE                 Location/Qualifiers
source                  1..267
                        mol_type = protein
                        organism = Zingiber zerumbet
SEQUENCE: 102
MRLEGKVALV TGGASGIGES IARLFIEHGA KICIVDVQDE LGQQVSQRLG GDPHACYFHC  60
DVTVEDDVRR AVDFTAEKYG TIDIMVNNAG ITGDKVIDIR DADFNEFKKV FDINVNGVFL  120
GMKHAARIMI PKMKGSIVSL ASVSSVIAGA GPHGYTGAKH AVVGLTKSVA AELGRHGIRV  180
NCVSPYAVPT RLSMPYLPES EMQEDALRGF LTFVRSNANL KGVDLMPNDV AEAVLYLATE  240
ESKYVSGLNL VIDGGFSIAN HTLQVFE                                       267

SEQ ID NO: 103          moltype = DNA  length = 804
FEATURE                 Location/Qualifiers
source                  1..804
                        mol_type = other DNA
                        organism = Zingiber zerumbet
SEQUENCE: 103
atgcgtctgg aaggcaaagt ggctctggtc acgggcggtg cgtcgggtat tggcgaatct  60
attgctcgtc tgtttattga acacggtgca aaaatttgca tcgtggatgt ccaggatgaa  120
ctgggtcaac aggtctctca gcgtctgggt ggcgatccgc acgcctgtta tttccactgt  180
gatgtgaccg tggaagatga cgttcgtcgc gcggtggatt ttacggcgga aaaatatggc  240
accattgaca ttatggttaa caatgcgggc attacgggcg ataaagtgat cgatattcgt  300
gatgcggatt tcaacgaatt taaaaaagtg ttcgacatta acgtgaatgg tgtctttctg  360
ggcatgaaac acgcagcgcg tattatgatc ccgaaaatga aaggctccat cgtttcgctg  420
gcgtccgtta gctcggtgat tgctggtgca ggtccgcatg gctataccgg cgcaaaacat  480
gcggttgtgg gtctgaccaa aagcgttgca gccgaactgg gtcgtcatgg tattcgcgtg  540
aactgcgttt cgccgtatgc ggtgccgacg cgcctgtcaa tgccgtatct gccggaatcg  600
gaaatgcagg aagatgcact gcgcggcttt ctgacctttg tgcgtagcaa tgcgaacctg  660
aaaggcgttg atctgatgcc gaatgatgtg gcggaagctg ttctgtatct ggcgaccgaa  720
gaaagcaaat atgtttcagg tctgaatctg gttattgacg gcggcttctc catcgctaat  780
catacctgc aagtgtttga ataa                                            804

SEQ ID NO: 104          moltype = AA  length = 505
FEATURE                 Location/Qualifiers
REGION                  1..505
                        note = Synthetic - Engineered valencene oxidase variant
source                  1..505
                        mol_type = protein
                        organism = synthetic construct
SEQUENCE: 104
MAWEYALIGL VVGIIIGAVA MRWYLKSYTS ARRSQSNRLP RVPEVPGVPL LGNLLQLKEK  60
KPYMTFTRWA ATYGPIYSIK TGATSMVVVS SNEIAKEALV TRFQSISTRN LSKALKVLTA  120
DKTMVAMSDY DDYHKTVKRH ILTAVLGPNA QKKHRIHRDI MMDNISTQLH EFVKNNPEQE  180
EVDLRKIFQS ELFGLAMRQA LGKDVESLYV EDLKITMNRD EILQVLVVDP MMGAIDVDWR  240
DFFPYLKWVP NKKFENTIQQ MYIRREAVMK SLIKEQKKRI ASGEKLNSYI DYLLSEAQTL  300
TDQQLLMSLW EPIIESSDTT MVTTEWAMYE LAKNPKLQDR LYRDIKSVCG SEKITEEHLS  360
QLPYITAIFH ETLRKHSPVP IIPLRHVHED TQLGGYHVPA GTELAVNIYG CNMDKNVWEN  420
PEEWNPERFM KENETADFQK TMAFGGGKRV CAGSLQALLT ASIGIGRMVQ EFEWKLKDMD  480
QEEVNTIGLT NQMLRPLRAI IKPRI                                         505

SEQ ID NO: 105          moltype = AA  length = 505
FEATURE                 Location/Qualifiers
REGION                  1..505
                        note = Synthetic - Engineered valencene oxidase variant
source                  1..505
                        mol_type = protein
                        organism = synthetic construct
SEQUENCE: 105
MAWEYALIGL VVGIIIGAVA MRWYLKSYTS ARRSQSNHLP RVPEVPGVPL LGNLLQLKEK  60
KPYMTFTKWA ATYGPIYSIK TGATSVVVVS SNEIAKEALV TRFQSISTRN LSKALKVLTA  120
DKQMVAMSDY DDYHKTVKRH ILTAVLGPNA QKKHRIHRDI MMDNISTQLH EFVKNNPEQE  180
EVDLRKIFQS ELFGLAMRQA LGKDVESLYV EDLKITMNRD EILQVLVVDP MMGAIDVDWR  240
DFFPYLKWVP NKKFENTIQQ MYIRREAVMK SLIKEQKKRI ASGEKLNSYI DYLLSEAQTL  300
TDQQLLMSLW EPIIESSDTT MVTTEWAMYE LAKNPKLQDR LYRDIKSVCG SEKITEEHLS  360
QLPYITAIFH ETLRKHSPVP ILPLRHVHED TVLGGYHVPA GTELAVNIYG CNMDKNVWEN  420
PEEWNPERFM KENETIDFQK TMAFGGGKRV CAGSLQALLI ASIGIGRMVQ EFEWKLKDMT  480
QEEVNTIGLT NQMLRPLRAI IKPRI                                         505

SEQ ID NO: 106          moltype = AA  length = 501
FEATURE                 Location/Qualifiers
```

```
REGION                  1..501
                        note = Synthetic - Engineered valencene oxidase variant
source                  1..501
                        mol_type = protein
                        organism = synthetic construct
SEQUENCE: 106
MALLLAVFAV ALAVALIFWY LKSYTSARRS QSNHLPRVPE VPGVPLLGNL LQLKEKKPYM  60
TFTRWAATYG PIYSIKTGAT SMVVVSSNEI AKEALVTRFQ SISTRNLSKA LKVLTADKTM  120
VAMSDYDDYH KTVKRHILTA VLGPNAQKKH RIHRDIMMDN ISTQLHEFVK NNPEQEEVDL  180
RKIFQSELFG LAMRQALGKD VESLYVEDLK ITMNRDEIFQ VLVVDPMMGA IDVDWRDFFP  240
YLKWVPNKKF ENTIQQMYIR REAVMKSLIK EHKKRIASGE KLNSYIDYLL SEAQTLTDQQ  300
LLMSLWEPII ESSDTTMVTT EWAMYELAKN PKLQDRLYRD IKSVCGSEKI TEEHLSQLPY  360
ITAIFHETLR RHSPVPIIPL RHVHEDTVLG GYHVPAGTEL AVNIYGCNMD KNVWENPEEW  420
NPERFMKENE TIDFQKTMAF GGGKRVCAGS LQALLTASIG IGRMVQEFEW KLKDMTQEEV  480
NTIGLTTQML RPLRAIIKPR I                                          501

SEQ ID NO: 107          moltype = AA  length = 501
FEATURE                 Location/Qualifiers
REGION                  1..501
                        note = Synthetic - Engineered valencene oxidase variant
source                  1..501
                        mol_type = protein
                        organism = synthetic construct
SEQUENCE: 107
MALLLAVFAV ALAVALIFWY LKSYTSARRS QSNHLPRVPE VPGVPLLGNL LQLKEKKPYM  60
TFTRWAATYG PIYSIKTGAT SMVVVSSNEI AKEALVTRFQ SISTRNLSKA LKVLTADKTM  120
VAMSDYDDYH KTVKRHILTA VLGPNAQKKH RIHRDIMMDN ISTQLHEFVK NNPEQEEVDL  180
RKIFQSELFG LAMRQALGKD VESLYVEDLK ITMNRDEIFQ VLVVDPMMGA IDVDWRDFFP  240
YLKWVPNKKF ENTIQQMYIR REAVMKSLIK EHKKRIASGE KLNSYIDYLL SEAQTLTDQQ  300
LLMSLWEPII ESSDTTMVTT EWAMYELAKN PKLQDRLYRD IKSVCGSEKI TEEHLSQLPY  360
ITAIFHETLR RHSPVPIIPL RHVHEDTVLG GYHVPAGTEL AVNIYGCNMD KNVWENPEEW  420
NPERFMKENE TIDFQKTMAF GGGKRVCAGS LQALLTASIG IGRMVQEFEW KLKDMTQEEV  480
NTIGLTNQML RPLRAIIKPR I                                          501

SEQ ID NO: 108          moltype = AA  length = 513
FEATURE                 Location/Qualifiers
REGION                  1..513
                        note = Synthetic - Engineered valencene oxidase variant
source                  1..513
                        mol_type = protein
                        organism = synthetic construct
SEQUENCE: 108
MDAVTGLLTV PATAITIGGT AVALAVALIF WYLKSYTSAR RSQSNHLPRV PEVPGVPLLG  60
NLLQLKEKKP YMTFTRWAAT YGPIYSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI FQVLVVDPMM  240
GAIDVDWRDF FPYLKWVPNK KFENTIQQMY IRREAVMKSL IKEHKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRRHSPVPII PLRHVHEDTV LGGYHVPAGT ELAVNIYGCN  420
MDKNVWENPE EWNPERFMKE NETIDFQKTM AFGGGKRVCA GSLQALLTAS IGIGRMVQEF  480
EWKLKDMTQE EVNTIGLTTQ MLRPLRAIIK PRI                              513

SEQ ID NO: 109          moltype = AA  length = 513
FEATURE                 Location/Qualifiers
REGION                  1..513
                        note = Synthetic - Engineered valencene oxidase variant
source                  1..513
                        mol_type = protein
                        organism = synthetic construct
SEQUENCE: 109
MDAVTGLLTV PATAITIGGT AVALAVALIF WYLKSYTSAR RSQSNHLPRV PEVPGVPLLG  60
NLLQLKEKKP YMTFTRWAAT YGPIYSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI FQVLVVDPMM  240
GAIDVDWRDF FPYLKWVPNK KFENTIQQMY IRREAVMKSL IKEHKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRRHSPVPII PLRHVHEDTV LGGYHVPAGT ELAVNIYGCN  420
MDKNVWENPE EWNPERFMKE NETIDFQKTM AFGGGKRVCA GSLQALLTAS IGIGRMVQEF  480
EWKLKDMTQE EVNTIGLTNQ MLRPLRAIIK PRI                              513

SEQ ID NO: 110          moltype = AA  length = 513
FEATURE                 Location/Qualifiers
REGION                  1..513
                        note = Synthetic - Engineered valencene oxidase variant
source                  1..513
                        mol_type = protein
                        organism = synthetic construct
SEQUENCE: 110
MDAVTGLLTV PATAITIGGT AVALAVALIF WYLKSYTSAR RSQSNRLPRV PEVPGVPLLG  60
```

```
NLLQLKEKKP YMTFTRWAAT YGPIYSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI LQVLVVDPMM  240
GAIDVDWRDF FPYLKWVPNK KFENTIQQMY IRREAVMKSL IKEQKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRKHSPVPII PLRHVHEDTQ LGGYHVPAGT ELAVNIYGCN  420
MDKNVWENPE EWNPERFMKE NETADFQKTM AFGGGKRVCA GSLQALLTAS IGIGRMVQEF  480
EWKLKDMDQE EVNTIGLTNQ MLRPLRAIIK PRI                               513

SEQ ID NO: 111          moltype = AA  length = 513
FEATURE                 Location/Qualifiers
REGION                  1..513
                        note = Synthetic - Engineered valencene oxidase variant
source                  1..513
                        mol_type = protein
                        organism = synthetic construct
SEQUENCE: 111
MDAVTGLLTV PATAITIGGT AVALAVALIF WYLKSYTSAR RSQSNHLPRV PEVPGVPLLG  60
NLLQLKEKKP YMTFTKWAAT YGPIYSIKTG ATSVVVVSSN EIAKEALVTR FQSISTRNLS  120
KALKVLTADK QMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI LQVLVVDPMM  240
GAIDVDWRDF FPYLKWVPNK KFENTIQQMY IRREAVMKSL IKEQKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRKHSPVPIL PLRHVHEDTV LGGYHVPAGT ELAVNIYGCN  420
MDKNVWENPE EWNPERFMKE NETIDFQKTM AFGGGKRVCA GSLQALLIAS IGIGRMVQEF  480
EWKLKDMTQE EVNTIGLTNQ MLRPLRAIIK PRI                               513

SEQ ID NO: 112          moltype = AA  length = 8
FEATURE                 Location/Qualifiers
REGION                  1..8
                        note = Synthetic - Leader sequence
source                  1..8
                        mol_type = protein
                        organism = synthetic construct
SEQUENCE: 112
MALLLAVF                                                           8

SEQ ID NO: 113          moltype = AA  length = 7
FEATURE                 Location/Qualifiers
REGION                  1..7
                        note = Synthetic - Linker sequence
source                  1..7
                        mol_type = protein
                        organism = synthetic construct
SEQUENCE: 113
GSGGGGS                                                            7

SEQ ID NO: 114          moltype = AA  length = 8
FEATURE                 Location/Qualifiers
REGION                  1..8
                        note = Synthetic - Linker sequence
source                  1..8
                        mol_type = protein
                        organism = synthetic construct
SEQUENCE: 114
GSGEAAAK                                                           8

SEQ ID NO: 115          moltype = AA  length = 13
FEATURE                 Location/Qualifiers
REGION                  1..13
                        note = Synthetic - Linker sequence
source                  1..13
                        mol_type = protein
                        organism = synthetic construct
SEQUENCE: 115
GSGEAAAKEA AAK                                                     13

SEQ ID NO: 116          moltype = AA  length = 9
FEATURE                 Location/Qualifiers
REGION                  1..9
                        note = Synthetic - Linker sequence
source                  1..9
                        mol_type = protein
                        organism = synthetic construct
SEQUENCE: 116
GSGMGSSSN                                                          9

SEQ ID NO: 117          moltype = AA  length = 5
FEATURE                 Location/Qualifiers
```

```
REGION                  1..5
                        note = Synthetic - Linker sequence
source                  1..5
                        mol_type = protein
                        organism = synthetic construct
SEQUENCE: 117
GSTGS                                                                5

SEQ ID NO: 118          moltype = AA  length = 20
FEATURE                 Location/Qualifiers
REGION                  1..20
                        note = Synthetic - N-terminal fragment of yhcB
source                  1..20
                        mol_type = protein
                        organism = synthetic construct
SEQUENCE: 118
MAWEYALIGL VVGIIIGAVA                                                20

SEQ ID NO: 119          moltype = DNA  length = 1647
FEATURE                 Location/Qualifiers
source                  1..1647
                        mol_type = genomic DNA
                        organism = Citrus sinensis
SEQUENCE: 119
atggcctccg gcgaaacctt ccgtccgacc gcagacttcc atccgtcact gtggcgtaat  60
cacttcctga aggcgcaag cgacttcaaa acggtggatc atacggcaac ccaggaacgt  120
cacgaagctc tgaaggaaga agtccgtcgc atgattaccg atgccgaaga caaaccggtg  180
cagaagctgc gtctgatcga tgaagttcaa cgcctgggcg tcgcgtatca ttttgaaaaa  240
gaaattggtg acgccatcca gaagctgtgc ccgatttaca tcgatagcaa ccgcgcagac  300
ctgcataccg tgtctctgca ctttcgtctg ctgcgccagc aaggcatcaa gatcagctgt  360
gatgttttcg aaaagttcaa ggatgacgaa ggccgtttca aaagctctct gattaatgat  420
gttcagggta tgctgtctct gtatgaagcg gcctacatgg cggtccgcgg tgaacatatt  480
ctggatgaag cgatcgcctt taccacgacc catctgaaaa gcctggtggc ccaggaccac  540
gttacgccga agctggcgga acaaattaac cacgccctgt atcgtccgct gcgcaaaacc  600
ctgccgcgtc tggaagcacg ctacttcatg agcatgatta atagtacgtc cgatcatctg  660
tgcaacaaaa ccctgctgaa ttttgctaag ctggacttca acatcctgct ggaactgcac  720
aaagaagaac tgaatgaact gaccaaatgg tggaaggatc tggactttac gaccaaactg  780
ccgtatgcac gtgatcgcct ggttgaactg tacttctggg acctgggcac gtattttgaa  840
ccgcagtacg ctttcggtcg taaaattatg acccaactga actatatcct gtcaattatc  900
gatgacacgt atgatgcgta cggcaccctg gaagaactgt cgctgtttac ggaagcggtg  960
cagcgttgga atattgaagc cgttgatatg ctgccggaat atatgaaact gatttaccgc  1020
accctgctgg atgcattcaa cgaaatcgaa gaagacatgg ctaaacaagg tcgtagtcat  1080
tgcgtgcgct atgcgaaaga agaaaatcag aaggttattg gcgcgtactc agtccaagcc  1140
aaatggtttt cggaaggtta tgttccgacg attgaagaat acatgccgat cgcactgacc  1200
tcatgtgctt atacgtttgt gatcaccaac tcgttcctgg gcatgggtga ttttgccacc  1260
aaagaagttt tcgaatggat tagcaacaat ccgaaagtgg ttaaggcagc ttctgtcatc  1320
tgccgtctga tggatgacat gcagggccat gaatttgaac aaaaacgcgg tcacgttgca  1380
agtgctattg aatgttatac caagcagcac ggcgtctcca aagaagaagc aattaagatg  1440
ttcgaagaag aagtggcgaa cgcctggaaa gatatcaatg aagaactgat gatgaagccg  1500
acggtcgtgg cacgtccgct gctgggcacc atcctgaatc tggcacgcgc tatcgatttc  1560
atctacaaag aagatgacgg ctacacccat agttacctga ttaaggatca gatcgcctcc  1620
gtcctgggtg accacgtgcc gttctaa                                      1647

SEQ ID NO: 120          moltype = DNA  length = 1671
FEATURE                 Location/Qualifiers
misc_feature            1..1671
                        note = Synthetic - Engineered valencene synthase
source                  1..1671
                        mol_type = other DNA
                        organism = synthetic construct
SEQUENCE: 120
atggcaaccc aggtgagcgc cagtagcctg gcacaaatcc cgcagcctaa aaaccgccct  60
gttgccaatt tccatccgaa catctggggc gaccacttta tcacctacac cccggaagac  120
aaagtgaccc gcgccaaaaa agaagagagg attgaagatc tgaaggaaga agtgaaacgc  180
aaactgaccg cagccgccgt ggccaatccg agtcaactgc tgaacttcat tgatgcagtt  240
cagcgcctgg gcgttgccta tcactttgag caggagatcg aggaggcatt acagcatatt  300
tgtaatagct ttcacgactg caatgatatg gatggcgacc tgtataatat cgccctgcta  360
tttcgtctgc tgcgccaaca gggttacaca atcagttgcg acatctttaa caagttcacc  420
gatgaagagg gccgctttaa agaagccctg attagcgacg tgcgcggtat gttaggcctg  480
tatgaagcag cccacctgcg cgttcacggc gaagacatcc tggcagaggc actggccttt  540
acaaccaccc acctgaaagc aatggttgaa tcgctgggct accatctggc cgagcaagtg  600
aggcacgcct taaaccgtcc gatccgtaaa ggcatggaac gtctggaagc acgttggtac  660
atcagcatat accaggatga ggcctttcat gacaaaaccc tgctggagct ggccaaactg  720
gacttcaacc tggtgcagag cctgcacaaa gaagagctga gcaatctggc acgctggtgg  780
aaggagctgg attttgccac caaactgcct tttgcccgcg accgtttagt tgaaggctac  840
ttttggatga tgggtgtgta ttttgagccg cagtatctgc gtggccgtcg catcctgaca  900
aaggtgatcg ccctgaccag catcattgac gacatccacg atgcctatgg caccccggag  960
gaactgaaac tgtttatcga ggccatcgaa aaatgggacg agagcagcat caaccaactg  1020
cctgagtaca tgaagctgtg ctatgtggcc ctgctggacg tgtataatga aatcgaagag  1080
```

```
gagatggaaa aggagggcaa ccaataccgt atccactacc tgaaggaggt tatgaaaaac  1140
caggtgcgtg cctactttgc agaggcaaaa tggctgcacg atgagcatgt gccggccttt  1200
gaagaataca tgcgcgttgc cctggccagc agtggttatt gtctgctggc cgttacaagt  1260
tttgtgggca tgggcgagat cgtgacaaag gaagcctttg actgggttac aagcgacccg  1320
cgcatcataa gcagcagcaa cacaattaca cgcctgatgg acgacattaa aagccataaa  1380
tttgaacaga aacgcggtca tgtgaccagc gccgtggaat gctacatgaa acagtacgcc  1440
gtgaccgaag agcaggttta cgaggaattt aaaaaacaga ttgaaaacgc atggctggac  1500
attaatcagg agtgtctgaa gccgaccgca gtgccgatgc cgctgttagc acgcctgctg  1560
aatttcaccc gcacaatgga tgtgatttat aaagaagaag acagctatac ccatgtgggc  1620
aagaccatgc gcgacaacat cgccagcgtg tttatcaacc ctgtgatcta a           1671

SEQ ID NO: 121          moltype = DNA  length = 1515
FEATURE                 Location/Qualifiers
misc_feature            1..1515
                        note = Synthetic - Engineered valencene oxidase
source                  1..1515
                        mol_type = other DNA
                        organism = synthetic construct
SEQUENCE: 121
atggcttggg aatatgcgct aattgggtta gtcgtcggca tcattattgg tgctgtggcc  60
ttctggtatc tgaaatctta cactagcgcg cgccgctctc agtccaacca cctgccgcgt  120
gtgccggaag ttccgggtgt gccactgctg ggcaacctgc tgcaactgaa agaaaagaaa  180
ccgtacatga cctttacccg ctgggcagcg acttatggtc ctatctacag cattaaaacc  240
ggcgctacgt ctatggttgt ggtttcttcc aacgaaatcg cgaaagaagc cctggtgact  300
cgtttccagt ccattagcac ccgcaacctg tccaaagcgc tgaaggttct gacggctgac  360
aagactatgg tggctatgag cgactatgat gactaccaca aaaccgttaa acgtcacatc  420
ctgaccgcag tactgggtcc gaacgcacag aaaaaacatc gcatccaccg cgacattatg  480
atggataaca tctccacgca gctgcatgag ttcgttaaga acaatccaga acaggaagag  540
gtagatctgc gtaaaatttt tcagtccgaa ctgttcggtc tggctatgcg tcaggcgctg  600
ggcaaagacg ttgaaagcct gtatgtcgaa gacctgaaaa ttaccatgaa ccgtgatgag  660
atcttccagg ttctggttgt agatccgatg atgggcgcca tcgacgtgga ttggcgtgac  720
ttctttccgt acctgaaatg ggtcccgaac aagaagttcg aaaacaccat ccagcaaatg  780
tacatccgtc gtgaagcggt gatgaaaagc ctgatcaaag aacacaaaaa gcgtattgct  840
tctggtgaga aactgaactc ctacatcgat tatctgctgt ccgaagcgca gaccctgacc  900
gaccaacagc tgctgatgtc tctgtgggaa ccgattatcg aaagcagcga caccactatg  960
gtcactaccg aatgggcaat gtatgagctg gccaaaaacc cgaaactgca ggatcgtctg  1020
taccgtgaca tcaaaagcgt ttgcggctcc gagaaaatca ctgaagaaca cctgtctcag  1080
ctgccgtaca tcactgctat tttccacgaa accctgcgtc gccattctcc ggttccgatc  1140
attccgctgc gtcacgttca cgaagatact gtgctgggtg gttaccatgt accggcaggc  1200
actgaactgg ctgtcaacat ctacggctgt aacatggata aaaacgtttg ggagaatcct  1260
gaagaatgga acccggaacg cttcatgaaa gagaacgaaa ccatcgactt ccagaaaacg  1320
atggctttcg gcggtggtaa acgtgtgtgc gcaggttctc tgcaggcgct gctgacggcg  1380
tccattggta tcggtcgcat ggtacaggaa tttgaatgga agctgaaaga catgacccaa  1440
gaagaggtga ataccattgg tctgactacc cagatgctgc gtccactgcg tgcaatcatc  1500
aaacctcgta tttaa                                                    1515

SEQ ID NO: 122          moltype = DNA  length = 1518
FEATURE                 Location/Qualifiers
misc_feature            1..1518
                        note = Synthetic - Engineered valencene oxidase
source                  1..1518
                        mol_type = other DNA
                        organism = synthetic construct
SEQUENCE: 122
atggcttggg aatatgcgct aattgggtta gtcgtcggca tcattattgg tgctgtggcc  60
atgcgttggt atctgaaatc ttacactagc gcgcgccgct ctcagtccaa ccacctgccg  120
cgtgtgccgg aagttccggg tgtgccactg ctgggcaacc tgctgcaact gaaagaaaag  180
aaaccgtaca tgacctttac ccgctgggca gcgacttatg gtcctatcta cagcattaaa  240
accggcgcta cgtctgtggt tgtggtttct tccaacgaaa tcgcgaaaga agccctggtg  300
actcgtttcc agtccattag cacccgcaac ctgtccaaag cgctgaaggt tctgacggct  360
gacaagacta tggtggctat gagcgactat gatgactacc acaaaaccgt taaacgtcac  420
atcctgaccg cattactggg tccgaacgca cagaaaaaac atcgcatcca ccgcgacatt  480
atgatggata acatctccac gcagctgcat gagttcgtta agaacaatcc agaacaggaa  540
gaggtagatc tgcgtaaaat ttttcagtcc gaactgttcg gtctggctat gcgtcaggcg  600
ctgggcaaag acgttgaaag cctgtatgtc gaagacctga aaattaccat gaaccgtgat  660
gagatcctac aggttctggt tgtagatccg atgatgggcg ccatcgacgt ggattggcgt  720
gacttctttc cgtacctgaa atgggtcccg aacaagaagt tcgaaaacac catccagcaa  780
atgtacatcc gtcgtgaagc ggtgatgaaa agcctgatca aagaacaaaa aaagcgtatt  840
gcttctggtg agaaactgaa ctcctacatc gattatctgc tgtccgaagc gcagaccctg  900
accgaccaac agctgctgat gtctctgtgg gaaccgatta tcgaaagcag cgacaccact  960
atggtcacta ccgaatgggc aatgtatgag ctggccaaaa acccgaaact gcaggatcgt  1020
ctgtaccgtg acatcaaaag cgtttgcggc tccgagaaaa tcactgaaga acacctgtct  1080
cagctgccgt acatcactgc tattttccac gaaaccctgc gtaagcattc tccggttccg  1140
atcctgccgc tgcgtcacgt tcacgaagat actgtgctgg gtggttacca tgtaccggca  1200
ggcactgaac tggctgtcaa catctacggc tgtaacatgg ataaaaacgt ttgggagaat  1260
cctgaagaat ggaacccgga acgcttcatg aaagagaacg aaaccatcga cttccagaaa  1320
acgatggctt tcggcggtgg taaacgtgtg tgcgcaggtt ctctgcaggc gctgctgatt  1380
gcgtccattg gtatcggtcg catggtacag gaatttgaat ggaagctgaa agacatgacc  1440
caagaagagg tgaataccat tggtctgact aatcagatgc tgcgtccact gcgtgcaatc  1500
```

```
atcaaacctc gtatttaa                                              1518

SEQ ID NO: 123          moltype = DNA  length = 1518
FEATURE                 Location/Qualifiers
misc_feature            1..1518
                        note = Synthetic - Engineered valencene oxidase
source                  1..1518
                        mol_type = other DNA
                        organism = synthetic construct
SEQUENCE: 123
atggcttggg aatatgcgct aattgggtta gtcgtcggca tcattattgg tgctgtggcc  60
atgcgttggt atctgaaatc ttacactagc gcgcgccgct ctcagtccaa ccacctgccg  120
cgtgtgccgg aagttccggg tgtgccactg ctgggcaacc tgctgcaact gaaagaaaag  180
aaaccgtaca tgacctttac caaatgggca gcgacttatg gtcctatcta cagcattaaa  240
accggcgcta cgtctatggt tgtggtttct tccaacgaaa tcgcgaaaga agccctggtg  300
actcgtttcc agtccattag cacccgcaac ctgtccaaag cgctgaaggt tctgacggct  360
gacaagcaga tggtggctat gagcgactat gatgactacc acaaaaccgt taaacgtcac  420
atcctgaccg cagtactggg tccgaacgca cagaaaaaac atcgcatcca ccgcgacatt  480
atgatggata acatctccac gcagctgcat gagttcgtta agaacaatcc agaacaggaa  540
gaggtagatc tgcgtaaaat ttttcagtcc gaactgttcg gtctggctat gcgtcaggcg  600
ctgggcaaag acgttgaaag cctgtatgtc gaagacctga aaattaccat gaaccgtgat  660
gagatcctac aggttctggt tgtagatccg atgatgggcg ccatcgacgt ggattggcgt  720
gacttctttc cgtacctgaa atgggtcccg aacaagaagt tcgaaaacac catccagcaa  780
atgtacatcc gtcgtgaagc ggtgatgaaa agcctgatca aagaacaaaa aaagcgtatt  840
gcttctggtg agaaactgaa ctcctacatc gattatctgc tgtccgaagc gcagaccctg  900
accgaccaac agctgctgat gtctctgtgg gaaccgatta tcgaaagcag cgacaccact  960
atggtcacta ccgaatgggc aatgtatgag ctggccaaaa acccgaaact gcaggatcgt  1020
ctgtaccgtg acatcaaaag cgtttgcggc tccgagaaaa tcactgaaga acacctgtct  1080
cagctgccgt acatcactgc tattttccac gaaaccctgc gtaagcattc tccggttccg  1140
atcctgccgc tgcgtcacgt tcacgaagat actgtgctgg gtggttacca tgtaccggca  1200
ggcactgaac tggctgtcaa catctacggc tgtaacatgg ataaaaacgt ttgggagaat  1260
cctgaagaat ggaacccgga acgcttcatg aaagagaacg aaaccatcga cttccagaaa  1320
acgatggctt tcggcggtgg taaacgtgtg tgcgcaggtt ctctgcaggc gctgctgatt  1380
gcgtccattg gtatcggtcg catggtacag gaatttgaat ggaagctgaa agacatgacc  1440
caagaagagg tgaataccat tggtctgact aatcagatgc tgcgtccact gcgtgcaatc  1500
atcaaacctc gtatttaa                                              1518

SEQ ID NO: 124          moltype = DNA  length = 1518
FEATURE                 Location/Qualifiers
misc_feature            1..1518
                        note = Synthetic - Engineered valencene oxidase
source                  1..1518
                        mol_type = other DNA
                        organism = synthetic construct
SEQUENCE: 124
atggcttggg aatatgcgct aattgggtta gtcgtcggca tcattattgg tgctgtggcc  60
atgcgttggt atctgaaatc ttacactagc gcgcgccgct ctcagtccaa ccatctgccg  120
cgtgtgccgg aagttccggg tgtgccactg ctgggcaacc tgctgcaact gaaagaaaag  180
aaaccgtaca tgacctttac ccgctgggca gcgacttatg gtcctatcta cagcattaaa  240
accggcgcta cgtctgtggt tgtggtttct tccaacgaaa tcgcgaaaga agccctggtg  300
actcgtttcc agtccattag cacccgcaac ctgtccaaag cgctgaaggt tctgacggct  360
gacaagcaga tggtggctat gagcgactat gatgactacc acaaaaccgt taaacgtcac  420
atcctgaccg cagtactggg tccgaacgca cagaaaaaac atcgcatcca ccgcgacatt  480
atgatggata acatctccac gcagctgcat gagttcgtta agaacaatcc agaacaggaa  540
gaggtagatc tgcgtaaaat ttttcagtcc gaactgttcg gtctggctat gcgtcaggcg  600
ctgggcaaag acgttgaaag cctgtatgtc gaagacctga aaattaccat gaaccgtgat  660
gagatcctac aggttctggt tgtagatccg atgatgggcg ccatcgacgt ggattggcgt  720
gacttctttc cgtacctgaa atgggtcccg aacaagaagt tcgaaaacac catccagcaa  780
atgtacatcc gtcgtgaagc ggtgatgaaa agcctgatca aagaacaaaa aaagcgtatt  840
gcttctggtg agaaactgaa ctcctacatc gattatctgc tgtccgaagc gcagaccctg  900
accgaccaac agctgctgat gtctctgtgg gaaccgatta tcgaaagcag cgacaccact  960
atggtcacta ccgaatgggc aatgtatgag ctggccaaaa acccgaaact gcaggatcgt  1020
ctgtaccgtg acatcaaaag cgtttgcggc tccgagaaaa tcactgaaga acacctgtct  1080
cagctgccgt acatcactgc tattttccac gaaaccctgc gtaagcattc tccggttccg  1140
atcctgccgc tgcgtcacgt tcacgaagat actgtgctgg gtggttacca tgtaccggca  1200
ggcactgaac tggctgtcaa catctacggc tgtaacatgg ataaaaacgt ttgggagaat  1260
cctgaagaat ggaacccgga acgcttcatg aaagagaacg aaaccatcga cttccagaaa  1320
acgatggctt tcggcggtgg taaacgtgtg tgcgcaggtt ctctgcaggc gctgctgatt  1380
gcgtccattg gtatcggtcg catggtacag gaatttgaat ggaagctgaa agacatgacc  1440
caagaagagg tgaataccat tggtctgact aatcagatgc tgcgtccact gcgtgcaatc  1500
atcaaacctc gtatttaa                                              1518

SEQ ID NO: 125          moltype = DNA  length = 1515
FEATURE                 Location/Qualifiers
misc_feature            1..1515
                        note = Synthetic - Engineered valencene oxidase
source                  1..1515
                        mol_type = other DNA
                        organism = synthetic construct
```

SEQUENCE: 125
atggcttggg aatatgcgct aattgggtta gtcgtcggca tcattattgg tgctgtggcc 60
gcttggtatc tgaaatctta cactagcgcg cgccgctctc agtccaacca tctgccgcgt 120
gtgccggaag ttccgggtgt gccactgctg ggcaacctgc tgcaactgaa agaaaagaaa 180
ccgtacatga cctttaccaa atgggcagcg acttatggtc ctatctacag cattaaaacc 240
ggcgctacgt ctatggttgt ggtttcttcc aacgaaatcg cgaaagaagc cctggtgact 300
cgtttccagt ccattagcac ccgcaacctg tccaaagcgc tgaaggttct gacggctgac 360
aagcagatgg tggctatgag cgactatgat gactaccaca aaaccgttaa acgtcacatc 420
ctgaccgcag tactgggtcc gaacgcacag aaaaaacatc gcatccaccg cgacattatg 480
atggataaca tctccacgca gctgcatgag ttcgttaaga acaatccaga acaggaagag 540
gtagatctgc gtaaaatttt tcagtccgaa ctgttcggtc tggctatgcg tcaggcgctg 600
ggcaaagacg ttgaaagcct gtatgtcgaa gacctgaaaa ttaccatgaa ccgtgatgag 660
atcctacagg ttctggttgt agatccgatg atgggcgcca tcgacgtgga ttggcgtgac 720
ttctttccgt acctgaaatg ggtcccgaac aagaagttcg aaaacaccat ccagcaaatg 780
tacatccgtc gtgaagcggt gatgaaaagc ctgatcaaag aacaaaaaaa gcgtattgct 840
tctggtgaga aactgaactc ctacatcgat tatctgctgt ccgaagcgca gaccctgacc 900
gaccaacagc tgctgatgtc tctgtgggaa ccgattatcg aaagcagcga caccactatg 960
gtcactaccg aatgggcaat gtatgagctg gccaaaaacc cgaaactgca ggatcgtctg 1020
taccgtgaca tcaaaagcgt ttgcggctcc gagaaaatca ctgaagaaca cctgtctcag 1080
ctgccgtaca tcactgctat tttccacgaa accctgcgta agcattctcc ggttccgatc 1140
ctgccgctgc gtcacgttca cgaagatact gtgctgggtg gttaccatgt accggcaggc 1200
actgaactgg ctgtcaacat ctacggctgt aacatggata aaaacgtttg ggagaatcct 1260
gaagaatgga acccggaacg cttcatgaaa gagaacgaaa ccatcgactt ccagaaaacg 1320
atggctttcg gcggtggtaa acgtgtgtgc gcaggttctc tgcaggcgct gctgattgcg 1380
tccattggta tcggtcgcat ggtacaggaa tttgaatgga agctgaaaga catgacccaa 1440
gaagaggtga ataccattgg tctgactaat cagatgctgc gtccactgcg tgcaatcatc 1500
aaacctcgta tttaa 1515

SEQ ID NO: 126 moltype = DNA length = 1518
FEATURE Location/Qualifiers
misc_feature 1..1518
note = Synthetic - Engineered valencene oxidase
source 1..1518
mol_type = other DNA
organism = synthetic construct
SEQUENCE: 126
atggcttggg aatatgcgct aattgggtta gtcgtcggca tcattattgg tgctgtggcc 60
atgcgttggt atctgaaatc ttacactagc gcgcgccgct ctcagtccaa ccacctgccg 120
cgtgtgccgg aagttccggg tgtgccactg ctgggcaacc tgctgcaact gaaagaaaag 180
aaaccgtaca tgacctttac caaatgggca gcgacttatg gtcctatcta cagcattaaa 240
accggcgcta cgtctgtggt tgtggtttct tccaacgaaa tcgcgaaaga agccctggtg 300
actcgtttcc agtccattag cacccgcaac ctgtccaaag cgctgaaggt tctgacggct 360
gacaagcaga tggtggctat gagcgactat gatgactacc acaaaaccgt taaacgtcac 420
atcctgaccg cagtactggg tccgaacgca cagaaaaaac atcgcatcca ccgcgacatt 480
atgatggata acatctccac gcagctgcat gagttcgtta agaacaatcc agaacaggaa 540
gaggtagatc tgcgtaaaat ttttcagtcc gaactgttcg gtctggctat gcgtcaggcg 600
ctgggcaaag acgttgaaag cctgtatgtc gaagacctga aaattaccat gaaccgtgat 660
gagatcctac aggttctggt tgtagatccg atgatgggcg ccatcgacgt ggattggcgt 720
gacttctttc cgtacctgaa atgggtcccg aacaagaagt tcgaaaacac catccagcaa 780
atgtacatcc gtcgtgaagc ggtgatgaaa agcctgatca aagaacaaaa aaagcgtatt 840
gcttctggtg agaaactgaa ctcctacatc gattatctgc tgtccgaagc gcagaccctg 900
accgaccaac agctgctgat gtctctgtgg gaaccgatta tcgaaagcag cgacaccact 960
atggtcacta ccgaatgggc aatgtatgag ctggccaaaa acccgaaact gcaggatcgt 1020
ctgtaccgtg acatcaaaag cgtttgcggc tccgagaaaa tcactgaaga acacctgtct 1080
cagctgccgt acatcactgc tattttccac gaaaccctgc gtaagcattc tccggttccg 1140
atcctgccgc tgcgtcacgt tcacgaagat actgtgctgg gtggttacca tgtaccggca 1200
ggcactgaac tggctgtcaa catctacggc tgtaacatgg ataaaaacgt ttgggagaat 1260
cctgaagaat ggaacccgga acgcttcatg aaagagaacg aaaccatcga cttccagaaa 1320
acgatggctt tcggcggtgg taaacgtgtg tgcgcaggtt ctctgcaggc gctgctgatt 1380
gcgtccattg gtatcggtcg catggtacag gaatttgaat ggaagctgaa agacatgacc 1440
caagaagagg tgaataccat tggtctgact aatcagatgc tgcgtccact gcgtgcaatc 1500
atcaaacctc gtatttaa 1518

SEQ ID NO: 127 moltype = DNA length = 1518
FEATURE Location/Qualifiers
misc_feature 1..1518
note = Synthetic - Engineered valencene oxidase
source 1..1518
mol_type = other DNA
organism = synthetic construct
SEQUENCE: 127
atggcttggg aatatgcgct aattgggtta gtcgtcggca tcattattgg tgctgtggcc 60
atgcgttggt atctgaaatc ttacactagc gcgcgccgct ctcagtccaa ccacctgccg 120
cgtgtgccgg aagttccggg tgtgccactg ctgggcaacc tgctgcaact gaaagaaaag 180
aaaccgtaca tgacctttac caaatgggca gcgacttatg gtcctatcta cagcattaaa 240
accggcgcta cgtctgtggt tgtggtttct tccaacgaaa tcgcgaaaga agccctggtg 300
actcgtttcc agtccattag cacccgcaac ctgtccaaag cgctgaaggt tctgacggct 360
gacaagacta tggtggctat gagcgactat gatgactacc acaaaaccgt taaacgtcac 420
atcctgaccg cagtactggg tccgaacgca cagaaaaaac atcgcatcca ccgcgacatt 480

```
atgatggata acatctccac gcagctgcat gagttcgtta agaacaatcc agaacaggaa  540
gaggtagatc tgcgtaaaat ttttcagtcc gaactgttcg gtctggctat gcgtcaggcg  600
ctgggcaaag acgttgaaag cctgtatgtc gaagacctga aaattaccat gaaccgtgat  660
gagatcctac aggttctggt tgtagatccg atgatgggcg ccatcgacgt ggattggcgt  720
gacttctttc cgtacctgaa atgggtcccg aacaagaagt tcgaaaacac catccagcaa  780
atgtacatcc gtcgtgaagc ggtgatgaaa agcctgatca aagaacaaaa aaagcgtatt  840
gcttctggtg agaaactgaa ctcctacatc gattatctgc tgtccgaagc gcagaccctg  900
accgaccaac agctgctgat gtctctgtgg gaaccgatta tcgaaagcag cgacaccact  960
atggtcacta ccgaatgggc aatgtatgag ctggccaaaa acccgaaact gcaggatcgt  1020
ctgtaccgtg acatcaaaag cgtttgcggc tccgagaaaa tcactgaaga acacctgtct  1080
cagctgccgt acatcactgc tattttccac gaaaccctgc gtaagcattc tccggttccg  1140
atcattccgc tgcgtcacgt tcacgaagat actgtgctgg gtggttacca tgtaccggca  1200
ggcactgaac tggctgtcaa catctacggc tgtaacatgg ataaaaacgt ttgggagaat  1260
cctgaagaat ggaacccgga acgcttcatg aaagagaacg aaaccatcga cttccagaaa  1320
acgatggctt tcggcggtgg taaacgtgtg tgcgcaggtt ctctgcaggc gctgctgatt  1380
gcgtccattg gtatcggtcg catggtacag gaatttgaat ggaagctgaa agacatgacc  1440
caagaagagg tgaataccat tggtctgact aatcagatgc tgcgtccact gcgtgcaatc  1500
atcaaacctc gtatttaa                                                1518

SEQ ID NO: 128         moltype = DNA  length = 1671
FEATURE                Location/Qualifiers
misc_feature           1..1671
                       note = Synthetic - Engineered valencene synthase
source                 1..1671
                       mol_type = other DNA
                       organism = synthetic construct
SEQUENCE: 128
atggcaaccc aggtgagcgc cagtagcctg gcacaaatcc cgcagcctaa aaaccgccct  60
gttgccaatt tccataaaaa catctggggc gaccacttta tcacctacac cccggaagac  120
aaagtgaccc gcgccaaaaa agaagagagg attgaagatc tgaaggaaga agtgaaacgc  180
aaactgaccg cagccgccgt ggccaatccg agtcaactgc tgaacttcat tgatgcagtt  240
cagcgcctgg gcgttgccta tcactttgag caggagatcg aggaggcatt acagcatatt  300
tgtaatagct ttcacgactg caatgatatg gatggcgacc tgtataatat cgccctgcta  360
tttcgtctgc tgcgccaaca gggttacaca atcagttgcg acatctttaa caagttcacc  420
gatgaagagg gccgctttaa agaagccctg attagcgacg tgcgcggtat gttaggcctg  480
tatgaagcag cctacctgcg cgttcacggc gaagacatcc tggcagaggc actggccttt  540
acaaccaccc acctgaaagc aatggttgaa tcgctgggct accatctggc cgagcaagtg  600
aggcacgcct taaaccgtcc gatccgtaaa ggcatggaac gtctggaagc acgttggtac  660
atcagcatat accaggatga ggcctttcat gacaaaaccc tgctggagct ggccaaactg  720
gacttcaacc tggtgcagag cctgcacaaa gaagagctga gcaatctggc acgctggtgg  780
aaggagctgg attttgccac caaactgcct tttgcccgcg accgtttagt tgaaggctac  840
ttttggatga tgggtgtgta ttttgagccg cagtatctgc gtggccgtcg catcctgaca  900
aaggtgatcg ccctgaccag catcattgac gacatccacg atgcctatgg caccccggag  960
gaactgaaac tgtttatcga ggccatcgaa aaatgggacg agagcagcat caaccaactg  1020
cctgagtaca tgaagctgtg ctataatgcc ctgctggacg tgtataatga aatcgaagag  1080
gagatggaaa aggagggcaa ccaataccgt atccactacc tgaaggaggt tatgaaaaac  1140
caggtgcgtg cctactttgc agaggcaaaa tggctgcacg atgagcatgt gccggccttt  1200
gaagaataca tgcgcgttgc cctggccagc agtggttatt gtctgctggc cgttacaagt  1260
tttgtgggca tgggcgagat cgtgacaaag gaagcctttg actgggttac aagcgacccg  1320
cgcatcataa gcagcagcaa cacaattaca cgcctgatgg acgacattaa aagccataaa  1380
tttgaacaga aacgcggtca tgtgtggagc gccgtggaat gctacatgaa acagtacgcc  1440
gtgaccgaag agcaggttta cgaggaattt aaaaaacaga ttgaaaacgc atggctggac  1500
attaatcagg agtgtctgaa gccgaccgca gtgccgatgc cgctgttagc acgcctgctg  1560
aatttcaccc gcacaatgga tgtgatttat aaagaagaag acagctatac ccatgtgggc  1620
aagaccatgc gcgacaacat cgccagcgtg tttatcaacc ctgtgatcta a           1671

SEQ ID NO: 129         moltype = AA  length = 556
FEATURE                Location/Qualifiers
REGION                 1..556
                       note = Synthetic - Engineered valencene synthase
source                 1..556
                       mol_type = protein
                       organism = synthetic construct
SEQUENCE: 129
MATQVSASSL AQIPQPKNRP VANFHKNIWG DHFITYTPED KVTRAKKEER IEDLKEEVKR  60
KLTAAAVANP SQLLNFIDAV QRLGVAYHFE QEIEEALQHI CNSFHDCNDM DGDLYNIALL  120
FRLLRQQGYT ISCDIFNKFT DEEGRFKEAL ISDVRGMLGL YEAAYLRVHG EDILAEALAF  180
TTTHLKAMVE SLGYHLAEQV RHALNRPIRK GMERLEARWY ISIYQDEAFH DKTLLELAKL  240
DFNLVQSLHK EELSNLARWW KELDFATKLP FARDRLVEGY FWMMGVYFEP QYLRGRRILT  300
KVIALTSIID DIHDAYGTPE ELKLFIEAIE KWDESSINQL PEYMKLCYNA LLDVYNEIEE  360
EMEKEGNQYR IHYLKEVMKN QVRAYFAEAK WLHDEHVPAF EEYMRVALAS SGYCLLAVTS  420
FVGMGEIVTK EAFDWVTSDP RIISSSNTIT RLMDDIKSHK FEQKRGHVWS AVECYMKQYA  480
VTEEQVYEEF KKQIENAWLD INQECLKPTA VPMPLLARLL NFTRTMDVIY KEEDSYTHVG  540
KTMRDNIASV FINPVI                                                  556

SEQ ID NO: 130         moltype = AA  length = 132
FEATURE                Location/Qualifiers
source                 1..132
                       mol_type = protein
```

-continued

```
                         organism = Escherichia coli
SEQUENCE: 130
MTWEYALIGL VVGIIIGAVA MRFGNRKLRQ QQALQYELEK NKAELDEYRE ELVSHFARSA  60
ELLDTMAHDY RQLYQHMAKS SSSLLPELSA EANPFRNRLA ESEASNDQAP VQMPRDYSEG  120
ASGLLRTGAK RD                                                     132

SEQ ID NO: 131           moltype = DNA  length = 1542
FEATURE                  Location/Qualifiers
source                   1..1542
                         mol_type = genomic DNA
                         organism = Stevia rebaudiana
SEQUENCE: 131
atggatgccg tcaccggttt gctgacagtt ccggcaaccg caataaccat cggcggtacg  60
gccgtcgcac tcgccgtcgc tctgatattc tggtacctca aaagctacac atctgcacgc  120
aggagccaat caaaccatct ccctcgggtt cccgaggtac ctggtgtgcc attattgggg  180
aatttattgc agttgaagga gaagaaacct tacatgactt ttacaagatg ggcggcaact  240
tatggtccga tttattcgat taaaaccgga gcaacttcta tggtggtcgt cagttcaaat  300
gaaattgcaa aggaggcatt ggttaccaga tttcaatcta tctcaaccag aaacctatca  360
aaggcattaa aggttctcac agcagataaa accatggtgg cgatgagtga ttatgatgat  420
tatcataaga ctgtcaaacg ccatatactg accgctgttt tgggaccaaa tgctcagaag  480
aaacaccgca tccatagggga catcatgatg gataatatat caacccaact tcatgaattt  540
gttaaaaata atcctgaaca agaggaagtg gatctaagga aaatattcca atccgaactt  600
tttggattag ctatgagaca agcattggga aaggatgtgg agagcttata tgttgaggat  660
cttaaaatca ccatgaaccg agacgagata tttcaggtat tggttgttga cccgatgatg  720
ggtgcaattg acgtcgactg gagagatttc ttcccgtatc taaagtgggt cccgaataaa  780
aagtttgaaa acacgatcca acaaatgtat atccggagag aagctgtgat gaagtctctt  840
attaaagaac ataaaaaacg tattgcatcc ggagagaaat taaacagcta cattgattac  900
ttgctatcgg aagcacaaac gttaaccgat caacaactac ttatgtctct atgggaacct  960
attattgaat catcagacac cactatggtt acaactgaat gggctatgta tgaacttgca  1020
aaaaacccca aacttcagga tcgtttgtat cgggatatca aaagtgtttg cgggtcagag  1080
aagattacag aagaacactt gtctcaactg ccatacataa ctgccatttt tcatgaaacc  1140
ttgagaaggc atagtccagt tcctataatt ccattaagac acgtgcatga agacacagtg  1200
ttaggagggt accatgtgcc agctggaacc gagctagcgg taaacattta tggatgtaac  1260
atggataaga atgtgtggga gaatcctgaa gaatggaatc cagagagatt catgaaggaa  1320
aatgaaacga tagatttcca gaaaacaatg gcgtttggag gtggaaagcg cgtatgtgct  1380
ggttcgcttc aagcattgtt gactgcttcc attggaattg gaagaatggt gcaagagttt  1440
gagtggaaac tgaaagatat gacccaagaa gaagttaata cgattgggct tacgacccag  1500
atgcttcgtc cactgcgggc cataataaag cccaggatat ga                    1542

SEQ ID NO: 132           moltype = DNA  length = 1518
FEATURE                  Location/Qualifiers
misc_feature             1..1518
                         note = Synthetic - Engineered valencene oxidase variant
source                   1..1518
                         mol_type = other DNA
                         organism = synthetic construct
SEQUENCE: 132
atggcttggg aatatgcgct aattgggtta gtcgtcggca tcattattgg tgctgtggcc  60
atgcgttggt atctgaaatc ttacactagc gcgcgccgct ctcagtccaa ccacctgccg  120
cgtgtgccgg aagttccggg tgtgccactg ctgggcaacc tgctgcaact gaaagaaaag  180
aaaccgtaca tgacctttac caaatgggca gcgacttatg gtcctatcta cagcattaaa  240
accggcgcta cgtctgtggt tgtggtttct tccaacgaaa tcgcgaaaga agccctggtg  300
actcgtttcc agtccattag cacccgcaac ctgtccaaag cgctgaaggt tctgacggct  360
gacaagcaga tggtggctat gagcgactat gatgactacc acaaaaccgt taaacgtcac  420
atcctgaccg cagtactggg tccgaacgca cagaaaaaac atcgcatcca ccgcgacatt  480
atgatggata acatctccac gcagctgcat gagttcgtta agaacaatcc agaacaggaa  540
gaggtagatc tgcgtaaaat ttttcagtcc gaactgttcg gtctggctat gcgtcaggcg  600
ctgggcaaag acgttgaaag cctgtatgtc gaagacctga aaattaccat gaaccgtgat  660
gagatcctac aggttctggt tgtagatccg atgatgggcg ccatcgacgt ggattggcgt  720
gacttctttc cgtacctgaa atgggtcccg aacaagaagt tcgaaaacac catccagcaa  780
atgtacatcc gtcgtgaagc ggtgatgaaa agcctgatca aagaacaaaa aaagcgtatt  840
gcttctggtg agaaactgaa ctcctacatc gattatctgc tgtccgaagc gcagaccctg  900
accgaccaac agctgctgat gtctctgtgg gaaccgatta tcgaaagcag cgacaccact  960
atggtcacta ccgaatgggc aatgtatgag ctggccaaaa acccgaaact gcaggatcgt  1020
ctgtaccgtg acatcaaaag cgtttgcggc tccgagaaaa tcactgaaga acacctgtct  1080
cagctgccgt acatcactgc tattttccac gaaaccctgc gtaagcattc tccggttccg  1140
atcctgccgc tgcgtcacgt tcacgaagat actgtgctgg gtggttacca tgtaccggca  1200
ggcactgaac tggctgtcaa catctacggc tgtaacatgg ataaaaacgt ttgggagaat  1260
cctgaagaat ggaacccgga acgcttcatg aaagagaacg aaaccatcga cttccagaaa  1320
acgatggctt tcggcggtgg taaacgtgtg tgcgcaggtt ctctgcaggc gctgctgatt  1380
gcgtccattg gtatcggtcg catggtacag gaatttgaat ggaagctgaa agacatgacc  1440
caagaagagg tgaataccat tggtctgact aatcagatgc tgcgtccact gcgtgcaatc  1500
atcaaacctc gtatttaa                                               1518
```

METHODS FOR PRODUCTION OF OXYGENATED TERPENES

CROSS-REFERENCE TO RELATED APPLICATIONS

This application is a Continuation of application Ser. No. 17/456,126, filed on Nov. 22, 2021, which is a Continuation of application Ser. No. 16/669,051, filed on Oct. 30, 2019, now U.S. Pat. No. 11,180,782, which is a Divisional of application Ser. No. 15/505,022, filed on Feb. 17, 2017, now U.S. Pat. No. 10,501,760, filed as application No. PCT/US2015/046421 on Aug. 21, 2015, which claims the benefit of, and priority to, U.S. Provisional Application No. 62/040,284 filed Aug. 21, 2014, all of which are hereby incorporated by reference in their entireties.

The contents of the electronic sequence listing (GIVP30746C_XMLSEQ; Size: 246,000 bytes; and Date of Creation: Jan. 15, 2024) are herein incorporated by reference in its entirety.

FIELD OF THE INVENTION

The present disclosure relates to oxygenated sesquiterpenes (e.g., nootkatone and/or nootkatol) and methods for their production and use. The disclosure also provides enzymes for the production of oxygenated sesquiterpenes (e.g., nootkatone and/or nootkatol) and methods for identifying, selecting, making and using these enzymes.

BACKGROUND OF THE INVENTION

The food and beverage industries as well as other industries such as the perfume, cosmetic and health care industries routinely use terpenes and/or terpenoid products as flavours and fragrances. By way of example, many sesquiterpene compounds are used in perfumery (e.g., patchoulol) and in the flavour industry (e.g., nootkatone) and many are extracted from plants. However, factors such as: (i) the availability and high price of the plant raw material; (ii) the relatively low terpene content in plant; and (iii) the tedious and inefficient extraction processes to produce sufficient quantities of terpene products on an industrial scale all have stimulated research on the biosynthesis of terpenes using plant-independent systems. Consequently, effort has been expended in developing technologies to engineer microorganisms for converting renewable resources such as glucose into terpenoid products. By comparison with traditional methods, microorganisms have the advantage of fast growth without the need for land to sustain development.

Many microorganisms use either the methylerythritol 4-phosphate (MEP) pathway or the melavonate (MVA) pathway to supply intermediates necessary to produce terpenoid products. These MEP or MVA pathways can include an endogenous or an engineered MEP or MVA pathway or both. A detailed understanding of isoprenoid pathway engineering and optimization is disclosed in WO 2011/060057, US 2011/0189717, US 2012/107893, U.S. Pat. No. 8,512,988 and Ajikumar et al (2010) *Science* 330 70-74, which discloses the production of various terpenoid compounds including sesquiterpene compounds such as nootkatone, which is an oxidised sesquiterpene produced from a valencene sesquiterpene substrate.

Nootkatone (4,4a,5,6,7,8-hexahydro-6-isopropenyl-4,4a-dimethyl-2(3II)-naphtalenone) is an important flavour constituent of grapefruit and is used commercially to flavour soft drinks and other beverages, as well as being used in perfumery. The conventional method for nootkatone preparation is by oxidation of valencene (see, e.g., U.S. Pat. Nos. 6,200,786 and 8,097,442). The starting material valencene is expensive and thus methods that consume valencene are less commercially acceptable. Because of these drawbacks, there is a need for commercially feasible and sustainable methods to prepare nootkatone and associated products.

SUMMARY OF THE INVENTION

An object of the present disclosure is to provide sustainable production of oxygenated sesquiterpene products. Specifically, the present disclosure provides enzyme catalysts for the ex vivo or in vivo production of certain oxygenated sesquiterpenes. In some embodiments, the disclosure provides host cells engineered for the biosynthesis of the oxygenated sesquiterpenes. Another object of the present disclosure is to provide engineered cytochrome P450 (CYP450) enzymes for synthesis of oxygenated sesquiterpenes, including in some embodiments functional expression alongside a reductase counterpart in *E. coli*, yeast, or other host cell. The disclosure thereby harnesses the unique capability of this class of enzymes to conduct oxidative chemistry.

In one aspect, the disclosure provides a method for making an oxygenated product of a sesquiterpene. The method comprises contacting the sesquiterpene with *Stevia rebaudiana* Kaurene Oxidase (SrKO) or a derivative thereof having sesquiterpene oxidizing activity. Surprisingly, the wild type SrKO enzyme was shown to have activity on a sesquiterpene substrate even though its natural activity is understood to act on a diterpene substrate. Further, SrKO enzyme showed unique activities, including oxygenation, by creating different stereoisomers of the hydroxylated product (alpha and beta nootkatol and further oxidizing to ketone, nootkatone), and produced different oxygenated terpene products including hydroxygermacra-1(10)5-diene, and murolan-3,9(11) diene-10-peroxy. This activity is distinct from other P450 enzymes tested, which produced only one of the stereoisomers of the hydroxylated product (e.g., 0-nootkatol), as the major product and produced only minor amounts of nootkatone. This activity of SrKO provides a unique sesquiterpene oil for flavoring applications.

In some embodiments, the method takes place in an ex vivo (e.g., cell free) system. In other embodiments, the sesquiterpene substrate and the SrKO or derivative thereof are contacted in a cell expressing the SrKO, such as a bacterium (e.g., *E. coli*). The oxygenated product of a sesquiterpene may be recovered, or may be the substrate for further chemical transformation. Functional expression of wild type cytochrome P450 in *E. coli* has inherent limitations attributable to the bacterial platforms (such as the absence of electron transfer machinery and cytochrome P450 reductases, and translational incompatibility of the membrane signal modules of P450 enzymes due to the lack of an endoplasmic reticulum). Thus, in some embodiments the SrKO enzyme is modified for functional expression in an *E. coli* host cell, for example, by replacing a portion of the SrKO N-terminal transmembrane region with a short peptide sequence that stabilizes interactions with the *E. coli* inner membrane and/or reduces cell stress.

In some embodiments, the SrKO derivative has at least one mutation with respect to the wild type SrKO that increases valencene oxidase activity, or increases production of nootkatone, α-nootkatol, and/or β-nootkatol. For example, the SrKO may have from 1 to 50 mutations independently selected from substitutions, deletions, or insertions relative to wild type SrKO (SEQ ID NOS: 37 and 108) or an SrKO modified for expression and activity in *E. coli* (e.g., SEQ ID NOS: 38 and 106). For example, the SrKO derivative may have from 1 to 40 mutations, from 1 to 30 mutations, from 1 to 20 mutations, or from 1 to 10 mutations relative to SrKO (SEQ ID NOS: 37 or 38). In these or other embodiments, the SrKO derivative may comprise an amino acid sequence having at least 50% sequence identity, or at least 60% sequence identity, or at least 70% sequence identity, or at least 80% sequence identity, or at least 90% sequence identity to SrKO (SEQ ID NOS: 37 or 38), and has valencene oxidase activity. The SrKO in various embodiments maintains valencene oxidase activity, or has increased valencene oxidase activity as compared to the wild type enzyme in an ex vivo or bacterial system (e.g., *E coli*). Various mutations of SrKO which maintain or enhance valencene oxidase activity are listed in Tables 2.1, 2.2, 2.3 and 6. Thus, in various embodiments, the SrKO may have at least 2, at least 3, at least 4, at least 5, at least 6, at least 7, at least 8, at least 9, or at least 10 mutations selected from Tables 2.1, 2.2, 2.3 and/or 6. Exemplary derivatives of SrKO, also referred to herein as "valencene oxidase" or "VO" are represented by, for example, SEQ ID NOS: 104 and 105, which may further be derivatized for improvements in desired activity. Mutations may be selected empirically for increases in oxygenated sesquiterpene titer, or selected by in silico evaluation, or both.

In accordance with aspects of the disclosure, oxygenated sesquiterpene products are obtainable by contacting a sesquiterpene substrate with *Stevia rebaudiana* Kaurene Oxidase (SrKO) or derivative thereof having valencene oxidizing activity. Unlike other CYP450 enzymes, when a SrKO enzyme is used with valencene sesquiterpene substrate, it produces a different oxygenated terpene product profile that can include hydroxygermacra-1(10)5-diene, murolan-3,9 (11) diene-10-peroxy, alpha-nootkatol, beta-nootkatol, and nootkatone. By comparison, other CYP450's having the activity of hydroxylating valencene only produced one of the stereoisomers (beta nootkatol) and did not produce significant amounts of the ketone (nootkatone), which requries two oxygenation cycles. See Table 4 and FIG. 7.

In various embodiments, the sesquiterpene substrate is (or the predominant sesquiterpene substrate is) valencene, germacrene (A, B, C, D, or E), famesene, farnesol, nootkatol, patchoulol, cadinene, cedrol, humulene, longifolene, and/or bergamotene, β-ylangene, β-santalol, β-santalene, α-santalene, α-santalol, ß-vetivone, a-vetivone, khusimol, bisabolene, β-aryophyllene, longifolene; α-sinensal; α-bisabolol, (−)-β-copaene, (−)-α-copaene, 4(Z),7(Z)-ecadienal, cedrol, cedrene, cedrol, guaiol, (−)-6,9-guaiadiene, bulnesol, guaiol, ledene, ledol, lindestrene, and alpha-bergamotene. In some embodiments, the predominant sesquiterpene substrate is valencene, and the predominant oxygenated product is nootkatone and/or nootkatol, which in some embodiments comprises both α and β nootkatol.

The disclosure, when applied in vivo, is applicable to a wide array of host cells. In some embodiments, the host cell is a microbial host, such as a bacterium selected from *E. coli, Bacillus subtillus*, or *Pseudomonas putida*; or a yeast, such as a species of *Saccharomyces, Pichia*, or *Yarrowia*, including *Saccharomyces cerevisiae, Pichia pastoris*, and *Yarrowia lipolytica*.

In some embodiments, the host cell produces isopentyl pyrophosphate (IPP), which acts as a substrate for the synthesis of the sesquiterpene. In some embodiments, the IPP is produced by metabolic flux through an endogenous or heterologous methylerythritol phosphate (MEP) or mevalonic acid (MVA) pathway. In some embodiments, the sesquiterpene is produced at least in part by metabolic flux through an MEP pathway, and wherein the host cell has at least one additional copy of a dxs, ispD, ispF, and/or idi gene.

In some embodiments, the host cell expresses a farnesyl pyrophosphate synthase (FPPS), which produces farnesyl pyrophosphate (FPP) from IPP or DMAPP. The host cell may further express a heterologous sesquiterpene synthase to produce the desired sesquiterpene scaffold. For example, in some embodiments the cell expresses a valencene synthase. Several valencene synthase enzymes are known including *Vitis vinifera* valencene synthase (VvVS) (SEQ ID NO: 1) or *Citrus sinensis* valencene synthase (CsVS) (SEQ ID NO: 12), which may be employed with the present disclosure, or alternatively a derivative of the VvVS or CsVS. Exemplary derivative VvVS enzymes are disclosed herein. In certain embodiments, the sesquiterpene synthase is a valencene synthase selected from Vv1M1 (SEQ ID NO: 3), Vv2M1 (SEQ ID NO: 5), Vv1M5 (SEQ ID NO: 7), Vv2M5 (SEQ ID NO: 9), VS2 (SEQ ID NO: 11), and VS3 (SEQ ID NO: 129), as disclosed herein.

The SrKO or derivative thereof acts on the sesquiterpene (e.g., valencene) to produce the oxygenated terpene product. In some embodiments the SrKO is a fusion protein with a cytochrome P450 reductase partner (e.g., SrCPR), allowing the cofactor to be efficiently regenerated. In other embodiments, a P450 reductase is provided (e.g., to in vitro system) or expressed in the host cell separately, and may be expressed in the same operon as the SrKO in some embodiments. In some embodiments, the CPR enzyme is expressed separately, and the gene may be integrated into the host cell genome in some embodiments. Various exemplary CPR enzymes are disclosed herein, and which may be derivatized to improve oxygenated sesquiterpenoid titer and/or to improve P450 efficiency.

In some embodiments, the host cell expresses one or more enzymes that further direct oxygenated product to nootkatone, such as the expression of one or more alcohol dehydrogenase (ADH) enzymes. Exemplary ADH enzymes are disclosed herein.

In other aspects, the disclosure provides a method for making a product containing an oxygenated sesquiterpene, which comprises incorporating the oxygenated sesquiterpene prepared and recovered according to the methods described herein into a consumer or industrial product. For example, the product may be a flavor product, a fragrance product, a cosmetic, a cleaning product, a detergent or soap, or a pest control product. In some embodiments, the oxygenated product recovered comprises nootkatol (e.g., α and/or β nootkatol) and/or nootkatone, and the product is a flavor product selected from a beverage, a chewing gum, a candy, or a flavor additive.

In other aspects, the disclosure provides engineered SrKO enzymes having enhanced valencene oxidase activity as compared to wild type, as well as host cells producing an oxygenated sesquiterpene as described herein, and which express all of the enzyme components for producing the desired oxygenated sesquiterpene from isopentyl pyrophosphate (IPP). For example, the host cell in various embodiments expresses a farnesyl pyrophosphate synthase, a sesquiterpene synthase, and the SrKO or derivative thereof. IPP may be produced through the MEP and/or MVA pathway, which may be endogenous to the host cell, and which may be enhanced through expression of heterologous enzymes or duplication of certain enzymes in the pathway. Host cells include various bacteria and yeast as described herein. The oxygenated sesquiterpene (e.g., nootkatone and/or nootkatol) may be recovered from the culture, and/or optionally may act as the substrate for further chemical transformation in the cell or ex vivo system.

In another aspect, the disclosure provides sesquiterpene-containing oil produced by the methods and host cells described herein. In some embodiments, the oil comprises hydroxygermacra-1(10)5-diene, murolan-3,9(11) diene-10-peroxy, alpha-nootkatol, beta-nootkatol, and nootkatone. In some embodiments, the predominant oxygenated products of valencene is nootkatone and nootkatol, and the oxygenated sesquiterpene product comprises both alpha and beta nootkatol.

In another aspect, there is provided an SrKO crystal model structure (CMS) based on the structural coordinates of P45017A1 (which catalyzes the biosynthesis of androgens). The CMS, including the terpene binding pocket domain (TBD) that comprises a terpene binding pocket (TBP) and a terpene (e.g., valencene) bound to the TBD, is illustrated in FIGS. 8A and 8B. This SrKO crystal model structure (CMS) facilitates in-silico testing of SrKO derivatives. In part aided by this homology model, the present disclosure illustrates the use of several mutational strategies to identify increases or improvements in sesquiterpene oxygenation activity, including back-to-consensus mutagenesis, site-saturation mutagenesis, and recombination library screening.

Additional aspects and embodiments of the invention will be apparent from the following detailed description.

DESCRIPTION OF THE DRAWINGS

FIG. 2 shows the number of VvVS mutants (y-axis) exhibiting certain levels of productivity (x-axis) versus the wild type.

FIG. 3 (A to H) provides the amino acid and nucleotide sequences of valencene synthases. FIGS. 3A to 3G shows amino acid and nucleotide sequences from *Vitis vinifera* wild-type (WT) (VvVS) (SEQ ID NOS: 1 and 2) and derivatives Vv1M1 (SEQ ID NOS: 3 and 4), Vv2M1 (SEQ ID NOS: 5 and 6), Vv1M5 (SEQ ID NOS: 7 and 8), Vv2M5 (SEQ ID NOS: 9 and 10), and VS2 (SEQ ID NOS: 11 and 120); as well as amino acid sequence for *Citrus sinensis* wild-type (CsVS) (SEQ ID NOS: 12 and 119). FIG. 3H shows an alignment of wild-type VvVS and CsVS sequences, and the engineered Vv2M5 and VS2 sequences.

FIG. 4 (A to R) provides the amino acid and nucleotide sequences of various CYP450 (Cytochrome P450) enzymes having activity on sesquiterpene scaffolds. FIGS. 4A to 4P shows sequences of wild type amino acid sequences and amino acid and nucleotide sequences engineered for bacterial expression: ZzHO (SEQ ID NO: 13, 14, and 15 respectively), BsGAO (SEQ ID NO: 16, 17, and 18, respectively), HmPO (SEQ ID NO: 19, 20, and 21 respectively), LsGAO (SEQ ID NO: 22, 23, and 24, respectively), NtEAO (SEQ ID NO: 25, 26, and 27, respectively), CpVO (SEQ ID NO: 28, 29, and 30, respectively), AaAO (SEQ ID NO: 31, 32, and 33, respectively), AtKO (SEQ ID NO: 34, 35, and 36 respectively), SrKO (SEQ ID NO: 37, 38, and 39 respectively), PpKO (SEQ ID NO: 40, 41, and 42, respectively), BmVO (SEQ ID NO: 43 and SEQ ID NO: 44, respectively), PsVO (SEQ ID NO: 45 and SEQ ID NO: 46, respectively), PoLO (SEQ ID NO: 47 and SEQ ID NO: 48, respectively), CiVO (SEQ ID NO: 49, 50, and 51 respectively), HaGAO (SEQ ID NO: 52, 53, and 54, respectively). FIGS. 4Q to 4R shows amino acid sequences of engineered Valencene Oxidase enzymes based on the SrKO scaffold (SEQ ID NOS: 55-61).

FIG. 5A shows strain configuration of upstream MEP pathway genes and the two plasmids harboring downstream pathway genes. FIG. 5B shows construction of P450 fusions, whereby N-terminal regions of both the P450 and CPR (Cytochrome P450 reductase) are truncated and an exemplary leader sequence (MALLLAVF—SEQ ID NO:112) (8RP) is added while the two are fused with a short linker peptide.

FIG. 6 (A-T) provides the amino acid and nucleotide sequences of various CPR (Cytochrome P450 reductase) enzymes with sequence alignments. In FIGS. 6A to 6L: *Stevia rebaudiana* (Sr)CPR (SEQ ID NOS: 62 and 63, *Stevia rebaudiana* (Sr)CPR1 SEQ ID NOS: 76 and 77), *Arabidopsis thaliana* (At) CPR (SEQ ID NOS: 64 and 65), *Taxus cuspidata* (Tc) CPR (SEQ ID NOS: 66 and 67), *Artemisia annua* (Aa)CPR) SEQ ID NOS: 68 and 69), *Arabidopsis thaliana* (At)CPR1 (SEQ ID NOS: 70 and 71), *Arabidopsis thaliana* (At)CPR2 (SEQ ID NOS: 72 and 73), *Arabidopsis thaliana* (At)R2 (SEQ ID NOS: 74 and 75); *Stevia rebaudiana* (Sr)CPR2 (SEQ ID NOS: 78 and 79); *Stevia rebaudiana* (Sr)CPR3 (SEQ ID NOS: 80 and 81); *Pelargonium graveolens* (Pg)CPR (SEQ ID NO: 82 and 83). FIGS. 6M to 6O shows an alignment of amino acid sequences for *Arabidopsis thaliana* and *Artemisia annua* CPR sequences (SEQ ID NOS:72, 74, 68, 64, and 70). FIGS. 6P to 6Q shows an alignment of *Stevia rebaudiana* CPR sequences (SEQ ID NOS: 78, 80, 62, and 76). FIGS. 6R to 6T shows an alignment of eight CPR amino acid sequences (SEQ ID NO: 74, 72, 82, 68, 80, 62, 78, and 76).

FIG. 8B depicts a structural model of SrKO active site with valencene docked in its α-binding mode. Secondary structure motifs (B-C Loop and I-Helix) and amino acids targeted for mutagenesis are shown.

FIG. 22 (A to G) depicts alcohol dehydrogenase enzymes. FIGS. 22A to 22E shows amino acid and nucleotide sequences including those for *Rhodococcus erythropolis* (Re)CDH (SEQ ID NOS: 84 and 85), *Citrus sinensis* (Cs) DH (SEQ ID NOS: 86 and 87), *Citrus sinensis* (Cs)DH1 (SEQ ID NOS: 88 and 89), *Citrus sinensis* (Cs)DH2 (SEQ ID NOS: 90 and 91), *Citrus sinensis* (Cs)DH3 (SEQ ID NOS: 92 and 93), *Vitis vinifera* (Vv)DH (SEQ ID NOS: 94 and 95), *Vitis vinifera* (Vv)DH1 (SEQ ID NOS: 96 and 97, *Citrus sinensis* (Cs)ABA2 (SEQ ID NOS: 98 and 99), Brachypodium distachyon (Bd)DH (SEQ ID NO: 100 and 101), *Zingiber zerumbet* (Zz)SDR (SEQ ID NOS: 102 and 103). FIGS. 22F to 22G shows an alignment of the amino acid sequences.

FIG. 23 (A to 23D) shows alignments of several engineered valencene oxidase (VO) variants. In FISG. 23A to 23B: 8rp-t20SrKO (SEQ ID NO: 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 499 (numbered according to wild-type SrKO). n22yhcB-t30VO1 (SEQ ID NO: 104) has a 30-amino acid truncation of the SrKO N-terminus, a membrane anchor based on 22 amino acids from *E. coli* yhcB, and eight point mutations at positions 46, 231, 284, 383, 400, 444, 488, and 499 (with respect to SrKO wild-type). n22yhcB-t30VO2 (SEQ ID NO: 105) has a 30-amino acid truncation of the SrKO N-terminus, a membrane anchor based on 22 amino acids from *E. coli* yhcB, and nine point mutations at positions 76, 94, 131, 231, 284, 383, 390, 468, and 499 (with respect to SrKO wild-type). In FIG. 23C to 23D, point mutations in VO0 (SEQ ID NO: 109), VO1 (SEQ ID NO: 110), and VO2 (SEQ ID NO: 111) are shown against wild-type SrKO (SEQ ID NO: 108) (all shown with the wild-type SrKO N-terminus for convenience).

DETAILED DESCRIPTION OF THE INVENTION

Figure 1:
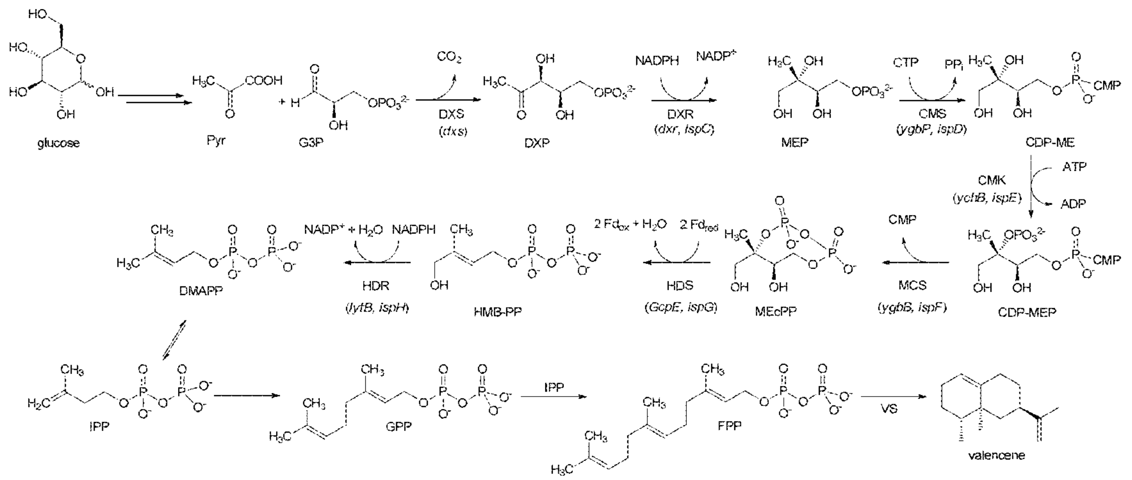
FIG. 1 shows a scheme for biosynthesis of valencene, which is a substrate for SrKO in accordance with the present disclosure.

The present disclosure in various aspects provides methods for making oxygenated terpenes or terpenoids in ex vivo or in cell systems. The disclosure further provides engineered or modified enzymes, polynucleotides, and host cells for use in such methods. The disclosure in various embodiments is directed to a method to produce nootkatone and/or nootkatol using an SrKO enzyme. Surprisingly, it was found that the SrKO enzyme can be used to catalyze sesquiterpene oxidation (e.g., valencene oxidation to nootkatol and nootkatone).

As used herein, SrKO refers to ent-kaurene oxidase CYP701A5 [*Stevia rebaudiana*] with Accession No AAQ63464.1 (SEQ ID NO: 37). SrKO and its activity on diterpenes (and kaurene in particular) are known and are described in, for example, US 2012/0164678, which is hereby incorporated by reference in its entirety. It is a member of the CYP70 family of cytochrome p450 enzymes (CYP450). An exemplary SrKO sequence modified for expression in *E. coli* is shown as SEQ ID NO: 38. As shown herein, SrKO is active on sesquiterpene substrates (e.g., valencene), producing nootkatol (both α and β) and nootkatone, which are valuable terpenoid compounds. Further, SrKO provides a unique product profile with unique sensory characteristics that is based on the oxygenation of valencene. These activities and product profiles can be further refined by mutagenesis of the SrKO using processes (and aided by in silico models) described in detail herein.

As used herein, the term "SrKO derivative," "modified SrKO polypeptide," "engineered SrKO," "SrKO variant," "engineered valencene oxidase," or "valencene oxidase variant" refers to an amino acid sequence that has substantial structural and/or sequence identity with SrKO, and catalyzes oxygenation of a sesquiterpene scaffold, such as valencene. SrKO enzymes engineered for the oxygentation of valencene are also referred to herein as "valencene oxidase" or "VO" enzymes. Generally, derivatives comprise mutated forms of SrKO having at least one mutation that increases the activity of the enzyme for the valencene substrate or for the production of nootkatone, nootkatol, and/or other products. Some SrKO mutations are provided in Tables 2.1, 2.2, and 2.3. Some such additional SrKO mutations are provided in Table 6.

The term "contacting" means that the components are physically brought together, whether in vivo through co-expression of relevant protein products (e.g., sesquiterpene synthase and CYP450) in a host cell, or by adding or feeding a substrate of interest to a host cell expressing an SrKO or derivative thereof, or in vitro (or "ex vivo") by adding sesquiterpene substrate to purified P450 enzyme or cellular extract or partially purified extract containing the same. The terms in vitro and ex vivo refer to a cell free system, and may be performed in a reaction tube or well.

As used herein, "terpenes" are a large and varied class of hydrocarbons that have a simple unifying feature, despite their structural diversity. According to the "isoprene rule", all terpenes consist of isoprene (C5) units. This fact is used for a rational classification depending on the number of such units. Monoterpenes comprise 2 isoprene units and are classified as (C10) terpenes, sesquiterpenes comprise 3 isoprene units and are classified as (C15) terpenes, diterpenes comprise 4 isoprene units and are classified as (C20) terpenes, sesterterpenes (C25), triterpenes (C30) and rubber (C5)n. They occur as acyclic or mono- to pentacyclic derivatives with alcohol, ether, ester, aldehyde, or ketone groups (the so called "terpenoids"), everywhere in organisms, particularly in higher plants, and are characteristic of the individual type of plants. Terpenes such as Monoterpenes (C10), Sesquiterpenes (C15) and Diterpenes (C20) are derived from the prenyl diphosphate substrates, geranyl diphosphate (GPP), farnesyl diphosphate (FPP) and geranylgeranyl diphosphate (GGPP) respectively through the action of a very large group of enzymes called the terpene (terpenoid) synthases. These enzymes are often referred to as terpene cyclases since the product of the reactions are cyclised to various monoterpene, sesquiterpene and diterpene carbon skeleton products. Many of the resulting carbon skeletons undergo subsequence oxygenation by cytochrome p450 hydrolysase enzymes to give rise to large families of derivatives. The technical syntheses of top-selling flavours and fragrances can start from terpenes which can also serve as excellent solvents or diluting agents for dyes and varnishes. Natural or synthetic resins of terpenes are used and also many pharmaceutical syntheses of vitamins and insecticides start from terpenes. As used herein, the term "terpene" or "sesquiterpene" (for example) includes corresponding terpenoid or sesquiterpenoid compounds.

As used herein, the term "oxygenated sesquiterpene" refers to a sesquiterpene scaffold having one or more oxygenation events, producing a corresponding alcohol, aldehyde, carboxylic acid and/or ketone. One or more oxygenated sesquiterpenes may be referred to herein as an "oxygenated product."

As used herein, the term "unoxygenated sesquiterpene" refers to a sesquiterpene scaffold that has not undergone any oxygenation events. An unoxygenated sesquiterpene may also be referred to herein as an "unoxygenated product."

As used herein, the term "oxygenated product titer" or "oxygenated titer" refers to the sum of titers of α-nootkatol, β-nootkatol, and (+)-nootkatone.

As used herein, the term "MEP pathway" refers to the (2-C-methyl-D-erythritol 4-phosphate) pathway, also called the MEP/DOXP (2-C-methyl-D-erythritol 4-phosphate/l-deoxy-D-xylulose 5-phosphate) pathway or the non-mevalonate pathway or the mevalonic acid-independent pathway. In the MEP pathway, pyruvate and D-glyceraldehyde-3-phosphate are converted via a series of reactions to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA.

As used herein, the "MVA pathway" refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MEP pathway, are described in U.S. Pat. No. 7,667,017, which is hereby incorporated by reference in its entirety.

As used herein, the term "cytochrome P450 reductase partner" or "CPR partner" refers to a cytochrome P450 reductase capable of regenerating the cofactor component of the cytochrome P450 oxidase of interest (e.g., SrKO) for oxidative chemistry. For example, SrCPR is a natural CPR partner for SrKO. In some embodiments, the CPR partner is not the natural CPR partner for SrKO. In some embodiments employing in vivo production of oxygenated sesquiterpene, the SrKO and SrCPR are co-expressed as separate proteins, or in some embodiments are expressed as a fusion protein.

As used herein, the term "natural product" refers to a product obtained, at least in part, from plant and/or animal material or obtained from microbial enzymatic biotransformations/bioconversions/biocatalysis and/or biosynthesis.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as “about” that particular value in addition to the value itself. For example, if the value “10” is disclosed, then “about 10” is also disclosed. It is also understood that each unit between two particular units are also disclosed. For example, if 10 and 15 are disclosed, then 11, 12, 13, and 14 are also disclosed.

The similarity of nucleotide and amino acid sequences, i.e., the percentage of sequence identity, can be determined via sequence alignments. Such alignments can be carried out with several art-known algorithms, such as with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) J. Mol. Biol. 215: 403-410. BLAST polynucleotide searches can be performed with the BLASTN program, score=100, word length=12.

BLAST protein searches may be performed with the BLASTP program, score=50, word length=3. To obtain gapped alignments for comparative purposes, Gapped BLAST is utilized as described in Altschul et al (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

“Conservative substitutions” may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:

(1) hydrophobic: Met, Ala, Val, Leu, He;
(2) neutral hydrophilic: Cys, Ser, Thr; Asn, Gin;
(3) acidic: Asp, Glu;
(4) basic: His, Lys, Arg;
(5) residues that influence chain orientation: Gly, Pro; and
(6) aromatic: Trp, Tyr, Phe.

As used herein, “conservative substitutions” are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt a-helices. Some preferred conservative substitutions within the above six groups are exchanges within the following sub-groups: (i) Ala, Val, Leu and He; (ii) Ser and Thr; (ii) Asn and Gin; (iv) Lys and Arg; and (v) Tyr and Phe.

As used herein, “non-conservative substitutions” or “non-conservative amino acid exchanges” are defined as exchanges of an amino acid by another amino acid listed in a different group of the six standard amino acid groups (1) to (6) shown above.

In one aspect, the disclosure provides a method for making an oxygenated product of a sesquiterpene. In various embodiments, the sesquiterpene substrate is (or the predominant sesquiterpene substrate is) valencene, germacrene (A, B, C, D, or E), famesene, farnesol, nootkatol, patchoulol, cadinene, cedrol, humulene, longifolene, and/or bergamotene, β-ylangene, β-santalol, β-santalene, α-santalene, α-santalol, ß-vetivone, a-vetivone, khusimol, bisabolene, β-aryophyllene, Longifolene; α-sinensal; α-bisabolol, (−)-β-copaene, (−)-α-copaene, 4(Z),7(Z)-ecadienal, cedrol, cedrene, cedrol, guaiol, (−)-6,9-guaiadiene, bulnesol, guaiol, ledene, ledol, lindestrene, and alpha-bergamotene. In some embodiments, the predominant sesquiterpene substrate is valencene, and the predominant oxygenated product is nootkatone and/or nootkatol, which in some embodiments comprises both α and β nootkatol. In this context, the term “predominant” means that the particular sesquiterpene is present at a level higher than all other terpene or terpenoid species individually. In some embodiments, the predominant sesquiterpene (either the substrate or the oxygenated product after the reaction) makes up at least 25%, at least 40%, at least 50%, or at least 75% of the terpene or terpenoid component of the composition. In various embodiments involving in vivo production of oxygenated sesquiterpenes, the oxygenated product is recovered from the culture media, and can be fractionated to isolate or enrich for various components of the product, such as nootkatone, nootkatol, and/or other components.

In various embodiments, the disclosure comprises contacting a sesquiterpene with a terpene oxidizing P450 enzyme, or a derivative thereof. The contacting may take place in a host cell or in a cell free system. The substrate for oxidation (e.g., the sesquiterpene), may be produced by the cells (e.g., through metabolic flux through the MEP or MVA pathways), or alternatively fed to the host cells expressing the P450 enzyme. The oxygenated product may be recovered, or be the substrate for further chemical transformation either in the cellular system or cell free system. Table 1 below provides a list of exemplary P450 enzymes. While in certain embodiments the disclosure involves the use of the following P450 enzymes (optionally engineered to increase the oxygenation of valencene to nootkatone and/or nootkatol), a preferred enzyme in accordance with this disclosure is SrKO. Exemplary oxygenated sesquiterpene products obtained by these reactions in accordance with the disclosure are shown in Table 4.

TABLE 1

| # | Species | Name | Native Substrate | Native Reaction Product |
|---|---|---|---|---|
| 1 | *Zingiber zerumbet* | zzHO | α-humulene | 8-hydroxy-α-humulene |
| 2 | *Barnadesia spinosa* | BsGAO | germacrene A | germacra-1(10),4,11(13)-trien-12-ol |
| 3 | *Hyoscyamus muticus* | HmPO | premnaspiro-diene | solavetivol |
| 4 | *Latuca spicata* | LsGAO | germacrene A | germacra-1(10),4,11(13)-trien-12-ol |
| 5 | *Nicotiana tabacum* | NtEAO | 5-epi-aristolochene | capsidiol |
| 6 | *Citrus × paradisi* | CpVO | valencene | nootkatol |

TABLE 1-continued

| # | Species | Name | Native Substrate | Native Reaction Product |
|---|---|---|---|---|
| 7 | *Artemesia annua* | AaAO | amorphadiene | artemisinic acid |
| 8 | *Arabidopsis thaliana* | AtKO | kaurene | kaurenoic acid |
| 9 | *Stevia rebaudiana* | SrKO | kaurene | kaurenoic acid |
| 10 | *Pseudomonas putida* | PpKO | kaurene | kaurenoic acid |
| 11 | *Bacillus megaterium* | BmVO | fatty acids | hydroxylated FAs |
| 12 | *Pleurotus sapidus* | PsVO | valencene | nootkatone |
| 13 | *Pleurotus ostreatus* | PoLO | unknown | unknown |
| 14 | *Cichorium intybus* | CiVO | valencene | nootkatone |
| 15 | *Helianthus annuus* | HaGAO | germacrene A | germacrene A acid |

In various embodiments, the method comprises contacting the sesquiterpene with a protein comprising *Stevia rebaudiana* Kaurene Oxidase (SrKO) or derivative thereof. In some embodiments the SrKO is expressed in a host cell as described below, or is provided in a cell free system. For example, certain in vitro and in vivo systems for oxidizing terpenes with P450 enzymes are disclosed in U.S. Pat. No. 7,211,420, which are hereby incorporated by reference. McDougle D R, Palaria A, Magnetta E, Meling D D, Das A. *Functional Studies of N-terminally modified CYP2J2 epoxygenase in Model Lipid Bilayers, Protein Sci.* 2013 22:964-79; Luthra, A., Gregory, M., Grinkova, Y. V., Denisov, I. G., Sligar, S. G. (2013) "Nanodiscs in the studies of membrane-bound cytochrome P450 enzymes." Methods Mol. Biol., 987, 115-127).

In some embodiments, the SrKO derivative comprises an amino acid sequence that has from about 1 to about 50 mutations independently selected from substitutions, deletions, or insertions relative to SrKO (SEQ ID NO: 37 or 38), or relative to an SrKO enzyme modified at its N-terminus for functional expression in *E. coli* (SEQ ID NO: 38 or 55). In various embodiments, the mutation or combination of mutations enhances the activity of the enzyme for oxygenation of valencene, such as the production of nootkatone and/or nootkatol. Protein modeling as described herein may be used to guide such substitutions, deletions, or insertions in the SrKO sequence. For example, a structural model of the SrKO amino acid sequence may be created using the coordinates for P45017A1. As demonstrated herein, such a homology model is useful for directing improvement of SrKO for valencene oxygenation. Thus, in various embodiments, the SrKO derivative may have from about 1 to about 45 mutations, about 1 to about 40 mutations, about 1 to about 35 mutations, from about 1 to about 30 mutations, about 1 to about 25 mutations, from about 1 to about 20 mutations, about 1 to about 15 mutations, about 1 to about 10 mutations, or from about 1 to about 5 mutations relative to SrKO (SEQ ID NO: 37, 38, or 55). In various embodiments, the SrKO comprises a sequence having at least 5 or at least 10 mutations with respect to SEQ ID NO: 37, 38, or 55, but not more than about 20 or 30 mutations. In various embodiments, the SrKO derivative may have about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, about 40 mutations, about 41 mutations, about 42 mutations, about 43 mutations, about 44 mutations, about 45 mutations, about 46 mutations, about 47 mutations, about 48 mutations, about 49 mutations, or about 50 mutations relative to SrKO (SEQ ID NO: 37, 38, or 55). SEQ ID NO: 37, and other WT enzymes disclosed herein, can optionally contain an Ala inserted at position 2 where not present in the wild-type.

In these or other embodiments, the SrKO derivative may comprise an amino acid sequence having at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity, to SrKO (SEQ ID NO: 37, 38, or 55). In various embodiments, the SrKO derivative has higher activity for the oxygenation of valencene than the wild type enzyme, such as a higher production of oxygenated oil upon contact with valencene substrate than the wild type enzyme (SEQ ID NO: 37) or the wild type enzyme as modified for functional expression in *E. coli* (e.g., SEQ ID NO: 38). For example, the SrKO derivative may comprise an amino acid sequence having at least: about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, about 90% identity, about 91% sequence identity, about 92% sequence identity, about 93% sequence identity, about 94% sequence identity, about 95% sequence identity, about 96% sequence identity, about 97% sequence identity, about 98% sequence identity, or about 99% sequence identity to SrKO (SEQ ID NO: 37, 38, or 55).

In some embodiments, mutants are selected for an increase in production of oxygenated valencene, such as nootkatone, α-nootkatol, and/or β-nootkatol. For example, the SrKO derivative may have one or more mutations at positions selected from 46, 76, 94, 131, 231, 284, 383, 390, 400, 444, 468, 488 and 499, numbered according to SEQ ID NO: 37. For example, in some embodiments, the SrKO is a derivative comprising an amino acid sequence having one or more (or all) of the mutations selected from H46R, R76K, M94V, T131Q, F231L, H284Q, R383K, I390L, V400Q, I444A, T468I, T488D, and T499N, numbered according to SEQ ID NO: 37. In certain embodiments, the SrKO is a derivative comprising an amino acid sequence having one or more (or all) of the mutations selected from R76K, M94V, T131Q, F231L, H284Q, R383K, I390L, T468I, and T499N, numbered according to SEQ ID NO: 37. In some embodiments, the SrKO derivative comprises an amino acid sequence selected from SEQ ID NOS: 55-61, which were engineered according to this disclosure to improve activity for oxygenation of valencene (e.g., production of nootkatone).

In some embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488, and 499 (numbered according to SEQ ID NO: 37), or the proviso that the SrKO derivative comprises an amino acid sequence having one or more (or all) of the mutations selected from H46R, R76K, M94V, T131Q, F231L, H284Q, R383K, I390L, V400Q, I444A, T468I, T488D, and T499N (numbered according to SEQ ID NO: 37). In certain embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488, and 499 (numbered according to SEQ ID NO: 37), or the proviso that the SrKO derivative comprises an amino acid sequence having one or more (or all) of the mutations selected from R76K, M94V, T131Q, F231L, H284Q, R383K, I390L, T468I, and T499N (numbered according to SEQ ID NO: 37).

In some embodiments, the disclosure provides a recombinant polynucleotide encoding the SrKO derivative described above, which may be inserted into expression vectors for expression and optional purification. In some embodiments, the polynucleotide is incorporated into the genome of valencene-producing cells, such as valencene-producing *E. coli* cells.

The SrKO or derivative in various embodiments has valencene oxidase activity. Assays for determining and quantifying valencene oxidase activity are described herein and are known in the art. Assays include expressing the SrKO (or derivative) in valencene-producing cells (e.g., *E. coli* expressing FPPS and valencene synthase), and extracting the oxygenated oil from the aqueous reaction media. The profile of terpenoid product can be determined quantitatively by GC/MS. Various mutations of SrKO tested for effect on valencene oxidase activity are listed in Tables 2.1, 2.2, 2.3 and/or 6. Thus, in various embodiments, the SrKO may have at least about 1, at least about 2, at least about 3, at least about 4, at least about 5, at least about 6, at least about 7, at least about 8, at least about 9, or at least about 10 mutations selected from Tables 2.1, 2.2, 2.3 and/or 6. In some embodiments, the SrKO derivative is a modified SrKO polypeptide comprising an amino acid sequence which has up to 25 mutations compared to the wild type protein according to SEQ ID NO: 37 (or its counterpart that is modified for expression in *E. coli*), and comprises at least the substitutions I310V, V375I or T487N in combination with at least any one or more of V375F, V375A, V375M, M120L, M120I, M120V, F129L, F129I, L114V, L114F and V121A (numbered according to SEQ ID NO: 38) (see Table 6), and optionally comprises a leader sequence (as shown in SEQ ID NO: 38) supporting functional expression in *E. coli*.

TABLE 2.1

Summary of some *Stevia rebaudiana* kaurene oxidase mutations tested, numbered according to wild type SrKO (SEQ ID NOS: 37 and 108), 8rp-t20SrKO (SEQ ID NOS: 38 and 106), n22yhcB-t30VO1 (SEQ ID NO: 104), and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/ SEQ ID NO: 38 (SEQ ID NO: 106) |
|---|---|---|---|---|
| 1 | L | 59/47 | 51 | I |
| 2 | Y | 71/59 | 63 | H |
| 3 | M | 72/60 | 64 | K |
| 4 | T | 75/63 | 67 | A |
| 5 | A | 79/67 | 71 | E |
| 6 | K | 88/76 | 80 | R |
| 7 | T | 92/80 | 84 | C |
| 8 | M | 94/82 | 86 | V |
| 9 | V | 97/85 | 89 | L |
| 10 | V | 97/85 | 89 | I |
| 11 | S | 98/86 | 90 | N |
| 12 | Q | 112/100 | 104 | S |
| 13 | N | 118/106 | 110 | K |
| 14 | K | 124/112 | 116 | T |
| 15 | A | 128/116 | 120 | R |
| 16 | T | 131/119 | 123 | S |
| 17 | M | 135/123 | 127 | T |
| 18 | M | 135/123 | 127 | Q |
| 19 | M | 135/123 | 127 | F |
| 20 | M | 135/123 | 127 | T |
| 21 | D | 139/127 | 131 | G |
| 22 | Y | 141/129 | 133 | F |
| 23 | A | 152/140 | 144 | R |
| 24 | K | 161/149 | 153 | R |
| 25 | H | 162/150 | 154 | F |
| 26 | N | 183/171 | 175 | D |

TABLE 2.1-continued

Summary of some *Stevia rebaudiana* kaurene oxidase mutations tested, numbered according to wild type SrKO (SEQ ID NOS: 37 and 108), 8rp-t20SrKO (SEQ ID NOS: 38 and 106), n22yhcB-t30VO1 (SEQ ID NO: 104), and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/ SEQ ID NO: 38 (SEQ ID NO: 106) |
|---|---|---|---|---|
| 27 | L | 192/180 | 184 | F |
| 28 | I | 195/183 | 187 | V |
| 29 | D | 220/208 | 212 | E |
| 30 | D | 244/232 | 236 | E |
| 31 | S | 279/267 | 271 | A |
| 32 | H | 284/272 | 276 | Q |
| 33 | S | 296/284 | 288 | C |
| 34 | I | 298/286 | 290 | L |
| 35 | Q | 306/294 | 298 | K |
| 36 | Q | 311/299 | 303 | E |
| 37 | I | 322/310 | 314 | T |
| 38 | I | 322/310 | 314 | V |
| 39 | R | 383/371 | 375 | K |
| 40 | R | 383/371 | 375 | I |
| 41 | V | 387/375 | 379 | T |
| 42 | V | 387/375 | 379 | I |
| 43 | V | 387/375 | 379 | L |
| 44 | I | 390/378 | 382 | V |
| 45 | H | 394/382 | 386 | Y |
| 46 | V | 400/388 | 392 | Q |
| 47 | V | 400/388 | 392 | M |
| 48 | H | 405/393 | 397 | D |
| 49 | L | 412/400 | 404 | I |
| 50 | V | 425/413 | 417 | D |
| 51 | V | 425/413 | 417 | K |
| 52 | F | 446/434 | 438 | L |
| 53 | G | 454/442 | 446 | A |
| 54 | S | 462/450 | 454 | A |
| 55 | L | 466/454 | 458 | M |
| 56 | G | 472/460 | 464 | A |
| 57 | M | 476/464 | 468 | L |
| 58 | M | 487/475 | 479 | G |
| 59 | T | 499/487 | 491 | N |
| 60 | P | 504/492 | 496 | K |
| 61 | I | 509/497 | 501 | L |
|  | T | 499/487 | 491 | S |
| 62 | M | 135/123 | 127 | Q |
|  | T | 499/487 | 491 | V |
| 63 | M | 135/123 | 127 | F |
|  | T | 499/487 | 491 | V |
| 64 | M | 135/123 | 127 | F |
|  | T | 499/487 | 491 | F |
| 65 | M | 135/123 | 127 | F |
|  | T | 499/487 | 491 | M |
| 66 | M | 135/123 | 127 | F |
|  | T | 499/487 | 491 | G |

TABLE 2.2

The following mutants were evaluated in the VO1 background (n22-yhcB-t30-VO1, SEQ ID NO: 110) according to wild type SrKO (SEQ ID NOS: 37 and 108), 8rp-t20SrKO (SEQ ID NOS: 38 and 106), n22yhcB-t30VO1 (SEQ ID NO: 104) and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/ SEQ ID NO: 38 (SEQ ID NO: 106) |
|---|---|---|---|---|
| 1 | A | 2 |  | T |
| 2 | H | 46/34 | 38 | R |
| 3 | E | 52/40 | 44 | A |
| 4 | R | 76/64 | 68 | K |

TABLE 2.2-continued

The following mutants were evaluated in the VO1 background (n22-yhcB-t30-VO1, SEQ ID NO: 110) according to wild type SrKO (SEQ ID NOS: 37 and 108), 8rp-t20SrKO (SEQ ID NOS: 38 and 106), n22yhcB-t30VO1 (SEQ ID NO: 104) and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/ SEQ ID NO: 38 (SEQ ID NO: 106) |
|---|---|---|---|---|
| 5 | M | 94/82 | 86 | V |
| 6 | T | 131/119 | 123 | K |
| 7 | T | 131/119 | 123 | Q |
| 8 | L | 150/138 | 142 | M |
| 9 | D | 191/179 | 183 | N |
| 10 | L | 231/219 | 223 | M |
| 11 | Q | 268/256 | 260 | T |
| 12 | E | 323/311 | 315 | L |
| 13 | K | 344/332 | 336 | D |
| 14 | R | 351/339 | 343 | Q |
| 15 | I | 389/377 | 381 | L |
| 16 | I | 389/377 | 381 | V |
| 17 | I | 389/377 | 381 | A |
| 18 | I | 390/378 | 382 | L |
| 19 | I | 390/378 | 382 | M |
| 20 | V | 400/388 | 392 | Q |
| 21 | I | 444/432 | 436 | A |
| 22 | T | 468/456 | 460 | I |
| 23 | T | 488/476 | 480 | D |
| 24 | E | 491/479 | 483 | K |
| 25 | I | 495/483 | 487 | V |

TABLE 2.3

Summary of mutations of several engineered SrKO derivatives based on alignments relative to wild type SrKO (SEQ ID NOS: 37 and 108). The point mutations for each of the SrKO derivatives (SEQ ID NOS: 38, 61, 104, 105, 106, and 107) are identified based on the shift value for each sequence relative to wild type SrKO. 8rp-t20SrKO (SEQ ID NOS: 38 and 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 487. n22yhcB-t30VO1 (SEQ ID NO: 104) has a 30-amino acid truncation of the SrKO N-terminus, a membrane anchor based on 22 amino acids from *E. coli* yhcB, and eight point mutations at positions 38, 223, 276, 375, 392, 436, 480, and 491, and a n22t30-yhcB mutation. n22yhcB-t30VO2 (SEQ ID NOS: 61 and 105) has a 30-amino acid truncation of the SrKO N-terminus, a membrane anchor based on 22 amino acids from *E. coli* yhcB, and nine point mutations at positions 68, 86, 123, 223, 276, 375, 382, 460, and 491, and a n22t30-yhcB mutation.

| Wild Type SrKO (SEQ ID NOS: 37 and 108) (Shift Value: 0) | 8rp-t20SrKO (SEQ ID NOS: 38 and 106) (Shift Value: −12) | 8rp-t20VO0 (SEQ ID NO: 107) (Shift Value: −12) | n22yhcB-t30VO1 (SEQ ID NO: 104) (Shift Value: −8) | n22yhcB-t30VO2 (SEQ ID NOS: 61 and 105) (Shift Value: −8) |
|---|---|---|---|---|
| H46 | H34 | | H38R | |
| R76 | R64 | | | R68K |
| M94 | M82 | | | M86V |
| T131 | T119 | | | T123Q |
| F231 | F219 | | F223L | F223L |
| H284 | H272 | | H276Q | H276Q |
| R383 | R371 | | R375K | R375K |
| I390 | 1378 | | | I382L |
| V400 | V388 | | V392Q | |
| I444 | I432 | | I436A | |
| T468 | T456 | | | T460I |
| T488 | T476 | | T480D | |
| T499 | T487 | T487N | T491N | T491N |

The SrKO may be expressed in a variety of host cells, either for recombinant protein production, or for sesquiterpene (e.g., valencene) oxidation. For example, the host cells include those described in U.S. Pat. No. 8,512,988, which is hereby incorporated by reference in its entirety. The host cell may be a prokaryotic or eukaryotic cell. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp.,

*Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, such as, for example, *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. In an embodiment, the host cell is a bacterium selected from *E. coli, Bacillus subtillus*, or *Pseudomonas putida. In an embodiment, the host cell is a yeast, and may be a species of Saccharomyces, Pichia*, or *Yarrowia*, including *Saccharomyces cerevisiae, Pichia pastoris*, and *Yarrowia lipolytica.*

In some embodiments, the host cell produces isopentyl pyrophosphate (IPP), which acts as a substrate for the synthesis of the sesquiterpene. In some embodiments, the IPP is produced by metabolic flux (e.g., starting with a carbon source supplied to the cell) through an endogenous or heterologous methylerythritol phosphate (MEP) or mevalonic acid (MVA) pathway. In certain embodiments, the MEP or MVA pathway may be enhanced through expression of heterologous enzymes or duplication of certain enzymes in the pathway.

The MEP (2-C-methyl-D-erythritol 4-phosphate) pathway, also called the MEP/DOXP (2-C-methyl-D-erythritol 4-phosphate/l-deoxy-D-xylulose 5-phosphate) pathway or the non-mevalonate pathway or the mevalonic acid-independent pathway refers to the pathway that converts glyceraldehyde-3-phosphate and pyruvate to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA. In some embodiments, the sesquiterpene is produced at least in part by metabolic flux through an MEP pathway, and wherein the host cell has at least one additional copy of a dxs, ispD, ispF, and/or idi gene (e.g., dxs and idi; or dxs, ispD, ispF, and/or idi).

The MVA pathway refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MEP pathway, are described in U.S. Pat. No. 7,667,017, which is hereby incorporated by reference in its entirety.

In some embodiments, the host cell expresses a farnesyl pyrophosphate synthase (FPPS), which produces farnesyl pyrophosphate from IPP or DMAPP. As shown in FIG. 1, farnesyl pyrophosphate is an intermediate for production of valencene. An exemplary farnesyl pyrophosphate synthase is ERG20 of *Saccharomyces cerevisiae* (NCBI accession P08524) and *E. coli* ispA. Various other prokaryotic, yeast, plant, and mammalian FPPS enzymes are known, and may be used in accordance with this aspect.

The host cell may further express a heterologous sesquiterpene synthase to produce the desired sesquiterpene, such as a valencene synthase. Several valencene synthase enzymes are known including valencene synthase from *Citrus×paradisi* or from *Citrus* sinensis. *Citrus sinensis* VS (e.g., AAQ04608.1) as well as various derivatives thereof are described in US 2012/0246767, which is hereby incorporated by reference. For example, the disclosure may employ an amino acid sequence of *Citrus sinensis* valencene synthase (CsVS) (SEQ ID NO: 12), or a derivative, having from 1 to 30 mutations or from 1 to 20 or from 1 to 10 mutations with respect to the wild type amino acid sequence (SEQ ID NO: 12). Such sequences may have at least 60% sequence identity, at least 70% sequence identity, at least 80% sequence identity, at least 90% sequence identity, at least 95% sequence identity, or at least about 96%, about 97%, about 98%, or about 99% sequence identity with the wild type sequence (SEQ ID NO: 12). Further, valencene synthase from *Vitis vinifera* (VvVS) (SEQ ID NO: 1) has been described by Licker et al. (Phytochemistry (2004) 65: 2649-2659). In an embodiment, a valencene synthase comprising the amino acid sequence of VvVS (SEQ ID NO: 1) or an engineered derivative thereof may be employed with the present disclosure. Various sesquiterpene synthase enzymes such as valencene synthase are known and are described in, for example, US 2012/0107893, US 2012/0246767, and U.S. Pat. No. 7,273,735, which are hereby incorporated by reference in their entireties.

For example, in some embodiments, the valencene synthase is a VvVS derivative that comprises an amino acid sequence having from about 1 to about 40 mutations, from about 1 to about 35 mutations, from about 1 to about 30 mutations, about 1 to about 25 mutations, from about 1 to about 20 mutations, about 1 to about 15 mutations, or from about 1 to about 10 mutations independently selected from substitutions, deletions, or insertions with respect to VvVS (SEQ ID NO: 1). For example, the VvVS derivative may comprise an amino acid sequence having at least about 5 or at least about 10, but less than about 30 or about 20 mutations with respect to SEQ ID NO: 1. In various embodiments, the VvVS derivative comprises an amino acid sequence that has about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, or about 40 mutations relative to VvVS (SEQ ID NO: 1). Such sequences may have at least 60% sequence identity, at least 70% sequence identity, at least 80% sequence identity, at least 90% sequence identity, at least 95% sequence identity, or at least about 96%, about 97%, about 98%, or about 99% sequence identity with SEQ ID NO:1. Exemplary mutations of VvVS are shown in Table 3. Mutations can be guided by a homology model of *Vitis vinifera* valencene synthase (VvVS) based on the 5-epi-aristolochene synthase crystal structure as a template (PDB: 5EAT).

TABLE 3.1

Summary of *Vitis vinifera* valencene synthase mutations with respect to wild type (SEQ ID NO: 1)

| No. | WT | Position | Mutation |
|---|---|---|---|
| 1 | N | 23 | D |
| 2 | T | 37 | R |
| 3 | P | 38 | S |
| 4 | V | 42 | R |
| 5 | A | 45 | E |
| 6 | C | 46 | K |
| 7 | Q | 50 | R |
| 8 | K | 56 | E |
| 9 | K | 59 | R |
| 10 | R | 60 | K |
| 11 | K | 61 | M |
| 12 | T | 63 | R |
| 13 | T | 63 | K |
| 14 | N | 69 | Q |
| 15 | N | 69 | K |
| 16 | S | 71 | I |
| 17 | Q | 72 | R |
| 18 | L | 73 | K |
| 19 | N | 75 | E |
| 20 | F | 76 | M |
| 21 | F | 76 | L |
| 22 | V | 80 | M |
| 23 | V | 80 | L |
| 24 | V | 85 | I |
| 25 | A | 86 | S |
| 26 | Q | 91 | D |
| 27 | A | 96 | I |
| 28 | Q | 98 | E |
| 29 | Q | 98 | D |
| 30 | C | 101 | Y |
| 31 | N | 102 | H |
| 32 | S | 103 | D |
| 33 | F | 104 | D |
| 34 | F | 104 | N |
| 35 | D | 111 | E |
| 36 | N | 116 | T |
| 37 | I | 117 | S |
| 38 | I | 117 | V |
| 39 | I | 117 | T |
| 40 | G | 120 | R |
| 41 | Q | 127 | H |
| 42 | T | 130 | N |
| 43 | I | 131 | V |
| 44 | I | 135 | V |
| 45 | T | 140 | K |
| 46 | E | 142 | K |
| 47 | E | 148 | D |
| 48 | A | 149 | S |
| 49 | A | 149 | D |
| 50 | I | 151 | S |
| 51 | R | 155 | K |
| 52 | M | 157 | L |
| 53 | G | 159 | S |
| 54 | G | 159 | N |
| 55 | E | 162 | Q |
| 56 | E | 162 | K |

TABLE 3.1-continued

Summary of *Vitis vinifera* valencene synthase mutations with respect to wild type (SEQ ID NO: 1)

| No. | WT | Position | Mutation |
|---|---|---|---|
| 57 | A | 164 | S |
| 58 | V | 168 | T |
| 59 | G | 170 | D |
| 60 | L | 174 | M |
| 61 | A | 175 | E |
| 62 | A | 175 | D |
| 63 | K | 176 | E |
| 64 | T | 183 | K |
| 65 | A | 187 | S |
| 66 | M | 188 | L |
| 67 | E | 190 | N |
| 68 | G | 193 | K |
| 69 | A | 201 | S |
| 70 | N | 205 | E |
| 71 | R | 206 | Q |
| 72 | I | 208 | L |
| 73 | R | 209 | H |
| 74 | G | 211 | R |
| 75 | L | 212 | M |
| 76 | E | 213 | P |
| 77 | I | 221 | L |
| 78 | V | 223 | R |
| 79 | Q | 225 | D |
| 80 | Q | 225 | E |
| 81 | D | 226 | K |
| 82 | D | 226 | E |
| 83 | A | 228 | E |
| 84 | F | 229 | I |
| 85 | H | 230 | V |
| 86 | D | 231 | N |
| 87 | K | 232 | E |
| 88 | T | 233 | A |
| 89 | T | 233 | V |
| 90 | S | 247 | D |
| 91 | L | 248 | M |
| 92 | L | 248 | K |
| 93 | K | 250 | Q |
| 94 | E | 251 | K |
| 95 | S | 254 | K |
| 96 | N | 255 | E |
| 97 | A | 257 | S |
| 98 | K | 261 | A |
| 99 | E | 262 | D |
| 100 | D | 264 | G |
| 101 | Y | 280 | F |
| 102 | M | 283 | I |
| 103 | H | 284 | M |
| 104 | H | 284 | A |
| 105 | G | 285 | A |
| 106 | Y | 287 | F |
| 107 | Q | 291 | N |
| 108 | R | 294 | L |
| 109 | R | 297 | I |
| 110 | L | 299 | M |
| 111 | M | 305 | A |
| 112 | M | 305 | L |
| 113 | I | 308 | M |
| 114 | T | 318 | S |
| 115 | P | 319 | L |
| 116 | P | 319 | I |
| 117 | K | 323 | Q |
| 118 | R | 331 | K |
| 119 | D | 333 | E |
| 120 | I | 334 | E |
| 121 | I | 334 | V |
| 122 | N | 335 | K |
| 123 | N | 335 | Q |
| 124 | N | 335 | S |
| 125 | S | 336 | A |
| 126 | Y | 343 | W |
| 127 | Y | 348 | F |
| 128 | V | 349 | L |
| 129 | L | 352 | I |
| 130 | D | 353 | E |
| 131 | D | 353 | N |

TABLE 3.1-continued

Summary of *Vitis vinifera* valencene synthase mutations with respect to wild type (SEQ ID NO: 1)

| No. | WT | Position | Mutation |
|---|---|---|---|
| 132 | V | 354 | T |
| 133 | Y | 355 | F |
| 134 | K | 356 | E |
| 135 | K | 356 | N |
| 136 | I | 358 | V |
| 137 | E | 359 | D |
| 138 | E | 360 | Y |
| 139 | E | 363 | K |
| 140 | E | 363 | L |
| 141 | G | 366 | A |
| 142 | Y | 369 | N |
| 143 | R | 370 | V |
| 144 | V | 371 | I |
| 145 | H | 372 | E |
| 146 | H | 372 | P |
| 147 | A | 374 | G |
| 148 | A | 374 | L |
| 149 | E | 376 | D |
| 150 | M | 378 | I |
| 151 | N | 380 | I |
| 152 | N | 380 | K |
| 153 | R | 383 | Q |
| 154 | E | 394 | Q |
| 155 | E | 394 | D |
| 156 | E | 395 | N |
| 157 | E | 395 | G |
| 158 | H | 396 | Y |
| 159 | H | 396 | Q |
| 160 | E | 402 | D |
| 161 | R | 405 | E |
| 162 | C | 414 | R |
| 163 | L | 415 | M |
| 164 | A | 417 | L |
| 165 | T | 418 | V |
| 166 | T | 419 | H |
| 167 | V | 422 | L |
| 168 | M | 424 | V |
| 169 | A | 428 | V |
| 170 | T | 429 | S |
| 171 | T | 437 | F |
| 172 | S | 438 | G |
| 173 | D | 439 | Y |
| 174 | K | 441 | R |
| 175 | I | 442 | M |
| 176 | I | 442 | L |
| 177 | M | 443 | V |
| 178 | S | 444 | R |
| 179 | N | 447 | S |
| 180 | F | 448 | T |
| 181 | M | 453 | A |
| 182 | G | 466 | E |
| 183 | T | 469 | A |
| 184 | Q | 478 | E |
| 185 | Y | 479 | F |
| 186 | G | 480 | A |
| 187 | V | 481 | A |
| 188 | S | 482 | T |
| 189 | Y | 487 | C |
| 190 | S | 488 | E |
| 191 | E | 489 | H |
| 192 | F | 490 | I |
| 193 | F | 490 | L |
| 194 | Q | 491 | K |
| 195 | Q | 491 | N |
| 196 | Q | 493 | L |
| 197 | I | 494 | M |
| 198 | N | 496 | D |
| 199 | D | 500 | E |
| 200 | L | 506 | M |
| 201 | T | 509 | S |
| 202 | V | 511 | M |
| 203 | S | 512 | P |
| 204 | S | 512 | T |
| 205 | M | 513 | K |
| 206 | P | 514 | D |

TABLE 3.1-continued

Summary of *Vitis vinifera* valencene synthase mutations with respect to wild type (SEQ ID NO: 1)

| No. | WT | Position | Mutation |
|---|---|---|---|
| 207 | L | 519 | A |
| 208 | D | 527 | E |
| 209 | V | 528 | F |
| 210 | E | 532 | D |
| 211 | Q | 533 | E |
| 212 | Q | 533 | G |
| 213 | S | 535 | G |
| 214 | V | 539 | S |
| 215 | V | 542 | L |
| 216 | V | 542 | T |
| 217 | M | 543 | I |
| 218 | N | 546 | H |
| 219 | V | 550 | L |
| 220 | F | 551 | L |
| 221 | I | 552 | V |
| 222 | N | 553 | D |
| 223 | N | 553 | E |
| 224 | A | 554 | P |
| 225 | V | 555 | I |

TABLE 3.2

Summary of mutations evaluated in the Vv2M5 background (SEQ ID NO: 9).

| No. | WT | Position | Mutation |
|---|---|---|---|
| 226 | N | 18 | V |
| 227 | V | 21 | S |
| 228 | N | 23 | D |
| 229 | N | 27 | S |
| 230 | Q | 32 | H |
| 231 | I | 34 | L |
| 232 | T | 35 | S |
| 233 | T | 37 | S |
| 234 | K | 41 | S |
| 235 | V | 42 | E |
| 236 | A | 45 | E |
| 237 | K | 46 | C |
| 238 | K | 47 | M |
| 239 | Q | 50 | R |
| 240 | I | 51 | V |
| 241 | D | 53 | E |
| 242 | K | 56 | E |
| 243 | V | 67 | A |
| 244 | A | 68 | N |
| 245 | N | 69 | D |
| 246 | N | 69 | Q |
| 247 | S | 71 | L |
| 248 | Q | 72 | R |
| 249 | V | 80 | I |
| 250 | A | 86 | S |
| 251 | Q | 91 | K |
| 252 | C | 101 | Y |
| 253 | N | 102 | D |
| 254 | N | 102 | H |
| 255 | M | 110 | D |
| 256 | D | 111 | E |
| 257 | G | 112 | D |
| 258 | I | 117 | S |
| 259 | T | 130 | N |
| 260 | R | 143 | E |
| 261 | R | 145 | N |
| 262 | A | 149 | S |
| 263 | S | 152 | N |
| 264 | G | 159 | N |
| 265 | G | 159 | S |
| 266 | V | 168 | T |
| 267 | K | 176 | E |
| 268 | K | 186 | E |
| 269 | A | 187 | S |
| 270 | S | 191 | H |

TABLE 3.2-continued

| Summary of mutations evaluated in the Vv2M5 background (SEQ ID NO: 9). | | | |
|---|---|---|---|
| No. | WT | Position | Mutation |
| 271 | Y | 194 | P |
| 272 | H | 195 | P |
| 273 | N | 205 | E |
| 274 | L | 212 | M |
| 275 | E | 213 | P |
| 276 | W | 219 | H |
| 277 | V | 223 | I |
| 278 | D | 226 | E |
| 279 | A | 228 | E |
| 280 | F | 229 | S |
| 281 | T | 233 | V |
| 282 | V | 245 | L |
| 283 | L | 248 | M |
| 284 | L | 256 | I |
| 285 | K | 261 | A |
| 286 | E | 262 | D |
| 287 | C | 347 | F |
| 288 | E | 363 | A |
| 289 | H | 372 | E |
| 290 | V | 377 | A |
| 291 | E | 395 | G |
| 292 | E | 395 | N |
| 293 | H | 396 | Y |
| 294 | A | 399 | T |
| 295 | C | 414 | R |
| 296 | E | 426 | D |
| 297 | S | 438 | G |
| 298 | M | 443 | I |
| 299 | T | 469 | A |
| 300 | S | 488 | E |
| 301 | K | 491 | R |
| 302 | M | 513 | K |
| 303 | A | 517 | E |
| 304 | L | 519 | V |
| 305 | E | 532 | D |
| 306 | V | 550 | L |
| 307 | N | 553 | D |

TABLE 3.3

| Summary of mutations evaluated in VS2 background (SEQ ID NO: 11). | | | |
|---|---|---|---|
| No. | WT | Position | Mutation |
| 308 | P | 20 | R |
| 309 | N | 23 | D |
| 310 | I | 28 | F |
| 311 | K | 41 | P |
| 312 | K | 41 | S |
| 313 | V | 42 | D |
| 314 | R | 44 | H |
| 315 | Q | 50 | D |
| 316 | Q | 50 | R |
| 317 | E | 52 | R |
| 318 | K | 61 | M |
| 319 | N | 69 | Q |
| 320 | Q | 72 | R |
| 321 | L | 73 | K |
| 322 | A | 79 | I |
| 323 | A | 86 | S |
| 324 | H | 88 | L |
| 325 | Q | 91 | H |
| 326 | A | 96 | I |
| 327 | Q | 98 | R |
| 328 | C | 101 | Y |
| 329 | N | 102 | H |
| 330 | C | 107 | F |
| 331 | I | 117 | S |
| 332 | G | 120 | L |
| 333 | T | 140 | K |
| 334 | R | 145 | N |

TABLE 3.3-continued

| Summary of mutations evaluated in VS2 background (SEQ ID NO: 11). | | | |
|---|---|---|---|
| No. | WT | Position | Mutation |
| 335 | S | 152 | V |
| 336 | V | 154 | I |
| 337 | V | 154 | P |
| 338 | R | 155 | K |
| 339 | M | 157 | L |
| 340 | G | 159 | M |
| 341 | A | 175 | D |
| 342 | K | 176 | E |
| 343 | A | 177 | P |
| 344 | L | 178 | I |
| 345 | H | 184 | Y |
| 346 | H | 184 | Q |
| 347 | A | 187 | S |
| 348 | S | 191 | H |
| 349 | H | 195 | N |
| 350 | L | 196 | P |
| 351 | A | 201 | R |
| 352 | L | 212 | M |
| 353 | E | 213 | P |
| 354 | A | 217 | Q |
| 355 | A | 228 | E |
| 356 | D | 231 | N |
| 357 | K | 232 | P |
| 358 | T | 233 | V |
| 359 | E | 236 | D |
| 360 | D | 241 | E |
| 361 | N | 255 | D |
| 362 | A | 257 | M |
| 363 | L | 276 | P |
| 364 | Y | 280 | F |
| 365 | M | 283 | I |
| 366 | V | 286 | A |
| 367 | T | 300 | M |
| 368 | T | 300 | I |
| 369 | T | 306 | L |
| 370 | T | 306 | I |
| 371 | L | 309 | I |
| 372 | A | 315 | V |
| 373 | E | 320 | D |
| 374 | K | 323 | R |
| 375 | S | 336 | T |
| 376 | E | 342 | D |
| 377 | C | 347 | L |
| 378 | A | 350 | I |
| 379 | N | 356 | H |
| 380 | E | 363 | G |
| 381 | Q | 368 | P |
| 382 | N | 380 | D |
| 383 | Q | 381 | L |
| 384 | E | 395 | G |
| 385 | A | 407 | G |
| 386 | A | 407 | S |
| 387 | C | 414 | P |
| 388 | A | 417 | I |
| 389 | A | 432 | I |
| 390 | V | 436 | L |
| 391 | I | 442 | P |
| 392 | I | 442 | L |
| 393 | S | 445 | R |
| 394 | S | 446 | M |
| 395 | T | 450 | C |
| 396 | S | 458 | T |
| 397 | H | 459 | Y |
| 398 | H | 459 | M |
| 399 | H | 467 | Q |
| 400 | T | 469 | A |
| 401 | E | 484 | P |
| 402 | Q | 485 | H |
| 403 | Q | 485 | E |
| 404 | V | 486 | A |
| 405 | Y | 487 | L |
| 406 | S | 488 | E |
| 407 | I | 494 | V |
| 408 | N | 496 | D |
| 409 | N | 496 | K |

TABLE 3.3-continued

Summary of mutations evaluated in VS2 background (SEQ ID NO: 11).

| No. | WT | Position | Mutation |
|---|---|---|---|
| 410 | M | 513 | T |
| 411 | T | 523 | I |
| 412 | D | 527 | L |
| 413 | I | 529 | L |
| 414 | I | 529 | M |
| 415 | E | 532 | H |
| 416 | E | 532 | Y |
| 417 | S | 535 | A |
| 418 | R | 544 | H |
| 419 | N | 546 | Y |
| 420 | N | 546 | F |
| 421 | A | 548 | I |
| 422 | V | 550 | L |
| 423 | V | 555 | I |

Thus, in various embodiments, the engineered VvVS may have at least about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, or about 40 mutations selected from Table 3. Exemplary recombinant valencene synthases Vv1M1 (SEQ ID NO: 3), Vv2M1 (SEQ ID NO: 5), Vv1M5 (SEQ ID NO: 7), Vv2M5 (SEQ ID NO: 9), and VS2 (SEQ ID NO: 11) are further depicted in FIG. 3, including an alignment in FIG. 3B. A further exemplary recombinant valencene synthase VS3 (SEQ ID NO: 129) is also depicted herein.

In certain aspects, the disclosure provides polynucleotides comprising a nucleotide sequence encoding a valencene synthase modified for increased expression of valencene as described above. Such polynucleotides may be expressed in host cells, either on extrachromosomal elements such as plasmids, or may be chromosomally integrated.

In various embodiments, the SrKO is expressed alongside a P450 reductase to regenerate the enzyme, or alternatively, the SrKO or derivative is expressed with the P450 reductase as a chimeric P450 enzyme. Functional expression of cytochrome P450 has been considered challenging due to the inherent limitations of bacterial platforms, such as the absence of electron transfer machinery and cytochrome P450 reductases, and translational incompatibility of the membrane signal modules of P450 enzymes due to the lack of an endoplasmic reticulum.

Accordingly, in some embodiments the SrKO is expressed as a fusion protein with a cytochrome P450 reductase partner. Cytochrome P450 reductase is a membrane protein found in the endoplasmic reticulum. It catalyzes pyridine nucleotide dehydration and electron transfer to membrane bound cytochrome P450s. Isozymes of similar structure are found in humans, plants, other mammals, and insects. Exemplary P450 reductase partners include, for example, *Stevia rebaudiana* (Sr)CPR (SEQ ID NOS: 62 and 63), *Stevia rebaudiana* (Sr)CPR1 (SEQ ID NOS: 76 and 77), *Arabidopsis thaliana* (At)CPR (SEQ ID NOS: 64 and 65),

*Taxus cuspidata* (Tc) CPR (SEQ ID NOS: 66 and 67), *Artemisia annua* (Aa)CPR (SEQ ID NOS: 68 and 69), *Arabidopsis thaliana* (At)CPR1 (SEQ ID NOS: 70 and 71), *Arabidopsis thaliana* (At)CPR2 (SEQ ID NOS: 72 and 73), *Arabidopsis thaliana* (At)R2 (SEQ ID NOS: 74 and 75); *Stevia rebaudiana* (Sr)CPR2 (SEQ ID NOS: 78 and 79); *Stevia rebaudiana* (Sr)CPR3 (SEQ ID NOS: 80 and 81); *Pelargonium graveolens* (Pg)CPR (SEQ ID NO: 82 and 83). Any of these P450s can be derivatized in some embodiments, for example, to introduce from 1 to about 20 mutations, or from about 1 to about 10 mutations. FIG. 6B shows an alignment of amino acid sequences for *Arabidopsis thaliana* and *Artemisia annua* CPR sequences (SEQ ID NOS: 72, 74, 68, 64, and 70). FIG. 6C shows an alignment of *Stevia rebaudiana* CPR sequences (SEQ ID NOS: 78, 80, 62, and 76). FIG. 6D shows an alignment of eight CPR amino acid sequences (SEQ ID NOS: 74, 72, 82, 68, 80, 62, 78, and 76).

Engineering of P450 fusion proteins is disclosed, for example, in US 2012/0107893 and US 2012/0164678, both of which are hereby incorporated by reference in their entireties. In certain embodiments, the SrKO is fused to the cytochrome P450 reductase partner through a linker. Exemplary linker sequences, which are predominantly serine, glycine, and/or alanine, and optionally from one to five charged amino acids such as lysine or arginine, include, for example, GSG, GSGGGGS (SEQ ID NO: 113), GSGEAAAK (SEQ ID NO: 114), GSGEAAAKEAAAK (SEQ ID NO: 115), GSGMGSSSN (SEQ ID NO: 116), and GSTGS (SEQ ID NO: 117). The linker is generally flexible, and contains no more than one, two, or three hydrophobic residues, and is generally from three to fifty amino acids in length, such as from three to twenty amino acids in length. In other embodiments, a P450 reductase is expressed in the host cell separately, and may be expressed in the same operon as the SrKO in some embodiments. In some embodiments, the P450 reductase enzyme is expressed separately in the host cell, and the gene is optionally integrated into the genome or expressed from a plasmid.

In certain embodiments the N-terminus of the P450 enzymes may be engineered to increase their functional expression. The N-terminus of membrane-bound P450 plays important roles in enzyme expression, membrane association and substrate access. It has been reported that the use of rare codons in the N-terminus of P450 significantly improved the expression level of P450. Further, since most plant P450 enzymes are membrane-bound and hydrophobic substrates are thought to enter the enzymes through channels dynamically established between the P450 and membrane, N-terminal engineering can affect the association of the membrane and P450 and therefore the access of substrate to the enzyme. Accordingly, in an embodiment, N-terminal engineering of SrKO generates an SrKO derivative that either maintains or shows enhanced valencene oxidase activity in a host system such as *E. coli* or yeast. An exemplary N-terminal sequence is 8rp or MALLLAVF (SEQ ID NO: 112), and other exemplary sequences include sequences of from four to twenty amino acids (such as from four to fifteen amino acids, or from four to ten amino acids, or about eight amino acids) that are predominately hydrophobic, for example, constructed predominately of (at least 50%, or at least 75%) amino acids selected from leucine, valine, alanine, isoleucine, and phenylalanine.

In some embodiments, the SrKO is a derivative having a deletion of at least a portion of its N-terminal transmembrane region, and the addition of an inner membrane transmembrane domain from *E. coli* yhcB or derivative thereof.

In these embodiments, the P450 enzyme has a more stable and/or productive association with the *E. coli* inner membrane, which reduces cell stress otherwise induced by the expression of a membrane-associated P450 enzyme. In some embodiments, the SrKO is a derivative having a deletion of from 15 to 35 amino acids of its N-terminal transmembrane domain, and the addition of from 15 to 25 amino acids of the transmembrane domain from *E. coli* yhcB or derivative thereof. In some embodiments, the N-terminal transmembrane domain of the derivative comprises the amino acid sequence MAWEYALIGLVVGIIIGAVA (SEQ ID NO: 118), or an amino acid sequence having from 1 to 10 or from 1 to 5 amino acid mutations with respect to SEQ ID NO: 118.

In some embodiments, the host cell further expresses one or more enzymes, such as an alcohol dehydrogenase (ADH). In certain embodiments, the host cell may express an ADH enzyme producing nootkatone from nootkatol, examples of which include *Rhodococcus erythropolis* CDH (SEQ ID NO: 84), *Citrus sinensis* DH (SEQ ID NO: 86), *Citrus sinensis* DH1 (SEQ ID NO: 88), *Citrus sinensis* DH2 (SEQ ID NO: 90), *Citrus sinensis* DH3 (SEQ ID NO: 92), *Vitis vinifera* DH (SEQ ID NO: 94), *Vitis vinifera* DH1 (SEQ ID NO: 96), *Citrus sinensis* ABA2 (SEQ ID NO: 98), Brachypodium distachyon DH (SEQ ID NO: 100), and *Zingiber zerumbet* SDR (SEQ ID NO: 102). The ADH may comprise an amino acid sequence having at least 70%, at least 80%, or at least 90% sequence identity to one or more of the enzymes described in this paragraph, and with the activity of converting nootkatol to nootkatone.

Sesquiterpenes (e.g., valencene and its oxygenated products) can be produced as biosynthetic products of the non-mevalonate pathway in *E. coli* comprising two modules: the native upstream pathway forming Isopentenyl Pyrophosphate (IPP) and a heterologous downstream terpenoid-forming pathway. A multivariate-modular approach to metabolic pathway engineering can be employed to optimize the production of sesquiterpenes in an engineered *E. coli*. The multivariate-modular pathway engineering approach is based on a systematic multivariate search to identify conditions that optimally balance the two pathway modules to minimize accumulation of inhibitory intermediates and flux diversion to side products.

WO 2011/060057, US 2011/0189717, US 2012/107893, and U.S. Pat. No. 8,512,988 (each of which are hereby incorporated by reference) describe methods and compositions for optimizing production of terpenoids in cells by controlling expression of genes or proteins participating in an upstream pathway and a downstream pathway. This can be achieved by grouping the enzyme pathways into two modules: an upstream (MEP) pathway module (e.g., containing one or more genes of the MEP pathway) and a downstream, heterologous pathway to sesquiterpene production. Using this basic configuration, parameters such as the effect of plasmid copy number on cell physiology, gene order and promoter strength in an expression cassette, and chromosomal integration are evaluated with respect to their effect on terpene and terpenoid (e.g., sesquiterpene) production. Expression of genes within the MEP pathway can thus be regulated in a modular method. As used herein, regulation by a modular method refers to regulation of multiple genes together. By way of example, multiple genes within the MEP pathway can be recombinantly expressed on a contiguous region of DNA, such as an operon. It should be appreciated that modules of genes within the MEP pathway, consistent with aspects of the disclosure, can contain any of the genes within the MEP pathway, in any order. In some embodiments, a gene within the MEP pathway is one of the following: dxs, ispC, ispD, ispE, ispF, ispG, ispH, idi, ispA or ispB. A non-limiting example of a module of genes within the MEP pathway is a module containing the genes dxs, idi, ispD and ispF, and referred to as dxs-idi-ispDF.

The manipulation of the expression of genes and/or proteins, including modules such as the dxs-idi-ispDF operon, and a FPPS-VS operon, can be achieved through methods known to one of ordinary skill in the art. For example, expression of the genes or operons can be regulated through selection of promoters, such as inducible promoters, with different strengths. Several non-limiting examples of promoters include Trc, T5 and T7. Additionally, expression of genes or operons can be regulated through manipulation of the copy number of the gene or operon in the cell.

The expression of one or more genes and/or proteins within the MEP pathway can be upregulated and/or downregulated. In certain embodiments, upregulation of one or more genes and/or proteins within the MEP pathway can be combined with downregulation of one or more genes and/or proteins within the MEP pathway. By way of example, in some embodiments, a cell that overexpresses one or more components of the non-mevalonate (MEP) pathway is used, at least in part, to amplify isopentyl diphosphate (IPP) and dimethylallyl diphosphate (DMAPP), substrates of GGPPS. In some embodiments, overexpression of one or more components of the non-mevalonate (MEP) pathway is achieved by increasing the copy number of one or more components of the non-mevalonate (MEP) pathway. In this regards, copy numbers of components at rate-limiting steps in the MEP pathway such as (dxs, ispD, ispF, idi) can be amplified, such as by additional episomal expression.

In some embodiments, the production of indole is used as a surrogate marker for sesquiterpene production, and/or the accumulation of indole in the culture is controlled to increase sesquiterpene production. For example, in various embodiments, accumulation of indole in the culture is controlled to below about 100 mg/L, or below about 75 mg/L, or below about 50 mg/L, or below about 25 mg/L, or below about 10 mg/L. The accumulation of indole can be controlled by balancing protein expression and activity using the multivariate modular approach described above, and/or is controlled by chemical means.

In other aspects, the disclosure provides a method for making a product containing an oxygenated sesquiterpene (as described), which comprises incorporating the oxygenated sesquiterpene prepared and recovered according to the method described above into a consumer or industrial product. For example, the product may be a flavor product, a fragrance product, a cosmetic, a cleaning product, a detergent or soap, or a pest control product (e.g., an insect repellant). In some embodiments, the oxygenated product recovered and optionally enriched by fractionation is nootkatol (e.g., α and β nootkatol) and/or nootkatone, and the product is a flavor product selected from a beverage, a chewing gum, a candy, or a flavor additive, or is a pest control product (e.g., an insect repellant).

The oxygenated product can be recovered by any suitable process, including partitioning the desired product into an organic phase. The production of the desired product can be determined and/or quantified, for example, by gas chromatography (e.g., GC-MS). The desired product can be produced in batch or continuous bioreactor systems. Production of product, recovery, and/or analysis of the product can be done as described in US 2012/0246767, which is hereby incorporated by reference in its entirety. For example, in some embodiments, oxygenated oil is extracted from aqueous reaction medium, which may be done by using an organic solvent, such as an alkane such as heptane, followed by fractional distillation. Sesquiterpene and sesquiterpenoid components of fractions may be measured quantitatively by GC/MS, followed by blending of the fractions to generate a desired nootkatone-containing ingredient for flavour (or other) applications.

In other aspects, the disclosure provides polynucleotides comprising a nucleotide sequence encoding a P450 derivative described herein. The polynucleotide may be codon optimized for expression in *E. coli* or yeast in some embodiments. In another example, the polynucleotide may comprise a nucleotide sequence encoding a SrKO fusion protein, optionally with a P450 reductase partner as described herein. In other embodiments, the disclosure provides polynucleotides comprising a nucleotide sequence encoding a sesquiterpene synthase variant described herein, which may likewise be codon optimized for expression in *E. coli* or yeast. Such polynucleotides may further comprise, in addition to sequences encoding the P450 or sesquiterpene synthase, one or more expression control elements. For example, the polynucleotide may comprise one or more promoters or transcriptional enhancers, ribosomal binding sites, transcription termination signals, and polyadenylation signals, as expression control elements. The polynucleotide may be inserted within any suitable vector, including an expression vector, and which may be contained within any suitable host cell for expression. The polynucleotide may be designed for introduction and/or protein expression in any suitable host cell, including bacterial cells and yeast cells, and may be expressed from a plasmid, or may be chromosomally integrated. In some embodiments, the recombinant nucleic acid molecule encodes an SrKO derivative with a higher activity for oxidation of valencene than the wild type enzyme (SEQ ID NO: 37), and having a leader sequence as described, such as the leader sequence MALLLAVF (SEQ ID NO: 112) or leader sequence derived from *E. coli* yhcB. In certain embodiments, the recombinant nucleic acid molecules further encodes either as an operon or as a fusion in frame with the SrKO derivative, an SrCPR or derivative thereof capable of regenerating the SrKO enzyme. When present as a fusion protein, the SrKO derivative and the SrCPR may be connected by a linking sequence of from 3 to 10 amino acids (e.g., 5 amino acids). In some embodiments, the linking sequence is predominately glycine, serine, and/or alanine and may comprise the sequence GSTGS.

In other aspects, the disclosure provides host cells producing an oxygenated sesquiterpene as described herein, and which express all of the enzyme components for producing the desired oxygenated sesquiterpene from isopentyl pyrophosphate (IPP). For example, the host cell in various embodiments expresses a farnesyl pyrophosphate synthase, a sesquiterpene synthase, and the SrKO or derivative thereof. IPP may be produced through the MEP and/or MVA pathway, which may be endogenous to the host cell or modified through expression of heterologous enzymes or duplication of certain enzymes in the pathway. Host cells include various bacteria and yeast as described herein.

In still other aspects, the disclosure provides sesquiterpene products produced by the methods and host cells described herein. As disclosed herein, SrKO enzyme showed unique activities by creating different stereoisomers of the hydroxylated product (alpha and beta nootkatol and further oxidizing to ketone, nootkatone), and produced different oxygenated terpene products including hydroxygermacra-1(10)5-diene, and murolan-3,9(11) diene-10-peroxy. This activity provides for the incorporation of a unique valencene oxidation profile into an oil suitable for flavouring applications.

In certain embodiments, the processes and methods disclosed herein provide compositions and formulations comprising an oxygenated product. In some embodiments, said compositions and formulations may further comprise an unoxygenated product, a sesquiterpene, valencene, a non-sesquiterpene component, and/or one or more additional ingredients. In particular embodiments, the compositions and formulations disclosed herein comprise at least one of valencene, hydroxygermacra-1(10)5-diene, murolan-3,9(11) diene-10-peroxy, α-nootkatol, β-nootkatol, and nootkatone. In certain embodiments of the compositions and formulations disclosed herein, the compositions and formulations comprise at least one of nootkatone, α-nootkatol, β-nootkatol, and valencene. For example, in certain such embodiments, the nootkatone content may be selected from about 50% to about 65% (w/w), about 52.5% to about 62.5% (w/w), and about 55% to about 60% (w/w); the α-nootkatol content may be selected from about 15% to about 30% (w/w), about 17.5% to about 27.5% (w/w), and about 20% to about 25% (w/w); the β-nootkatol content may be selected from about 1% to about 15% (w/w), about 3% to about 12% (w/w), and about 5% to about 10% (w/w); and the valencene content may be selected from about 1% to about 15% (w/w), about 3% to about 12% (w/w), and about 5% to about 10% (w/w).

In specific embodiments of the compositions and formulations disclosed herein, the compositions and formulations comprise at least one of nootkatone, α-nootkatol, and β-nootkatol. For example, in certain such embodiments, the nootkatone content may be selected from about 50% to about 65% (w/w), about 52.5% to about 62.5% (w/w), and about 55% to about 60% (w/w); the α-nootkatol content may be selected from about 15% to about 30% (w/w), about 17.5% to about 27.5% (w/w), and about 20% to about 25% (w/w); and the β-nootkatol content may be selected from about 1% to about 15% (w/w), about 3% to about 12% (w/w), and about 5% to about 10% (w/w).

In one embodiment, the composition or formulation comprise nootkatone, α-nootkatol, and β-nootkatol, wherein the nootkatone is present in an amount ranging from about 55% to about 60% (w/w), the α-nootkatol is present in an amount ranging from about 20% to about 25% (w/w), and the β-nootkatol is present in an amount ranging from about 5% to about 10% (w/w).

In another embodiment, the composition or formulation comprise valencene, nootkatone, α-nootkatol, and β-nootkatol, wherein the valencene is present in an amount ranging from about 5% to about 10% (w/w), the nootkatone is present in an amount ranging from about 55% to about 60% (w/w), the α-nootkatol is present in an amount ranging from about 20% to about 25% (w/w), and the β-nootkatol is present in an amount ranging from about 5% to about 10% (w/w).

Figure 7:
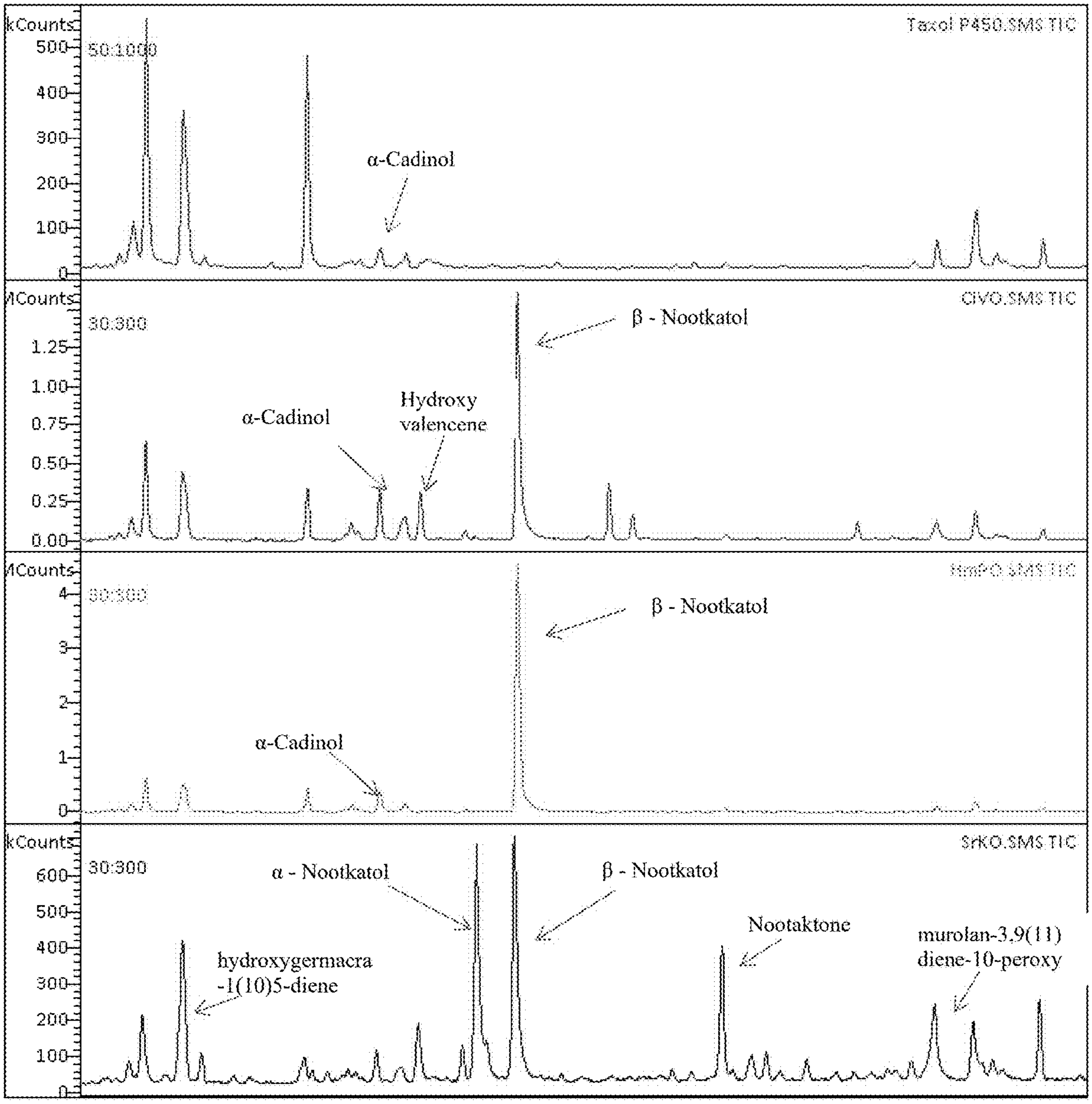
FIG. 7 provides GC-chromatographs which show the different activities of various CYP450 enzymes, as expressed in valencene-producing *E. coli* along with CPR partners as described in Example 2. Strains were cultured for four days and extracted with Methyl Tert-Butyl Ether (MTBE). 1 μl of MTBE was injected through GC-MS and the product profiles were monitored by comparing with a MS library. From top to bottom: *Taxus* 5-alpha hydroxylase, *Cichorium intybus* (CiVO) P450 (SEQ ID NO:50), *Hyoscyamus muticus* (HmPO) P450 (SEQ ID NO:20), and SrKO (SEQ ID NO:38).

Further, other P450 enzymes tested, including previously known sesquiterpene CYP450's or P450's having hydroxylating activity on the valencene substrate produced one of the stereoisomers (beta nootkatol) and only minor amounts of the ketone (nootkatone). Specifically, the other sesquiterpene CYP450 enzymes produced beta-nootkatol and hydroxyl valencene as major products, while Taxol CYP450 enzyme did not produce any oxygenated valencene (Table 4 and FIG. 7). The different blend of sesquiterpene products produced by SrKO provides a unique profile with a unique sensory/taste profile.

In certain aspects, the disclosure relates to SrKO derivative enzymes. In certain embodiments, the SrKO derivative polypeptide comprises an amino acid sequence that has up to 25 mutations compared to the wild type protein according to SEQ ID NO: 37. For example, the SrKO derivative may comprise an amino acid sequence that has one or more mutations at positions selected from 46, 76, 94, 131, 231, 284, 383, 390, 400, 444, 468, 488 and 499, numbered according to SEQ ID NO: 37. For example, in some embodiments, the SrKO is a derivative comprising an amino acid sequence having one or more (or all) of the mutations selected from H46R, R76K, M94V, T131Q, F231L, H284Q, R383K, I390L, V400Q, I444A, T468I, T488D, and T499N, numbered according to SEQ ID NO:37. In certain embodiments, the SrKO is a derivative comprising an amino acid sequence having one or more (or all) of the mutations selected from R76K, M94V, T131Q, F231L, H284Q, R383K, I390L, T468I, and T499N, numbered according to SEQ ID NO: 37. In some embodiments, the SrKO derivative comprises an amino acid sequence selected from SEQ ID NOS: 55-61, which were engineered according to this disclosure to improve activity for oxygenation of valencene (e.g., production of nootkatone and/or nootkatol). In some embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488 and 499 (numbered according to SEQ ID NO: 37), or the proviso that the SrKO derivative comprises an amino acid sequence having one or more (or all) of the mutations selected from H46R, R76K, M94V, T131Q, F231L, H284Q, R383K, I390L, V400Q, I444A, T468I, T488D, and T499N (numbered according to SEQ ID NO: 37). In certain embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488 and 499 (numbered according to SEQ ID NO: 37), or the proviso that the SrKO derivative comprises an amino acid sequence having one or more (or all) of the mutations selected from R76K, M94V, T131Q, F231L, H284Q, R383K, I390L, T468I, and T499N (numbered according to SEQ ID NO: 37). As shown herein, these mutations increase the level of SrKOs valencene oxidation activity.

In these or other embodiments, the SrKO is a derivative having a deletion of at least a portion of its N-terminal transmembrane region, and the addition of an inner membrane transmembrane domain from *E. coli* yhcB or derivative thereof. In some embodiments, the SrKO is a derivative having a deletion of from 15 to 35 amino acids of its N-terminal transmembrane domain, and the addition of from 15 to 25 amino acids of the transmembrane domain from *E. coli* yhcB or derivative thereof. In some embodiments, the N-terminal transmembrane domain of the derivative comprises the amino acid sequence MAWEYALIGLVVGIIIGAVA (SEQ ID NO:118), or an amino acid sequence having from 1 to 10 or from 1 to 5 amino acid mutations with respect to SEQ ID NO: 118.

In still other aspects, the disclosure provides a method of preparing the modified SrKO polypeptide, wherein the method comprises the steps of: (i) culturing a host cell expressing the modified polypeptide under conditions which permit expression of the polypeptide; and (ii) optionally recovering the polypeptide.

In still other aspects, the disclosure provides a method of producing an oxygenated sesquiterpene comprising the steps of: (i) providing the modified SrKO polypeptide, (ii) contacting a sesquiterpene with the modified SrKO polypeptide, and (iii) recovering the produced oxygenated sesquiterpene. The method may further comprise providing a CPR enzyme for regenerating the SrKO cofactor (e.g., SrCPR). In some embodiments, the oxygenated sesquiterpene is recovered as an oil. In some embodiments, the sesquiterpene is valencene. In some embodiments, the oxygenated sesquiterpene comprises hydroxygermacra-1(10)5-diene, murolan-3,9(11) diene-10-peroxy, alpha-nootkatol, beta-nootkatol, and nootkatone. In some embodiments, the predominant oxygenated product is nootkatone and/or nootkatol. In some embodiments, the oxygenated product comprises both alpha and beta nootkatol.

Figure 8A:
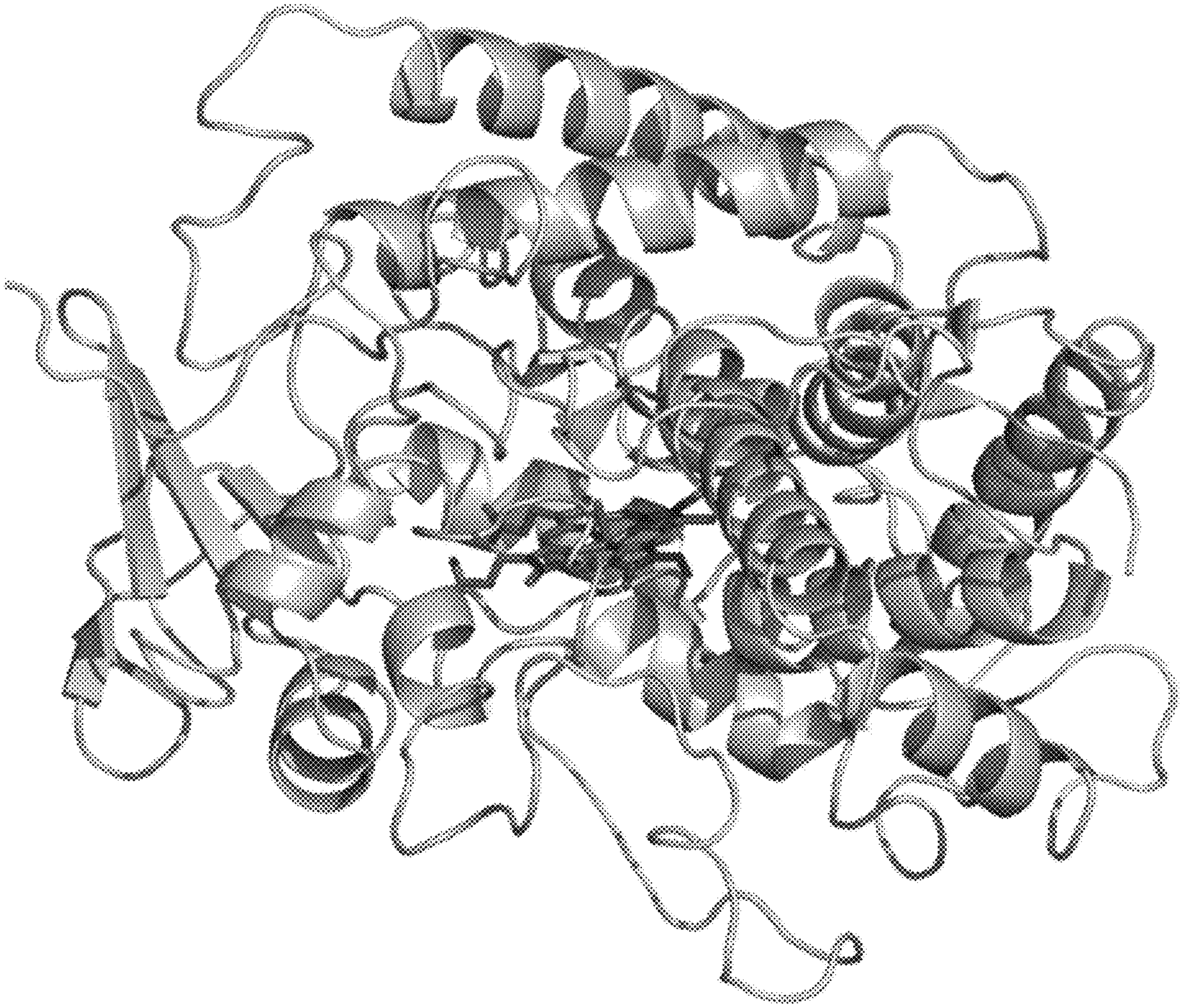
FIGS. 8A and 8B illustrate a homology model of SrKO and its active site. The SrKO homology model is based on the known mutant P45017A1 (the crystal structure of membrane-bound cytochrome P450 17 A1 as disclosed in DeVore NM and Scott E E (*Nature,* 482, 116-119, 2012), which catalyzes the biosynthesis of androgens in human. The position of the heme is shown as sticks.
Figure 8B:
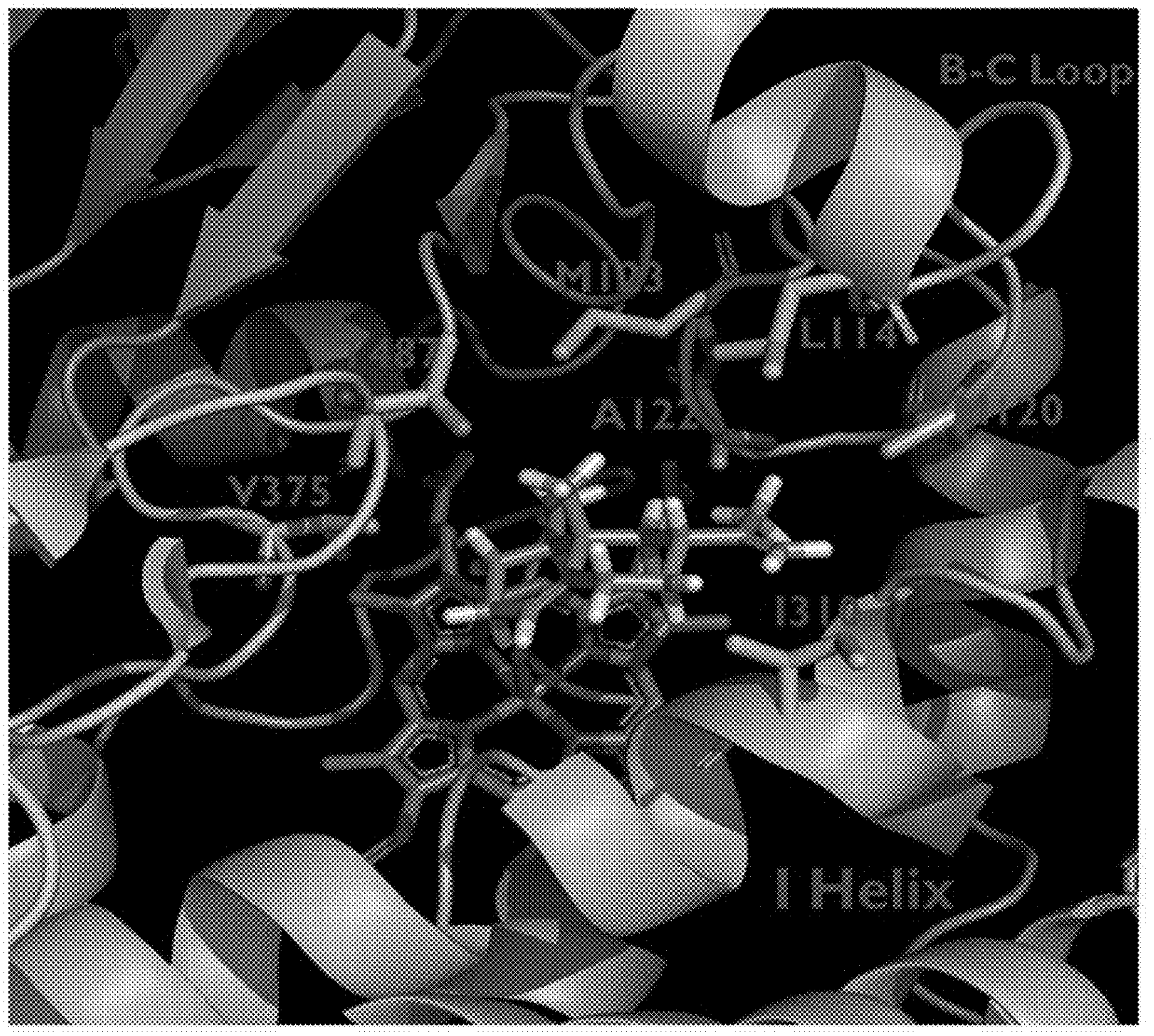

In another aspect, there is provided an SrKO crystal model structure (CMS) based on the structural coordinates of P45017A1, with an amino acid sequence of SrKO or derivative described herein. The CMS comprises a terpene binding pocket domain (TBD) that comprises a terpene binding pocket (TBP) and a terpene (e.g., valencene) bound to the TBD. FIGS. 8A and 8B. This SrKO crystal model structure (CMS) facilitates in-silico testing of SrKO derivatives.

Thus, in still other embodiments, the disclosure provides a method of screening for a terpene capable of binding to a TBD wherein the method comprises the use of the SrKO CMS. In another aspect, the disclosure provides a method for screening for a terpene capable of binding to the TBP, and the method comprises contacting the TBP with a test compound, and determining if said test compound binds to said TBP. In some embodiments, the method is to screen for a test compound (e.g., terpenes) useful in modulating the activity of a SrKO enzyme.

In another aspect, the disclosure provides a method for predicting, simulating or modelling the molecular characteristics and/or molecular interactions of a terpene binding domain (TBD) comprising the use of a computer model, said computer model comprising, using or depicting the structural coordinates of a terpene binding domain as defined above to provide an image of said ligand binding domain and to optionally display said image.

EXAMPLES

Example 1: Construction of Sesquiterpene Precursor (Valencene) Producing *E. coli* Strain

*E. coli* overexpressing upstream MEP pathway genes dxs, ispD, ispF, and idi was created, which facilitates flux to the isoprenoid precursor isopentyl-pyrophosphate (IPP) supporting more than 1 g/L titers of a heterologous diterpenoid product (3). Strains were constructed producing a variety of terpenoids including mono- and sesquiterpenes by replacing the geranylgeranyl pyrophosphate synthase (GGPS) and diterpene synthase with a farnesyl pyrophosphate synthase (FPPS) and sesquiterpene synthase or a geranyl pyrophosphate synthase (GPPS) and monoterpene synthase. For developing a sesquiterpene producing strain to test the CYP450s for novel oxygenated terpenes, a valencene synthase enzyme was cloned and expressed in the MEP pathway overexpressed *E. coli* strain. The high substrate flux helps identify the activity of the CYP450. Previously, research on an oxygenated taxadiene producing strain showed a significant drop in the productivity upon transferring the CYP450 pathway to the taxadiene producing strain (300 mg/L to ~10 mg/L).

Further, multivariate modular metabolic engineering (MMME) was applied for balancing the pathway for high level production of valencene. Naturally occurring valencene synthases, such as that from *Vitis vinifera*, often perform sub-optimally (~5 mg/L) even after MMME optimization, compared to previous results obtaining 100's of mg/L diterpenoids. Enzymes involved in the sesquiterpene biosynthesis can be difficult to express in *E. coli*, and also are deficient in kinetics relative to those involved in primary metabolism (17).

A homology model for the *Vitis vinifera* valencene synthase (VvVS) was constructed using the BioLuminate® software package (Schrodinger, Inc.) with the 5-epi-aristolochene synthase crystal structure as a template (PDB: 5EAT). Further, to identify the natural mutational landscape of terpene synthases, an extensive multiple sequence alignment incorporating hundreds of related terpene synthase sequences was created. Using this information, mutations were designed using a combination of back-to-consensus, in silico energetics, and structural analysis. Back-to-consensus mutations have been shown to be an important tool for improving stability (19,20) and expression (21). Energetics calculations based on atomic force-field models in BioLuminate were used to assess the ΔΔG of folding for individual mutations predicted for positions with low solvent-accessible surface area, which were predicted to affect folding and stability.

By applying the MMME approach, a balanced upstream and downstream valencene production strain was identified incorporating a codon-optimized version of VvVS on a plasmid with a p15A origin of replication and a T7 promoter. This strain background was then used to screen designed synthase enzyme mutations. Using the aforementioned protein engineering tools we designed over 200 unique point mutations (Table 3) which were then constructed in the p15A-T7 screening plasmid using site-directed mutagenesis. Mutated enzyme variants were transformed into the screening strain, triplicate colonies were cultured in selective LB cell culture medium overnight, and then inoculated into a minimal R-medium and cultured for four days at 22° C. Cultures were extracted using methyl tert-butyl ether (MTBE) and analyzed by combined gas chromatography/mass spectrometry for productivity of valencene.

Figure 2:
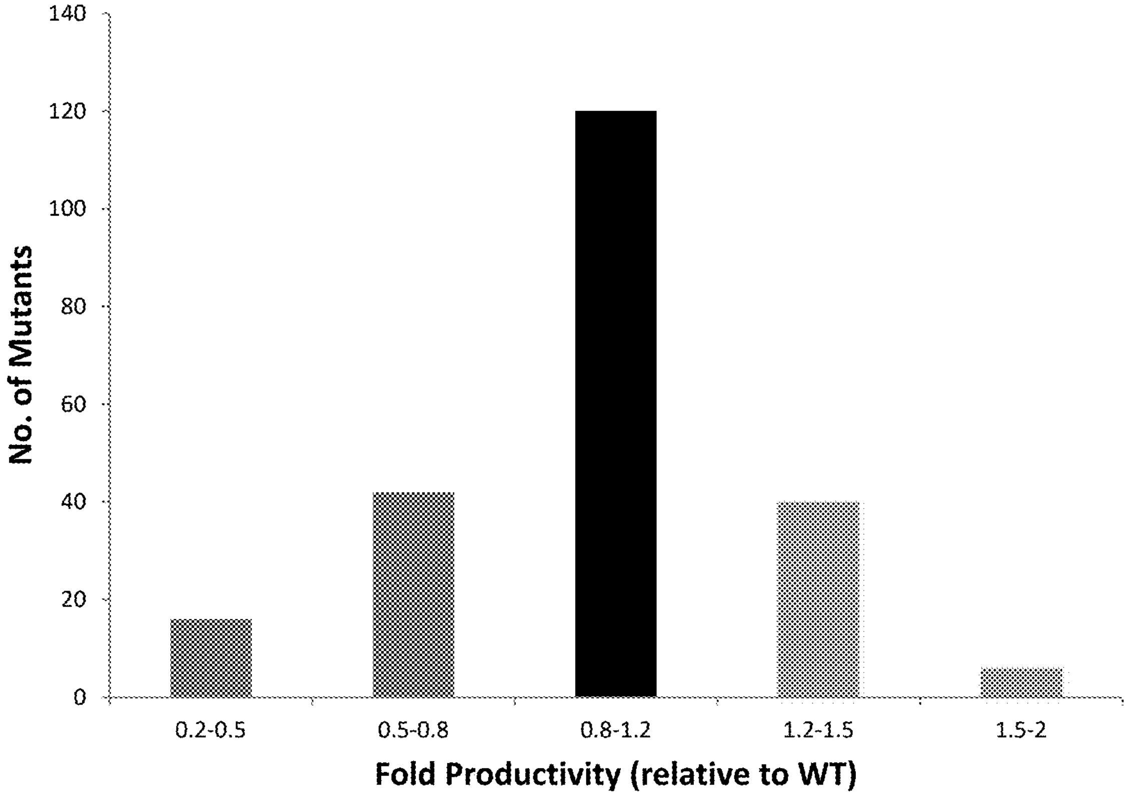
FIG. 2 depicts the fold productivities for site-directed mutants made to VvVS. 46 of the 225 point mutations convey an average improvement in productivity of valencene of at least 20% compared to the wild-type WT VvVS.

Approximately one-fifth of the designed point mutations increased valencene productivity in our screening strain by at least 20% (FIG. 2). Beneficial point mutations were then strategically combined to confer increasingly advantageous phenotypes. Recombined valencene synthase sequences are provided as Vv1M1 (Mutations—R331K, I334E, N335S, V371I, A374L, T418V, S482T, S512P, K356N, Q491K, E394D, A428V, Y348F, T318S, L352I, I442L, A554P), Vv2M1 (Mutations-R331K, I334E, N335S, V371I, A374L, T418V, S482T, S512P, K356N, Q491K, E394D, A428V, V542T, G480A, M305L, K441R, A554P), Vv1M5 (Mutations-R331K, I334E, N335S, V371I, A374L, T418V, S482T, S512P, K356N, Q491K, E394D, A428V, Y348F, T318S, L352I, I442L, A554P, H284M, C46K, F448T, Q533E), and Vv2M5 (Mutations-R331K, I334E, N335S, V371I, A374L, T418V, S482T, S512P, K356N, Q491K, E394D, A428V, V542T, G480A, M305L, K441R, A554P, H284M, C46K, F448T, Q533E) (FIG. 3). When either of these enzymes was overexpressed in our MEP pathway strain with dxs-idi-ispDF overexpressed, and balanced using MMME, the titers of valencene obtained were sufficient to motivate incorporation of P450 enzymes to test their ability to catalyze the formation of oxygenated valencene. Titers of valencene before P450 incorporation were about 30 mg/L.

Example 2: Functional Activity of CYP450 Library on Valencene Scaffold

Valencene was used as a model system to validate the power of CYP450-based oxygenation chemistry for production terpene chemicals.

Figure 5A:
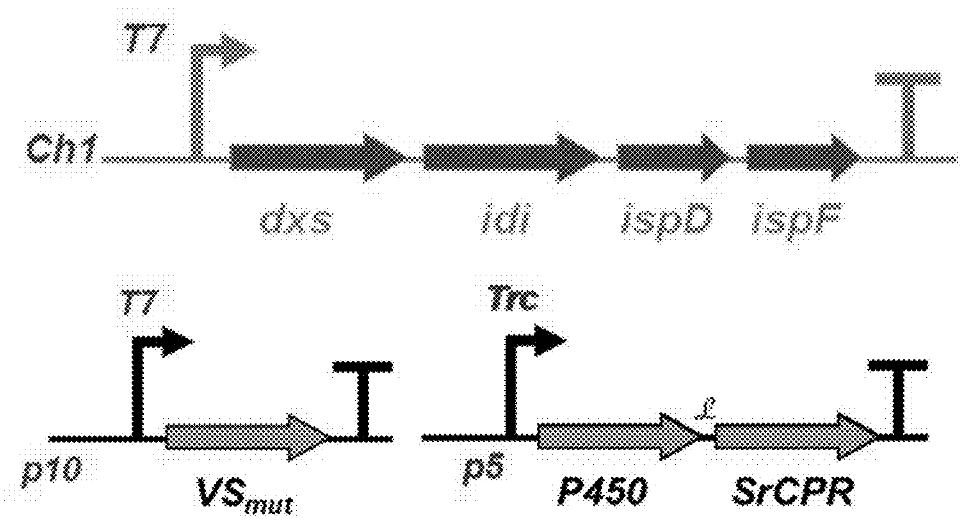
FIGS. 5A and 5B depict construct designs for expression of MEP, terpene and terpenoid synthases, and P450 enzymes in *E. coli*.
Figure 5B:
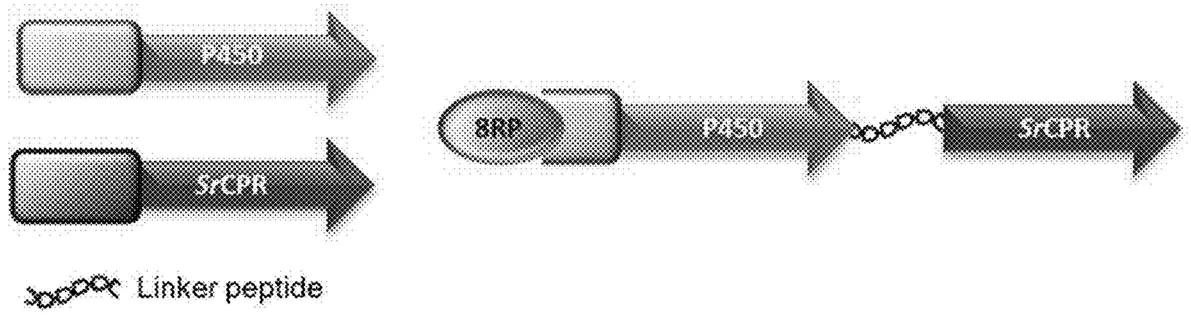

The CYPP450 candidate screening was conducted using the valencene producing *E. coli* strains as host background. For constructing the CYP450 for functional expression, a proprietary plasmid system, p5Trc (plasmid derived from pSC101) was used to construct a plasmid containing the candidate P450 fused to an N-terminal truncated *Stevia rebaudiana* cytochrome P450 reductase (SrCPR) through a flexible 5-amino acid linker (GSTGS, SEQ ID NO: 117). The sequences of the various candidate P450s are shown in FIG. 4. The candidate CYP450's were analyzed for N-terminal membrane associating regions which were truncated and a 8-amino acid leader sequence (MALLLAVF, SEQ ID NO: 112) was added to the fusion (FIGS. 5A and 5B). CPR red/ox partners from *Arabidopsis thaliana* and *Taxus cuspidata* were also prepared in similar genetic constructions. Since the native SrCPR was effective, the level of activity of these constructs was not determined. The sequences of the various CPR red/ox partners are shown in FIG. 6. Following transformation of p5Trc-CYP450-L-SrCPR to valencene producing strain, the strains were cultured overnight at 30° C. in antibiotic selective LB media. These cultures were then used to inoculate 2 mL antibiotic selective R-media cultures in hungate tubes with 15 g/L glycerol and 0.1 mM IPTG which were subsequently cultured for 4-days at 22° C. before being extracted with methyl tert-butyl ether (MTBE).

A set of CYP450 enzymes, from those listed in Table 4, was selected and classified for both sesqui- and diterpene oxygenation in this *E. coli* system. Among the various CYP450 enzymes tested for oxygenation on valencene, kaurene oxidase from *Stevia rebaudiana* (SrKO) (16) was discovered to have a unique oxygenation chemistry on the valencene scaffold. SrKO natively oxidizes the diterpene (−)-kaurene at the C19 position to (−)-kaurenoic acid. SrKO enzyme showed unique activities in the present studies by creating different stereoisomers of the hydroxylated product (alpha and beta nootkatol and further oxidizing to the ketone, nootkatone), and produced different oxygenated terpene products including hydroxygermacra-1(10)5-diene, murolan-3,9(11) diene-10-peroxy, in addition to the alpha-nootkatol, beta-nootkatol, and nootkatone. Other P450's, including the previously known sesquiterpene CYP450's for hydroxylating valencene produced only one of the isomers (beta nootkatol) and only detectable amounts of ketone (nootkatone). Specifically, the other sesquiterpene CYP450 enzymes produced beta-nootkatol and hydroxyl valencene as major products, while another diterpene CYP450 enzymes (e.g., *Taxus* 5-alpha hydroxylase) produced nootkatol as only a minor (detectable) product (Table 4 and FIG. 7).

TABLE 4

| Major Products Formed From Valencene by Select P450 Enzymes in *E. coli* | | |
|---|---|---|
| SPECIES | NAME | MAJOR PRODUCTS |
| *Cichorium intybus* | CiVO | β-nootkatol, α-cadinol, hydroxyl valencene. |
| *Hyoscyamus muticus* | HmPO | β-nootkatol, α-cadinol, hydroxyl valencene, nootkatone |
| *Latuca spicata* | LsGAO | β-nootkatol, α-cadinol, isovalencenol, nootkat-11-en-10-ol. |
| *Barnadesia spinosa* | BsGAO | β-nootkatol, α-cadinol, isovalencenol. |
| *Nicotiana tabacum* | NtEAO | α-cadinol, nootkat-11-en-10-ol. |
| *Stevia rebaudiana* | SrKO | α-nootkatol, hydroxy germacra-1(10)5-diene, β-nootkatol, nootkatone, murolan-3,9(11) diene-10-peroxy |
| *Zingiber zerumbet* | ZzHO | α-cadinol, nootkat-11-en-10-ol. |
| *Citrus × paradisi* | CpVO | α-cadinol, nootkat-11-en-10-ol. |
| *Mentha spicata* | MsL6OH | α-cadinol. |
| *Nicotiana tabacum* | NtVO | α-cadinol, nootkat-11-en-10-ol. |
| *Solanum tuberosum* | StVO | α-cadinol, β-nootkatol, globulol. |
| *Arabidopsis thaliana* | AtKO | α-cadinol, nootkat-11-en-10-ol. |
| *Cichorium intybus* | Ci2VO | β-nootkatol, α-cadinol, isovalencenol. |
| *Artemesia annua* | AaAO | α-cadinol, murolol, nootkat-11-en-10-ol. |
| Taxus 5-alpha hydroxylase P450 | | α-cadinol |

Example 3: Structural and Mutational Studies of SrKO

Once the unique activities of SrKO were identified, experiments were conducted to improve its ability to conduct its diverse oxidation of valencene. The crystal structure for SrKO has not been described. Blast search of SrKO against RCSB Protein Data Bank shows the sequence identity of SrKO to P450 enzymes with crystal structures are low (~20%). Given the conservative folding structures of P450s regardless of its low sequence identity, state-of-the-art protein modeling tools were used to build on SrKO. The crystal structure of membrane-bound cytochrome P450 17 A1 (see DeVore N. M., Scott E. E., *Nature,* 482, 116-119, 2012) which catalyses the biosynthesis of androgens in human was selected as the template for model development. Using BioLuminate protein modeling software, a homology model was developed (FIG. 8A) such that the positioning of key residues and characteristic motifs (see Gotoh O., *J. Biol Chem,* 267, 83-90, 1992) aligned well with the template. Furthermore, a homology model for SrKO which included the prosthetic heme-iron complex was also constructed. AutoDock VINA was then used to create an ensemble of possible binding modes for valencene in the SrKO active site (FIG. 8B) (29).

In addition, a Blast search of SrKO against NCBI non-redundant protein sequence library returned no orthologs with sequence identity greater than 80% (except the SrKO itself). The top hits are listed in the Table 5.

TABLE 5

| BLAST search with SrKO in preparation of Homology Model | | | |
|---|---|---|---|
| Enzyme Name | Species | Sequence Identity | Accession |
| kaurene oxidase | *Stevia rebaudiana* | 99% | AAQ63464.1 |
| ent-kaurene oxidase 2 | *Lactuca sativa* | 79% | BAG71198.1 |
| ent-kaurene oxidase 1 | *Lactuca sativa* | 71% | BAG71197.1 |
| ent-kaurene oxidase | *Ricinus communis* | 63% | XP_002510288.1 |

Once the unique activities of SrKO were identified, experiments were conducted to improve its ability to conduct its diverse oxidation of valencene. Using the back-to-consensus mutagenesis strategy, a multiple sequence alignment of P450 enzymes was constructed including sequences (after clustering and elimination of sequences with greater than 90% identity) from a BLAST search of the Uniref100 database using 4 seed kaurene oxidase genes, from a BLAST search of the bacterial proteome using $P450_{BM3}$, $P450_{CAM}$, and $P450_{cryF}$ as seed genes, and the most closely related SrKO homologs. Based on the homology model, the multiple sequence alignment, and the literature, various point mutations and double mutations were designed and tested. These cytochrome P450 derivatives were assessed for improvements in total oxygenated terpene productivity (e.g., total of the major peaks observed by GC/MS) in the in vivo testing system described above. Mutagenesis on active site positions guided by the model revealed several variants with significantly improved oxygenated products (Table 6 and Table 7 below).

TABLE 6

Binding pocket mutations and their fold productivity of total oxygenated oil according to wild type SrKO (SEQ ID NOS: 37 and 108), 8rp-t20SrKO (SEQ ID NOS: 38 and 106), n22yhcB-t30VO1 (SEQ ID NO: 104) and n22yhcB-t30VO2 (SEQ ID NOS: 61 and 105).

| Mutant # (Table 2.1) | Mutants (numbered according to SEQ ID NO: 38) (SEQ ID NO: 106) | Mutants (numbered according to SEQ ID NO: 37) (SEQ ID NO: 108) (Shift value relative to SEQ ID NO: 38: +12) | Mutants (numbered according to SEQ ID NO: 104/SEQ ID NO: 105 (SEQ ID NO: 61)) (Shift value relative to SEQ ID NO.: 38: +4) | Fold productivity (as measured in mg/L) |
|---|---|---|---|---|
| 38 | I310V | I322V | I314V | 1.5 |
| 37 | I310T | I322T | I314T | 0.0 |
| 42 | V375I | V387I | V379I | 1.4 |

TABLE 6-continued

Binding pocket mutations and their fold productivity of total oxygenated oil according to wild type SrKO (SEQ ID NOS: 37 and 108), 8rp-t20SrKO (SEQ ID NOS: 38 and 106), n22yhcB-t30VO1 (SEQ ID NO: 104) and n22yhcB-t30VO2 (SEQ ID NOS: 61 and 105).

| Mutant # (Table 2.1) | Mutants (numbered according to SEQ ID NO: 38) (SEQ ID NO: 106) | Mutants (numbered according to SEQ ID NO: 37) (SEQ ID NO: 108) (Shift value relative to SEQ ID NO: 38: +12) | Mutants (numbered according to SEQ ID NO: 104/SEQ ID NO: 105 (SEQ ID NO: 61)) (Shift value relative to SEQ ID NO.: 38: +4) | Fold productivity (as measured in mg/L) |
|---|---|---|---|---|
| 41 | V375T | V387T | V379T | 0.0 |
| 19 | M123F | M135F | M127F | 0.0 |
| 20 | M123T | M135T | M127T | 0.3 |
| 18 | M123Q | M135Q | M127Q | 0.0 |
| 59 | T487N | T499N | T491N | 2.5 |
| 66 | M123F_T487G | M135F_T499G | M127F_T491G | 0.0 |
| 63 | M123F_T487V | M135F_T499V | M127F_T491V | 0.0 |
| 62 | M123Q_T487V | M135Q_T499V | M127Q_T491V | 0.0 |
| 59 | T487N_V375F | T499N_V387F | T491N_V379F | 2.2 |
| 59 | T487N_V375A | T499N_V387A | T491N_V379F | 1.8 |
| 59 | T487N_V121A | T499N_V133A | T491N_V125A | 2.0 |
| 59 | T487N_V375M | T499N_V387M | T491N_V379M | 1.9 |
| 59 | T487N_M120L | T499N_M132L | T491N_M124L | 1.8 |
| 59 | T487N_M120I | T499N_M132I | T491N_M124I | 1.8 |
| 59 | T487N_L114V | T499N_L126V | T491N_L118V | 1.4 |
| 59 | T487N_F219L | T499N_F231L | T491N_F223L | 3.5 |
| 59 | T487N_M120V | T499N_M132V | T491N_M124V | 1.1 |
| 59 | T487N_F219I | T499N_F231I | T491N_F223I | 3.3 |
| 59 | T487N_L114F | T499N_L126F | T491N_L118F | 1.2 |

TABLE 7

Non-binding pocket point mutations and productivity of total oxygenated oil compared to the wild type SrKO (SEQ ID NOS: 38 and 106).

| Mutant # (Table 2.1) | Mutants (numbered according to SEQ ID NOS: 38 and 106) | Mutants (numbered according to SEQ ID NO: 37) (SEQ ID NO: 108) (Shift value relative to SEQ ID NO: 38: +12) | Mutants (numbered according to SEQ ID NO: 104/SEQ ID NO: 105 (SEQ ID NO: 61)) (Shift value relative to SEQ ID NO: 38: +4) | Fold productivity (as measured in mg/L) |
|---|---|---|---|---|
| 53 | G442A | G454A | G446A | 0.849153 |
| 55 | L454M | L466M | L458M | 0.717318 |
| 44 | I378V | I390V | I382V | 0.349005 |
| 47 | V388M | V400M | V392M | 0.792428 |
| 9 | V85I | V97I | V89I | 0.795913 |
| 51 | V413K | V425K | V417K | 0.902039 |
| 60 | P492K | P504K | P496K | 0.131657 |
| 40 | R371I | R383I | R375I | 0.657808 |
| 7 | T80C | T92C | T84C | 0.342501 |
| 23 | A140R | A152R | A144R | 0.014872 |
| 2 | Y59H | Y71H | Y63H | 0.406787 |
| 5 | A67E | A78E | A71E | 0.937429 |
| 8 | M82V | M94V | M86V | 1.585588 |
| 11 | S86N | S98N | S90N | 0.977752 |
| 22 | Y129F | Y141F | Y133F | 0.686276 |
| 24 | K149R | K161R | K153R | 0.990776 |
| 29 | D208E | D220E | D212E | 0.853446 |
| 31 | S267A | S279A | S271A | 0.79152 |
| 32 | H272Q | H284Q | H276Q | 0.958227 |
| 33 | S284C | S296C | S288C | 0.652348 |
| 39 | R371K | R383K | R375K | 1.443497 |
| 45 | H382Y | H394Y | H386Y | 0.609951 |
| 46 | V388Q | V400Q | V392Q | 0.924043 |
| 49 | L400I | L412I | K404I | 0.682775 |
| 50 | V413D | V425D | V417D | 0.039261 |
| 52 | F434L | F446L | F438L | 0.793926 |
| 57 | M464L | M476L | M468L | 0.689696 |
| 58 | M475G | M487G | M479G | 0.573906 |

TABLE 7-continued

Non-binding pocket point mutations and productivity of total oxygenated oil compared to the wild type SrKO (SEQ ID NOS: 38 and 106).

| Mutant # (Table 2.1) | Mutants (numbered according to SEQ ID NOS: 38 and 106) | Mutants (numbered according to SEQ ID NO: 37) (SEQ ID NO: 108) (Shift value relative to SEQ ID NO: 38: +12) | Mutants (numbered according to SEQ ID NO: 104/SEQ ID NO: 105 (SEQ ID NO: 61)) (Shift value relative to SEQ ID NO: 38: +4) | Fold productivity (as measured in mg/L) |
|---|---|---|---|---|
| 61 | I497L | I509L | I501L | 0.679949 |
| 15 | A116R | A128R | A120R | 0.216353 |
| 1 | L47I | L59I | L51I | 0.88992 |
| 25 | H150F | H162F | H154F | 0.666723 |

Example 4: Isolation and Evaluation of Oxygenated Product

The product derived from oxidation of valencene by the cytochrome P450 enzyme SrKO (SEQ ID NO: 38) was analysed by GC/MS (Agilent 6800; Column: Rtx-5, 0.32 mm×60 m×1.0 μm film thickness; GC Temp. Program: 40° C. for 5 min, increased at 4° C./min to 300° C. and held for 30 min.) resulting in the data provided in Table 8A and 8B.

TABLE 8A

SrKO oxidation of valencene

| Ret. Time | Compound Name | CAS # | GC-FID Area % |
|---|---|---|---|
| 33.762 | dodecane | 112-40-3 | 6.70 |
| 35.440 | glyceryl diacetate I | | 5.26 |
| 38.767 | triacetin | 102-76-1 | 4.48 |
| 39.518 | unknown | | 10.17 |
| 40.176 | unknown | | 7.52 |
| 42.012 | unknown | | 2.53 |
| 44.437 | unknown | | 20.25 |
| 44.816 | valencene | 4630-07-3 | 1.97 |
| 45.546 | nootkatene | 5090-61-9 | 1.09 |
| 46.260 | unknown | | 2.14 |
| 46.395 | unknown | | 6.77 |
| 46.869 | unknown | | 4.01 |
| 47.394 | germacrene D-4-ol | 74841-87-5 | 1.23 |
| 48.273 | unknown | | 1.86 |
| 49.659 | T-muurolol | 19912-62-0 | 0.69 |
| 49.753 | an unknown sesquiterpene | | 0.56 |
| 50.336 | an unknown sesquiterpene | | 0.58 |
| 51.025 | epinootkatol (or alpha nootkatol) | 50763-66-1 | 1.96 |
| 51.430 | Nootkatol (or beta nootkatol) | 50763-67-2 | 3.54 |
| 54.138 | nootkatone | 4674-50-4 | 15.87 |
| 54.501 | 6-isopropenyl-4,8a-dimethyl-4a,5,6,7,8,8a-hexahydro-2(1H)-naphthalenone | 76784-84-4 | 0.84 |
| | | TOTAL | 100.00 |

TABLE 8B

SrKO oxidation of valencene

| Ret. Time | Compound Name | CAS # | GC-FID Area % |
|---|---|---|---|
| 33.763 | dodecane | 112-40-3 | 7.26 |
| 35.470 | glyceryl diacetate I | | 7.07 |
| 38.773 | triacetin | 102-76-1 | 6.19 |
| 39.526 | unknown | | 11.56 |
| 40.179 | unknown | | 8.10 |
| 44.440 | unknown | | 23.95 |
| 44.821 | valencene | 4630-07-3 | 6.88 |

TABLE 8B-continued

SrKO oxidation of valencene

| Ret. Time | Compound Name | CAS # | GC-FID Area % |
|---|---|---|---|
| 45.545 | nootkatene | 5090-61-9 | 2.22 |
| 46.404 | unknown | | 5.08 |
| 46.879 | unknown | | 3.66 |
| 47.399 | germacrene D-4-ol | 74841-87-5 | 2.89 |
| 48.279 | unknown | | 2.27 |
| 49.665 | T-muurolol | 19912-62-0 | 0.94 |
| 50.342 | an unknown sesquiterpene | | 1.71 |
| 51.027 | epinootkatol | 50763-66-1 | 2.48 |
| 51.444 | nootkatol | 50763-67-2 | 5.24 |
| 54.152 | nootkatone | 4674-50-4 | 2.49 |
| | | TOTAL | 100.00 |

Similar analysis was conducted on the product produced by SrKO derivatives. It was confirmed that product profiles are comparable, and that the major products of nootkatone, α-nootkatol, and β-nootkatol can be produced at higher levels based on mutagenesis of SrKO.

The oxygenated oil product can then be extracted from the aqueous reaction medium using an appropriate solvent (e.g., heptane) followed by fractional distillation. The chemical composition of each fraction can be measured quantitatively by GC/MS. Fractions can be blended to generate the desired alpha/beta nootkatol and/or nootkatone ingredients for use in flavour or other applications.

Verification of acceptability can be carried out by direct comparison to a reference nootkatone flavouring product (for example, an existing natural flavouring commercial product obtained from Frutarom) with analysis provided in Table 9.

TABLE 9

Analysis of commercially available natural flavouring nootkatone from rutarom

| Ret. Time | Compound Name | CAS # | GC-FID Area % |
|---|---|---|---|
| 42.307 | limonene glycol | 1946-00-5 | 0.201 |
| 42.792 | decanoic acid | 334-48-5 | 0.115 |
| 49.405 | valencene | 4630-07-3 | 0.039 |
| 50.362 | delta-cadinene | 483-76-1 | 0.268 |
| 52.757 | alpha-elemol | 639-99-6 | 2.178 |
| 53.11 | spathulenol | 6750-60-3 | 0.264 |
| 53.423 | caryophyllene oxide | 1139-30-6 | 0.394 |
| 53.748 | viridiflorol | 552-02-3 | 0.061 |
| 54.225 | unknown sesquiterpenoid | | 0.113 |

TABLE 9-continued

Analysis of commercially available natural flavouring nootkatone from rutarom

| Ret. Time | Compound Name | CAS # | GC-FID Area % |
|---|---|---|---|
| | (MW = 220, tent) | | |
| 54.853 | unknown | | 2.985 |
| 55.386 | unknown | | 2.251 |
| 55.97 | T-muurolol | 19912-62-0 | 0.399 |
| 56.192 | bulnesol | 22451-73-6 | 0.722 |
| 56.523 | 7(11), 4b-selinenol; tentative | | 1.425 |
| 56.65 | unknown (MW = 232, tent) | | 0.663 |
| 56.937 | beta-sinensal | 3779-62-2 | 0.914 |
| 57.449 | unknown | | 0.285 |
| 57.589 | cedrenal; tentative | | 0.438 |
| 58.189 | unknown sesquiterpenoid(s) | | 1.077 |
| 58.73 | unknown sesquiterpenoids (MW = 220, 222, tent) | | 0.537 |
| 59.102 | beta,gamma-nootkatone | 35936-67-5 | 1.805 |
| 59.32 | myristic acid | 544-63-8 | 0.058 |
| 59.537 | 1,10-dihydronootkatone | 20489-53-6 | 0.582 |
| 59.75 | a nootkatone isomer | | 0.442 |
| 60.507 | nootkatone isomers (2); tentative | | 0.812 |
| 60.782 | unknowns (2) | | 0.605 |
| 61.034 | hexadecanal | 629-80-1 | 0.302 |
| 62.93 | nootkatone | 4674-50-4 | 74.287 |
| 63.057 | 3,11-eudesmadiene-2-one (5S,7R,10R) | 86917-81-9 | 1.909 |
| 63.14 | unknown (MW = 234, tent) | | 0.18 |
| 63.26 | unknown (MW = 232, tent) | | 0.105 |
| 64.112 | heptadecanal | 629-90-3 | 0.344 |
| 64.403 | unknown sesquiterpenoid | | 0.446 |
| 65.16 | unknown sesquiterpenoid | | 0.147 |
| 65.384 | palmitic acid | 57-10-3 | 0.154 |
| 65.599 | alpha-camphorene | 532-87-6 | 0.249 |
| 65.75 | unknown(s) | | 0.054 |
| 65.878 | dehydro-alpha-vetivenone; tentative | | 0.115 |
| 66.056 | nootkatone, 9-oxo | 86925-44-2 | 0.172 |
| 66.371 | ethyl palmitate | 628-97-7 | 0.185 |
| 66.856 | cis-9-octadecenal | 2423-10-1 | 0.239 |
| 66.986 | unknown sesquiterpenoids | | 0.114 |
| 67.556 | octadecanal | 638-66-4 | 0.096 |
| 74.551 | osthol | 484-12-8 | 0.367 |
| 80.543 | isomerazin | 1088-17-1 | 0.112 |
| 84.671 | unknown (MW = 298) | | 0.07 |
| | | TOTAL | 99.28 |

Two exemplary methods of verification are: 1) Duo-Trio Test, 2) Forced-Choice Preference Test. In one method, the SrKO derived product can be compared to the reference product (for example a commercial Frutarom sourced nootkatone ingredient) in a duo-trio test to determine if the ingredients can be distinguished with statistical significance. This test will determine if the two nootkatone containing ingredients at least match one another based on perception of overall taste and aroma profiles. In the second test, assuming the two products are determined to be distinguishable in a duo trio test, one could determine if the SrKO derived nootkatone is preferred by conducting a forced-choice preference test. More details on these tests are provided as follows.

Duo-Trio Test:

A Duo-Trio Test can be conducted to determine if the blended fractions obtained from the SrKO derived nootkatone flavouring can be distinguished with statistical significance from a reference nootkatone product (for example, a commercially available nootkatone flavouring sourced from Frutarom). The test will determine if the nootkatone flavouring ingredients at least match in terms of overall taste and aroma profile typically conducted in a sugar/acid solution but could also be evaluated in water or sugar water.

TABLE 10

| Name | Finished Beverage |
|---|---|
| Spring Water | 1000 g |
| Citric Acid | 0.1% |
| Sucrose | 8% |
| Nootkatone flavouring | 2.5 ppm |

Methodology: One ounce of the reference sample, labelled "REF" is presented first followed by a one ounce sample of the reference and a one ounce sample of the test sample presented blindly in random order to a minimum of 15 discriminator panellists. The panellists are asked which blind sample is the same as the reference sample. The data are subjected to a statistical analysis to determine the degree of difference between the test sample and the reference control.

Forced-Choice Preference Test

Assuming a difference is observed between nootkatone flavouring derived from SrKO oxidation and the reference nootkatone product (for example, a Frutarom nootkatone flavouring), a Forced-Choice Preference Test can be conducted to determine if one sample is preferred over the other as a nootkatone flavouring ingredient. The test can be conducted in sugar/acid solution, sugar water or water.

TABLE 11

| Name | Finished Beverage |
|---|---|
| Spring Water | 1000 g |
| Citric Acid | 0.1% |
| Sucrose | 8% |
| Nootkatone flavouring | 2.5 ppm |

Methodology: One ounce of each test sample is presented blindly in random order to a minimum of 40 discriminator panellists. The panellists are asked which blind sample is preferred based on aroma and taste when consumed orally and are forced to make a decision. The data are subjected to a statistical analysis to determine the degree of preference for one sample over the other.

Example 5: N-Terminal Anchor Engineering

Figure 9:
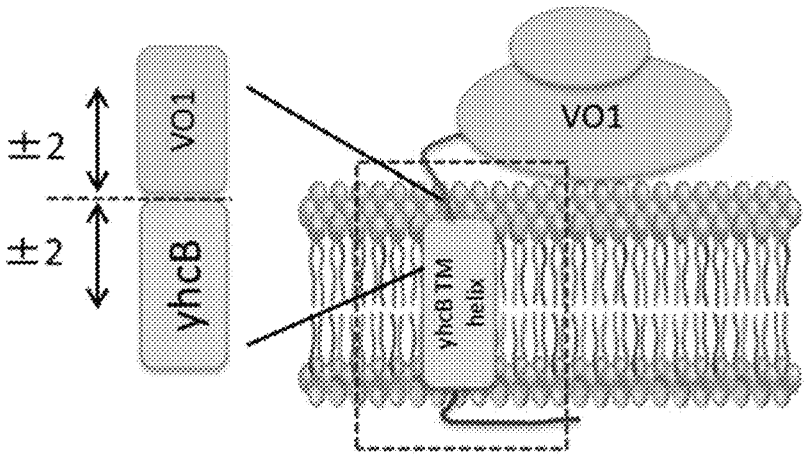
FIG. 9 shows optimizing the valencene oxidase (VO) N-terminal membrane anchor. The N-terminus of *E. coli* yhcB was selected as a membrane anchor sequence, which provides a single-pass transmembrane helix. The length of the anchor (from 20 to 24 amino acids) and the VO N-terminal truncation length (from 28 to 32 amino acids) were screened for improvements in oxygenation titer.

To optimize membrane interaction of the initial SrKO variants (referred to in these examples as Valencene Oxidase 1, or VO1), *E. coli* proteins anchored in the inner membrane with a cytoplasmic C-terminus were identified. An N-terminal sequence of *E. coli* yhcB was selected, which provides a single-pass transmembrane domain. 20-24 amino acids from the N-terminus of yhcB was exchanged for the original membrane anchor sequence MALLLAVF (SEQ ID NO:112), and the size of the SrKO N-terminal truncation was varied from 28 to 32. See FIG. 9. VO1 was expressed under control of a T7 promoter on a p5 plasmid. SrCPR was expressed independently from the chromosome. Strains were cultured in 96 deepwell plates at 30° C. for 48 hours, in R-medium plus glycerol and dodecane overlay as already described.

Figure 10:
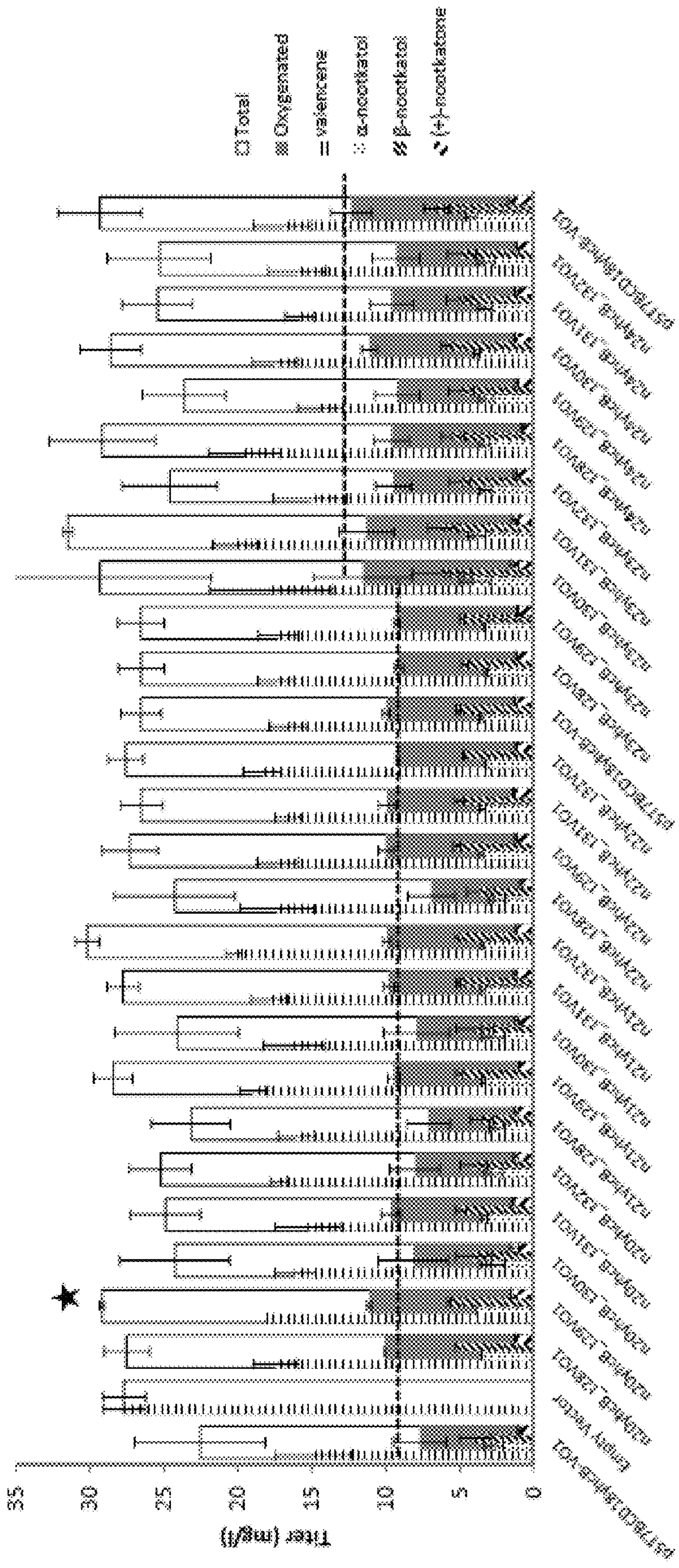
FIG. 10 shows that a truncation length of 29, and a 20 amino acid N-terminal anchor based on *E. coli* yhcB, led to a 1.2-fold increase in total oxygenated titer compared to the average of controls.
Figure 11:
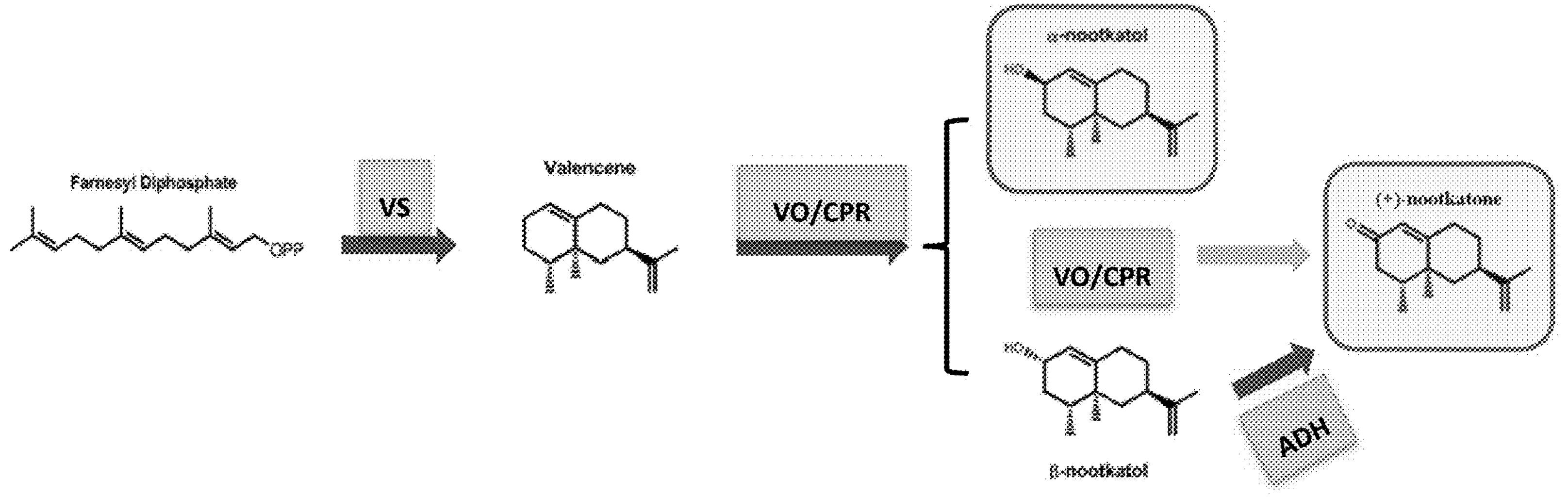
FIG. 11 illustrates an exemplary downstream pathway for expression in the host cell, for conversion of farnesyl diphosphate to nootkatone. Farnesyl diphosphate (produced from IPP/DMAPP by an expressed Farnesyl Pyrophosphate Synthase) is converted to valencene by the action of a Valencene Synthase (VS), which is oxidized by a Valencene Oxidase (VO), such as SrKO or an SrKO derivative described herein. The VO cofactor is regenerated by a cytochrome P450 reductase (CPR). The products of oxidation by VO can include nootkatol (α and β) and nookatone, which can be further directed to nootkatone by the action of an Alcohol Dehydrogenase (ADH).
Figure 12A:
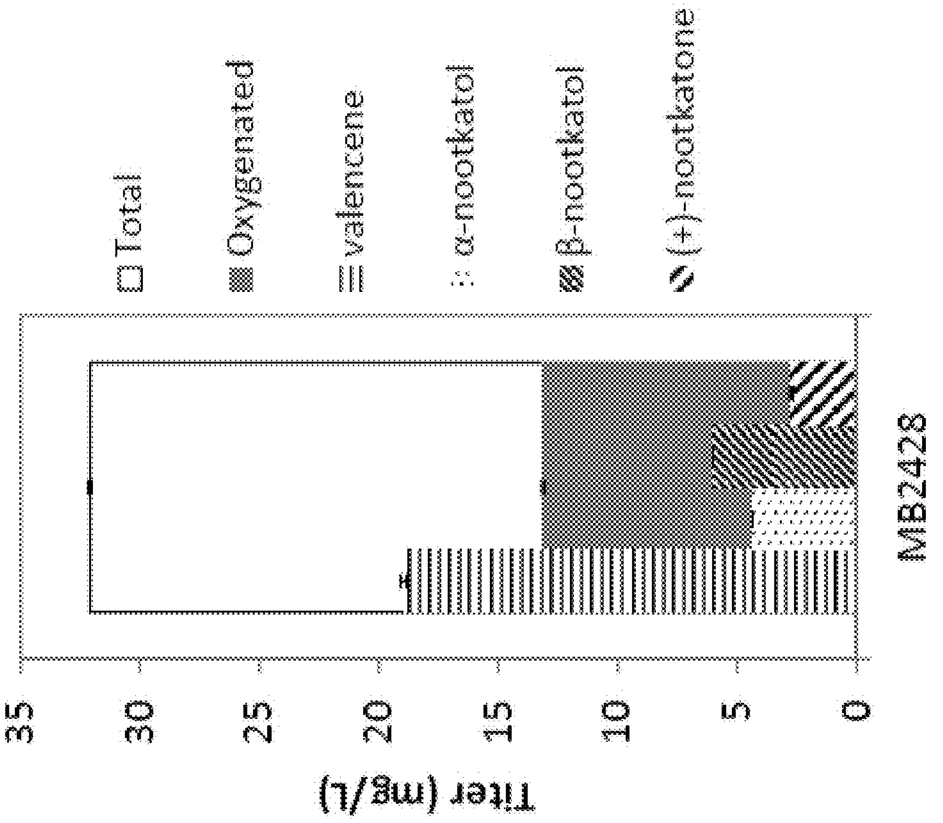
FIG. 12 (A and B) shows the oxygenation profile for a strain expressing VO1-L-SrCPR. The oxygenation profile includes the single oxygenation products of β-nootkatol and α-nootkatol along with the two-step oxygenation product, nootkatone. Panel (A) shows the profile in mg/L. Panel (B) shows the profile by percent of total oxygenated product (the legend for panels (A) and (B) are the same).
Figure 12B:
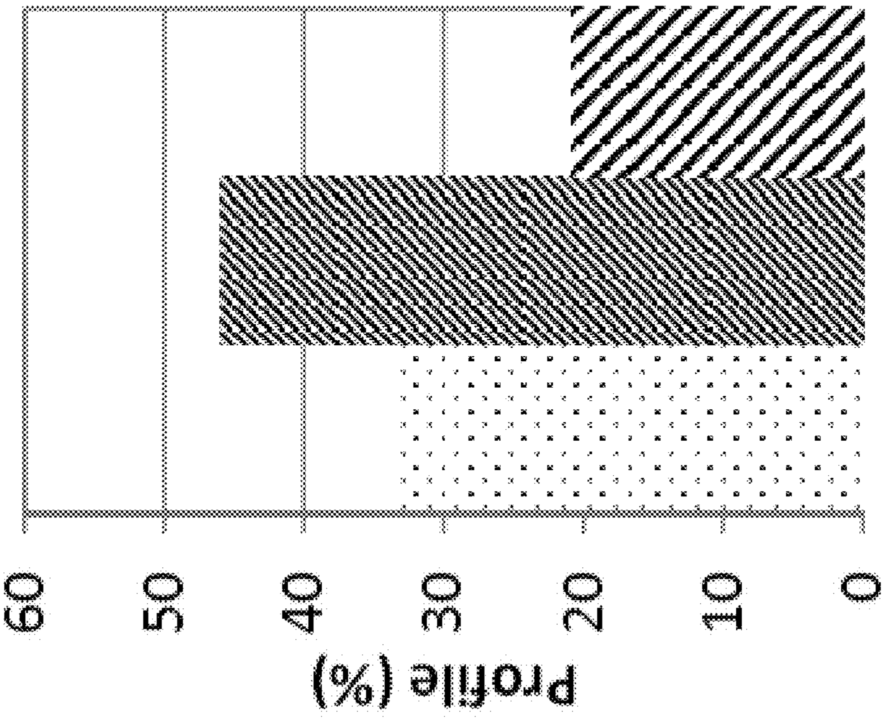

As shown in FIG. 10, n20yhcB_t29VO1 exhibited 1.2-fold productivity in total oxygenated titer compared to the average of controls. N20yhcB_t29VO1 exhibited a total oxygentated titer approximately 1.8 fold of the original 8RP anchor (not shown).

Example 6: Mutational Analysis of VO1

Mutational analysis of VO1 was conducted in an effort to increase oxygenated titers, as well as to produce altered product profiles. Strain MB2509 (MP6-MEP MP1-ScFPPS Fab46-VS2 MP6-ScCPR) was used as the background, which when transformed with a p5-T7-yhcB-VO1 plasmid produces about 18% nootkatone, about 35% α-nootkatol, and about 47% β-nootkatol, with a complete conversion of valencene. Strains were evaluated for higher production of nootkatone and α-nootkatol.

Guided by the homology model based on P450 17A1 (Example 3) site-saturation mutagenesis of the VO active site was conducted at 18 positions, and 5 paired position libraries were constructed. First shell residues were identified through substrate docking, and non-conserved first shell residues were selected based on relative proximity and position for altering the binding pocket geometry. Paired position libraries were constructed by overlap extension PCR and Gibson assembly.

TABLE 12

Paired Position Libraries (numbered according to SEQ ID NOS: 37 and 108)

| Library | Pos. 1 | Allowed AA | Pos. 2 | Allowed AA |
|---|---|---|---|---|
| 1 | V387 | F, L, I, S, P, T, A, M | P388 | S, T, A |
| 2 | M132 | F, L, I, V, S, P, T, A | V133 | F, L, I, S, P, T, A, M |
| 3 | L123 | F, I, V, S, T, A, P, M | L126 | F, I, V, S, T, A, P, M |
| 4 | V387 | F, L, I, S, P, T, A, M | I322 | F, L, V, S, P, A, M, T |
| 5 | I322 | F, L, V, S, P, A, M, T | V133 | F, L, I, S, P, T, A, M |

Strains were evaluated as in Example 4 for total oxygenation of valencene, and ratio of α- to β-nootkatol. Strains were evaluated at 30° C. and 22° C.

Primary screening of paired position libraries revealed that many of the variants lost activity. Library 3 contained variants with improved activity at 22° C. but not 30° C. Thus, introducing two or more mutations simultaneously in the first shell residues can be determimental to activity.

TABLE 13

The following single position SSM was conducted (numbered according to SEQ ID NOS: 37 and 108)

| Residue | Location | |
|---|---|---|
| I390 | Channel | |
| L392 | Channel | |
| V387 | 1st Shell | |
| E323 | 1st Shell | I helix |
| I322 | 1st Shell | I helix |
| T499 | 1st Shell | |
| Q500 | 1st Shell | |
| L231 | 1st Shell | F helix |
| L123 | 1st Shell | B-C loop |
| L126 | 1st Shell | B-C loop |
| V125 | 1st Shell | B-C loop |
| V133 | 1st Shell | F87 on BM3 |
| T131 | Channel | |
| M135 | 1st Shell | |
| L234 | 1st Shell | F helix |
| P238 | 1st Shell | F-G loop |
| M132 | 1st Shell | B-C loop |
| P388 | 1st Shell | |

Several variants improved oxygenated titers up to 1.7-fold or improved α/β-LGN ratios up to 3.8-fold. Mutations at positions E323, 1390, and Q500 showed several hits with improved oxygenation titer and/or improved α/β profile, and these positions were selected for secondary screening.

Figure 13A:
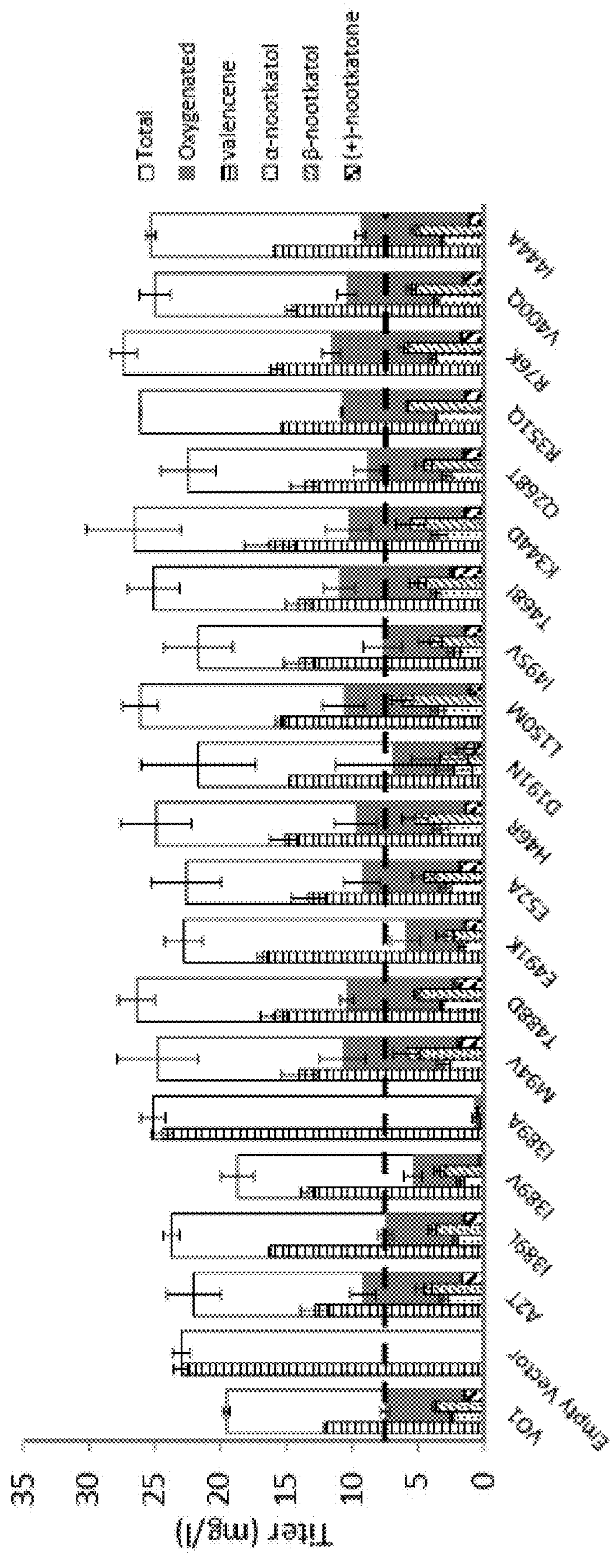
FIG. 13 (A and B) shows evaluation of mutations identified using a back-to-consensus strategy in wild-type SrKO, translated into an engineered valencene oxidase background (n22yhcB_t30VO1 (SEQ ID NO: 104)). More than 50% of the mutations resulted in a 1.2 to 1.45 fold improvement in total oxygenated titers. Panel (A) shows titer in mg/L. Panel (B) shows fold change in oxygenated titer and ratio of α/β nootkatol.
Figure 13B:
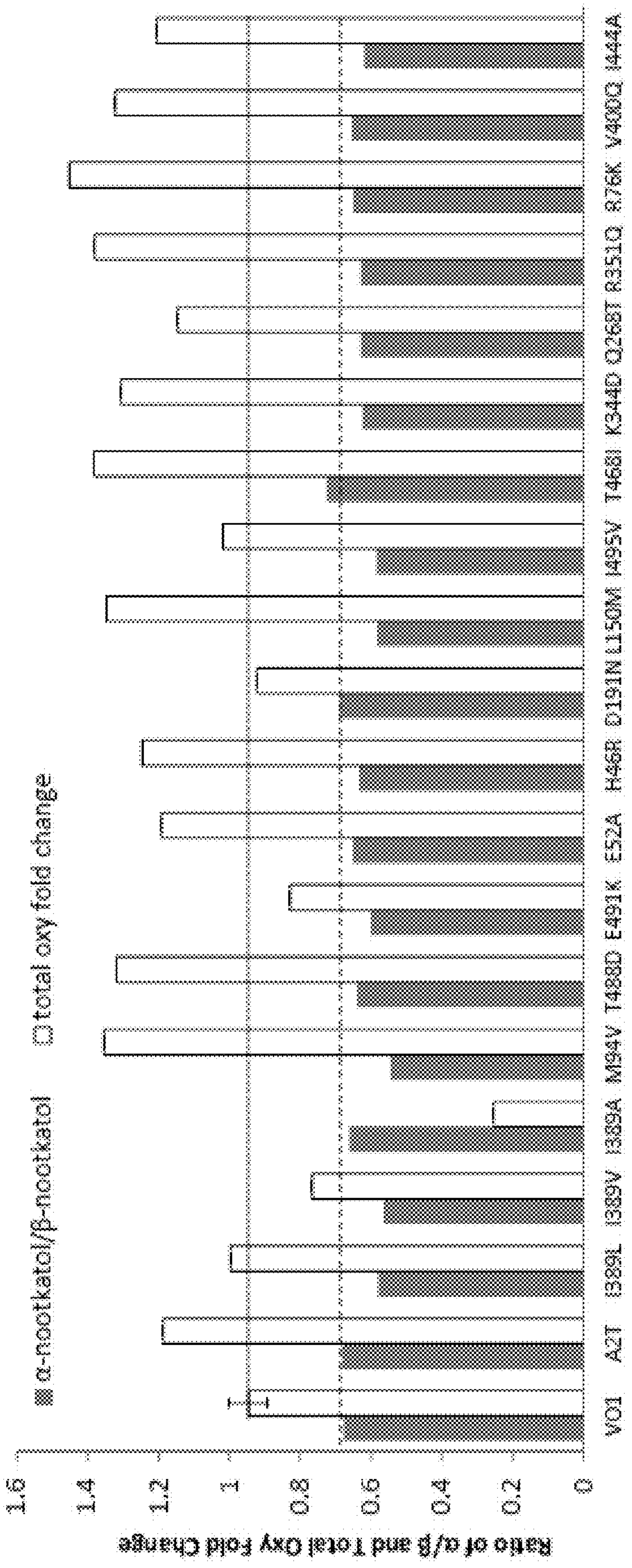

Next, back-to-consensusmutations (19 mutants) were screened in the VO1 background. Using the screening process described in Example 3, the following mutations were screened: A2T, I389L, I389V, I389A, M94V, T488D, E491K, E52A, H46R, D191N, L150M, I495V, T468I, K344D, Q268T, R351Q, R76K, V400Q, and I444A (numbered according to SEQ ID NO: 37). As shown in FIG. 13A, more than 50% of the mutations resulted in 1.2 to 1.45 times oxygenated titers (shown as mg/L), without dramatic shifts in product profile. Improvements were seen with A2T, M94V, T488D, E52A, H46R, L150M, T468I, K344D, Q268T, R351Q, R76K, V400Q, and I444A, which were selected for secondary screening. FIG. 13B shows the same screen plotted versus fold total oxygenated product change and α/β-nootkatol ratio.

Figure 14:
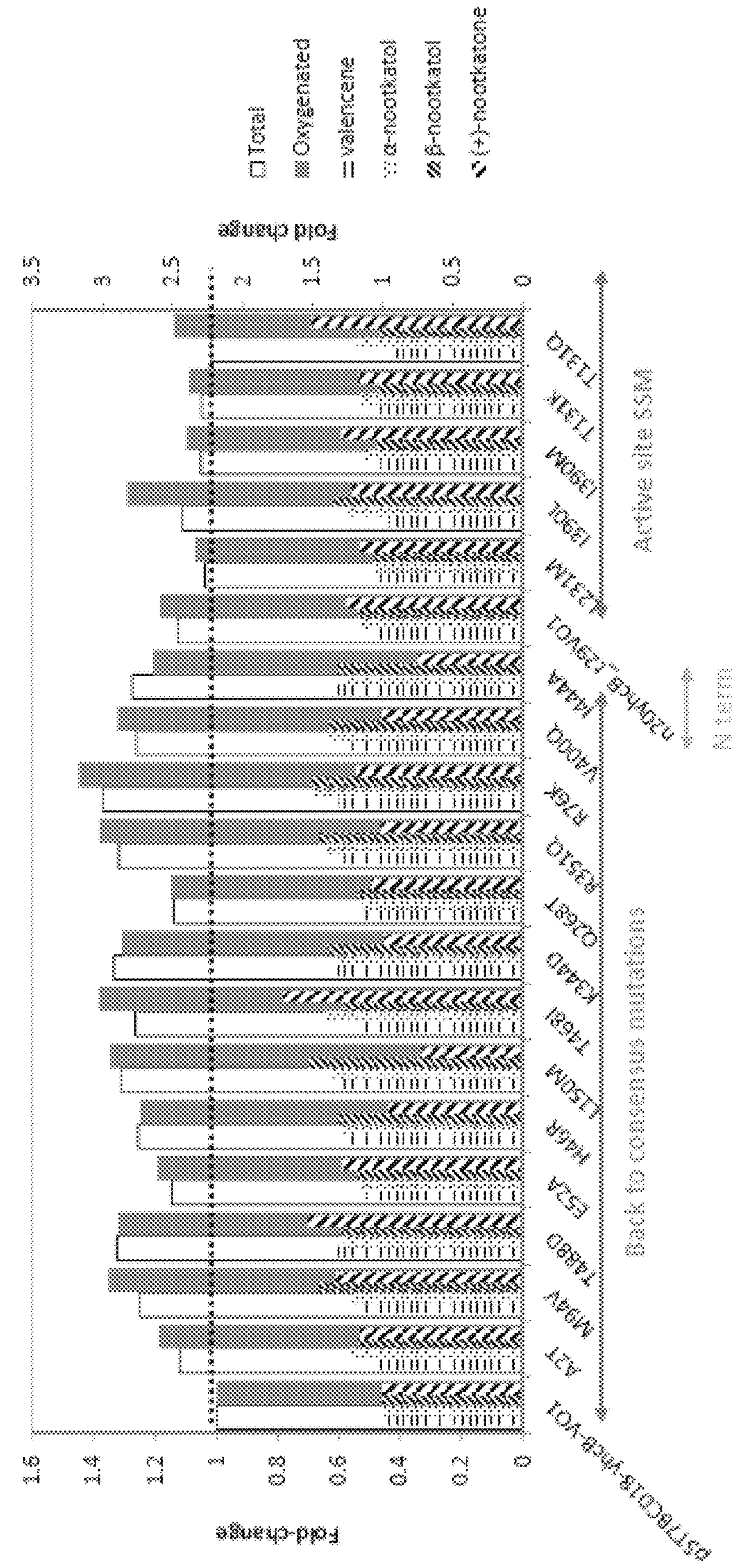
FIG. 14 shows results of secondary screening of back-to-consensus mutations, N-terminal anchor optimization, and site-saturation mutagenesis (SSM). Several mutations were identified that show a 1.1 to 1.4-fold improvement in oxygenated titers.

Lead variants from active site SSM (L231M, I390L, I390M, T131K, and T131Q), the N-terminal anchor variant n20yhcB_t29VO1, and back-to-consensus mutagenesis were selected, and re-screened. The results of this secondary screen are shown in FIG. 14.

Figure 15:
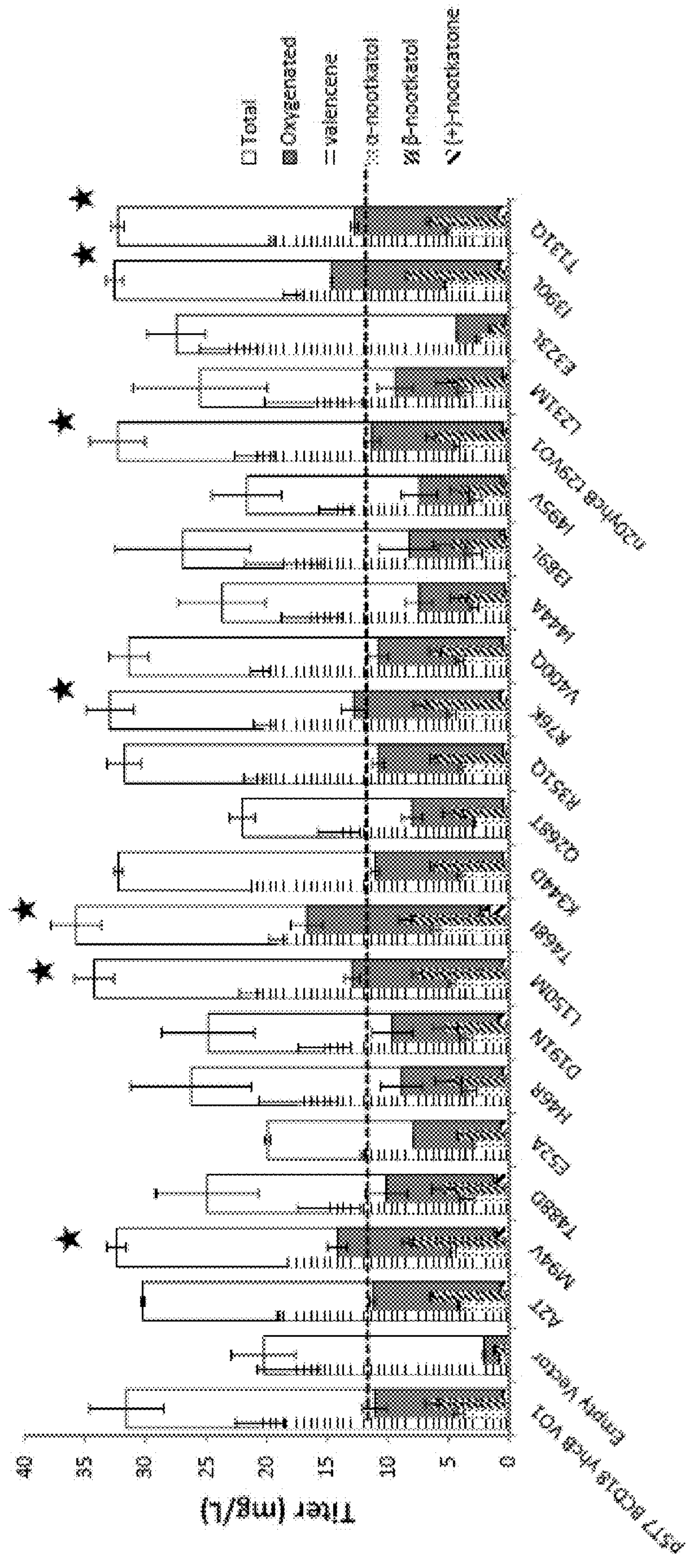
FIG. 15 shows performance of select VO1 variants at 33° C. Six mutations were identified that maintained improved productivities at 33° C.

Several mutations showed a 1.1-1.4-fold improvement in oxygenated titers. To narrow the list of mutations for recombination, the same mutations were screened at 33° C. to differentiate stabilizing mutations which could enable a process shift to higher temperature. As shown in FIG. 15, six mutations (M94V, L150M, T468I, R76K, I390L, and T131Q) maintained improved productivities at 33° C. These six mutations, in addition to the lead N-terminal anchor, were selected for recombination.

Example 7: SrKO Recombination Library Screening

The seven mutations selected after secondary screening (Example 6) were randomly incorporated into a VO recombination library by allowing either the variant or wild type at each site. The background strain was MB2509 (EGV G2 MP6-CPR)+pBAC-T7-BCD7-yhcB-VO.

Figure 16A:
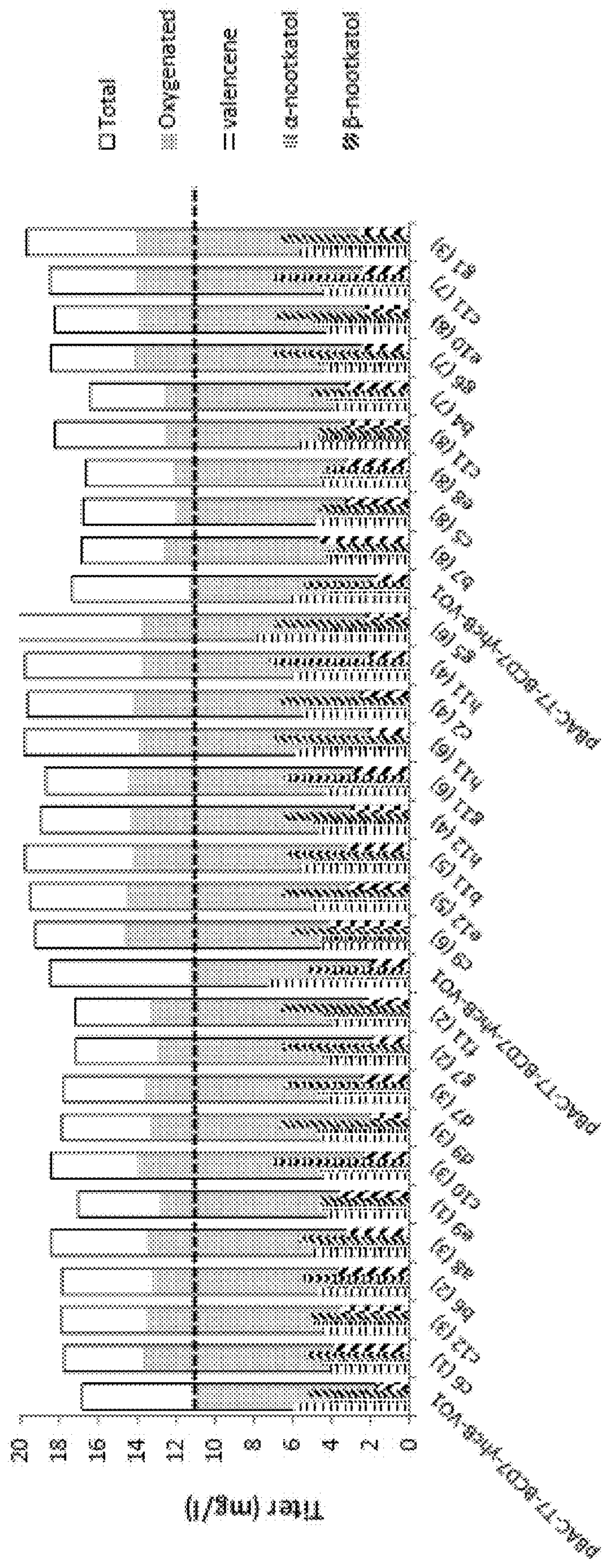
FIG. 16 (A and B) shows results from primary screening of the recombination library. Several variants (shown) exhibited up to 1.35-fold improvement in oxygenated product titer. There was a shift in profile to more (+)-nootkatone and higher oxygenation capacity for select variants. Panel (A) shows oxygenated product in mg/L. Panel (B) plots the fold change in oxygenation capacity (nootkatols require only one oxygenation cycle from valencene, while nootkatone requires two oxygenation cycles).
Figure 16B:
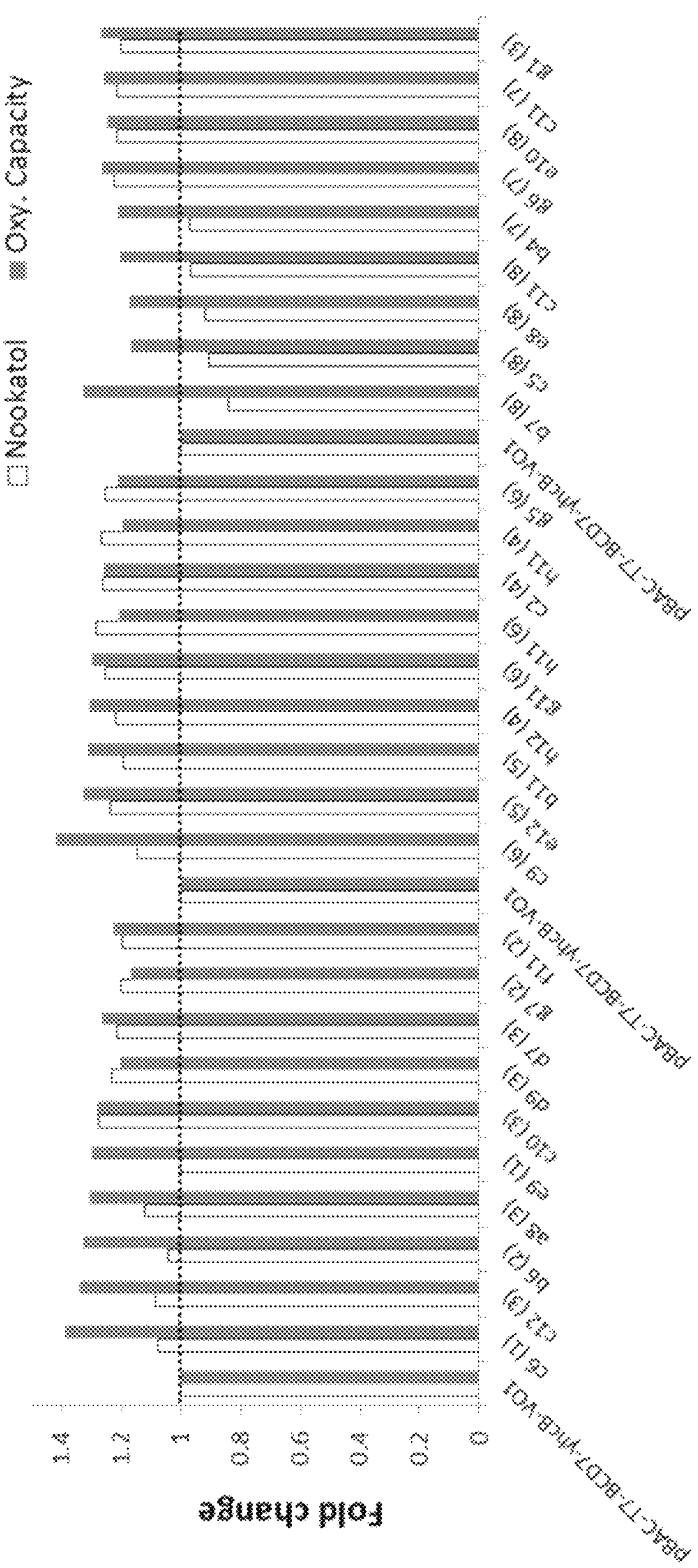

Primary screening at 30° C. (using the same process described in Example 5) identified several variants with up to 1.35-fold improvement in oxygenated product titers, compared to VO1. Further, select variants showed a shift in production to nootkatone, suggesting higher P450 activity (since production of nootkatone requires two oxygenation cycles). Results of primary screening are shown in FIG. 16A (strain versus titer in mg/L). FIG. 16B presents the same screen shown based on oxygenation capacity (total of nootkatone, α-nootkatol, and β-nootkatol).

Figure 17:
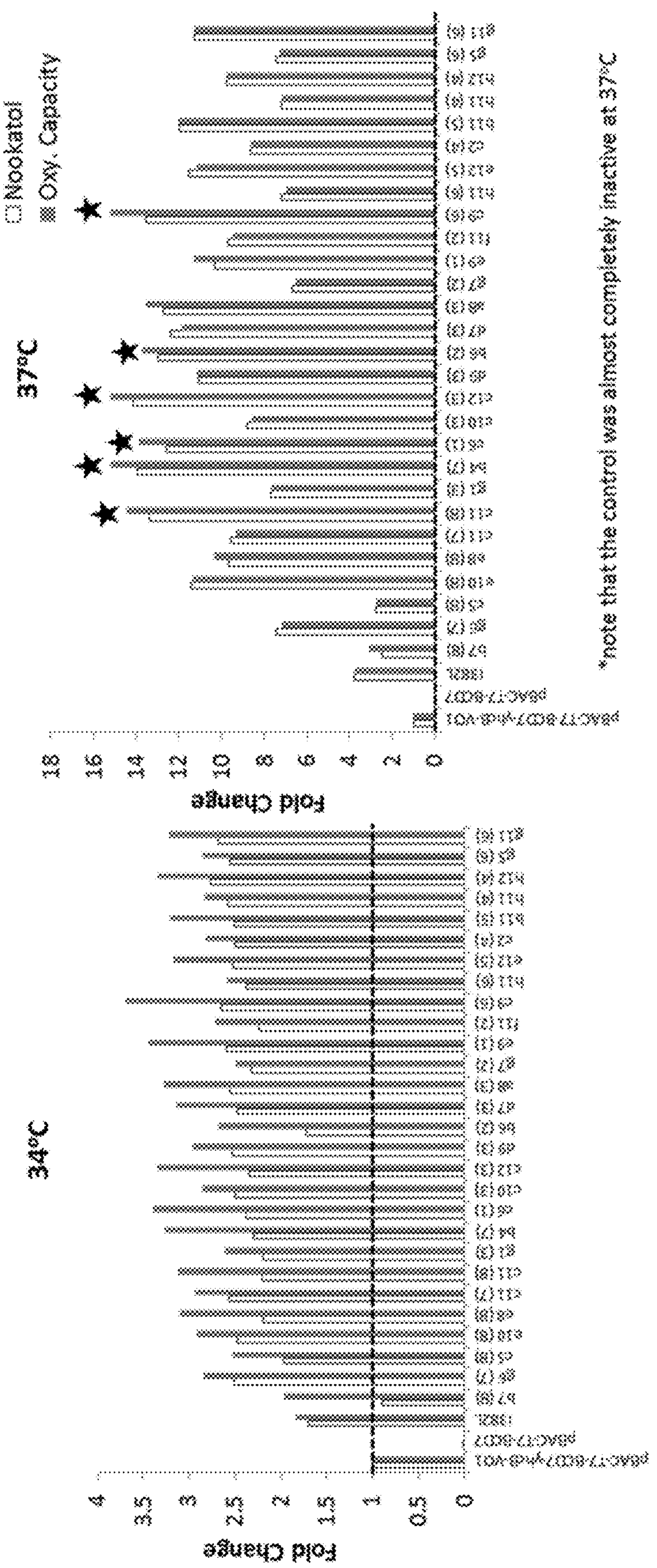
FIG. 17 shows oxygenation capacity at 34° C. and 37° C. for select VO recombination library variants.
Figure 18:
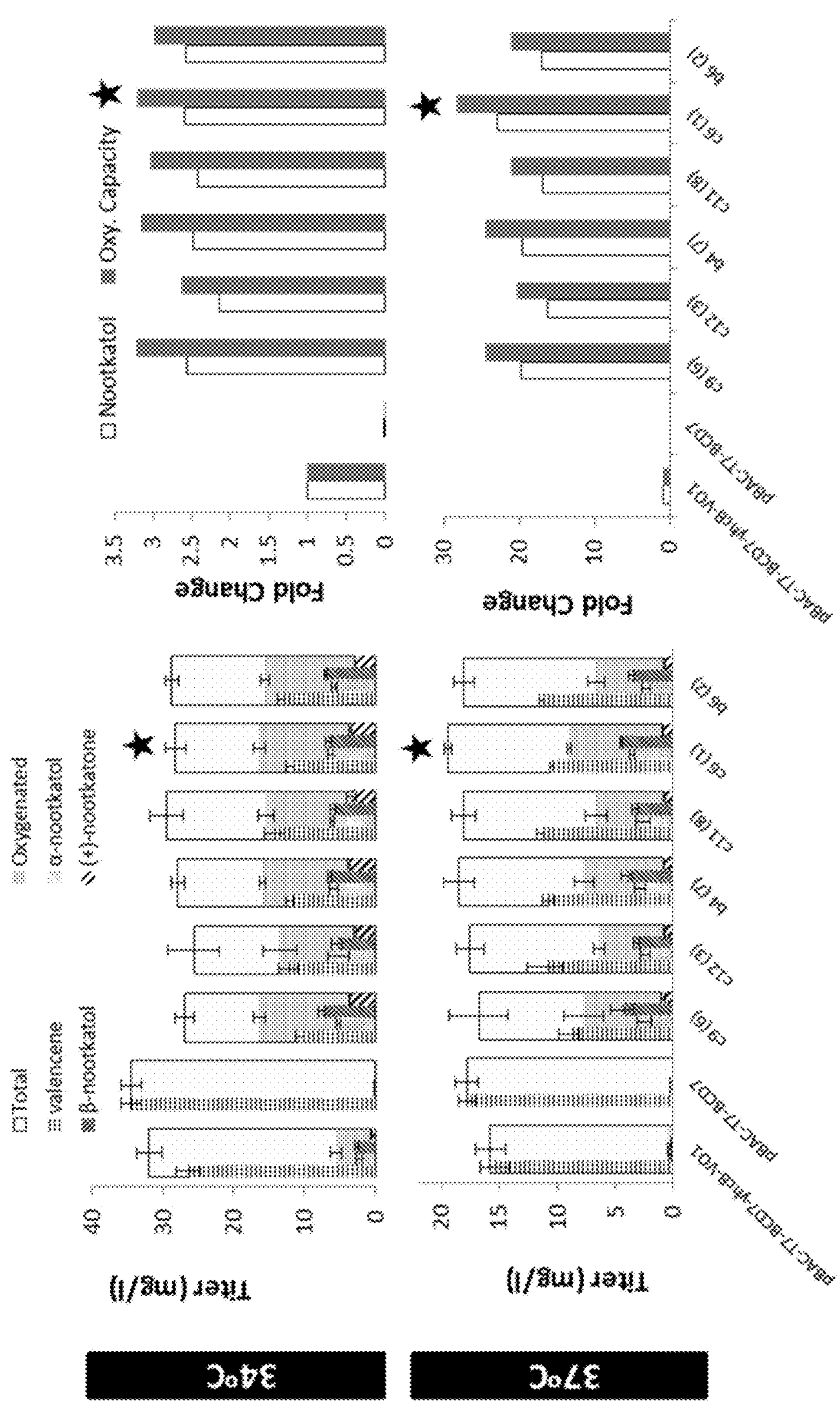
FIG. 18 shows oxygenation titer at 34° C. and 37° C. after re-screen of lead VO variants. C6(1) (R76K, M94V, T131Q, I390L, T468I) had the highest oxygenation capacity at 37° C., and was designated VO2 (SEQ ID NO: 111).
Figure 19:
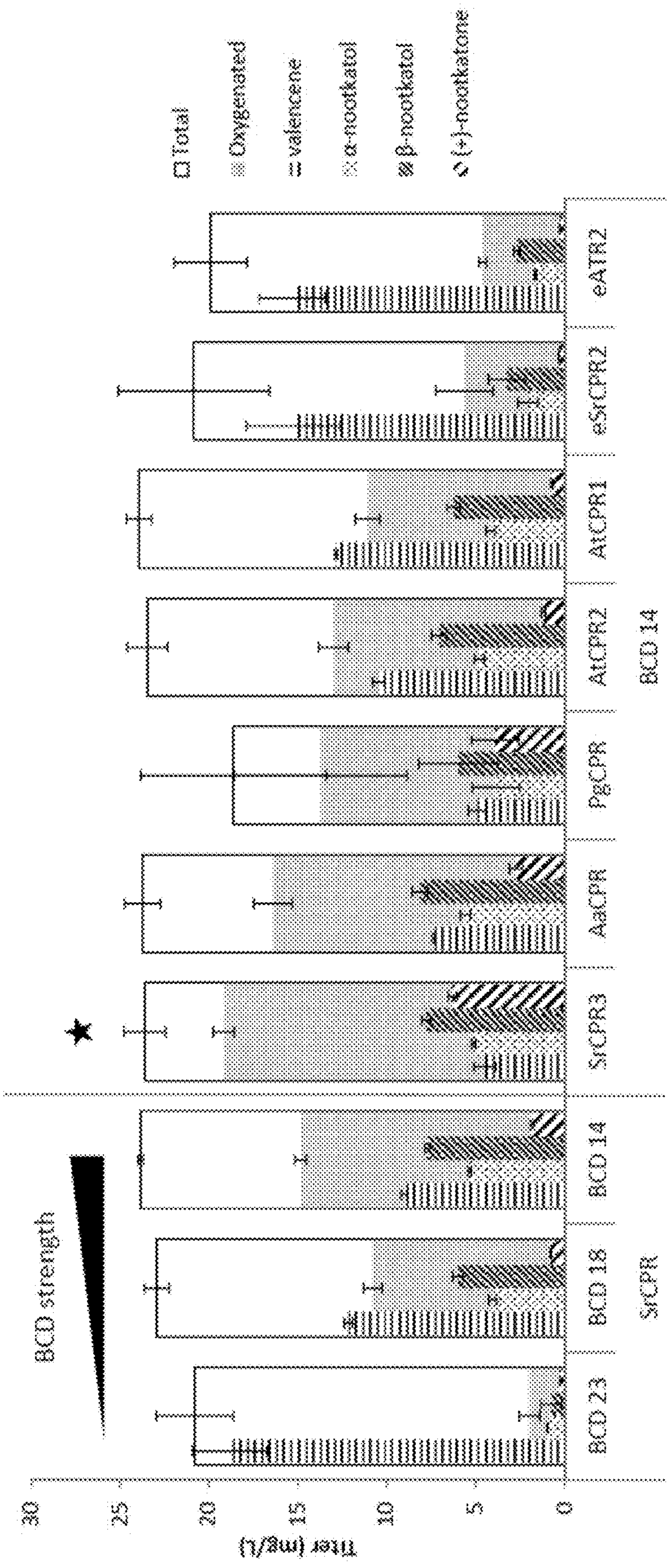
FIG. 19 shows screening of cytochrome P450 reductase (CPR) orthologs for enhanced valencene oxidase activity (30° C.). SrCPR3 shows increased oxygenation titer and higher production of Nootkatone.

The recombination variants were then screened at 34° C. and 37° C. to select leads with improved activity and stability at higher temperature. The results of the secondary screen are shown in FIG. 17. While the control was almost completely inactive at 37° C., six leads showed promising activity at the higher temperatures, and were selected for further screening (c11(8), b4(7), c6(1), c12(3), b6(2), and c9(6)). Based on this further screening (FIG. 18) c6(1) was selected as the best variant based on oxygenation capacity. Variant c6(1) was further modified to generate VO2 (SEQ ID NO: 111). The six leads contain the following sets of mutations.

TABLE 14

Sets of mutations in lead variants from recombination library (shown relative to SEQ ID NOS: 37 and 108).

| | N20_t29yhcB | R76K | M94V | T131Q | L150M | I390L | T468I | A39H | Others |
|---|---|---|---|---|---|---|---|---|---|
| c9(6) | | | X | | | X | X | | V146L |
| c12(3) | | X | | X | | X | X | | |
| b4(7) | | | X | X | | X | X | X | |
| c11(8) | X | X | | X | | X | X | X | |
| c6(1) | | X | X | X | | X | X | | |
| b6(2) | | X | X | | | | X | | |

FIG. 23 (A and B) shows alignments of several engineered valencene oxidase (VO) variants as described herein, and highlights select mutations evaluated in the screening process. In FIG. 23A: 8rp-t20SrKO (SEQ ID NO: 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 499 (numbered according to wild-type SrKO). n22yhcB-t30VO1 (SEQ ID NO: 104) has a 30-amino acid truncation of the SrKO N-terminus, a membrane anchor based on 22 amino acids from *E. coli* yhcB, and eight point mutations at positions 46, 231, 284, 383, 400, 444, 488, and 499 (with respect to SrKO wild-type). n22yhcB-t30VO2 (SEQ ID NOS: 61 and 105) has a 30-amino acid truncation of the SrKO N-terminus, a membrane anchor based on 22 amino acids from *E. coli* yhcB, and nine point mutations at positions 76, 94, 131, 231, 284, 383, 390, 468, and 499 (with respect to SrKO wild-type). In FIG. 23B, point mutations in VO0 (SEQ ID NO: 109), VO1 (SEQ ID NO: 110), and VO2 (SEQ ID NO: 111) are shown against wild-type SrKO (SEQ ID NO: 108) (all shown with the wild-type SrKO N-terminus for convenience).

Example 8: Cytochrome P450 Reductase Screening

A set of cytochrome P450 reductases were screened for improved activity with VO1. This example was done using the strain MB2459 as the background, with pBAC-T7-BCD7-VO1(I382L)-T7BCDx-CPRx. BCD stands for BiCistronic Design, and is described in Mutalik et. al. *Nature Methods* 2013(10)4:354. Lower BCD numbers refer to higher translation rate. CPRs included SrCPR (SEQ ID NO: 62), SrCPR3 (SEQ ID NO: 80), AaCPR (SEQ ID NO: 68), PgCPR (SEQ ID NO: 82), AtCPR2 (SEQ ID NO: 72), AtCPR1 (SEQ ID NO: 70), eSrCPR1 (SEQ ID NO: 76), and eATR2 (SEQ ID NO: 74). Strains were tested as in Example 5, at 30° C.

Figure 20:
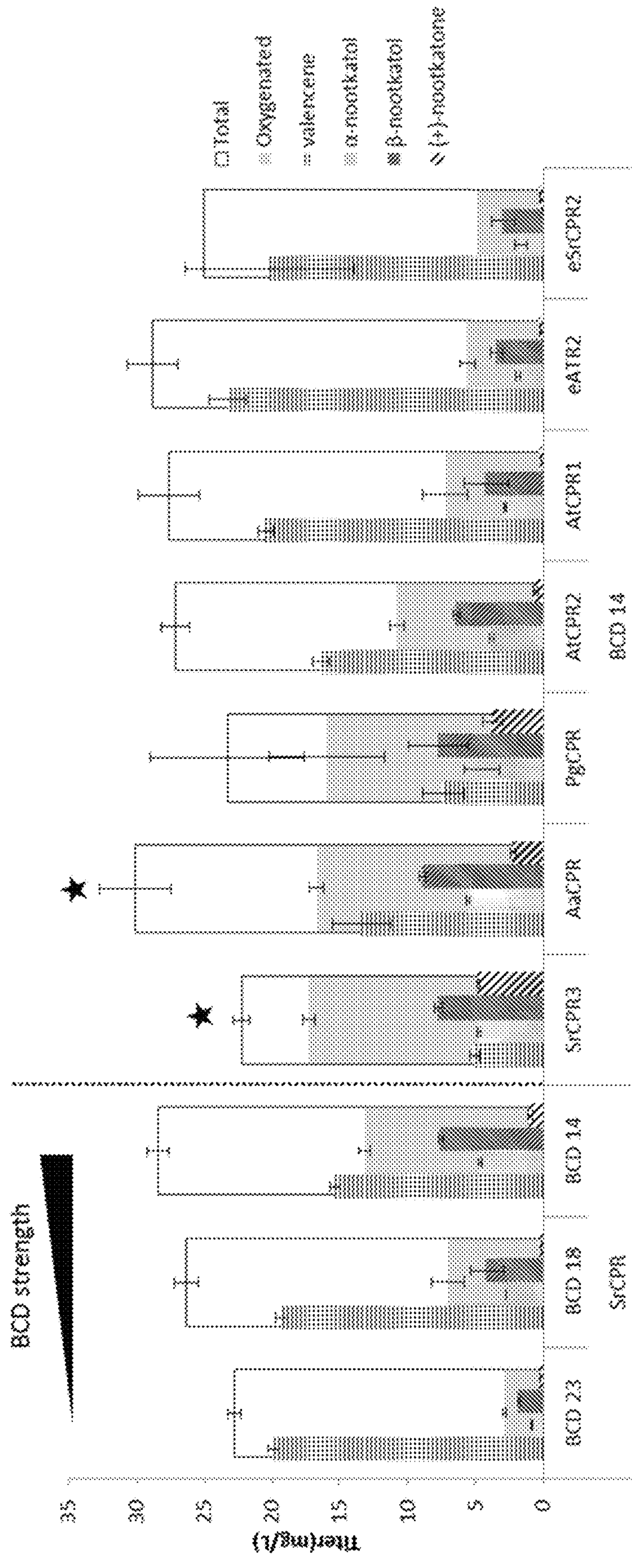
FIG. 20 shows screening of CPR orthologs at 34° C. SrCPR3 and AaCPR exhibit ~1.3-fold improvement in oxygenated titer, even at the higher temperature.

As shown in FIG. 20, SrCPR3, which was obtained through RNA sequencing studies, exhibited a 1.3-fold improvement in oxygenated titer.

The CPR orthologs were retested at 34° C. The results are shown in FIG. 20. Both SrCPR3 (SEQ ID NO: 80) and AaCPR (SEQ ID NO: 68) exhibited a 1.3-fold improvement in oxygenated titer, even at the higher temperature. Oxygenated titers are comparable to those obtained at 30° C.

Example 9: Alcohol Dehydrogenase Enzymes to Alter Product Profile

The ability of alcohol dehydrogenases to convert nootkatols to nootkatone was evaluated. The following ADH enzymes were evaluated:

TABLE 15

CPR enzymes

| Gene | UniProtID | Organism |
|---|---|---|
| reCDH | Q9RA05 | *Rhodococcus erythropolis* |
| csDH1 | A0A067H4B8 | *Citrus sinensis* |
| csDH2 | A0A067H4S0 | *Citrus sinensis* |
| csDH3 | | *Citrus sinensis* |
| vvDH | F6GX78 | *Vitis vinifera* |
| voDH1 | | |
| csABA2 | A0A067DRA0 | *Citrus sinensis* |
| csDH | A0A0A0KNF1 | *Cucumis sativus* |
| bdDH | I1GLS4 | *Brachypodium distachyon* |
| zzSDR | F1SWA0 | *Zingiber zerumbet* |

Strains were evaluated as in Example 5, using MB2490 as the background strain (MP6-MEP FAB46-ScFPPS-L-VS1 MP6-VO1-o-SrCPR+p5-T7-BCD14-ADH). Briefly, MP6, Fab46 and T7 refer to the promoter for the attached gene or operon. Here MEP is an operon overexpressing *E. coli* dxs, idi, and ispDF genes. The L between ScFPPS and VS1 refers to a short polypeptide linker encoding (GSTGS) while -o- between VO1 and SrCPR refers to an operonic construction in which an RBS sequence is inserted between the two genes. The plus denotes a plasmid following which is described as a p5 (five copy) plasmid with a promoter, BCD (described above) and the ADH in question.

Figure 21:
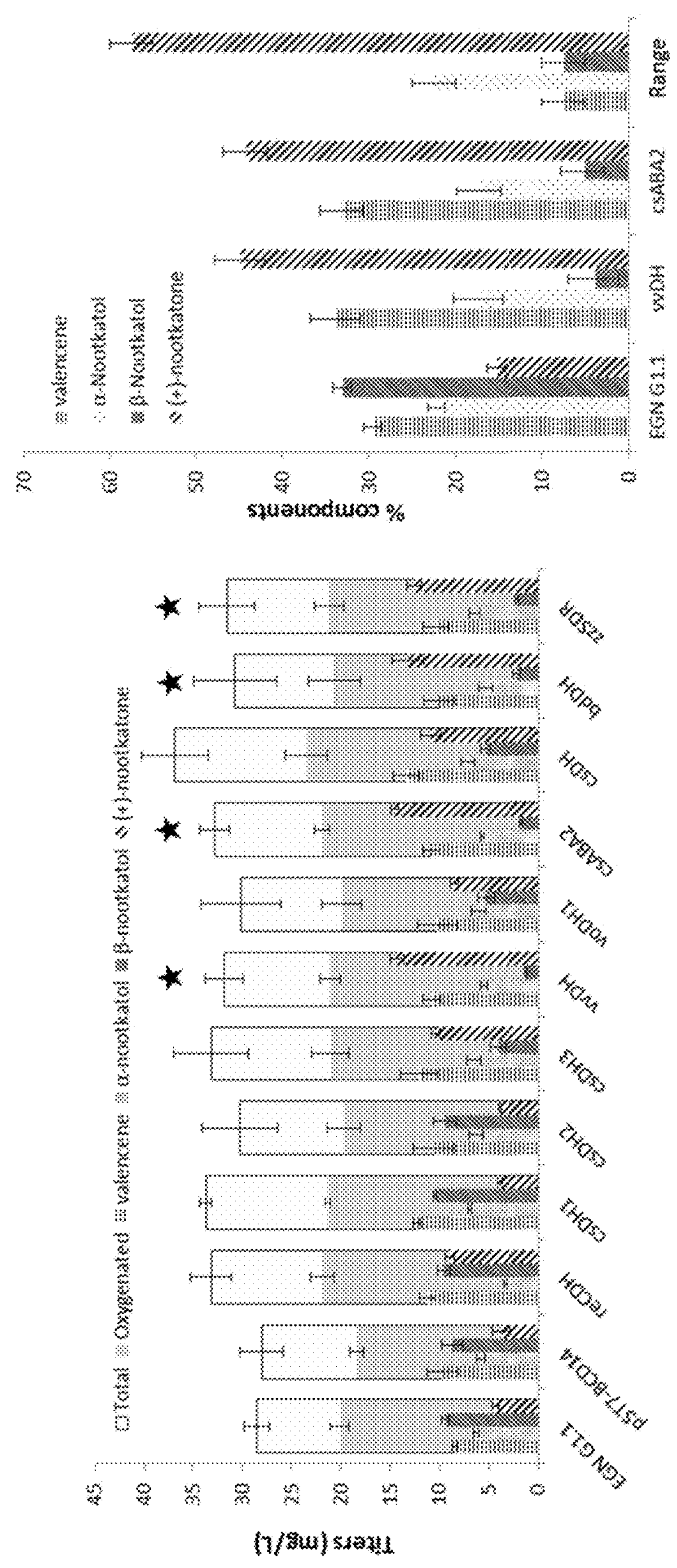
FIG. 21 shows conversion of nootkatols to nootkatone with an alcohol dehydrogenase (ADH). Four ADH orthologs (vvDH, csABA2, bdDH, and zzSDR) were identified that convert β-nootkatol to (+)-nootkatone, resulting in a 3-fold increase in (+)-nootkatone titers and an increase in proportion of α-nootkatol.

Four orthologs were identified (vvDH, csABA2, bdDH, and zzSDR) that convert β-nootkatol to nootkatone, resulting in more than a 3-fold increase in nootkatone titers. FIG. 21.

REFERENCES

1. Qualley A, Dudareva N. Plant Volatiles. Encycl. Life Sci. 2010; 1-9.
2. Ajikumar P, Tyo K, Carlsen S. Terpenoids: opportunities for biosynthesis of natural product drugs using engineered microorganisms. Mol. Pharm. [Internet]. 2008 [cited 2013 May 16]; 5(2):167-90.
3. Ajikumar P K, Xiao W-H, Tyo K E J, Wang Y, Simeon F, Leonard E, et al. Isoprenoid pathway optimization for Taxol precursor overproduction in *Escherichia coli*. Science [Internet]. 2010 Oct. 1 [cited 2013 May 22]; 330(6000):70-4.
4. Ro D-K, Paradise E M, Ouellet M, Fisher K J, Newman K L, Ndungu J M, et al. Production of the antimalarial drug precursor artemisinic acid in engineered yeast. Nature [Internet]. 2006 Apr. 13 [cited 2013 Mar. 1]; 440(7086):940-3.
5. Sevrioukova I F, Li H, Zhang H, Peterson J a, Poulos T L. Structure of a cytochrome P450-redox partner electron-transfer complex. Proc. Natl. Acad. Sci. U.S.A. [Internet]. 1999 Mar. 2; 96(5):1863-8.

6. Sevrioukova I F, Poulos T L. Structural biology of redox partner interactions in P450cam monooxygenase: a fresh look at an old system. Arch. Biochem. Biophys. [Internet]. Elsevier Inc.; 2011 Mar. 1 [cited 2013 Mar. 26]; 507(1):66-74.
7. Ekroos M, Sjögren T. Structural basis for ligand promiscuity in cytochrome P450 3A4. Proc. Natl. Acad. Sci. U.S.A. [Internet]. 2006 Sep. 12; 103(37):13682-7.
8. Takahashi S, Yeo Y-S, Zhao Y, O'Maille P E, Greenhagen B T, Noel J P, et al. Functional characterization of premnaspirodiene oxygenase, a cytochrome P450 catalyzing regio- and stereo-specific hydroxylations of diverse sesquiterpene substrates. J. Biol. Chem. [Internet]. 2007 Oct. 26 [cited 2013 Mar. 10]; 282(43): 31744-54.
9. Morrone D, Chen X, Coates R M, Peters R J. Characterization of the kaurene oxidase CYP701A3, a multifunctional cytochrome P450 from gibberellin biosynthesis. Biochem. J. [Internet]. 2010 Nov. 1 [cited 2013 Feb. 6]; 431(3):337-44.
10. Zhang Z, Sibbesen O. The substrate specificity of cytochrome P450 cam. Bioorganic Med. . . . [Internet]. 1998 [cited 2013 Sep. 24]; 6:1501-8.
11. Stjemschantz E, van Vugt-Lussenburg B M a, Bonifacio A, de Beer S B a, van der Zwan G, Gooijer C, et al. Structural rationalization of novel drug metabolizing mutants of cytochrome P450 BM3. Proteins [Internet]. 2008 April [cited 2013 May 16]; 71(1):336-52.
12. Chen M M Y, Snow C D, Vizcarra C L, Mayo S L, Arnold F H. Comparison of random mutagenesis and semi-rational designed libraries for improved cytochrome P450 BM3-catalyzed hydroxylation of small alkanes. Protein Eng. Des. Sel. [Internet]. 2012 April [cited 2013 Mar. 11]; 25(4):171-8.
13. Harford-Cross C F, Carmichael a B, Allan F K, England P a, Rouch D a, Wong L L. Protein engineering of cytochrome p450(cam) (CYP101) for the oxidation of polycyclic aromatic hydrocarbons. Protein Eng. [Internet]. 2000 February; 13(2):121-8.
14. Bell S G, Chen X, Sowden R J, Xu F, Williams J N, Wong L, et al. Molecular Recognition in (+)-r-Pinene Oxidation by Cytochrome P450cam. J. Am. Chem. Soc. 2003; 125:705-14.
15. Sowden R, Yasmin S, Rees N, Bell S G, Wong L-L. Biotransformation of the sesquiterpene (+)-valencene by cytochrome P450cam and P450BM-3. Org. Biomol. Chem. [Internet]. 2005 [cited 2013 May 16]; 3:57-64.
16. Brandle J E, Richman A, Swanson A K, Chapman B P. Leaf Ests from *Stevia rebaudiana*: a resource for gene discovery in diterpene synthesis. Plant Mol. Biol. [Internet]. 2002 November [cited 2013 Feb. 12]; 50(4-5):613-22.
17. Bar-even A, Noor E, Savir Y, Liebermeister W, Davidi D, Tawfik D S, et al. The Moderately Efficient Enzyme: Evolutionary and Physicochemical Trends Shaping Enzyme Parameters. Biochemistry. 2011;
18. Pleiss J. Protein design in metabolic engineering and synthetic biology. Curr. Opin. Biotechnol. [Internet]. 2011 October [cited 2013 Mar. 5]; 22(5):611-7.
19. Lehmann M, Pasamontes L, Lassen S F, Wyss M. The consensus concept for thermostability engineering of proteins. Biochim. Biophys. Acta [Internet]. 2000 Dec. 29 [cited 2013 Oct. 17]; 1543(2):408-15.
20. Vazquez-Figueroa E, Yeh V, Broering J M, Chaparro-Riggers J F, Bommarius A S. Thermostable variants constructed via the structure-guided consensus method also show increased stability in salts solutions and homogeneous aqueous-organic media. Protein Eng. Des. Sel. [Internet]. 2008 November [cited 2013 Oct. 17]; 21(11):673-80.
21. Dai M, Fisher H E, Temirov J, Kiss C, Phipps M E, Pavlik P, et al. The creation of a novel fluorescent protein by guided consensus engineering. Protein Eng. Des. Sel. [Internet]. 2007 February [cited 2013 Sep. 19]; 20(2):69-79.
22. Fraatz M a., Riemer S J L, Stober R, Kaspera R, Nimtz M, Berger R G, et al. A novel oxygenase from *Pleurotus sapidus* transforms valencene to nootkatone. J. Mol. Catal. B Enzym. [Internet]. 2009 December [cited 2013 Apr. 17]; 61(3-4):202-7.
23. Krügener S, Krings U, Zorn H, Berger R G. A dioxygenase of *Pleurotus sapidus* transforms (+)-valencene regio-specifically to (+)-nootkatone via a stereo-specific allylic hydroperoxidation. Bioresour. Technol. [Internet]. Elsevier Ltd; 2010 January [cited 2013 Apr. 12]; 101(2):457-62.
24. Zorn H, Fraatz M A, Riemer S J L, Takenberg M. Enzymatic synthesis of nootkatone. GERMANY; 2010.
25. Kaspera R, Krings U, Nanzad T, Berger R G. Bioconversion of (+)-valencene in submerged cultures of the ascomycete *Chaetomium globosum*. Appl. Microbiol. Biotechnol. [Internet]. 2005 June [cited 2013 May 16]; 67(4):477-83.
26. Cankar K, van Houwelingen A, Bosch D, Sonke T, Bouwmeester H, Beekwilder J. A chicory cytochrome P450 mono-oxygenase CYP71AV8 for the oxidation of (+)-valencene. FEBS Lett. [Internet]. Federation of European Biochemical Societies; 2011 January 3 [cited 2013 Mar. 6]; 585(1):178-82.
27. Girhard M, Machida K, Itoh M, Schmid R D, Arisawa A, Urlacher V B. Regioselective biooxidation of (+)-valencene by recombinant *E. coli* expressing CYP109B1 from *Bacillus subtilis* in a two-liquid-phase system. Microb. Cell Fact. [Internet]. 2009 January [cited 2013 May 16]; 8(4):36.
28. Bm-P, Sowden R J, Yasmin S, Rees N H, Bell S G, Wong L. Biotransformation of the sesquiterpene (+)-valencene by cytochrome P450. 2005; 57-64.
29. Trott O, Olson A. AutoDock Vina: improving the speed and accuracy of docking with a new scoring function, efficient optimization, and multithreading. J. Comput. Chem. [Internet]. 2010 [cited 2013 Jul. 26]; 31(2):455-61.1

The invention claimed is:

1. A method of making a product for providing oxygenated terpenes, comprising: obtaining a formulation by contacting valencene with *Stevia rebaudiana* Kaurene Oxidase (SrKO) or an SrKO derivative comprising a sequence having at least 70% sequence identity to SEQ ID NO: 37, SEQ ID NO: 38, or SEQ ID NO: 55, and having valencene oxidizing activity in an in vitro or in vivo system to produce an oxygenated product comprising nootkatone, α-nootkatol, and β-nootkatol, and incorporating the formulation into a consumer product, an industrial product, a flavor product, a fragrance product, a cosmetic product, a cleaning product, a detergent product, a soap product, or a pest control product.

2. The method of claim 1, wherein the flavor product is a beverage, a chewing gum, a candy, a natural flavor, an artificial flavor, or a flavor additive.

3. The method of claim 1, wherein obtaining the formulation comprises contacting valencene with *Stevia rebaudiana* Kaurene Oxidase (SrKO) or an SrKO derivative comprising a sequence having at least 70% sequence identity to SEQ ID NO: 37, SEQ ID NO: 38, or SEQ ID NO: 55, and having valencene oxidizing activity in an in vivo or in vitro system to yield an oxygenated product.

4. The method of claim 1, further comprising processing the oxygenated product by fractional distillation to yield two or more fractions of the oxygenated product.

5. The method of claim 4, further comprising blending the two or more fractions of the oxygenated product.

6. The method of claim 1, further comprising adding an unoxygenated product to the oxygenated product, one or more fractions of the oxygenated product, or the formulation.

7. The method of claim 6, wherein the unoxygenated product comprises valencene.

8. The method of claim 7, wherein the valencene is present in the formulation in an amount ranging from about 5% to about 10% (w/w).

9. The method of claim 1, wherein the formulation further comprises one or more non-sesquiterpene components or sesquiterpene components.

10. The method of claim 9, wherein the one or more non-sesquiterpene components or sesquiterpene components is selected from Table 8A, Table 8B, and Table 9.

* * * * *